US012702394B2

(12) United States Patent
Lashinski et al.

(10) Patent No.: US 12,702,394 B2
(45) Date of Patent: Aug. 11, 2026

(54) DEVICES, SYSTEMS, AND METHODS FOR TREATING THE LEFT ATRIAL APPENDAGE

(71) Applicant: Laminar, Inc., Santa Rosa, CA (US)

(72) Inventors: Randall T. Lashinski, Windsor, CA (US); Joshua J. Dwork, Santa Rosa, CA (US); Michael James Lee, Santa Rosa, CA (US); Finn Olavi Rinne, Santa Rosa, CA (US)

(73) Assignee: Laminar, Inc., Santa Rosa, CA (US)

( * ) Notice: Subject to any disclaimer, the term of this patent is extended or adjusted under 35 U.S.C. 154(b) by 1269 days.

(21) Appl. No.: 17/368,715

(22) Filed: Jul. 6, 2021

(65) Prior Publication Data

US 2022/0022854 A1 Jan. 27, 2022

Related U.S. Application Data

(60) Provisional application No. 63/171,011, filed on Apr. 5, 2021, provisional application No. 63/072,035, filed
(Continued)

(51) Int. Cl.
*A61B 17/00* (2006.01)

(52) U.S. Cl.
CPC ............................... *A61B 17/0057* (2013.01); *A61B 2017/00477* (2013.01); *A61B 2017/00619* (2013.01);
(Continued)

(58) Field of Classification Search
CPC ...... A61B 17/0057; A61B 2017/00477; A61B 2017/00619; A61B 2017/12095; A61B 2017/12122
See application file for complete search history.

(56) References Cited

U.S. PATENT DOCUMENTS 5,006,106 A 4/1991 Angelchik
5,919,207 A 7/1999 Taheri
(Continued)

FOREIGN PATENT DOCUMENTS

EP 1441649 B1 8/2011
EP 3342354 A1 7/2018
(Continued)

OTHER PUBLICATIONS

U.S. Appl. No. 16/828,782 (U.S. Pat. No. 11,219,462), filed Mar. 24, 2020, Devices, Systems, and Methods for Treating the Left Atrial Appendage.
(Continued)

*Primary Examiner* — Brooke Labranche
(74) *Attorney, Agent, or Firm* — FBT Gibbons LLP

(57) ABSTRACT

A device for treating a left atrial appendage, including an implant having a contact member configured to engage an inside tissue surface of the left atrial appendage and configured to rotate in at least a first direction from a first position to at least a second position so as to twist the left atrial appendage when the contact member is engaged with an inside tissue surface of the left atrial appendage. Some embodiments can also include a securing element configured to move between a first position in which the securing element is decoupled from the contact member and a second position in which the securing element is coupled with the contact member.

35 Claims, 116 Drawing Sheets

Related U.S. Application Data on Aug. 28, 2020, provisional application No. 63/049,077, filed on Jul. 7, 2020.

(52) U.S. Cl.
CPC ............... *A61B 2017/00623* (2013.01); *A61B 2017/00632* (2013.01)

(56) References Cited

U.S. PATENT DOCUMENTS 6,290,674 B1 9/2001 Roue et al.
6,463,331 B1 10/2002 Edwards
6,626,930 B1 9/2003 Allen et al.
6,652,556 B1 11/2003 VanTassel et al.
6,773,440 B2 8/2004 Gannoe et al.
6,969,396 B2 11/2005 Krolik et al.
7,025,756 B2 4/2006 Frazier et al.
7,044,134 B2 5/2006 Khairkhahan et al.
7,115,110 B2 10/2006 Frazier et al.
7,122,043 B2 10/2006 Greenhalgh et al.
7,128,073 B1 10/2006 van der Burg et al.
7,226,458 B2 6/2007 Kaplan et al.
7,320,665 B2 1/2008 Vijay
7,357,815 B2 4/2008 Shaoulian et al.
7,442,207 B2 10/2008 Rafiee
7,559,936 B2 7/2009 Levine
7,566,336 B2 7/2009 Corcoran et al.
7,645,285 B2 1/2010 Cosgrove et al.
7,648,532 B2 1/2010 Greenhalgh et al.
7,655,040 B2 2/2010 Douk et al.
7,695,510 B2 4/2010 Bloom et al.
7,713,282 B2 5/2010 Frazier et al.
7,722,641 B2 5/2010 van der Burg et al.
7,727,249 B2 6/2010 Rahmani
7,736,392 B2 6/2010 Starkebaum
7,758,639 B2 7/2010 Mathis
7,780,683 B2 8/2010 Roue et al.
7,828,716 B2 11/2010 Burton et al.
7,984,717 B2 7/2011 Tropsha et al.
8,043,329 B2 10/2011 Khairkhahan et al.
8,070,671 B2 12/2011 Deem et al.
8,097,015 B2 1/2012 Devellian
8,197,496 B2 6/2012 Roue et al.
8,236,050 B2 8/2012 Bolling et al.
8,287,557 B2 10/2012 To et al.
8,323,309 B2 12/2012 Khairkhahan et al.
8,443,808 B2 5/2013 Brensel et al.
8,512,403 B2 8/2013 Navia et al.
8,523,897 B2 9/2013 van der Burg et al.
8,551,161 B2 10/2013 Dolan
8,603,137 B2 12/2013 Voss et al.
8,690,911 B2 4/2014 Miles et al.
8,758,395 B2 6/2014 Kleshinski et al.
8,764,793 B2 7/2014 Lee
8,771,297 B2 7/2014 Miller et al.
8,777,926 B2 7/2014 Chang et al.
8,784,469 B2 7/2014 Kassab
8,784,482 B2 7/2014 Rahdert et al.
8,840,641 B2 9/2014 Miles et al.
8,845,711 B2 9/2014 Miles et al.
8,851,077 B2 10/2014 Brensel et al.
8,968,284 B2 3/2015 Thomas et al.
9,023,080 B2 5/2015 Ciobanu et al.
9,089,311 B2 7/2015 Fortson et al.
9,095,363 B2 8/2015 Van Bladel et al.
9,186,152 B2 11/2015 Campbell et al.
9,220,487 B2 12/2015 Davis et al.
9,314,249 B2 4/2016 Kreidler et al.
9,326,857 B2 5/2016 Carledge et al.
9,358,009 B2 6/2016 Yock et al.
9,427,220 B2 8/2016 Whitman et al.
9,554,804 B2 1/2017 Erzberger et al.
9,572,584 B2 2/2017 Miles et al.
9,592,058 B2 3/2017 Erzberger et al.
9,597,086 B2 3/2017 Larsen et al.
9,615,926 B2 4/2017 Lashinski et al.
9,649,115 B2 5/2017 Edmiston et al.
9,662,117 B2 5/2017 Forsell
9,675,360 B2 6/2017 Baker
9,693,780 B2 7/2017 Miles et al.
9,693,781 B2 7/2017 Miles et al.
9,707,124 B2 7/2017 Brensel et al.
9,717,488 B2 8/2017 Kassab
9,763,666 B2 9/2017 Wu et al.
9,795,480 B2 10/2017 Bolling et al.
9,795,481 B2 10/2017 Callas et al.
9,808,253 B2 11/2017 Li et al.
9,826,980 B2 11/2017 Figulla et al.
9,883,864 B2 2/2018 Miles et al.
9,918,719 B2 3/2018 Konstantino et al.
9,937,042 B2 4/2018 Cabiri et al.
9,987,017 B2 6/2018 Smith et al.
10,064,628 B2 9/2018 Edmiston et al.
10,071,226 B2 9/2018 Hsueh et al.
10,098,640 B2 10/2018 Bertolero et al.
10,143,456 B2 12/2018 Javois
10,143,478 B2 12/2018 Forbes
10,238,398 B2 3/2019 Hughett, Sr. et al.
10,278,705 B2 5/2019 Amin et al.
10,299,799 B1 5/2019 DeMeritt
10,307,165 B2 6/2019 Henderson et al.
10,307,620 B2 6/2019 Burdette
10,386,990 B2 8/2019 Shikham et al.
10,405,866 B2 9/2019 Chakroborty et al.
10,420,564 B2 9/2019 Miles et al.
10,433,998 B2 10/2019 Keren et al.
10,441,258 B2 10/2019 Corcoran et al.
10,531,878 B2 1/2020 Slaughter et al.
10,537,332 B2 1/2020 Edmiston et al.
10,582,929 B2 3/2020 Miles et al.
10,582,930 B2 3/2020 Miles et al.
10,624,648 B2 4/2020 Li et al.
10,631,969 B2 4/2020 Edmiston et al.
10,695,070 B2 6/2020 Miles et al.
10,702,274 B2 7/2020 Groothuis et al.
10,709,432 B2 7/2020 Ma
10,709,454 B2 7/2020 Li et al.
10,722,240 B1 7/2020 Melanson et al.
10,758,241 B1 9/2020 Lashinski et al.
10,898,202 B2 1/2021 Slaughter et al.
11,039,822 B2 6/2021 Wang et al.
11,116,510 B2 9/2021 Melanson et al.
11,123,080 B2 9/2021 Lashinski et al.
11,219,462 B2 1/2022 Lashinski et al.
11,399,843 B2 8/2022 Lashinski et al.
11,432,809 B2 9/2022 Inouye et al.
11,497,505 B2 11/2022 Slaughter et al.
11,540,835 B2 1/2023 Groothuis et al.
11,540,836 B2 1/2023 Wang et al.
11,547,417 B2 1/2023 Li et al.
11,596,533 B2 3/2023 Inouye et al.
2003/0040771 A1 2/2003 Hyodoh et al.
2003/0057156 A1 3/2003 Peterson et al.
2003/0181942 A1 9/2003 Sutton et al.
2004/0186566 A1 9/2004 Hindrichs et al.
2004/0220610 A1 11/2004 Kreidler et al.
2005/0004652 A1 1/2005 van der Burg et al.
2005/0177180 A1 8/2005 Kaganov et al.
2005/0187568 A1 8/2005 Klenk et al.
2005/0273119 A1 12/2005 Widomski et al.
2005/0288722 A1 12/2005 Eigler et al.
2006/0287661 A1 12/2006 Bolduc et al.
2007/0073337 A1 3/2007 Abbott et al.
2007/0118213 A1 5/2007 Loulmet
2007/0198057 A1 8/2007 Gelbart et al.
2008/0294175 A1 11/2008 Bardsley et al.
2008/0319254 A1 12/2008 Nikolic et al.
2009/0171386 A1 7/2009 Amplatz et al.
2009/0209986 A1 8/2009 Stewart et al.
2010/0030328 A1 2/2010 Sequin et al.
2010/0185235 A1 7/2010 Kassab et al.
2011/0054515 A1 3/2011 Bridgeman et al.
2011/0178537 A1 7/2011 Whitman
2012/0221042 A1 8/2012 Schwartz et al.

(56) References Cited

U.S. PATENT DOCUMENTS

| | | | | |
|---|---|---|---|---|
| 2012/0265296 | A1 | 10/2012 | McNamara et al. | |
| 2012/0283585 | A1* | 11/2012 | Werneth | A61B 17/1214 606/200 |
| 2012/0316584 | A1 | 12/2012 | Miles et al. | |
| 2013/0197570 | A1 | 8/2013 | Ebata et al. | |
| 2013/0338686 | A1 | 12/2013 | Ruiz | |
| 2014/0018841 | A1 | 1/2014 | Peiffer et al. | |
| 2014/0135817 | A1 | 5/2014 | Tischler et al. | |
| 2015/0005809 | A1 | 1/2015 | Ayres et al. | |
| 2015/0005810 | A1 | 1/2015 | Center et al. | |
| 2015/0209049 | A1 | 7/2015 | Bernstein et al. | |
| 2015/0342612 | A1 | 12/2015 | Wu et al. | |
| 2016/0058434 | A1 | 3/2016 | Delaloye et al. | |
| 2016/0095603 | A1 | 4/2016 | McGuckin, Jr. et al. | |
| 2016/0270810 | A1 | 9/2016 | Vardi et al. | |
| 2016/0278749 | A1 | 9/2016 | Javois et al. | |
| 2017/0095256 | A1 | 4/2017 | Lindgren et al. | |
| 2017/0202575 | A1 | 7/2017 | Stanfield et al. | |
| 2017/0224354 | A1 | 8/2017 | Tischler et al. | |
| 2017/0258475 | A1 | 9/2017 | Mellmann et al. | |
| 2017/0340336 | A1 | 11/2017 | Osypka | |
| 2018/0055496 | A1 | 3/2018 | Hou et al. | |
| 2018/0235640 | A1* | 8/2018 | Slaughter | A61B 17/12177 |
| 2018/0289487 | A1 | 10/2018 | Alexander et al. | |
| 2018/0303488 | A1 | 10/2018 | Hill | |
| 2018/0310925 | A1 | 11/2018 | Inouye et al. | |
| 2018/0310926 | A1 | 11/2018 | Delaloye et al. | |
| 2019/0069901 | A1 | 3/2019 | Forbes | |
| 2019/0083075 | A1 | 3/2019 | Onushko et al. | |
| 2019/0099195 | A1 | 4/2019 | Carroll et al. | |
| 2019/0167242 | A1 | 6/2019 | Rowe et al. | |
| 2019/0183512 | A1 | 6/2019 | Subramaniam et al. | |
| 2019/0192754 | A1 | 6/2019 | Kassab et al. | |
| 2019/0209179 | A1 | 7/2019 | Subramaniam et al. | |
| 2019/0209180 | A1 | 7/2019 | Kealey et al. | |
| 2019/0321176 | A1 | 10/2019 | Lashinski et al. | |
| 2019/0374229 | A1 | 12/2019 | Anderson et al. | |
| 2020/0008870 | A1 | 1/2020 | Gruba et al. | |
| 2020/0038004 | A1 | 2/2020 | Corcoran et al. | |
| 2020/0107836 | A1 | 4/2020 | O'Halloran et al. | |
| 2020/0107837 | A1 | 4/2020 | Slaughter et al. | |
| 2020/0139102 | A1 | 5/2020 | Ziebol et al. | |
| 2020/0155164 | A1 | 5/2020 | Edmiston et al. | |
| 2020/0178981 | A1* | 6/2020 | Anderson | A61B 17/12172 |
| 2020/0214714 | A1 | 7/2020 | Li et al. | |
| 2020/0305887 | A1 | 10/2020 | Lashinski et al. | |
| 2021/0093325 | A1 | 4/2021 | Wang et al. | |
| 2021/0113212 | A1 | 4/2021 | Lashinski et al. | |
| 2021/0137507 | A1* | 5/2021 | Keren | A61B 17/12172 |
| 2021/0212674 | A1 | 7/2021 | Wang et al. | |
| 2021/0298728 | A1 | 9/2021 | Lashinski et al. | |
| 2021/0369284 | A1 | 12/2021 | Lashinski et al. | |
| 2022/0040451 | A1 | 2/2022 | Urbanski et al. | |
| 2022/0087741 | A1 | 3/2022 | Lashinski et al. | |
| 2022/0175390 | A1 | 6/2022 | Lee et al. | |
| 2022/0175392 | A1 | 6/2022 | Jayaraman | |
| 2022/0211386 | A1 | 7/2022 | Amplatz et al. | |
| 2022/0218356 | A1 | 7/2022 | Inouye et al. | |
| 2022/0240941 | A1 | 8/2022 | Lashinski et al. | |
| 2022/0257955 | A1 | 8/2022 | Zarbatany et al. | |
| 2022/0370056 | A1 | 11/2022 | Inouye et al. | |
| 2022/0401109 | A1 | 12/2022 | Zarbatany et al. | |
| 2023/0033509 | A1 | 2/2023 | Lashinski et al. | |
| 2023/0048873 | A1 | 2/2023 | Onushko et al. | |
| 2023/0084301 | A1 | 3/2023 | Groff et al. | |
| 2023/0130379 | A1 | 4/2023 | Akpinar et al. | |
| 2023/0263531 | A1 | 8/2023 | Lashinski et al. | |
| 2023/0310018 | A1 | 10/2023 | Lashinski et al. | |

FOREIGN PATENT DOCUMENTS

| | | | |
|---|---|---|---|
| EP | 3013249 | | 8/2018 |
| EP | 3 494 902 | | 6/2019 |
| EP | 3 632 337 | | 4/2020 |
| EP | 3340890 | B1 | 7/2022 |
| JP | 2010527742 | A | 8/2010 |
| JP | 2016168173 | A | 9/2016 |
| WO | WO 2008/150346 | A1 | 12/2008 |
| WO | WO 2013/009998 | A2 | 1/2013 |
| WO | WO 2015/189307 | | 12/2015 |
| WO | WO 2017/035363 | A1 | 3/2017 |
| WO | WO 2018/071717 | A1 | 4/2018 |
| WO | WO 2018/178979 | | 10/2018 |
| WO | WO 2019/212894 | | 11/2019 |
| WO | WO 2020/074738 | | 4/2020 |
| WO | WO 2020/198259 | | 10/2020 |
| WO | WO 2021/194964 | | 9/2021 |
| WO | WO 2022/010931 | A1 | 1/2022 |
| WO | WO 2022/047333 | | 3/2022 |
| WO | WO 2023/137343 | A1 | 7/2023 |
| WO | WO 2023/192189 | A1 | 10/2023 |

OTHER PUBLICATIONS

U.S. Appl. No. 16/863,995 (U.S. Pat. No. 10,758,241), filed Apr. 30, 2020, Devices, Systems, and Methods for Treating the Left Atrial Appendage.

U.S. Appl. No. 17/006,660, filed Aug. 28, 2020, Devices, Systems, and Methods for Treating the Left Atrial Appendage.

U.S. Appl. No. 17/180,121 (U.S. Pat. No. 11,123,080), filed Feb. 19, 2021, Devices, Systems, and Methods for Treating the Left Atrial Appendage.

U.S. Appl. No. 17/402,438 (U.S. Pat. No. 11,399,843), filed Aug. 13, 2021, Devices, Systems, and Methods for Treating the Left Atrial Appendage.

U.S. Appl. No. 17/572,503, filed Jan. 10, 2022, Devices, Systems, and Methods for Treating the Left Atrial Appendage.

U.S. Appl. No. 17/461,718, filed Jul. 11, 2022, Devices, Systems, and Methods for Treating the Left Atrial Appendage.

U.S. Appl. No. 17/208,435, filed Mar. 22, 2021, Devices, Systems, and Methods for Occluding Cavities Within the Body.

U.S. Appl. No. 17/461,718, filed Aug. 30, 2021, Devices, Systems, and Methods for Treating a Tissue of the Heart.

U.S. Appl. No. 18/153,311, Jan. 11, 2023, Devices, Systems, and Methods for Treating the Left Atrial Appendage.

U.S. Appl. No. 18/190,661, filed Mar. 27, 2023, Devices, Systems, and Methods for Transseptal Puncture.

PCT Search Report and Written Opinion for International Application No. PCT/US2021/040563 dated Dec. 20, 2021, 28 pages.

U.S. Appl. No. 17/461,718, filed Aug. 30, 2021, Lashinski et al.

U.S. Appl. No. 17/402,438, filed Aug. 13, 2021, Lashinski et al.

Watchman® Left Atrial Appendage Closure Device, Patient Information Guide; Boston Scientific; 9 pages.

Watchman® Left Atrial Appendage Closure Device, Product Brochure; 6 pages dated as copyright 2018.

"Watchman Stroke Device Lawsuit;" https://www.nationalinjuryhelp.com/watchman-stroke-device-lawsuit/; 7 pages.

Cardia Delivery System, 1 page, dated as available at http://www.cardia.com/ds.html on Mar. 7, 2019 by the Wayback Machine internet archive (accessed and printed on May 6, 2020).

Cardia Fenestrated Fontan Closure System, 1 page, dated as available at http://www.cardia.com/fontan.html on Feb. 11, 2019 by the Wayback Machine internet archive (accessed and printed on May 6, 2020).

Densford, Fink, "Prominent cardiologist calls for a halt to Watchman implants;" https://www.massdevice.com/prominent-cardiologist-calls-for-a-halt-to-watchman-implants/; Nov. 10, 2016; 12 pages.

Kelley Drye & Warren LLP, "Texas Court dismisses off-label device marketing FCA case;" Lexology; Oct. 27, 2010; 2 pages.

Perriello, Brad, "Jury hands Covidien's ev3 subsidiary a possible $275M loss;" https://www.massdevice.com/jury-hands-covidiens-ev3-subsidiary-possible-275m-loss/; Aug. 13, 2013; 12 pages.

Rosenthal et al., "What is the efficacy and safety of devices for left atrial appendage (LAA) closure/litigation in atrial fibrillation (Afib) AF)?; " Medscape; Jul. 25, 2019; 2 pages.

(56) References Cited

OTHER PUBLICATIONS

Ultrasept Cribriform Device, 1 page, dated as available at http://www.cardia.com/cribriform.html on Feb. 11, 2019by the Wayback Machine internet archive (accessed and printed on May 6, 2020).
Ultrasept Left Atrial Appendage Closure Device, 1 page, dated as available at http://www.cardia.com/laa.html on Mar. 7, 2019 by the Wayback Machine internet archive (accessed and printed on May 6, 2020).
Ultrasept Patent Foramen Ovale Closure Device, 1 page dated as available at http://www.cardia.com/pfo.html on of Mar. 7, 2019 by the Wayback Machine internet archive (accessed and printed on May 6, 2020).
Ultrasept Atrial Septal Defect Closure Device, http://www.cardia.com/asd.html, 1 page, dated as available as of Mar. 7, 2019by the Wayback Machine internet archive (accessed and printed on May 6, 2020).
U.S. Appl. No. 16/828,782, filed Mar. 24, 2020, Devices, Systems, and Methods for Treating the Left Atrial Appendage.
U.S. Appl. No. 17/180,121, filed Feb. 19, 2021, Devices, Systems, and Methods for Treating the Left Atrial Appendage.
U.S. Appl. No. 17/402,438, filed Aug. 13, 2021, Devices, Systems, and Methods for Treating the Left Atrial Appendage.
U.S. Appl. No. 18/153,311, filed Jan. 11, 2023, Lashinski et al.
U.S. Appl. No. 18/190,661, filed Mar. 27, 2023, Lashinski et al.
U.S. Appl. No. 17/862,241, filed Jul. 11, 2022, Lashinski et al.
European Communication dated Sep. 26, 2025, for Application No. 21748744.6, 7 pages.
Japanese first Office Action dated Jul. 22, 2025, for Application No. 2023-501300, 5 pages.

* cited by examiner

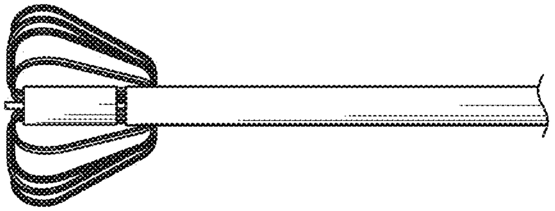
FIG. 62G1
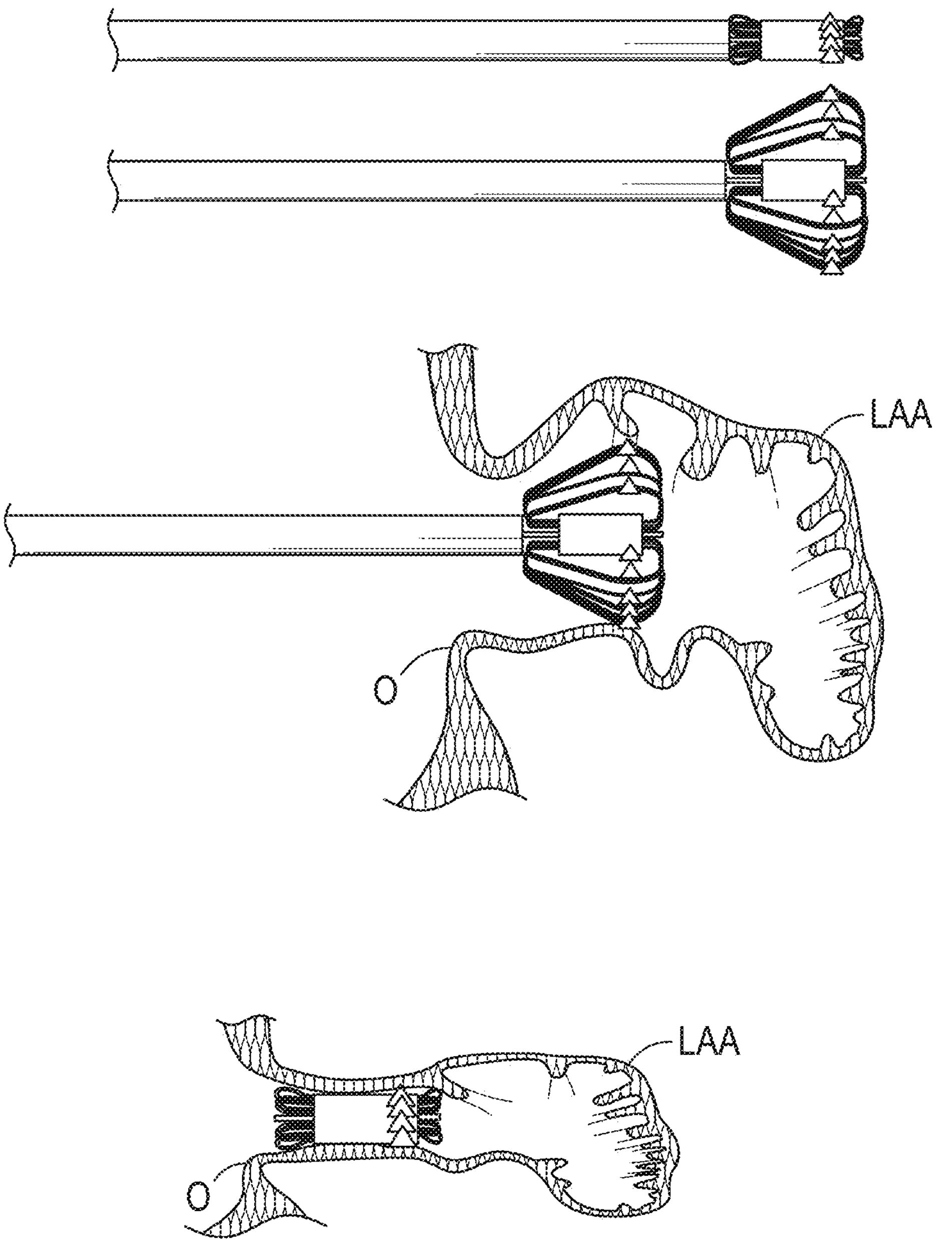
FIG. 62G2

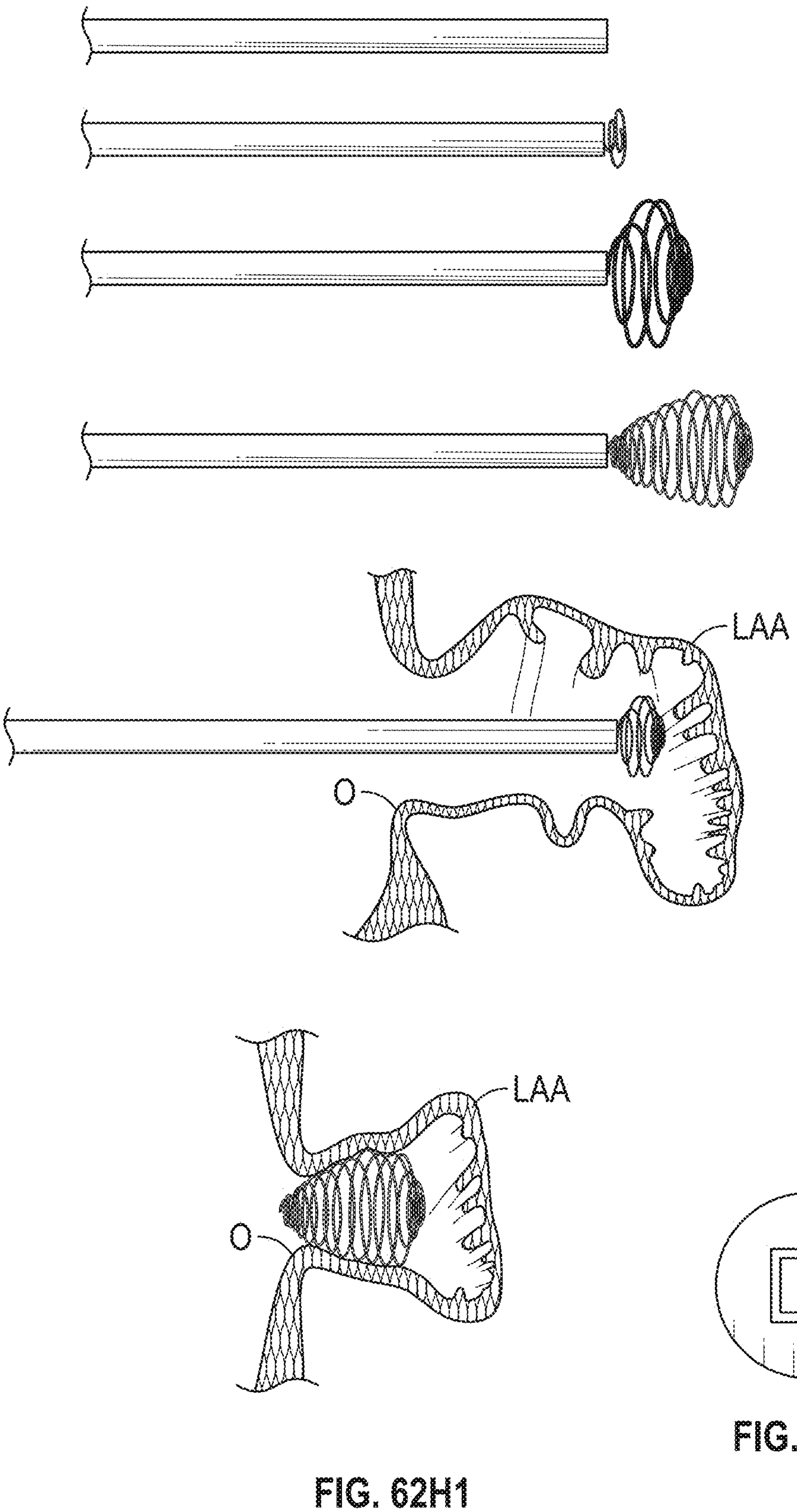
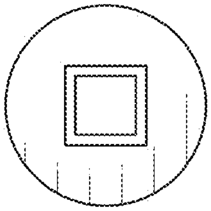
FIG. 62H2
FIG. 62H1

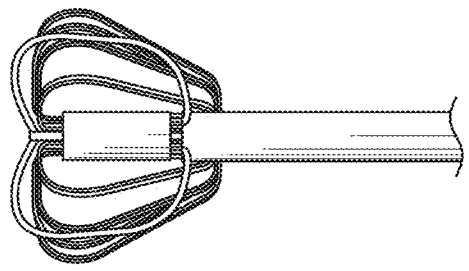
FIG. 62R1
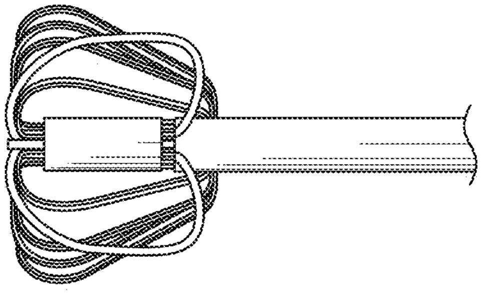
FIG. 62R2
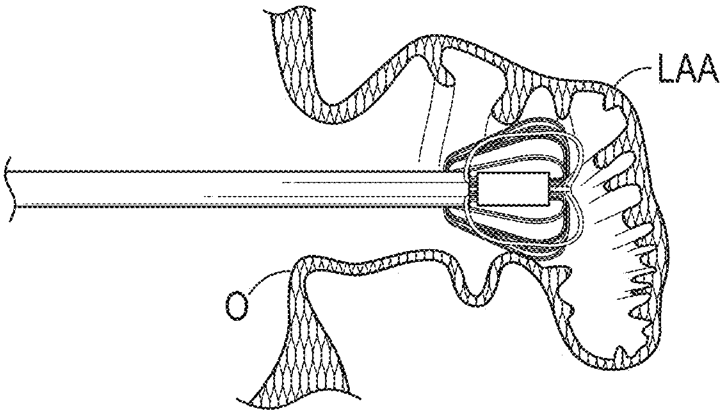
FIG. 62R3
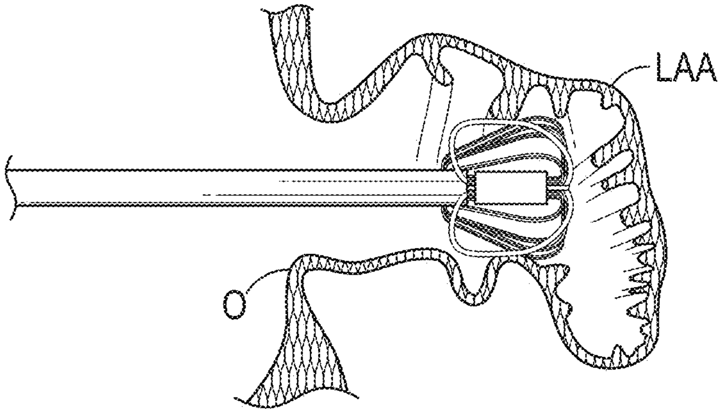
FIG. 62R4

100
3110
3102
100
3100
3102
3110
LAA
3114
3110
3102
3116
3106
3104
LAA
3120
3120
3110
3120
3102
3120
3103
3120
H
LAA
BR
LV
RV
PS
RC
S
X
AL
CC
CC 4000
4016
4016b
4004
4012
4040
4042
4004b
4018
4004a
4013
4014a
4014
4000
4016
4016b
4004
4012
4040
4042
4004b
4004a
4013
4014a
4014
4000
4016
4016b
4004
4012
4040
4042
4004b
4004a
4013
4009
4008
4010
4014
4014a
4016
4000
4004
4012
4010
4009
4030
4025
4014
4016
4016
4004a
4008

4012
4014
4025
4000
4002
4010
4004
4005

4012
4014
4033
4036
4013
4000
4008
4010
4008a
4025
4013b
4004
4032
4033
4017
4005

4012
4014
4025
4033
4013
4000
4010
4008
4008a
4004
4032
4005
4008
4034

DEVICES, SYSTEMS, AND METHODS FOR TREATING THE LEFT ATRIAL APPENDAGE

PRIORITY CLAIM AND INCORPORATION BY REFERENCE

The present application claims the benefit under 35 U.S.C. § 119(e) to U.S. Patent Application No. 63/171,011, filed on Apr. 5, 2021, U.S. Patent Application No. 63/072,035, filed on Aug. 28, 2020, and U.S. Patent Application No. 63/049,077, filed on Jul. 7, 2020, the contents of each of these priority applications are hereby incorporated by reference herein in their entirety as if fully set forth herein for all purposes. Any and all applications for which a foreign or domestic priority claim is identified in the Application Data Sheet as filed with the present application are hereby incorporated by reference herein in their entirety and made a part of this specification.

FIELD OF THE DISCLOSURE

Embodiments of the present disclosure relate to devices, apparatuses, and methods for closing or occluding a left atrial appendage.

BACKGROUND

Left atrial appendage (LAA) closure has been typically performed in high-risk patients due to possible stroke risk. LAA closure techniques are generally performed to block emboli from exiting the LAA. Typical surgical closure includes stitching the opening closed via left atrium entry. Other techniques include the application of external clamps such as ATRICLIP manufactured by Atricure where a Nitinol device is used to clamp the appendage without opening the left atrium to exclude the appendage from left atrium blood circulation.

Other solutions have used a plug to close the appendage from the inside of the left atrium. Such plugs can be constructed from a laser cut Nitinol tube expanded to a semi-spherical shape. The portion exposed to the left atrium can be covered with cover—such as a thin micron membrane made from polyethylene terephthalate. The membrane can act as a blood barrier to prevent flow from flowing through and between one or more struts of the plug. Typical sizes range between approximately 20 mm and 35 mm in diameter and approximately 20 mm and 40 mm in depth. The device can have anchors protruding from an outer surface of the device intended to engage the wall of the appendage and prevent movement post deployment. The device can be delivered via venous access through the groin and a transseptal crossing into the left atrium where a guide catheter and coaxial delivery catheter are positioned proximal to the left atrial appendage. The implant for appendage exclusion is typically positioned at the distal most portion of the delivery catheter. The device is typically positioned and deployed using fluoroscopy and echocardiography for guidance. Typical issues with conventional devices include complicated pre-procedural sizing algorithms used to determine the appropriate device size, migration of the implant, leakage around or through the implant, and/or fracture of the implant, all which may exacerbate the thrombus and stroke problem the device was designed to reduce. A typical drug regimen associated with conventional LAA treatment devices includes warfarin anticoagulation for 45 days (approximately 6 weeks) followed by dual antiplatelet therapy (DAPT) for six months post-procedure and aspirin thereafter. Another procedure typically required with conventional LAA treatment devices includes a follow up transesophageal echogram at six weeks following the procedure. The incidence of device-related thrombus in patients with LAA imaging has been reported to be 7.2% per year.

SUMMARY OF SOME EXEMPLIFYING EMBODIMENTS

The systems, methods and devices of this disclosure each have several innovative aspects, implementations, or aspects, no single one of which is solely responsible for the desirable attributes disclosed herein.

Disclosed herein are embodiments of methods of treating a left atrial appendage. In some embodiments, the method can include twisting the left atrial appendage and/or securing the left atrial appendage in a twisted position. Any embodiments of the methods, devices and systems of treating a left atrial appendage disclosed herein can include, in additional embodiments, one or more of the following steps, features, components, and/or details, in any combination with any of the other steps, features, components, and/or details of any other embodiments disclosed herein: wherein twisting the left atrial appendage can include engaging a wall portion on an inside of the left atrial appendage with a contact member and rotating the contact member from a first rotational position (also referred to herein as a first position) to a second rotational position (also referred to herein as a second position) to twist the left atrial appendage; wherein engaging a wall portion on an inside of the left atrial appendage with a contact member can include advancing a deployment device into the left atrial appendage; wherein engaging a wall portion on an inside of the left atrial appendage can include engaging a wall portion on an inside of the left atrial appendage with one or more tissue anchors; wherein the contact member can be a balloon; wherein the contact member can be positioned on an implant coupled with the deployment device; wherein the implant can be self-expanding, balloon expandable and/or mechanically expandable; further including applying a vacuum through the contact member to engage the left atrial appendage; wherein rotating a component of the deployment device rotates the contact member from the first rotational position to the second rotational position to twist the left atrial appendage; wherein rotating the contact member from the first rotational position to the second rotational position to twist the left atrial appendage can include rotating the contact member at least approximately 90 degrees in either direction from the first rotational position; wherein rotating the contact member from the first rotational position to the second rotational position to twist the left atrial appendage can include rotating the contact member at least approximately 180 degrees in either direction from the first rotational position; wherein rotating the contact member from the first rotational position to the second rotational position to twist the left atrial appendage can include rotating the contact member from approximately 90 degrees to approximately 360 degrees in either direction from the first rotational position; wherein rotating the deployment device can include exerting a torque on the deployment device between 0.25 in-oz of torque and 10 in-oz of torque; wherein the method further includes allowing the contact member to rotate from the second direction to a third rotational position that can be between the first rotational position and the second rotational position (for example and without limitation, as a result of the tissue relaxing); and/or wherein the contact member includes at least one vacuum port configured to communicate a suction force through the at least one vacuum port from a source of suction.

Further, any embodiments of the methods, devices and systems of treating a left atrial appendage disclosed herein can include, in additional embodiments, one or more of the following steps, features, components, and/or details, in any combination with any of the other steps, features, components, and/or details of any other embodiments disclosed herein: wherein twisting the left atrial appendage can include rotating a portion of the left atrial appendage about an axis from a first rotational position to a second rotational position to twist the left atrial appendage; wherein rotating a portion of the left atrial appendage about an axis from a first rotational position to a second rotational position to twist the left atrial appendage can include rotating the portion of the left atrial appendage at least approximately 90 degrees in either direction from the first rotational position; wherein rotating a portion of the left atrial appendage about an axis from a first rotational position to a second rotational position to twist the left atrial appendage can include rotating the portion of the left atrial appendage at least approximately 180 degrees in either direction from the first rotational position; wherein rotating a portion of the left atrial appendage about an axis from the first rotational position to the second rotational position to twist the left atrial appendage can include rotating the portion of the left atrial appendage from approximately 90 degrees to approximately 360 degrees in either direction from the first rotational position; wherein rotating a portion of the left atrial appendage about an axis from a first rotational position to a second rotational position to twist the left atrial appendage can include twisting the left atrial appendage until an ostium of the LAA can be substantially or completely closed; wherein securing the left atrial appendage in a twisted position can include engaging tissue of the heart that has been twisted; wherein engaging tissue of the heart that has been twisted can include engaging tissue wall with an anchor element; wherein the anchor element can include a suture; wherein securing the left atrial appendage in a twisted position can include securing a tissue of the heart outside of an occluded portion of the left atrial appendage with an anchor element; and/or wherein the anchor element can include a plurality of tissue anchors on at least one surface thereof configured to engage with the internal wall of the heart outside of the left atrial appendage.

Also disclosed herein are embodiments of a method of closing the ostium of a left atrial appendage. In some embodiments, the method can include twisting tissue of the heart to constrict the ostium of the left atrial appendage and/or securing tissue that has gathered as a result of twisting tissue of the heart in a gathered position. Any embodiments of the methods, devices and systems of closing the ostium of a left atrial appendage disclosed herein can include, in additional embodiments, one or more of the following steps, features, components, and/or details, in any combination with any of the other steps, features, components, and/or details of any other embodiments disclosed herein: wherein securing the tissue of the heart in the gathered position can include advancing a securing element into the gathered tissue; wherein the securing element can be a suture; and/or wherein the securing element can be a tissue anchor.

Disclosed herein are embodiments of devices and systems for treating an LAA that can include an implant comprising a contact member, and a securing element, wherein the contact member is configured to rotate at least in a first direction from a first rotational position to a second rotational position, wherein the contact member is configured to twist at least a portion of the LAA when the contact member is rotated from the first rotational position to the second rotational position, and wherein the securing element is configured to prevent a rotation of the implant in a second direction that is opposite to the first direction when the securing element is in an operable state. The contact member can be, in some embodiments, configured to move between a first state and a second state, wherein the contact member is larger or is expanded in the second state. Some embodiments of the contact member can be configured to move from the first state to the second state so that at least a portion of the contact member engages a wall portion of the LAA when the contact member is advanced into the LAA. In any embodiments disclosed herein wherein the contact member moves or expands from a first state to a second state, the contact member can be moved or expanded from the first state to the second state in the LA or in the LAA. Further, in any embodiments, the contact member can be configured to remain in a fixed state and/or size during the entire procedure, wherein the contact member can be extended past a distal end of the delivery catheter (or an outside tube of the delivery catheter can be withdrawn) and advanced into contact or engagement with a wall portion of the LAA, and then twisted. This can be done without changing a size of the contact member and/or without expanding the contact member.

Also disclosed herein are embodiments of devices and systems for treating an LAA can include an implant configured to move between a first state and a second state, a catheter configured to advance the implant into the LAA when the implant is in the first state and to cause the implant to move from the first state to the second state so that an outside surface of the implant moves against an inner wall surface of the LAA after the implant has been advanced into the LAA, wherein the catheter is configured to rotate the implant in a first direction from a first rotational position to a second rotational position so that the implant can twist at least a portion of the LAA when the implant is in the second state.

Also disclosed herein are embodiments of devices and systems for drawing a first tissue surface toward a second tissue surface, including a contact member configured to expand from a first state to a second state and a securing element configured to move from a first state to a second state, wherein the contact member can be configured to expand from the first state to the second state so that at least a portion of the contact member engages at least a distal portion of the first tissue surface and at least a distal portion of the second tissue surface, the contact member can be configured to rotate at least in a first direction from a first rotational position to a second rotational position, wherein the rotation of the contact member in the first direction causes at least a proximal portion of the first tissue surface to twist and to move toward a proximal portion of the second tissue surface, and wherein the securing element is configured to prevent a rotation of the implant in a second direction when the securing element is in an operable state and engaged with a tissue portion adjacent to and/or comprising the proximal portions of the first and second tissue surfaces, wherein the second direction is opposite to the first direction. Further, in any device and/or system embodiments disclosed herein, the device can be configured to occlude or close a cavity in a body having the first and second tissue surfaces, the first and second tissue surfaces can be tissue surfaces within any cavity within the body, and/or wherein the rotation of the contact member further causes the proximal portion of the second tissue surface to twist and to move toward the proximal portion of the first tissue surface.

Any embodiments of the devices and systems disclosed herein can include, in additional embodiments, one or more of the following features, components, and/or details, in any combination with any of the other features, components, and/or details of any other embodiments disclosed herein: wherein the implant is self-expandable such that the implant automatically expands from the first state to the second state when a restraint is removed from the implant; wherein the contact member is self-expandable such that at least a portion of the contact member automatically expands from the first state to the second state when a restraint is removed from the contact member; wherein the implant is substantially collapsed when the implant is in the first state and is expanded when the implant is in the second state such that a size of the implant is bigger when the implant is in the second state than when the implant is in the first state; wherein the contact member is biased to remain in the second state after deployment into the LAA; wherein the contact member is configured to be rotated in a clockwise or a counter-clockwise direction; wherein the device is configured to cause a tissue of the left atrium and/or the LAA to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element has a plurality of tissue anchors configured to engage with an internal wall of the heart adjacent to the LAA; wherein the securing element has a helical shape and is configured to rotate about a body portion of the implant during the implantation procedures; wherein the implant is configured to rotate in a first direction from the first rotational position to the second rotational position; wherein the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the LAA after the contact member has been moved to the second state; wherein the implant comprises a securing element configured to engage with a tissue portion of the heart adjacent to the LAA; wherein the second rotational position is at least one-quarter of a complete rotation relative to the first rotational position; wherein the second rotational position is at least one-half of a complete rotation relative to the first rotational position; and/or wherein the second rotational position is from approximately one-quarter of a complete rotation to one or more complete rotations relative to the first rotational position.

Further, any embodiments of the devices and systems disclosed herein can include, in additional embodiments, one or more of the following features, components, and/or details, in any combination with any of the other features, components, and/or details of any other embodiments disclosed herein: further comprising a catheter selectively coupled with the contact member and configured to exert a torque on the contact member to rotate the contact member from the first rotational position until a threshold predetermined torque level is reached; wherein a threshold predetermined torque level is from approximately 0.25 in-oz of torque to approximately 10 in-oz of torque; wherein a threshold predetermined torque level is from approximately 0.5 in-oz of torque to approximately 5 in-oz of torque; further comprising a retention element configured to bias the securing element toward a tissue wall of the LAA; further comprising a retention element configured to bias the securing element toward the contact member; further comprising a retention element configured to couple the securing element with the contact member; wherein the retention element comprises a threaded shaft; wherein the device is configured such that a rotation of the retention element in a first direction causes the securing element to move toward the contact member; wherein the contact member is configured to rotate at least in a first direction from a first rotational position to a second rotational position when a torque is applied to the contact member; wherein the device is configured such that the contact member can be removed from the LAA after the securing element has been deployed to the operable state of the securing element; wherein the device is configured such that the contact member can be removed from the LAA after the securing element has been deployed to the operable state of the securing element, and wherein the securing element is configured to prevent a rotation of the tissue of the left atrium and/or the LAA that has been constricted as a result of the rotation of the contact member from the first rotational position to the second rotational position; wherein only a portion of the securing element extends into the left atrium after deployment of the device, and all other portions of the device are internal to the LAA after deployment of the device; wherein only approximately 10% or less of an overall length of the deployed device extends into the left atrium after deployment of the device; wherein the device is configured for use by a surgical robot device or system; a surgical robotic device, comprising one or more robotic arms and wherein the device of any embodiments disclosed herein is configured for use by the surgical robotic device; wherein the contact member and the securing element are integrally formed and/or monolithically formed; wherein the device is configured to cause a tissue of the left atrium and/or the LAA to constrict around an outer surface of a body portion of the implant when the contact member is rotated to the second rotational position, and the securing element is configured to compress the tissue that has constricted around the outer surface of the body portion of the implant between a distal surface of the securing element and the contact member to prevent rotation of the implant in the second direction.

Some embodiments of devices and systems for closing or occluding a left atrial appendage (LAA) disclosed herein can include an implant configured to move between a first state and a second state and a catheter configured to advance the implant into the left atrial appendage when the implant is in the first state, wherein the implant can be configured to move from the first state to the second state so that at least a portion of the implant engages a wall portion of the left atrial appendage after the implant has been advanced into the left atrial appendage, and wherein the implant can be configured to twist at least a portion of the left atrial appendage when the implant is rotated from a first rotational position to a second rotational position when the implant is in the second state. In any embodiments disclosed herein, the twisting movement or step can be accomplished by a torque catheter.

Any embodiments of the devices and systems disclosed herein can, in additional embodiments, include one or more of the following features or details, in any combination: wherein the implant is configured to automatically rotate from the first rotational position to the second rotational position after the implant is in the second state; wherein the implant can be configured to be triggered or activated to thereafter automatically rotate from the first rotational position to the second rotational position; wherein the device has a spring that is coupled with the implant, the spring being configured to automatically rotate the implant when the spring is released or activated; wherein the implant can be self-expandable such that the implant automatically expands from the first state to the second state when a restraint is removed from the implant; wherein the implant can be self-expandable such that at least a portion of the implant automatically expands from the first state to the second state when the implant is advanced past a distal end of an outer sleeve of the catheter; wherein the implant is substantially collapsed when the implant is in the first state and can be expanded when the implant is in the second state such that a size of the implant can be bigger when the implant is in the second state than when the implant is in the first state; wherein the implant can be biased to remain in the second state after deployment into the left atrial appendage; wherein the implant can be configured to be rotated in a clockwise or a counter-clockwise direction; wherein the implant can include a securing element configured to engage with an internal wall of the heart outside of the left atrial appendage; wherein the implant can include a securing element configured to engage with an internal wall of the heart outside of the left atrial appendage, wherein the securing element has a helical shape and is configured to rotate about a body portion of the implant during the implantation procedures; wherein the implant can include a corkscrew shaped securing element configured to engage with an internal wall of the heart outside of the left atrial appendage; wherein the implant can include a securing element having a corkscrew tissue anchor to engage the internal wall of the heart and/or LAA tissue; wherein the implant can include a securing element having a plurality of tissue anchors configured to engage with an internal wall of the heart adjacent to the left atrial appendage; wherein the implant can be configured to prevent the implant from rotating back to the first rotational position after the implant has been fully deployed; wherein the implant can be configured to rotate in a first direction from the first rotational position to the second rotational position, and the implant can be configured to prevent rotation of the implant in a second direction after the implant has been fully deployed, the second direction being opposite to the first direction.

Any embodiments of the devices and systems disclosed herein can, in additional embodiments, include one or more of the following features or details, in any combination: wherein the implant has a plurality of tissue anchors on an outside surface thereof; wherein the plurality of tissue anchors on the outside surface of the implant configured to engage an inner wall surface of the left atrial appendage after the implant has been moved to the second state; wherein the implant can include a securing element configured to engage with a tissue portion of the heart adjacent to the left atrial appendage; wherein the second rotational position can be at least one-quarter or approximately one-quarter of a complete rotation (i.e., 90 degrees or approximately 90 degrees) relative to the first rotational position; wherein the second rotational position can be at least one-half or approximately one-half of a complete rotation (i.e., 180 degrees or approximately 180 degrees) relative to the first rotational position; wherein the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position; wherein the catheter can be configured to exert a torque on the implant to rotate the implant from the first rotational position until a threshold predetermined torque level is reached; wherein a threshold predetermined torque level can be from 0.25 or approximately 0.25 in-oz of torque to 10 or approximately 10 in-oz of torque; and/or wherein a threshold predetermined torque level can be from 0.5 or approximately 0.5 in-oz of torque to 5 or approximately 5 in-oz of torque.

Any embodiments of the devices and systems disclosed herein can include an implant having a contact member configured to move between a first state and a second state and a catheter configured to advance the contact member into the LAA when the contact member is in the first state and to cause the contact member to move from the first state to the second state so that an outside surface of the contact member expands against an inner wall surface of the LAA after the contact member has been advanced into the LAA, wherein the catheter is configured to exert a torque on the contact member when at least a portion of the catheter is rotated until a predetermine torque level is reached to rotate the contact member from a first rotational position to a second rotational position so that the contact member can twist at least a portion of the LAA.

Any embodiments of the devices and systems disclosed herein can include an expandable implant configured to move between a first state and a second state, a catheter configured to advance the implant into the left atrial appendage when the implant is in the first state and to cause the implant to move from the first state to the second state so that an outside surface of the implant expands against at least a portion of an inner wall surface of the left atrial appendage after the implant has been advanced into the left atrial appendage. In any embodiments of the device for closing or occluding an LAA disclosed herein, the catheter can be configured to exert a torque on the implant to rotate the implant from a first rotational position to a second rotational position so that the implant can twist at least a portion of the left atrial appendage until a predetermine torque level is reached, or in some embodiments, until the user decides to stop, whichever comes first.

Also disclosed herein are devices and systems for treating the LAA, which include a device configured to be inserted into the LAA and to engage the LAA tissue while the device is rotated to a rotated position to close the blood communication between the LAA and the left atrium. In any embodiments of the apparatus, the device can be configured to be selectively lockable in the rotated position to at least substantially maintain the device in the rotated position after implantation, the device can include a securing element configured to engage a tissue surface adjacent to the LAA to maintain the device in the rotated position after implantation, the device can be round, spherical, or disc shaped when the device is in a deployed state in the LAA, the device can be expandable from a first collapsed state to a second expanded state, and/or the device can be self-expanding from a first collapsed state to a second expanded state.

Also disclosed herein are embodiments of methods for treating the LAA, including engaging a tissue of the LAA, and rotating the tissue of the LAA to close or occlude a blood communication between the LAA and a left atrium. In any embodiments of the methods disclosed herein, rotating the tissue of the LAA to close or occlude the blood communication between the LAA and the left atrium can include rotating the tissue of the LAA to close or occlude the ostium of the LAA. Further, any embodiments of the methods disclosed herein can further include securing the LAA in a rotated position to hold the LAA in a closed or occluded state.

Any embodiments of a method of closing or occluding an LAA disclosed herein can include advancing a deployment device having an implant into the left atrial appendage, wherein the implant can be configured to be moved from a first state to a second state. In some embodiments, at least a portion of the implant can be enlarged in a radial direction when the implant is in the second state as compared to the first state. The method can further include moving the implant from the first state to the second state within the left atrial appendage so as to move at least a portion of an outside wall of the implant or one or more tissue anchors extending away from an outer surface of the implant against at least a portion of an inner wall surface of the left atrial appendage, rotating the implant from a first rotational position to a second rotational position to twist the left atrial appendage, and preventing the implant from rotating back to the first rotational position.

Any embodiments of methods of closing or occluding an LAA disclosed herein can, in some additional embodiments, include one or more of the following steps, in any combination and in any combination with any of the other steps, features, or other details of any other embodiments: wherein the implant is self-expanding and wherein moving the implant from the first state to the second state comprises advancing the implant out of a distal end of the deployment device; wherein engaging a wall portion on an inside of the LAA comprises engaging a wall portion on an inside of the LAA with one or more tissue anchors positioned on an outside surface of the implant; wherein preventing the implant from rotating back to the first rotational position comprises engaging a tissue wall with an anchor element to prevent relative movement between the implant and the tissue wall; wherein preventing the implant from rotating back to the first rotational position comprises engaging a tissue wall with an anchor element, and wherein the anchor element is configured to be secured to the implant to prevent a rotation between the implant and the anchor element; wherein preventing the implant from rotating back to the first rotational position comprises engaging a tissue wall of the heart with an anchor element, wherein the anchor element is rotationally fixed relative to the implant and configured to prevent the implant from rotating back to the first rotational position; wherein preventing the implant from rotating back to the first rotational position comprises engaging a tissue of the heart outside of the closed portion of the LAA with an anchor element, wherein the anchor element is rotationally fixed relative to the implant and configured to prevent the implant from rotating back to the first rotational position; wherein the anchor element comprises a plurality of tissue anchors on at least one surface thereof configured to engage with the internal wall of the heart outside of the LAA; wherein rotating the implant from the first rotational position to the second rotational position to twist the LAA comprises rotating the implant until an ostium of the LAA is substantially or completely closed; wherein rotating the implant from the first rotational position to the second rotational position to twist the LAA comprises rotating the implant at least approximately 90 degrees in either direction from the first rotational position; wherein rotating the implant from the first rotational position to the second rotational position to twist the LAA comprises rotating the implant at least approximately 180 degrees in either direction from the first rotational position; wherein rotating the implant from the first rotational position to the second rotational position to twist the LAA comprises rotating the implant from approximately 90 degrees to approximately 360 degrees in either direction from the first rotational position; wherein rotating the implant from the first rotational position to the second rotational position to twist the LAA comprises rotating the implant from approximately 90 degrees to approximately 180 degrees in either direction from the first rotational position; wherein rotating the implant from the first rotational position to the second rotational position to twist the LAA comprises exerting a torque on the implant to rotate the implant in either direction from the first rotational position until a threshold predetermined torque level is reached, holding the implant in the second rotational position, and securing the implant in approximately the second rotational position relative to a tissue surface surrounding the LAA; wherein a maximum predetermined torque level is from approximately 0.25 in-oz of torque to approximately 10 in-oz of torque; and/or wherein a maximum predetermined torque level is from approximately 0.5 in-oz of torque to approximately 5 in-oz of torque.

Any embodiments of the methods of closing or occluding an LAA disclosed herein can, in some additional embodiments, include one or more of the following steps, in any combination and in any combination with any of the other steps, features, or other details of any other embodiments: wherein the implant is self-expanding and wherein moving the implant from the first state to the second state can include advancing the implant out of a distal end of the deployment device; wherein engaging a wall portion on an inside of the left atrial appendage can include engaging at least a portion of a wall portion on an inside of the left atrial appendage or surrounding the left atrial appendage with one or more tissue anchors positioned on an outside surface of the implant; wherein preventing the implant from rotating back to the first rotational position can include engaging a tissue wall outside of the left atrial appendage with an anchor element; wherein the anchor element can be rotationally fixed to the implant to prevent relative movement between the anchor element and the implant; wherein preventing the implant from rotating back to the first rotational position can include engaging a tissue wall of the heart with an anchor element; wherein the anchor element can be rotationally fixed relative to the implant and configured to prevent the implant from rotating back to the first rotational position; wherein preventing the implant from rotating back to the first rotational position can include engaging an internal wall of the heart outside of the left atrial appendage with an anchor element; wherein the anchor element can be rotationally fixed relative to the implant and configured to prevent the implant from rotating back to the first rotational position; wherein the anchor element can include a plurality of tissue anchors on at least one surface thereof configured to engage with the internal wall of the heart outside of the left atrial appendage; and/or wherein rotating the implant from the first rotational position to the second rotational position to twist the left atrial appendage can include rotating the implant until an ostium of the LAA can be substantially or completely closed or occluded, or collapsed about an outer surface of the implant.

Any embodiments of the methods of closing or occluding an LAA disclosed herein can, in any additional embodiments, include one or more of the following steps, in any combination and in any combination with any of the other steps, features, or other details of any other embodiments: wherein rotating the implant from the first rotational position to the second rotational position to twist the left atrial appendage can include rotating the implant at least one-quarter or approximately one-quarter of a complete rotation (i.e., 90 degrees or approximately 90 degrees) relative to the first rotational position; wherein rotating the implant from the first rotational position to the second rotational position to twist the left atrial appendage can include rotating the implant at least one-half or approximately one-half of a complete rotation (i.e., 180 degrees or approximately 180 degrees) in either direction from the first rotational position; wherein rotating the implant from the first rotational position to the second rotational position to twist the left atrial appendage can include rotating the implant from one-quarter or approximately one-quarter of a complete rotation (i.e., 90 degrees or approximately 90 degrees) to one full turn or approximately one full turn (i.e., 360 degrees or approximately 360 degrees), or to more than one full turn (i.e., more than 360 degrees) in either direction from the first rotational position; wherein rotating the implant from the first rotational position to the second rotational position to twist the left atrial appendage can include rotating the implant from one-quarter or approximately one-quarter of a complete rotation (i.e., 90 degrees or approximately 90 degrees) to one-half of a full turn or approximately one-half of a full turn (i.e., 180 degrees or approximately 180 degrees), or to more than one full turn (i.e., more than 360 degrees) in either direction from the first rotational position; wherein rotating the implant from the first rotational position to the second rotational position to twist the left atrial appendage can include exerting a torque on the implant to rotate the implant in either direction from the first rotational position until a threshold predetermined torque level is reached; wherein rotating the implant from the first rotational position to the second rotational position to twist the left atrial appendage can include holding the implant in the second rotational position; wherein rotating the implant from the first rotational position to the second rotational position to twist the left atrial appendage can include securing the implant in approximately the second rotational position relative to a tissue surface surrounding the left atrial appendage; wherein a maximum predetermined torque level can be from approximately 0.25 in-oz of torque to approximately 10 in-oz of torque; and/or wherein a maximum predetermined torque level can be from approximately 0.5 in-oz of torque to approximately 5 in-oz of torque.

Some embodiments of an implant for deployment within a cavity or vessel disclosed herein include an expandable body, a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Any embodiments of the devices and systems disclosed herein can include an expandable implant having a plurality of tissue anchors on an outside surface thereof, the expandable implant being configured to move between a first state in which the implant is substantially collapsed and a second state in which at least a portion of the implant is expanded, and a catheter configured to advance the implant into the left atrial appendage when the implant is in the first state and to cause the implant to move from the first state to the second state so that at least some of the plurality of tissue anchors engage an inner wall surface of the left atrial appendage after the implant has been advanced into the left atrial appendage. In some embodiments, the catheter can be configured to rotate the implant in a first direction from a first rotational position to a second rotational position so that the implant can twist the wall of the left atrial appendage.

Some embodiments of the devices and systems for closing or occluding an LAA disclosed herein can include an implant configured to move between a first state and a second state, and a catheter configured to advance the implant into the left atrial appendage when the implant is in the first state and to cause the implant to move from the first state to the second state so that an outside surface of the implant moves against an inner wall surface of the left atrial appendage after the implant has been advanced into the left atrial appendage. In some embodiments, the catheter can be configured to rotate the implant in a first direction from a first rotational position to a second rotational position so that the implant can twist at least a portion of the left atrial appendage when the implant is in the second state.

Any embodiments of the methods of treating the left atrial appendage disclosed herein can include engaging a tissue of the left atrial appendage and rotating the tissue of the left atrial appendage to close or significantly close, or inhibit or substantially inhibit, a blood communication between the left atrial appendage and a left atrium. Any embodiments of the method(s) disclosed herein can include, in additional embodiments, one or more of the following features, components, steps, and/or details, in any combination with any of the other features, components, steps, and/or details of any other treatment method embodiments disclosed herein: further including rotating the tissue of the left atrial appendage to close the blood communication between the left atrial appendage and the left atrium can include rotating the tissue of the left atrial appendage to close the ostium of the left atrial appendage, and/or further including securing the left atrial appendage in a rotated position to hold the left atrial appendage in a closed state.

Some embodiments of apparatuses for treating the left atrial appendage disclosed herein can include a device configured to be inserted into the left atrial appendage and to engage the left atrial appendage tissue while the device is rotated to a rotated position to close the blood communication between the left atrial appendage and the left atrium. In some embodiments, the device can be configured to be locked in the rotated position to maintain the device in the rotated position after implantation, wherein the device can include a securing element configured to engage a tissue surface adjacent to the left atrial appendage to maintain the device in the rotated position after implantation, wherein the device can be round, spherical, or disc shaped when the device is in a deployed state in the left atrial appendage, wherein the device can be expandable from a first collapsed state to a second expanded state, and/or wherein the device can be self-expanding from a first collapsed state to a second expanded state.

Disclosed herein are embodiments of devices for treating a left atrial appendage that include an implant having a contact member and a catheter configured to advance the contact member into the left atrial appendage and to cause the contact member to move against an inner wall surface of the left atrial appendage, wherein the catheter is configured to exert a torque on the contact member when at least a portion of the catheter is rotated until a predetermine torque level is reached to rotate the contact member from a first rotational position to a second rotational position so that the contact member can twist at least a portion of the left atrial appendage. In any embodiments disclosed herein, the contact member can be configured to be moved against the inner wall surface of the left atrial appendage without changing a state or shape of the contact member, and/or the contact member can be configured to be movable or expandable from a first state to a second state.

Disclosed herein are embodiments of devices for reducing an opening of the left atrial appendage that include a contact member and a securing element, wherein the contact member is configured to engage a tissue surface of the left atrial appendage, the contact member is configured to rotate at least a portion of the left atrial appendage in a first direction from a first rotational position to a second rotational position and to cause the opening of the left atrial appendage to reduce in size from a first size to a second size, and/or the securing element is configured to engage with at least a portion of tissue adjacent to the opening of the left atrial appendage and to prevent the opening of the left atrial appendage from expanding to the first size. In any embodiments disclosed herein, the contact member can be configured to engage a tissue surface on an outside surface of the left atrial appendage. Further, in any embodiments disclosed herein, the contact member can be configured to engage the tissue surface of the left atrial appendage without changing a state or shape of the contact member.

Any embodiments of the devices disclosed herein can include, in additional embodiments, one or more of the following features, components, and/or details, in any combination with any of the other features, components, and/or details of any other embodiments disclosed herein: wherein the device further includes a delivery catheter; wherein the device further includes an implant of any of the implant embodiments disclosed herein that is advanceable through the delivery catheter when the implant is in a first state; wherein the implant includes a first stage portion and a second stage portion that are each independently deployable to at least a second operable or deployed state; wherein the first stage portion is configured to be at least partially deployed before a second stage portion is deployed; wherein the first stage portion is configured to be positioned near a distal end portion of the LAA; wherein the second stage portion is configured to constrict an opening of the LAA when the second stage portion is in the second state; wherein second stage portion is configured to close the opening of the LAA when the second stage portion is in the second state; wherein second stage portion is configured to fold one or more tissue portions surrounding or adjacent to the opening of the LAA when the second stage portion is in the second state; wherein the second stage portion is configured to twist one or more portions of tissue surrounding the opening of the LAA to constrict or close the opening of the LAA when the second stage portion is in a second state; wherein the second stage portion comprises a means for constricting or closing the opening of the LAA; wherein the second stage portion comprises a hinge mechanism for constricting or closing the opening of the LAA; further including at least one of a passive activation mechanism and an active activation mechanism to activate the hinge mechanism; and/or wherein at least one of the first stage portion and the second stage portion is self-expanding.

Disclosed herein are additional embodiments of treatment methods that include advancing a deployment device having an implant into the left atrial appendage, moving at least a portion of an outside surface of the implant or one or more tissue anchors extending away from an outer surface of the implant against an inner wall surface of the left atrial appendage, rotating the implant from a first rotational position to a second rotational position to twist the left atrial appendage, and preventing the implant from rotating back to the first rotational position. In any embodiments, the method can include moving at least a portion of an outside surface of the implant or one or more tissue anchors extending away from an outer surface of the implant against an inner wall surface of the left atrial appendage without changing a shape or size of the implant, and/or moving the implant from a first state to a second state, and wherein at least a portion of the implant is enlarged in a radial direction when the implant is in the second state as compared to the first state.

Disclosed herein are additional embodiments of devices and systems for closing an LAA that can include a clamp device having a first member and a second member and be configured to move between a closed position and an open position, a first guide device configured to be advanceable into the LAA, and a second guide device configured to be advanceable into a pericardial space outside of the LAA and moved so that an end portion of the second guide device is in approximate axial alignment with an end portion of the first guide device. In any embodiments disclosed herein, at least one of the first and second members of the clamp device can be substantially rigid; the clamp device can have an opening sized so that the clamp device can be passed over the LAA when the clamp device is in the open position; and/or at least one of the first and second members of the clamp device can be configured to substantially flatten and close a portion of the LAA when the clamp device is moved to the closed position. In any additional embodiments disclosed herein, the clamp device can include only the first member and the second member. In additional embodiments, the clamp device can further include a third member and a fourth member connected together in an end to end arrangement and defining an opening in the clamp device that is sized and configured to pass over an outside surface of the LAA. In any additional embodiments disclosed herein, the device can further include a delivery catheter having an outer sheath and a guide lumen, the guide lumen configured to receive and track over the second guide device. Additionally, the first member of the clamp device can be rigid and the second member of the clamp device can comprise a suture.

Disclosed herein are additional embodiments of methods of closing or occluding an LAA. In any embodiments disclosed herein, the method can include advancing a first guide device into the LAA, advancing a second guide device into a pericardial space outside of the LAA, approximately aligning an end portion of the second guide device with an end portion of the first guide device, advancing a delivery catheter over the second guide device, advancing a clamp device having a first member and a second member from the delivery catheter, opening the clamp device from a closed position to an open position, advancing the clamp device over an outside surface of the LAA toward a neck portion of the LAA, and/or substantially flattening and closing the neck portion of the LAA by closing the clamp device from the open position to the closed position.

Any embodiments of the methods of closing or occluding the LAA can include, in additional embodiments, one or more of the following features, components, steps, and/or details, in any combination with any of the other features, components, steps, and/or details of any other embodiments disclosed herein: wherein moving the clamp device from the closed position to the open position comprises advancing the clamp device past a distal end of the delivery catheter so that the clamp device can automatically move to the open position; wherein the delivery catheter has a guide lumen, the guide lumen being configured to receive and track over the second guide device; wherein the delivery catheter has an outer sheath; wherein at least one of the first and second members of the clamp device is substantially rigid; wherein at least one of the first and second members of the clamp device has a substantially planar contact surface, the contact surface being the surface configured to contact an outside surface of the LAA; wherein the delivery catheter has an outer sheath; wherein the clamp device comprises a least four substantially rigid members connected together in an end to end arrangement and defining an opening in the clamp device that is sized and configured to pass over an outside surface of the LAA; and/or wherein the clamp device comprises at least one rigid member and at least one flexible member interconnected with the at least one rigid member.

Additionally, any implant and/or device or system embodiments disclosed herein can be adapted and/or used for treatment of any tissue condition in a body that is desired to be occluded, restricted, or closed. For example and without limitation, some embodiments of the devices and systems for treating a tissue condition disclosed herein can include an implant comprising a contact member that can be (but is not required to be) configured to move between a first state and a second state and a securing element, wherein the contact member can be configured to move from the first state to the second state so that at least a portion of the contact member engages a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member that can be (but is not required to be) configured to move between a first state and a second state, a catheter configured to advance the contact member into the tissue condition when the contact member is in the first state and to cause the contact member to move from the first state to the second state so that an outside surface of the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, wherein the implant can be (but is not required to be) configured to be moved from a first state to a second state, and wherein at least a portion of the implant can be enlarged in a radial direction when the implant is in the second state as compared to the first state, moving the implant from the first state to the second state within the tissue condition so as to move at least a portion of an outside surface of the implant or one or more tissue anchors extending away from an outer surface of the implant against at least one wall surface of the tissue condition, rotating the implant from a first rotational position to a second rotational position to twist the tissue condition, and/or preventing the implant from rotating back to the first rotational position.

Additionally, any implant and/or device or system embodiments disclosed herein can be adapted and/or used for treatment of any tissue condition in a body that is desired to be occluded, reshaped, restricted, or closed. For example and without limitation, some embodiments of the devices and systems for treating a tissue condition disclosed herein can include an implant comprising a contact member that is configured to engage a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member, a catheter configured to advance the contact member into the tissue condition so that the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, and wherein at least a portion of the implant engages a wall surface of the tissue condition, rotating the implant from a first rotational position to a second rotational position to twist the tissue condition, and/or preventing the implant from rotating back to the first rotational position.

Disclosed herein are embodiments of a device for treating a left atrial appendage that can include an implant that can have a contact member configured to engage an inside tissue surface of the left atrial appendage and configured to rotate in at least a first direction from a first position to at least a second position so as to twist the left atrial appendage when the contact member is engaged with an inside tissue surface of the left atrial appendage, and a securing element configured to move between a first position in which the securing element is decoupled from the contact member and a second position in which the securing element is coupled with the contact member. In some embodiments, the contact member can be configured to rotate at least in the first direction from the first position to the second position when a torque is applied to the contact member.

Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: wherein the contact member can be configured to rotate at least in the first direction from a first position to at least a second position to twist the left atrial appendage and reduce a size of an ostium of the left atrial appendage from a first size to a second size when the contact member is engaged with an inside tissue surface or the left atrial appendage; wherein the implant can be configured to inhibit the ostium of the left atrial appendage from enlarging back to the first size; wherein the device can be configured such that the contact member can be removed from the left atrial appendage after the securing element has been deployed to the operable state of the securing element; wherein the device can be configured such that the contact member can be removed from the left atrial appendage after the securing element has been deployed to the operable state of the securing element, and wherein the securing element can be configured to prevent a rotation of the tissue of the left atrium and/or the left atrial appendage that has been constricted as a result of the rotation of the contact member from the first position to the second position; wherein the contact member can be configured to move between a first state and a second state, wherein an outside dimension of the contact member can be greater in the second state than in the first state; wherein the contact member can be biased to remain in the second state after deployment into the left atrial appendage; wherein the contact member can be configured to have an approximately fixed and unchangeable size and shape; wherein the contact member can be self-expandable such that the contact member will automatically expand from the first state to the second state when a restraint is removed from the implant without further intervention from a user; wherein the contact member can be configured to automatically move from the first state to the second state when a restraint is removed from the contact member, and wherein the contact member can be configured to engage a wall portion of the left atrial appendage when the contact member is in the second state and advanced into the left atrial appendage; wherein the contact member can have a plurality of tissue anchors on an outer surface thereof; and/or wherein the plurality of tissue anchors on or adjacent to the outer surface of the contact member are configured to engage an inner wall surface of the left atrial appendage after the contact member has been moved to the second state.

Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: wherein the device can be configured to cause a tissue of the left atrium and/or the left atrial appendage to constrict around an outer surface of a body portion of the implant when the contact member is rotated to the second position; wherein the securing element can be configured to engage with the tissue that has constricted around the outer surface of the body portion of the implant to prevent rotation of the implant in a second direction that is opposite to the first direction; wherein, in an operable position, the securing element can be configured to at least inhibit the contact member from rotating back to the first position; wherein the securing element can be configured to prevent a rotation of at least a portion of the left atrial appendage in a second direction when the securing element is implanted in a tissue surface surrounding an ostium of the left atrial appendage, wherein the second direction is opposite to the first direction; wherein the securing element can be configured to at least expand from a first state to a second state, wherein an outside dimension of the securing element can be greater in the second state than in the first state; wherein the securing element can include a plurality of arms; wherein the securing element can have a plurality of struts and a plurality of interconnections between adjacent struts of the plurality of struts; wherein at least an end portion of each of the plurality of arms of the securing element point generally away from the contact member when the securing element is in the first state and point generally toward the contact member when the securing element is in the second state; including a restraint configured to be movable in an axial direction relative to at least a portion of the securing element from a first position in which the plurality of arms of the securing element are restrained by the restraint to a second position in which the plurality of arms of the securing element are not restrained by the restraint;

Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: including a restraint configured to be movable in an axial direction relative to at least a portion of the securing element between a first position in which the plurality of arms of the securing element are restrained by the restraint and a second position in which the plurality of arms of the securing element are not restrained by the restraint, wherein the second axial position can be closer to the first portion of the implant than the first axial position; wherein the restraint can be configured to be movable in an axial direction relative to at least a portion of the securing element from the second position in which the plurality of arms of the securing element are not restrained by the restraint to the first position in which the plurality of arms of the securing element are restrained by the restraint to facilitate repositioning and/or removal of the implant; including a threaded member configured such that rotating the threaded member will cause the restraint to move from the first position to the second position; wherein the restraint can be rotatable relative to the threaded member so that the restraint is not forced to rotate as the threaded member is rotated; wherein the securing element can have a helical shape and can be configured to rotate about a body portion of the implant during the implantation procedure; wherein only a portion of the securing element extends into the left atrium after deployment of the device, and all other portions of the device are internal to the left atrial appendage after deployment of the device; wherein the securing element can be movable between a first state in which the securing element can spin freely relative to the contact member and a second state in which the securing element can be rotationally locked to the contact member; wherein one of the securing element and the contact member can have recesses and the other of the securing element and the contact member can have protrusions configured to selectively engage with the recesses such that the protrusions are spaced apart from the recesses when the securing element is in the first state and the protrusions are engaged with the recesses when the securing element is in the second state; further including a retention element configured to selectively couple the securing element to the contact member at any of a range of selectable distances when the securing element is in the second position; wherein the retention element can have a threaded shaft configured to threadedly engage with the contact member, the threaded shaft being coupled with the securing element; wherein the retention element can be adjustable so as to move the securing element between at least a first position and a second position, wherein the securing element can be closer to the contact member when the retention element is in the second position as compared to when the retention element is in the first position; wherein the retention element can have a threaded member, wherein a rotation of the threaded member in a first direction causes the securing element to move toward the contact member and a rotation of the threaded member in a second direction causes the securing element to move away from the contact member; wherein the retention element can be configured to slide at least in an axial direction over an inner core component of a delivery catheter; wherein the second position can be at least one-quarter of a complete rotation relative to the first position; wherein the second position can be at least one-half of a complete rotation relative to the first position; wherein the second position can be from approximately one-quarter of a complete rotation to one or more complete rotations relative to the first position; including a catheter selectively coupled with the contact member and configured to exert a torque on the contact member to rotate the contact member from the first position until a threshold predetermined torque level is reached; wherein a threshold predetermined torque level can be from approximately 0.25 in-oz of torque to approximately 10 in-oz of torque; and/or wherein a threshold predetermined torque level can be from approximately 0.5 in-oz of torque to approximately 5 in-oz of torque; and/or wherein only approximately 10% or less of an overall length of the deployed device extends into the left atrium after deployment of the device.

Also disclosed herein are embodiments of a method of treating a left atrial appendage that can include advancing a deployment device having an implant into the left atrium, moving at least a portion of an outer surface of a first portion of the implant and/or one or more tissue anchors on or adjacent to the outer surface of the first portion of the implant against an inner wall surface of the left atrial appendage, and rotating the first portion of the implant from a first position to a second position to twist the left atrial appendage from a first position to a second position, and moving a second portion of the implant from a first state in which the second portion of the implant spins freely relative to the first portion of the implant to a second state in which the second portion of the implant can be rotationally locked to the first portion of the implant. Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: wherein the second portion of the implant can be spaced apart from the first portion of the implant when the second portion of the implant is in the first state and the second portion of the implant is engaged with the first portion of the implant when the second portion of the implant is in the second state; including rotating the first portion of the implant until at least a portion of the left atrial appendage constricts around a portion of the implant; including rotating the first portion of the implant until an ostium of the left atrial appendage constricts around a portion of the implant; wherein the method can have engaging with the second portion of the implant a tissue that has constricted as a result of the rotation of the first portion of the implant; and/or wherein moving the second portion of the implant from the first state to the second state causes the second portion of the implant to inhibit a rotation of the left atrial appendage toward the first position of the left atrial appendage.

Also disclosed herein are embodiments of a device for treating a left atrial appendage that can include an implant device that can include a first implant member configured to engage an inside tissue surface of a first portion of the left atrial appendage and a second implant member configured to engage an inside tissue surface of a second portion of the left atrial appendage spaced apart from the first portion of the left atrial appendage. In some embodiments, the device can be configured to rotate the first implant member in a first direction. In some embodiments, the device can be configured to rotate the second implant member in a second direction that is opposite to the first direction.

Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: further including a first core member coupled with the first implant member and configured to cause a rotation of the first implant member when the first core member is rotated; wherein the first implant member can be selectively removably coupled with the first core member so that the first implant member can remain in the left atrial appendage after the first core member has been withdrawn; further including a second core member coupled with the second implant member and configured to cause a rotation of the second implant member when the second core member is rotated; wherein the second implant member can be selectively removably coupled with the second core member so that the second implant member can remain in the left atrial appendage after the second core member has been withdrawn; and/or further including a securing element configured to inhibit a rotation of the first implant member and/or the second implant member in an operable state.

Disclosed herein are embodiments of a device for treating a left atrial appendage that can include an implant device that can include a first implant member configured to engage an inside tissue surface of a first portion of the left atrial appendage and a second implant member configured to engage an inside tissue surface of a second portion of the left atrial appendage spaced apart from the first portion of the left atrial appendage. In some embodiments, the device can be configured to rotate the first implant member in a first direction. Further, in some embodiments, the device can be configured to also rotate the second implant member in the first direction. Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: further including a first core member coupled with the first implant member and configured to cause a rotation of the first implant member when the first core member is rotated; wherein the first implant member can be selectively removably coupled with the first core member so that the first implant member can remain in the left atrial appendage after the first core member has been withdrawn; further including a second core member coupled with the second implant member and configured to cause a rotation of the second implant member when the second core member is rotated; wherein the second implant member can be selectively removably coupled with the second core member so that the second implant member can remain in the left atrial appendage after the second core member has been withdrawn; and/or further including a securing element configured to inhibit a rotation of the first implant member and/or the second implant member in an operable state.

Disclosed herein are embodiments of a device for treating a left atrial appendage that can include an implant that can include a contact member and a securing element coupled with or coupleable with the contact member, the securing element including a plurality of struts and a plurality of interconnections between adjacent struts of the plurality of struts. In some embodiments, the contact member can be configured to rotate at least in a first direction from a first rotational position to a second rotational position to twist at least a portion of the left atrial appendage in the first direction when the contact member is rotated from the first rotational position to the second rotational position. Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: wherein the contact member can be configured to configured to move at least from a first state to a second state so that at least a portion of the contact member can expand radially to engage a wall portion inside the left atrial appendage; wherein the plurality of interconnections provide a point of connection between the adjacent struts of the plurality of struts; wherein the plurality of struts can have a plurality of pairs of struts, wherein each of the pairs of struts can have two struts that are interconnected at a distal end portion of the struts; wherein the plurality of struts can have a first strut, a second strut, and a third strut, the second strut can be positioned between the first strut and the third strut and the second strut can be interconnected with the first strut at a distal end of the first and second struts; wherein the second strut can be interconnected with the third strut at a middle portion of the second and third struts; wherein the implant further can have a retention element coupled with the securing element, the retention element configured to move the securing element in an axial direction toward or away from the contact member or to hold the securing element in a stationary position relative to the contact member; wherein the securing element can be configured to prevent a rotation of at least a portion of the left atrial appendage in a second direction when the securing element is in an operable state, wherein the second direction is opposite to the first direction; wherein the contact member can be self-expandable such that at least a portion of the contact member automatically expands from the first state to the second state when a restraint is removed from the contact member; wherein the implant can be substantially collapsed when the implant is in the first state and is expanded when the implant is in the second state such that a size of the implant can be bigger when the implant is in the second state than when the implant is in the first state; wherein the contact member can be biased to remain in the second state after deployment into the left atrial appendage; wherein the contact member can be configured to be rotated in a clockwise or a counter-clockwise direction; wherein the device can be configured to cause a tissue of the left atrium and/or the left atrial appendage to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element can have a plurality of tissue anchors configured to engage with an internal wall of the heart adjacent to the left atrial appendage; wherein the securing element can have a helical shape and can be configured to rotate about a body portion of the implant during the implantation procedures; wherein the implant can be configured to rotate in a first direction from the first rotational position to the second rotational position; and/or wherein the implant can be configured to prevent rotation of the implant in a second direction after the implant has been fully deployed, wherein the second direction is opposite to the first direction.

Any embodiments of the methods, devices and systems for treating a left atrial appendage disclosed herein can include, in additional embodiments, one or more of the following steps, features, components, and/or details, in any combination with any of the other steps, features, components, and/or details of any other embodiments disclosed herein: wherein the contact member can have a plurality of tissue anchors on an outside surface thereof; wherein the plurality of tissue anchors on the outside surface of the contact member are configured to engage an inner wall surface of the left atrial appendage after the contact member has been moved to the second state; wherein the tissue anchors of the contact member have a proximal facing surface that is angled toward a proximal end of the contact member by 5 degrees; wherein the tissue anchors wherein the tissue anchors of the contact member have a proximal facing surface that is angled toward a proximal end of the contact member at an angle from 2 degrees to 10 degrees; wherein the implant can have a securing element configured to engage with a tissue portion of the heart adjacent to the left atrial appendage; wherein the second rotational position can be at least one-quarter of a complete rotation relative to the first rotational position; wherein the second rotational position can be at least one-half of a complete rotation relative to the first rotational position; wherein the second rotational position can be from approximately one-quarter of a complete rotation to one or more complete rotations relative to the first rotational position; including a catheter selectively coupled with the contact member and configured to exert a torque on the contact member to rotate the contact member from the first rotational position until a threshold predetermined torque level is reached; wherein a threshold predetermined torque level can be from approximately 0.25 in-oz of torque to approximately 10 in-oz of torque; wherein a threshold predetermined torque level can be from approximately 0.5 in-oz of torque to approximately 5 in-oz of torque; including a retention element configured to bias the securing element toward a tissue wall of the LAA; including a retention element configured to bias the securing element toward the contact member; including a retention element configured to couple the securing element with the contact member; wherein the retention element can have a threaded shaft; wherein the device can be configured such that a rotation of the retention element in a first direction causes the securing element to move toward the contact member;

wherein the contact member can be configured to rotate at least in a first direction from a first rotational position to a second rotational position when a torque is applied to the contact member; wherein the device can be configured such that the contact member can be removed from the left atrial appendage after the securing element has been deployed to the operable state of the securing element; wherein the device can be configured such that the contact member can be removed from the left atrial appendage after the securing element has been deployed to the operable state of the securing element, and wherein the securing element can be configured to prevent a rotation of the tissue of the left atrium and/or the left atrial appendage that has been constricted as a result of the rotation of the contact member from the first rotational position to the second rotational position; wherein only a portion of the securing element extends into the left atrium after deployment of the device, and all other portions of the device are internal to the left atrial appendage after deployment of the device; wherein only approximately 10% or less of an overall length of the deployed device extends into the left atrium after deployment of the device; wherein the device can be configured for use by a surgical robot device or system; wherein the contact member and the securing element are integrally and/or monolithically formed; and/or wherein the device can be configured to cause a tissue of the left atrium and/or the left atrial appendage to constrict around an outer surface of a body portion of the implant when the contact member is rotated to the second rotational position, and the securing element can be configured to compress the tissue that has constricted around the outer surface of the body portion of the implant between a distal surface of the securing element and the contact member to prevent rotation of the implant in the second direction.

Some embodiments enclosed herein include a surgical robotic device that can include one or more robotic arms and the device of any of the embodiments disclosed herein, wherein the device can be configured for use by the surgical robotic device.

Some embodiments of methods of treating a left atrial appendage disclosed herein can include rotating the left atrial appendage and securing the left atrial appendage in a rotated position. Any embodiments of the methods of treating, closing, or occluding the LAA can include, in additional embodiments, one or more of the following features, components, steps, and/or details, in any combination with any of the other features, components, steps, and/or details of any other embodiments disclosed herein: wherein rotating the left atrial appendage comprises rotating the left atrial appendage to deform or occlude the left atrial appendage; wherein securing the left atrial appendage in a rotated position comprises securing the left atrial appendage in a rotated position in which the left atrial appendage is reduced in volume; wherein securing the left atrial appendage in a rotated position comprises securing the left atrial appendage in a rotated position in which the left atrial appendage is deformed or occluded; wherein rotating the left atrial appendage comprises bending or contorting the left atrial appendage; wherein securing the left atrial appendage in a rotated position comprises securing the left atrial appendage in a position in which a blood communication between the left atrial appendage and a left atrium is inhibited, eliminated, or substantially eliminated; wherein rotating the left atrial appendage comprises engaging a wall portion on an inside of the left atrial appendage and/or an ostium of the left atrial appendage with a contact member and rotating the contact member; wherein the contact member is positioned on an implant coupled to the delivery system; wherein the contact member is self-expanding, balloon expandable, mechanically expanded, and/or a balloon; wherein rotating the left atrial appendage comprises engaging a wall portion on an inside of the left atrial appendage with one or more tissue anchors, one or more tissue grippers, and/or one or more other tissue holding features; wherein rotating the left atrial appendage comprises advancing a device into the left atrial appendage and rotating at least a component of the device to rotate the left atrial appendage; wherein rotating at least a component of the device comprises rotating at least the component of the device from approximately 90 degrees to approximately 360 degrees in either direction from an initial position; wherein rotating the left atrial appendage comprises rotating a portion of the left atrial appendage about an axis to twist the left atrial appendage; wherein rotating a portion of the left atrial appendage about one or more axes from an initial position comprises rotating the portion of the left atrial appendage from approximately 90 degrees to approximately 360 degrees in either direction from the initial position; wherein rotating a portion of the left atrial appendage comprises rotating the left atrial appendage until an opening of the left atrial appendage is substantially or completely closed; wherein rotating a portion of the left atrial appendage comprises rotating the left atrial appendage until a blood communication between the left atrial appendage and a left atrium is inhibited; wherein rotating a portion of the left atrial appendage comprises rotating the left atrial appendage until a communication of blood or other matter between the left atrial appendage and the left atrium is eliminated or substantially eliminated; wherein securing the left atrial appendage in a rotated position comprises engaging tissue of the heart that has been twisted; wherein engaging tissue of the heart that has been twisted comprises engaging tissue wall with an anchor element or gripping element; wherein securing the left atrial appendage in a rotated position comprises securing a tissue of the heart outside of an occluded portion of the left atrial appendage with an anchor element; wherein securing the left atrial appendage in a rotated position comprises securing a tissue of an occluded portion of the left atrial appendage with an anchor element; and/or wherein the anchor element comprises a plurality of tissue grippers on at least one surface thereof configured to engage with the internal wall of the heart outside of the left atrial appendage.

Some embodiments of the method of reducing an ostium of a left atrial appendage disclosed herein can include twisting tissue of the heart to constrict the ostium of the left atrial appendage and securing tissue that has deformed or constricted as a result of twisting tissue of the heart. Any embodiments of the methods of treating, closing, or occluding the LAA can include, in additional embodiments, one or more of the following features, components, steps, and/or details, in any combination with any of the other features, components, steps, and/or details of any other embodiments disclosed herein: wherein securing the tissue that has deformed or constricted comprises advancing a securing element into the tissue that has deformed or constricted as a result of twisting tissue of the heart; wherein the securing element comprises a tissue anchor or tissue gripper; wherein securing the tissue that has deformed or constricted as a result of twisting tissue of the heart comprises advancing a securing element into the tissue that has deformed or constricted to compress the tissue that has deformed or constricted; and/or wherein securing tissue that has deformed or constricted as a result of twisting tissue of the heart comprises advancing one or more sutures or one or more staples into the tissue that has deformed or constricted as a result of twisting tissue of the heart.

Some embodiments of the method of treating a left atrial appendage disclosed herein can include twisting the left atrial appendage such that the left atrial appendage becomes reduced in volume and securing the left atrial appendage in a reduced volume configuration. In some embodiments, securing the left atrial appendage in a reduced volume configuration can include occluding the left atrial appendage with an implant that is smaller in size than a size of the inside of the left atrial appendage. In some embodiments, the method of treating the left atrial appendage can include unsecuring and untwisting the left atrial appendage.

BRIEF DESCRIPTION OF THE DRAWINGS

FIGS. 62C1-62Z show additional embodiments of contact members and/or implant devices that can be used with any of the embodiments of the treatment devices disclosed herein.

FIG. 67M shows the embodiment of the treatment device shown in FIG. 67L, showing the contact member being expanded within the LAA and engaging an inside surface of a wall portion of the LAA.

FIG. 67N shows the embodiment of the treatment device shown in FIG. 67L, showing the contact member being rotated to twist the LAA and cause a neck or opening of the LAA to constrict around a portion of the implant device.

FIG. 67O shows the embodiment of the treatment device shown in FIG. 67L, showing a securing element being advanced toward the contact member.

FIG. 67P shows the embodiment of the treatment device shown in FIG. 67L, showing the securing element engaged with the tissue that has constricted as a result of the twisting of the LAA and/or the tissue adjacent to the tissue that has constricted as a result of the twisting of the LAA.

FIG. 68A shows another embodiment of a device that can be configured to be used as a contact member and/or a securing element in any treatment device embodiments disclosed herein.

FIG. 68B shows another embodiment of a treatment device for occluding the LAA, showing the contact member in a collapsed state being advanced into the LAA.

FIG. 68C shows the embodiment of the treatment device shown in FIG. 68B, showing the contact member being expanded within the LAA and engaging an inside surface of a wall portion of the LAA.

FIG. 68D shows the embodiment of the treatment device shown in FIG. 68B, showing the contact member being rotated to twist the LAA and cause a neck or opening of the LAA to constrict around a portion of the implant device.

FIG. 68E shows the embodiment of the treatment device shown in FIG. 68B, showing a securing element being advanced toward the contact member.

FIG. 68F shows the embodiment of the treatment device shown in FIG. 68B, showing the securing element engaged with the tissue that has constricted as a result of the twisting of the LAA and/or the tissue adjacent to the tissue that has constricted as a result of the twisting of the LAA.

FIG. 69A shows another embodiment of a device that can be used as a contact member and/or a securing element in any treatment device embodiments disclosed herein.

FIG. 69B shows an embodiment of a treatment device for occluding the LAA showing an implant device having a contact member in a collapsed state being advanced into the LAA.

Figure 69A:
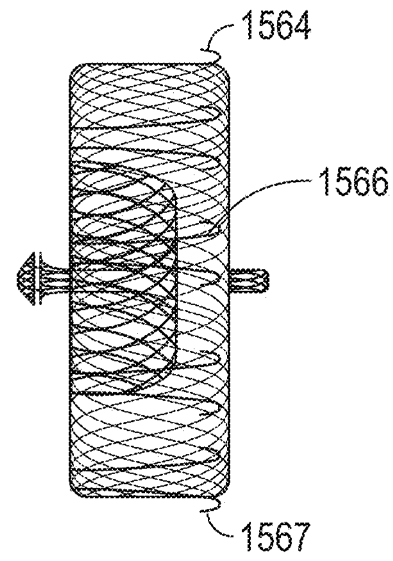
Figure 69B:
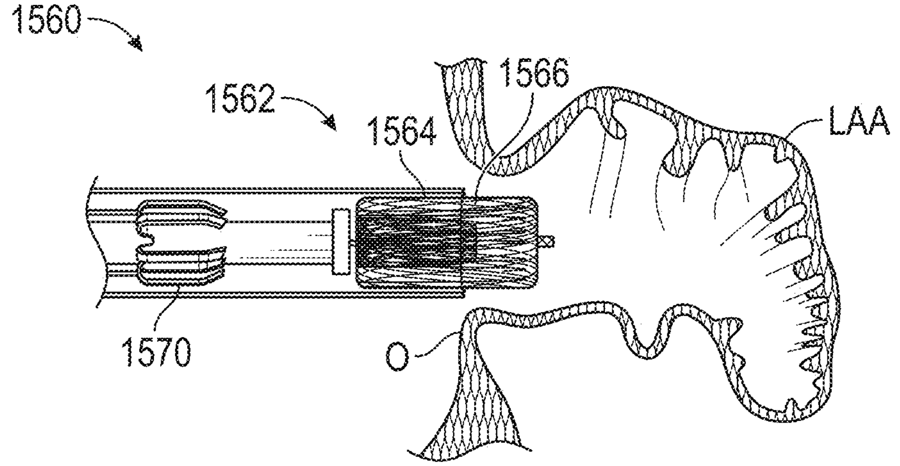
Figure 69C:
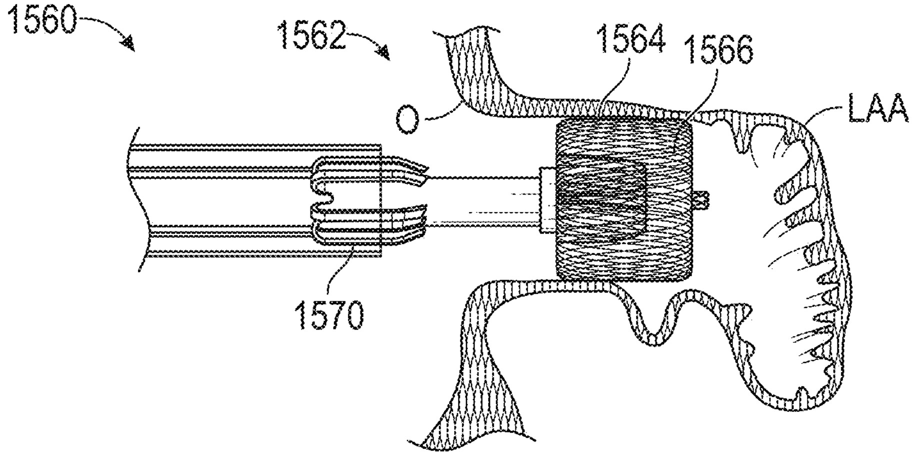

FIG. 69C shows the embodiment of the treatment device shown in FIG. 69B, showing the contact member being expanded within the LAA and engaging an inside surface of a wall portion of the LAA.

Figure 69D:
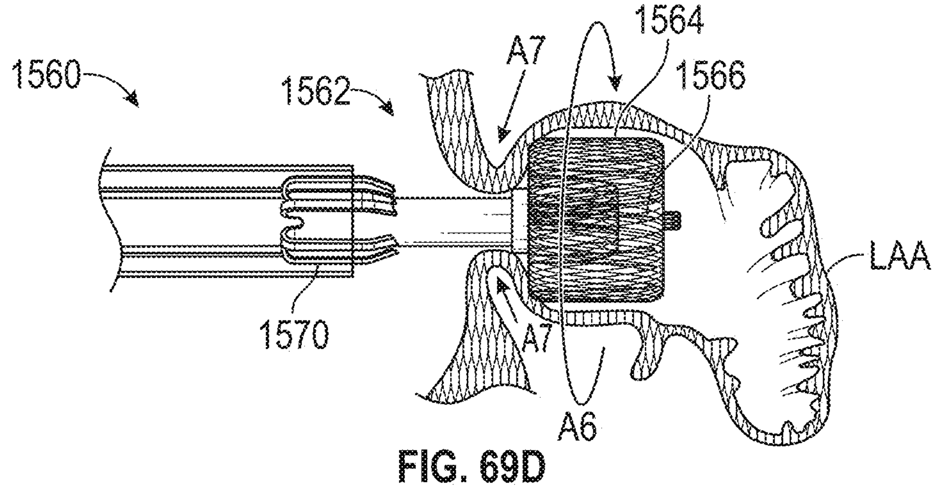

FIG. 69D shows the embodiment of the treatment device shown in FIG. 69B, showing the contact member being rotated to twist the LAA and cause a neck or opening of the LAA to constrict around a portion of the implant device.

Figure 69E:
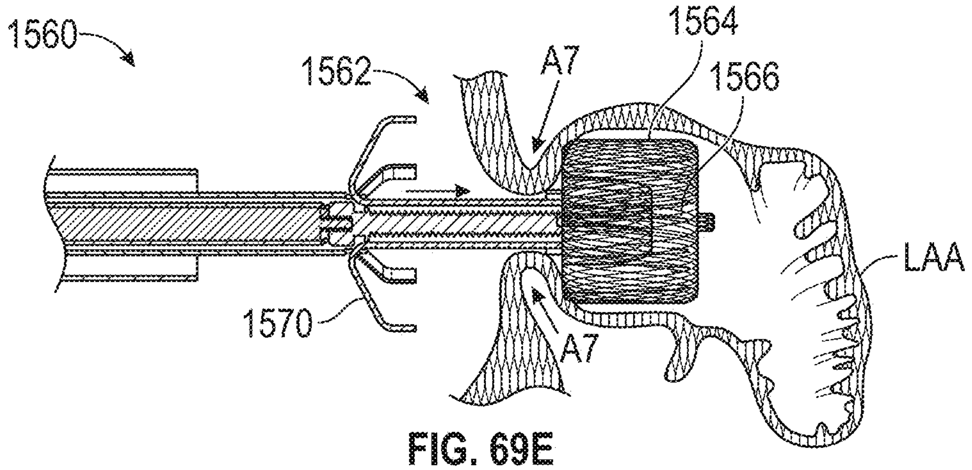

FIG. 69E shows the embodiment of the treatment device shown in FIG. 69B, showing a securing element of the embodiment of the implant device being advanced toward the contact member.

Figure 69F:
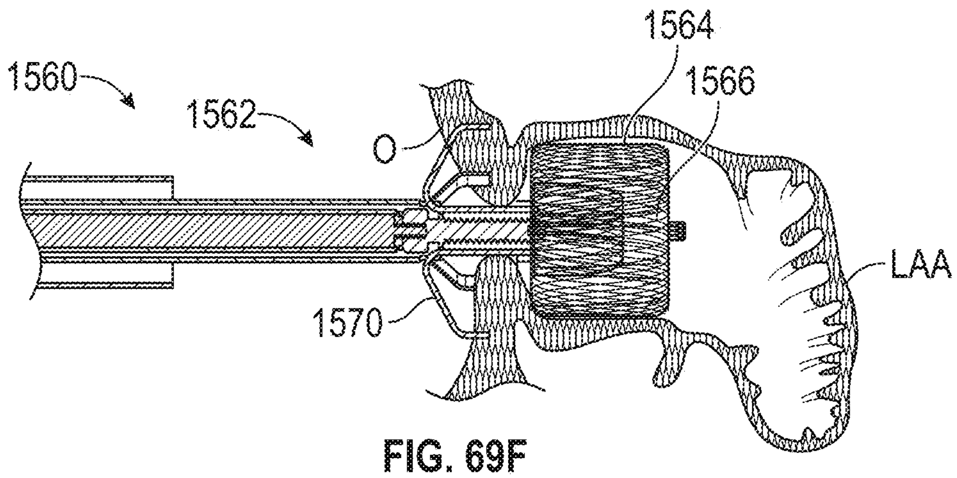

FIG. 69F shows the securing element of the treatment device shown in FIG. 69B engaged with the patient's tissue that has constricted as a result of the twisting of the LAA and/or adjacent to the patient's tissue that has constricted as a result of the twisting of the LAA.

Figure 70A:
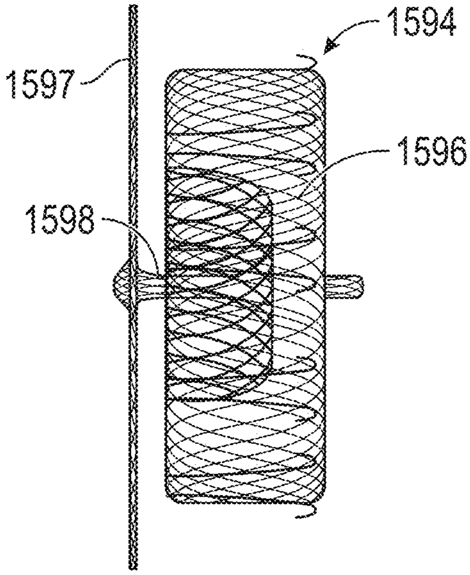

FIG. 70A shows another embodiment of an implant that can be used as a contact member and/or a securing element in any treatment device embodiments disclosed herein.

Figure 70B:
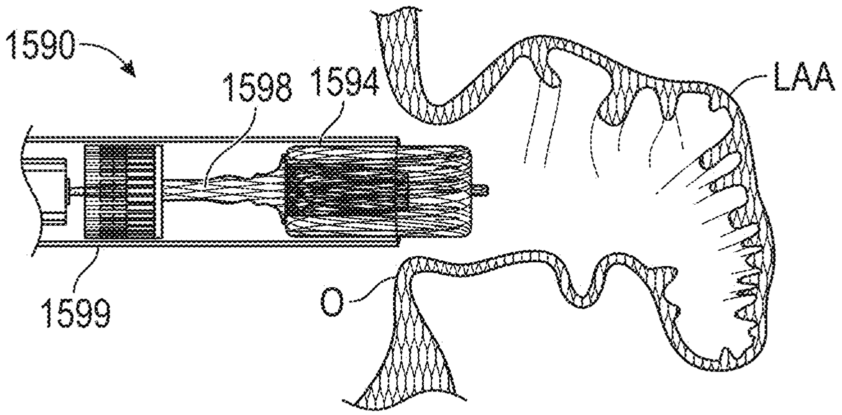

FIG. 70B shows an embodiment of a treatment device for occluding the LAA, showing an implant device having a contact member in a collapsed state being advanced into the LAA.

Figure 70C:
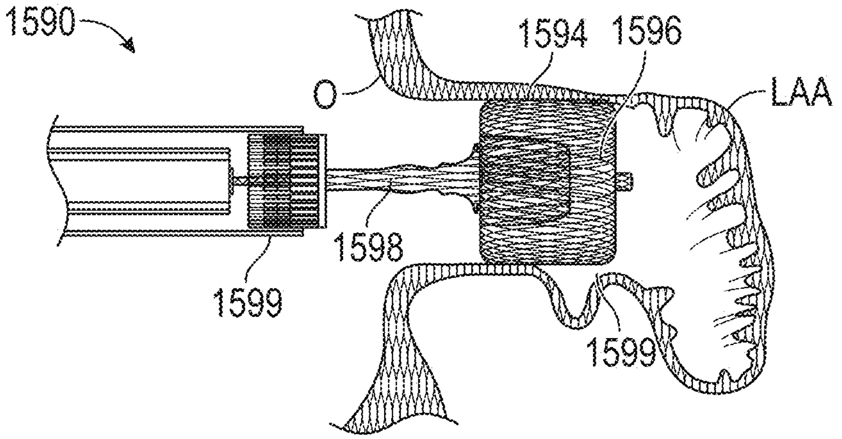

FIG. 70C shows the embodiment of the treatment device shown in FIG. 70B, showing the contact member being expanded within the LAA and engaging an inside surface of a wall portion of the LAA.

Figure 70D:
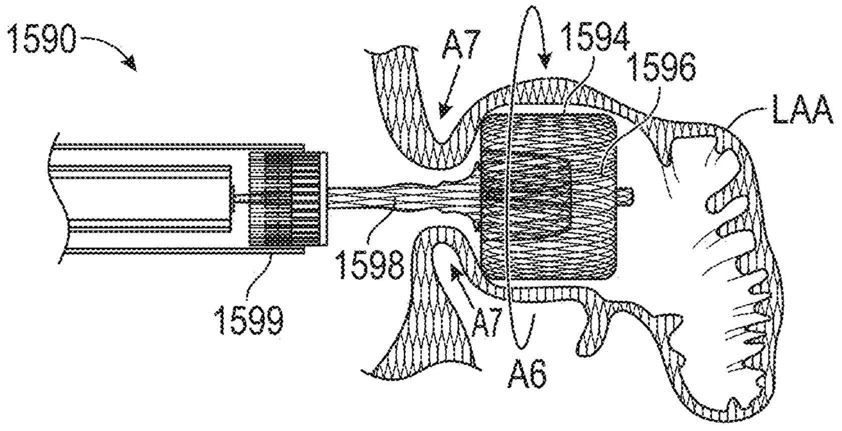

FIG. 70D shows the embodiment of the treatment device shown in FIG. 70B, showing the contact member being rotated to twist the LAA and cause a neck or opening of the LAA to constrict around a portion of the implant device.

Figure 70E:
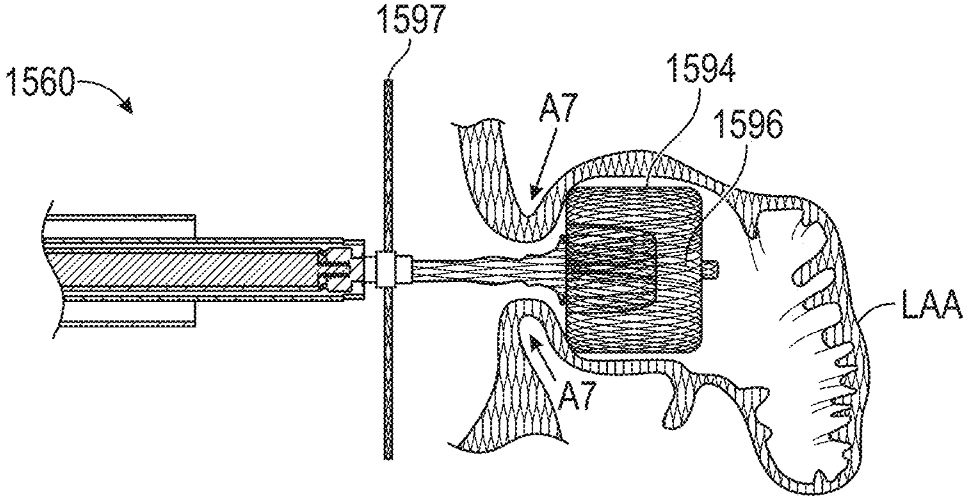

FIG. 70E shows the embodiment of the treatment device shown in FIG. 70B, showing a securing element of the embodiment of the implant device being advanced toward the contact member.

Figure 70F:
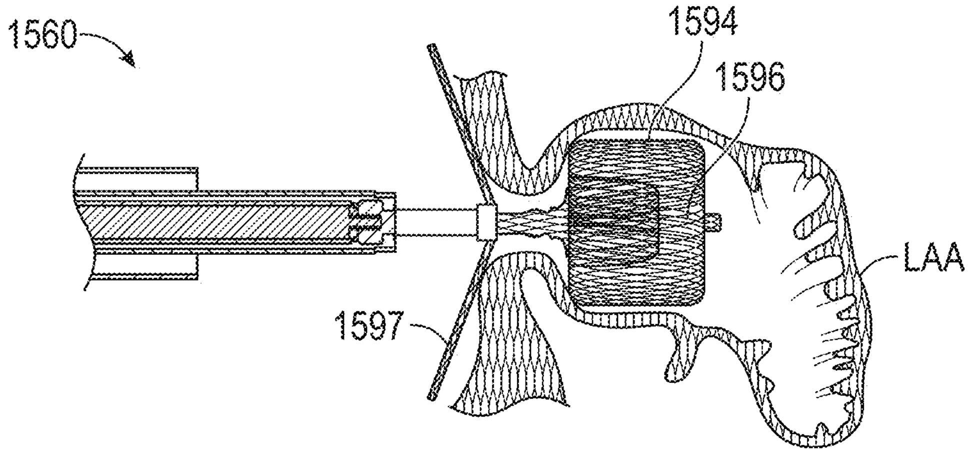

FIG. 70F shows the securing element of the treatment device shown in FIG. 70B engaged with the patient's tissue that has constricted as a result of the twisting of the LAA and/or adjacent to the patient's tissue that has constricted as a result of the twisting of the LAA.

Figure 70G:
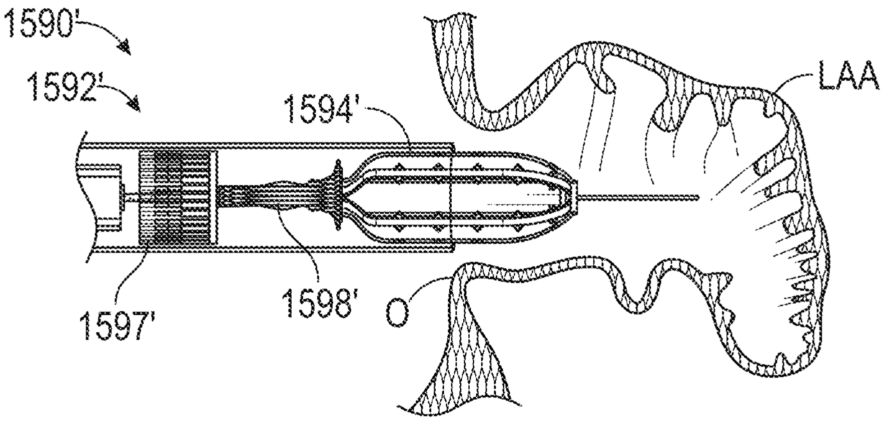

FIG. 70G shows another embodiment of a treatment device for occluding the LAA, showing an implant device having a contact member in a collapsed state being advanced into the LAA.

Figure 70H:
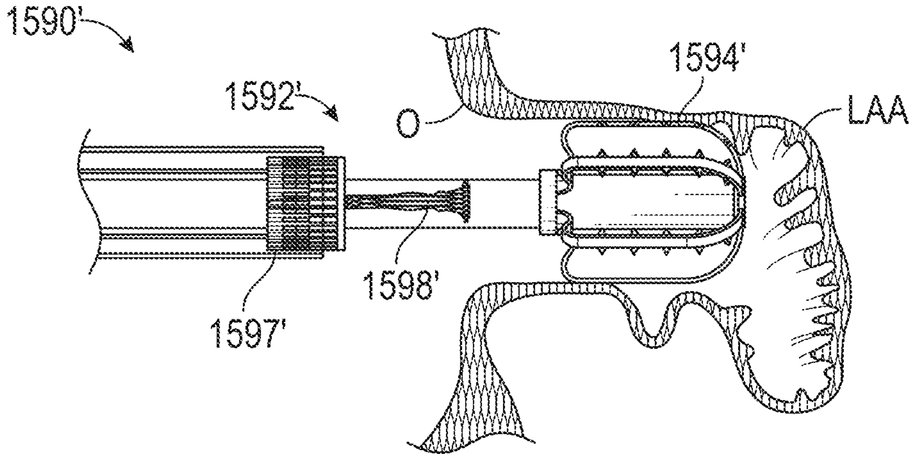

FIG. 70H shows the embodiment of the treatment device shown in FIG. 70B, showing the contact member being expanded within the LAA and engaging an inside surface of a wall portion of the LAA.

Figure 70I:
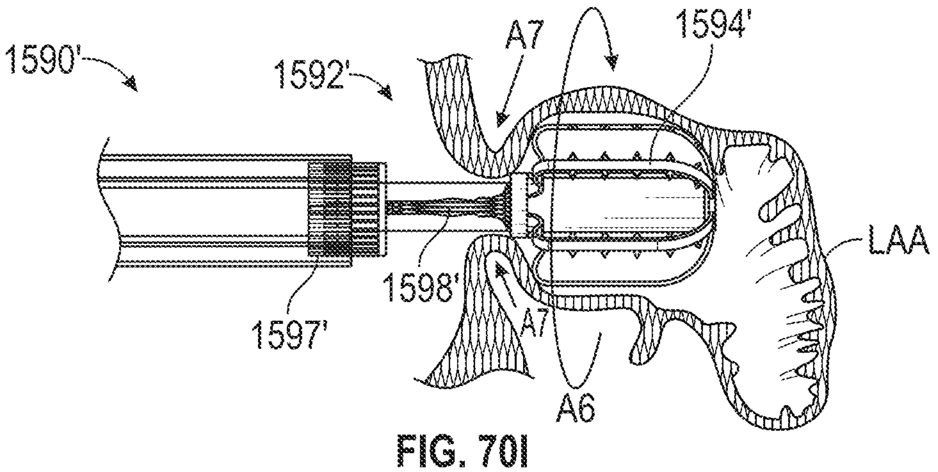

FIG. 70I shows the embodiment of the treatment device shown in FIG. 70B, showing the contact member being rotated to twist the LAA and cause a neck or opening of the LAA to constrict around a portion of the implant device.

Figure 70J:
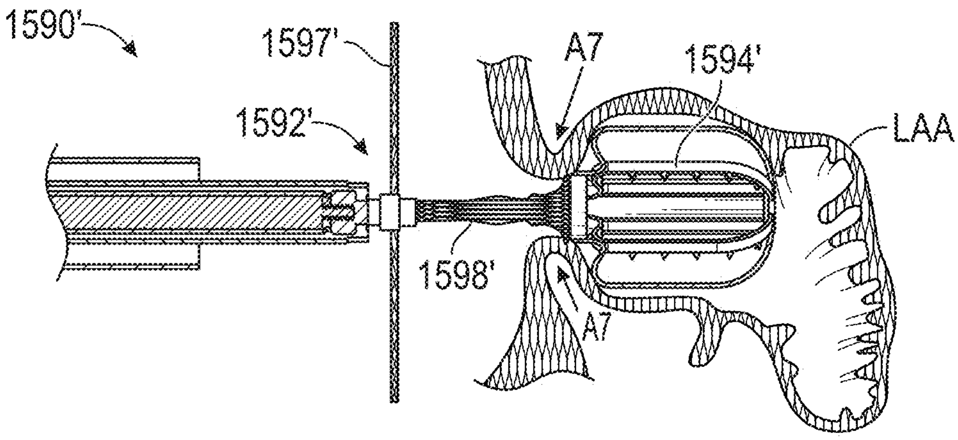

FIG. 70J shows the embodiment of the treatment device shown in FIG. 70B, showing a securing element of the embodiment of the implant device being advanced toward the contact member.

Figure 70K:
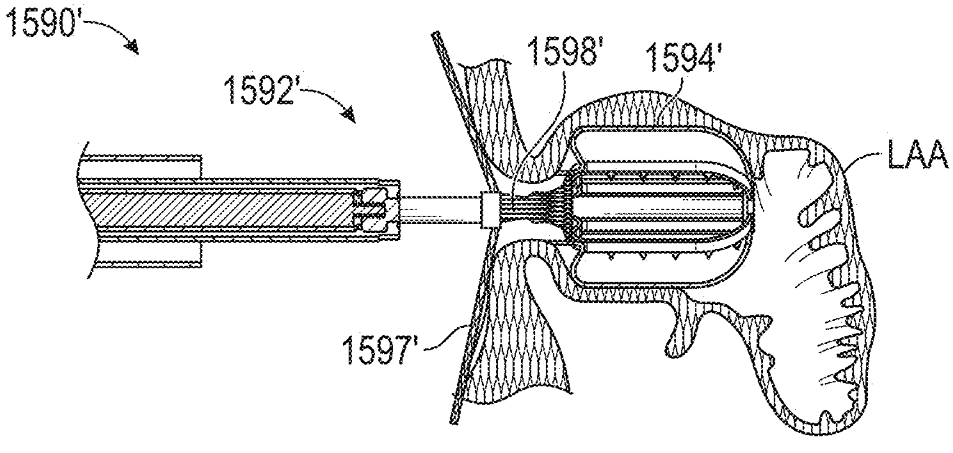
Figure 70L:
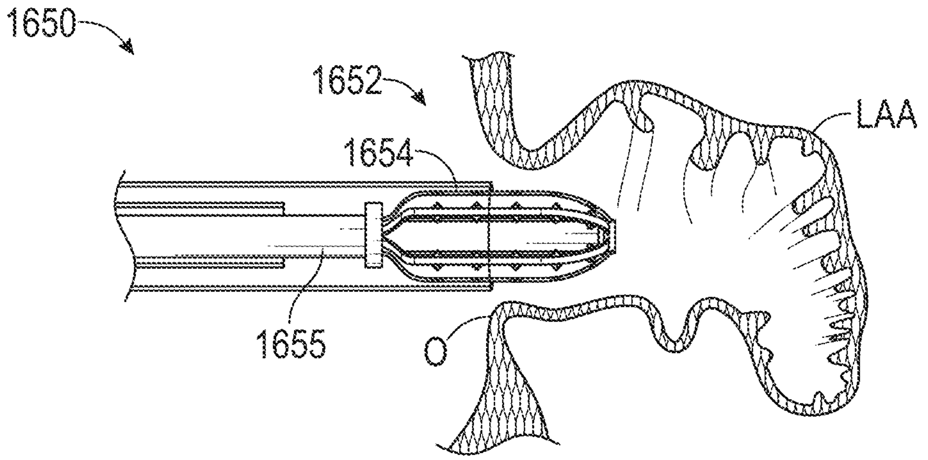

FIG. 70K shows the securing element of the treatment device shown in FIG. 70B engaged with the patient's tissue that has constricted as a result of the twisting of the LAA and/or adjacent to the patient's tissue that has constricted as a result of the twisting of the LAA.

FIGS. 70L-70T show another embodiment of a treatment system for treating or occluding an LAA.

Figure 71A:
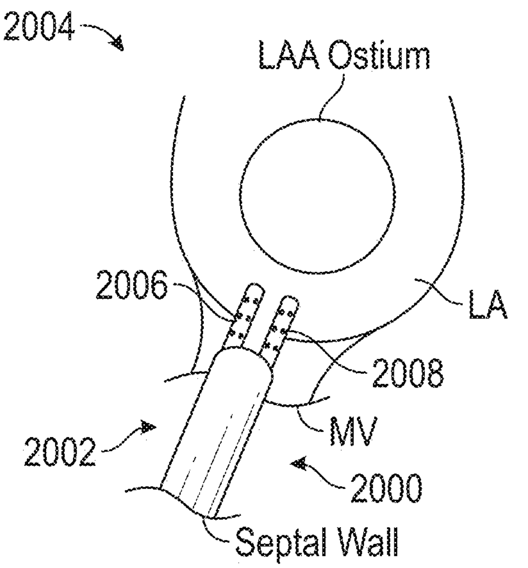

FIG. 71A shows another embodiment of a treatment device for treating or occluding an LAA, showing an implant device being advanced past a distal end of the delivery device toward the LAA.

Figure 71B:
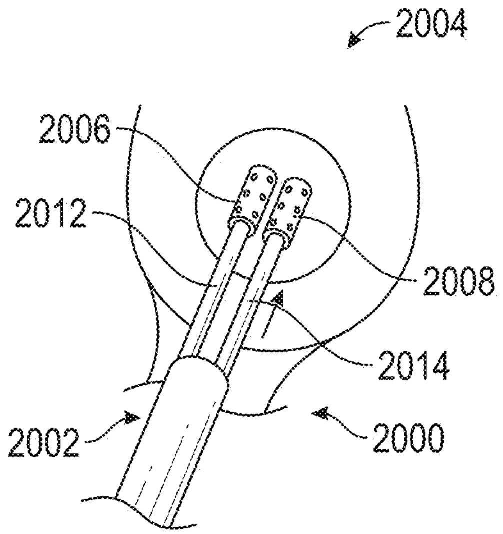

FIG. 71B shows the embodiment of the treatment device shown in FIG. 71A, showing the implant device being advanced into the LAA.

Figure 71C:
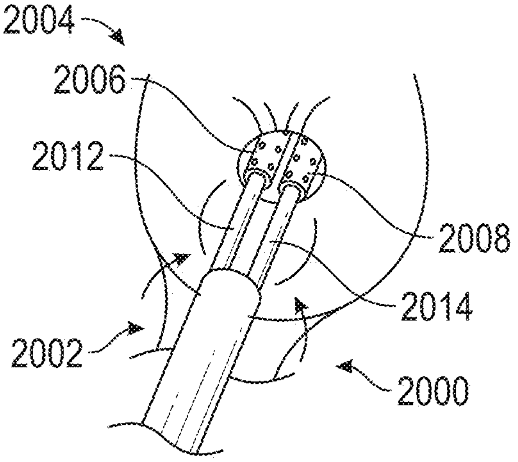

FIG. 71C shows the embodiment of the treatment device shown in FIG. 71A, showing a first and a second implant members of the implant device being rotated to twist the tissue of the LAA to occlude the ostium of the LAA.

Figure 71D:
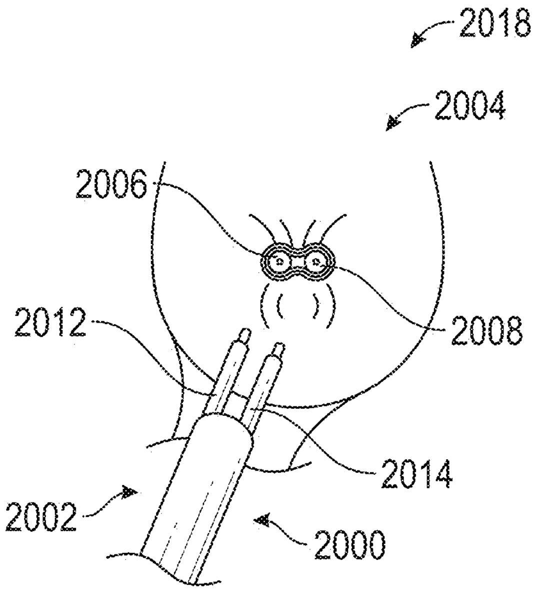

FIG. 71D shows the embodiment of the treatment device shown in FIG. 71A, showing a first and a second implant member of the implant device after occluding the LAA, the first and second implant members being secured together and disconnected from the delivery device.

Figure 72A:
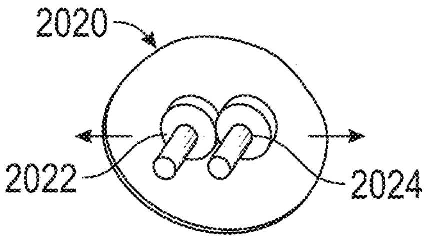

FIG. 72A shows another embodiment of a treatment device for treating or occluding an LAA, showing an implant device having a first implant member and a second implant member positioned within the ostium of the LAA.

Figure 72B:
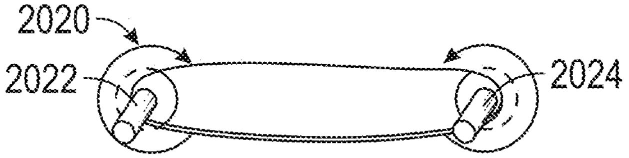

FIG. 72B shows the embodiment of the treatment device shown in FIG. 72A, showing a first and a second implant member of the implant device being rotated to twist the tissue of the LAA to occlude the ostium of the LAA.

Figure 73A:
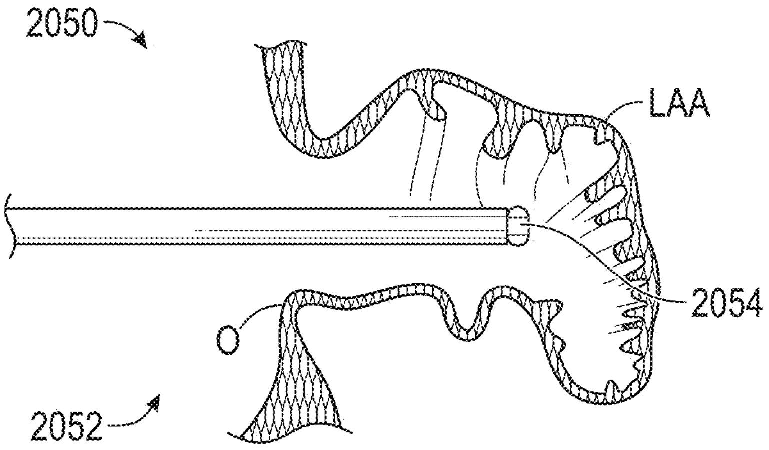

FIG. 73A shows another embodiment of a treatment device for treating or occluding an LAA, showing a deployment device having a suction member being advanced into the LAA.

Figure 73B:
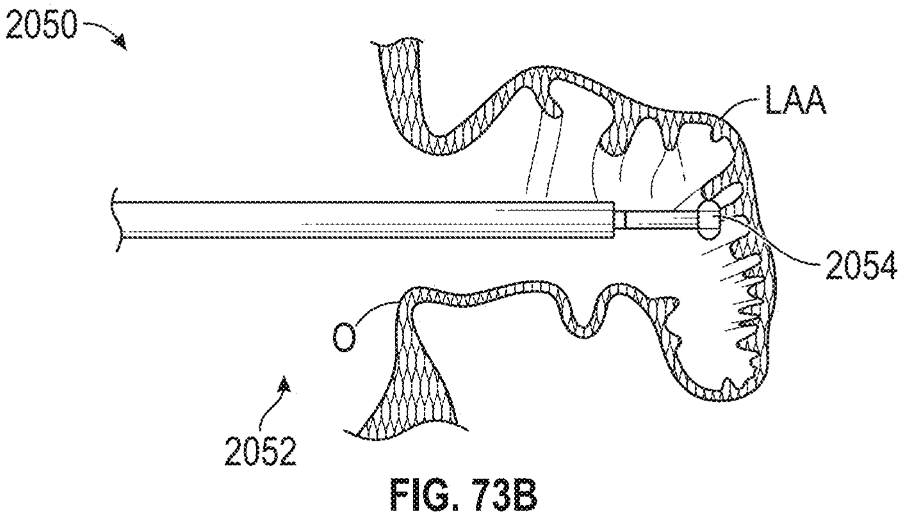

FIG. 73B shows the embodiment of the treatment device shown in FIG. 73A, showing the suction member being advanced toward a distal wall of the LAA.

Figure 73C:
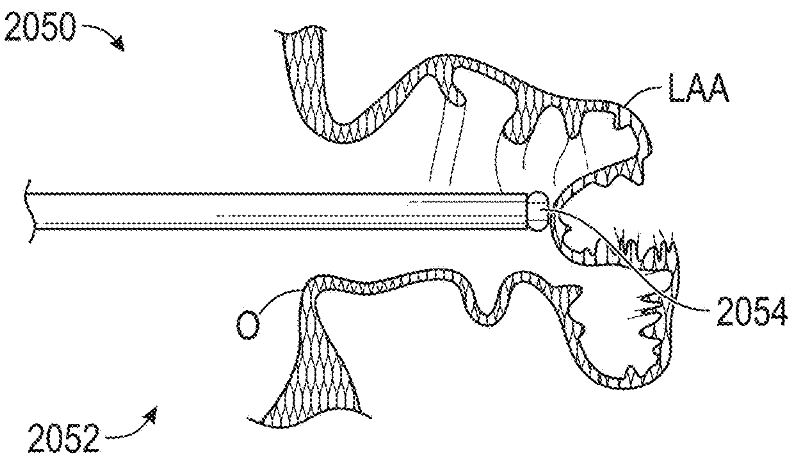

FIG. 73C shows the embodiment of the treatment device shown in FIG. 73A, showing the suction member engaging a distal wall of the LAA with suction and withdrawing a portion of the distal portion of the wall of the LAA.

Figure 73D:
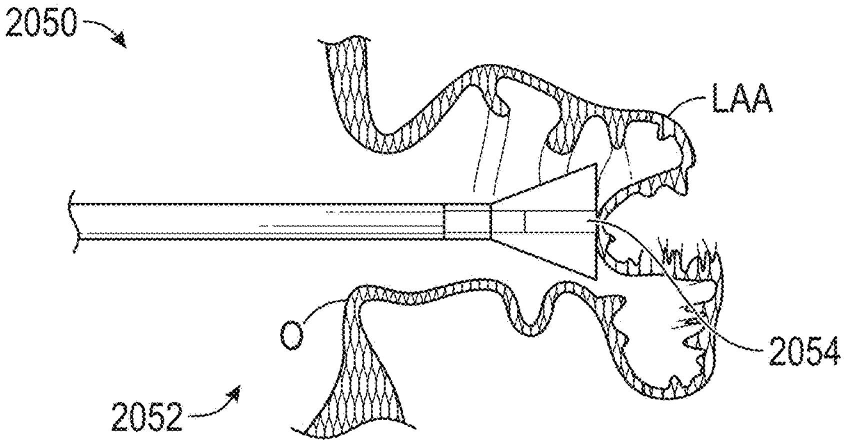

FIG. 73D shows another embodiment of a treatment device for treating or occluding an LAA, showing the suction member engaging a distal wall of the LAA with suction member and withdrawing a portion of the distal portion of the wall of the LAA.

Figure 73E:
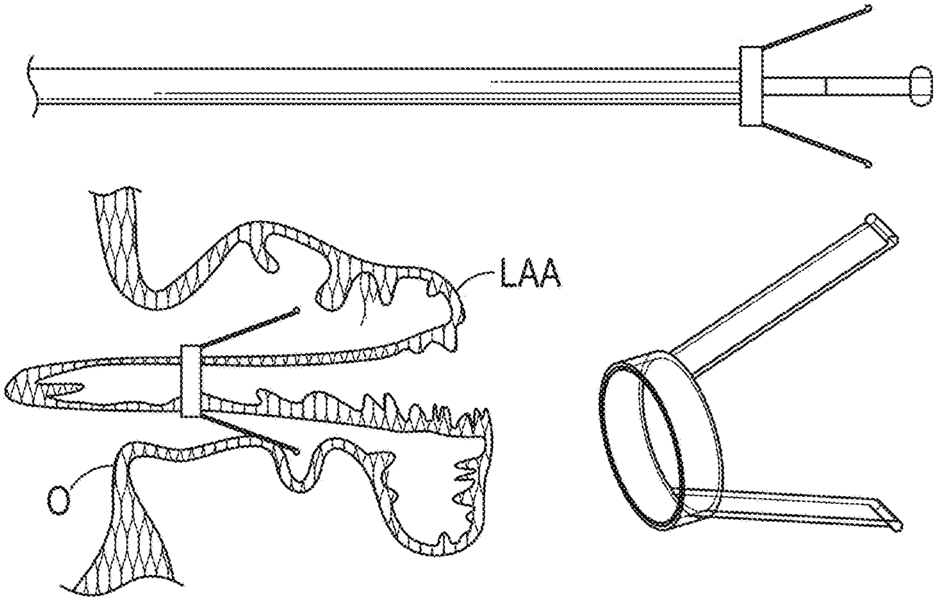

FIG. 73E shows another embodiment of a treatment device for treating or occluding an LAA, showing a clamp member surrounding a portion of the tissue that has been inverted by the withdrawal of the suction member.

Figures 74, 75, 76A, 76B, 76C, 76D:
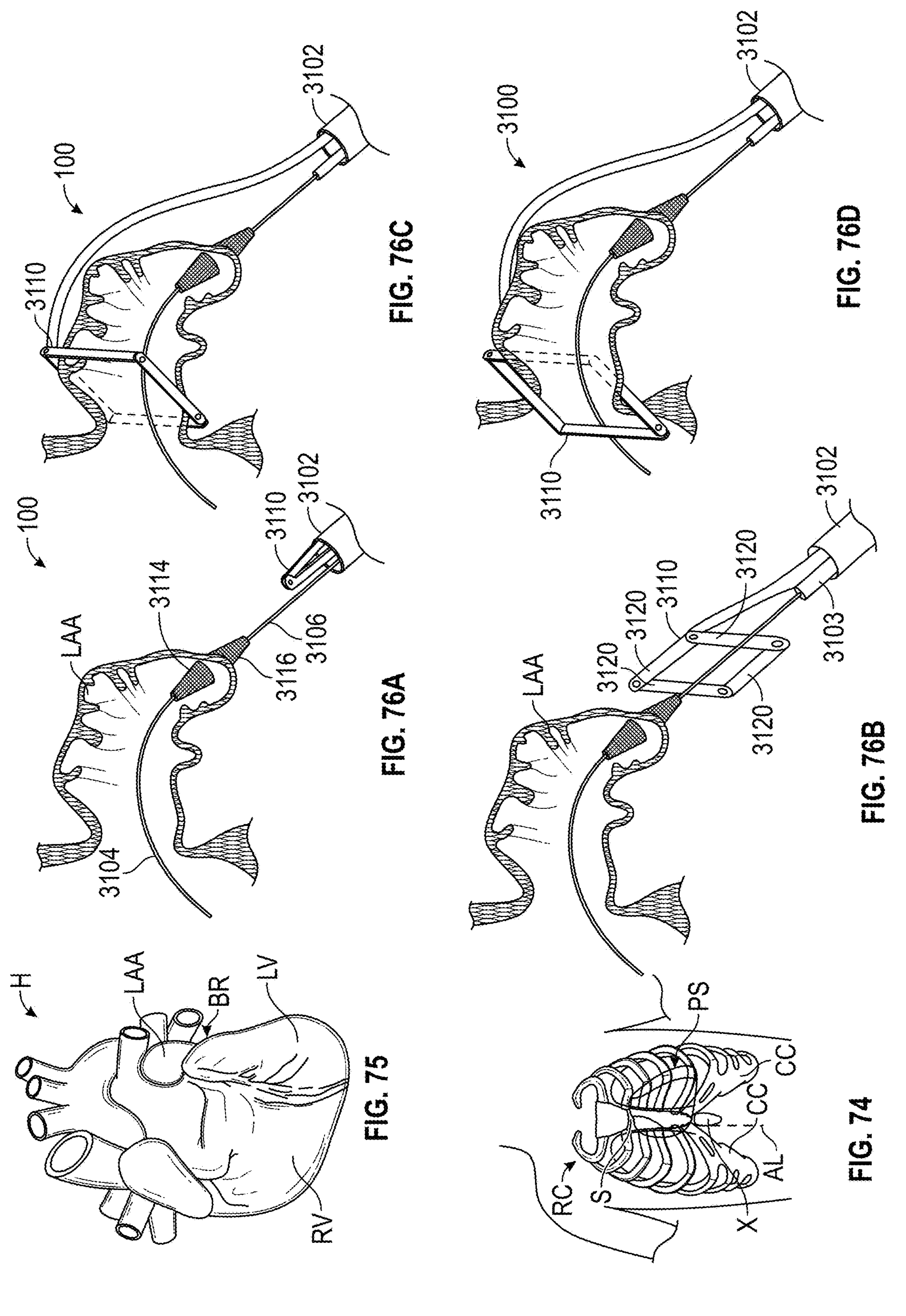

FIG. 74 is an anterior view of a heart illustrating the right ventricle, the left ventricle, and the LAA.

FIG. 75 illustrates the heart, located within the pericardial space located beneath the patient's rib cage.

FIGS. 76A-76F show an embodiment of a treatment device and method of using such device to treat the LAA.

FIGS. 77A-77E show an embodiment of a treatment device and method of using such device to treat the LAA.

FIGS. 78A-78E show an embodiment of a treatment device and method of using such device to treat the LAA.

FIGS. 79A-79H show another embodiment of a treatment device for occluding an LAA.

Figure 80A:
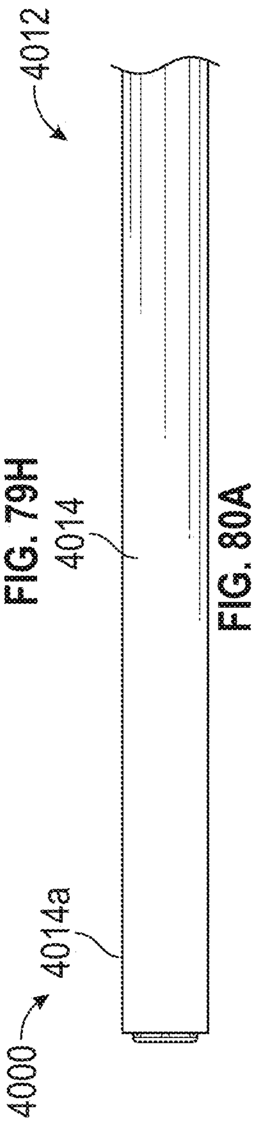
Figure 80B:
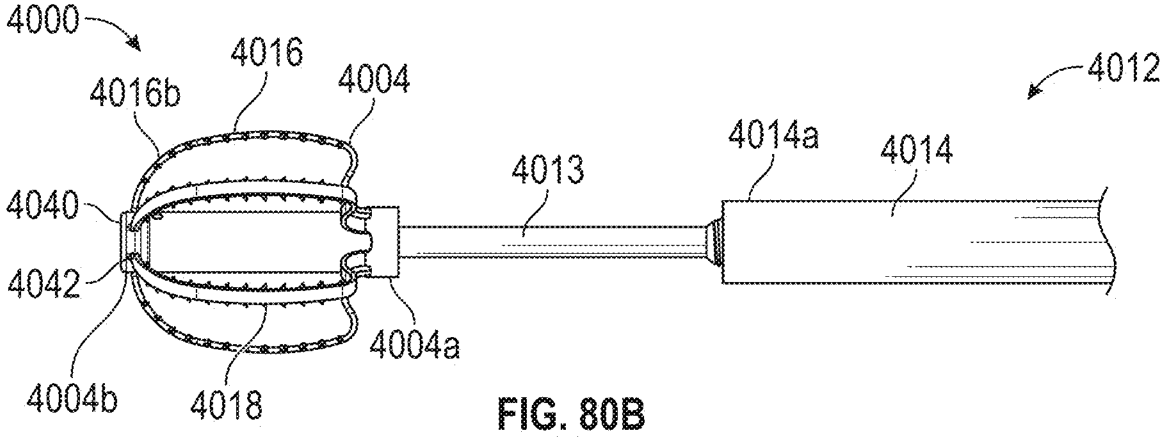
Figure 80C:
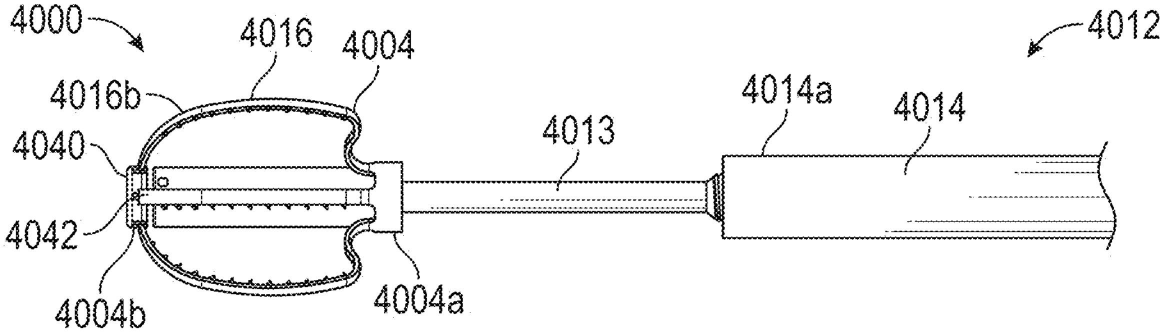
Figure 80D:
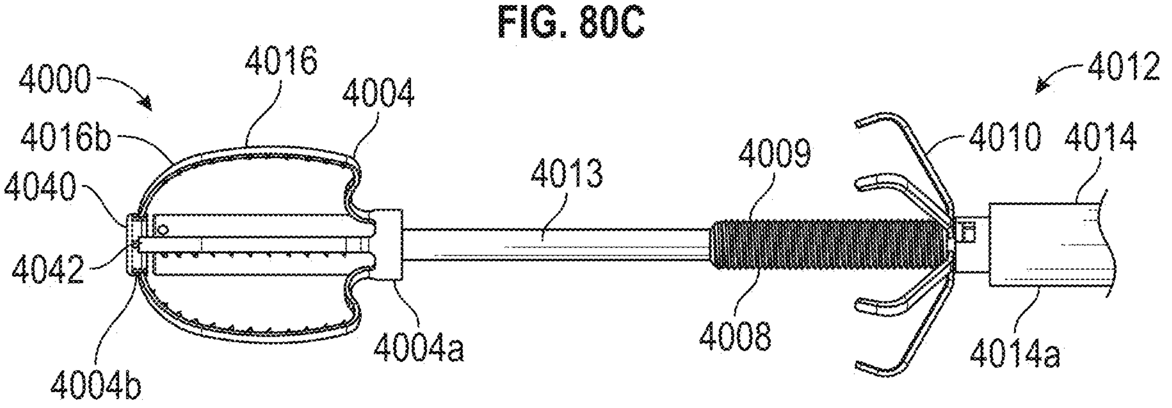
Figure 80E:
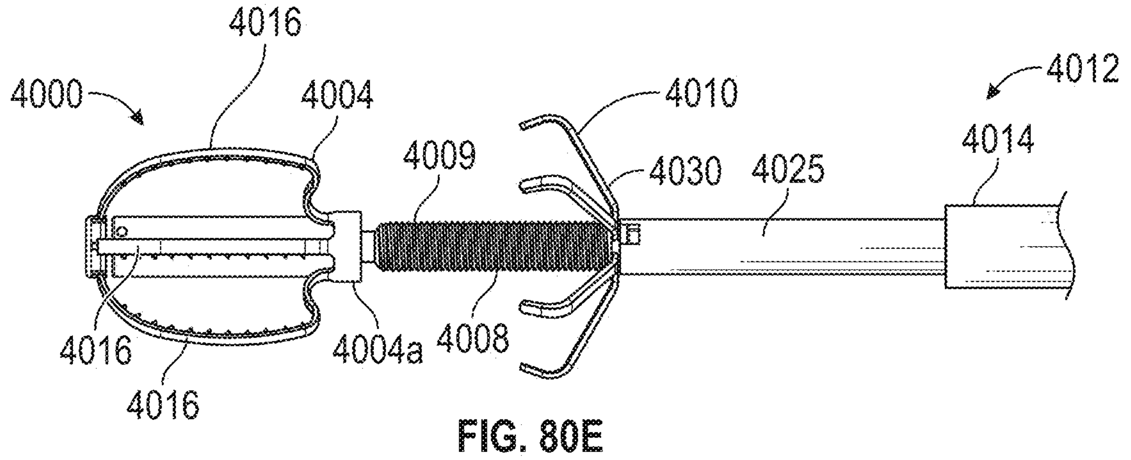
Figure 80F:
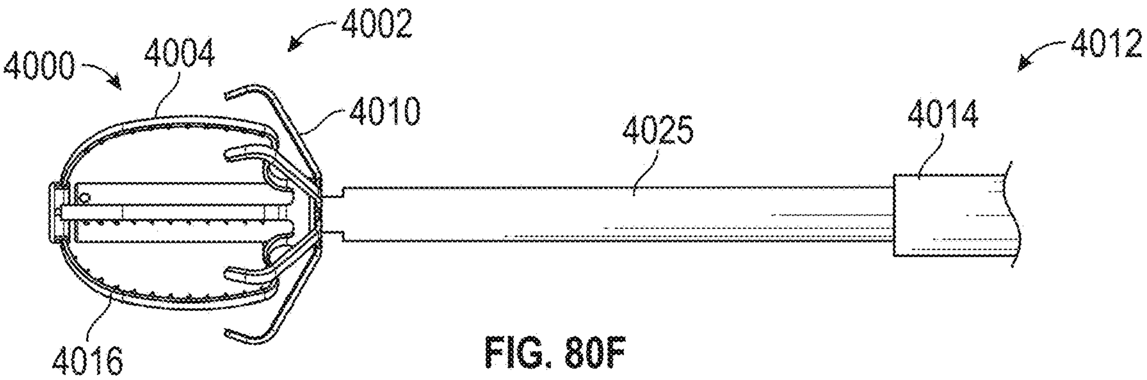
Figure 80G:
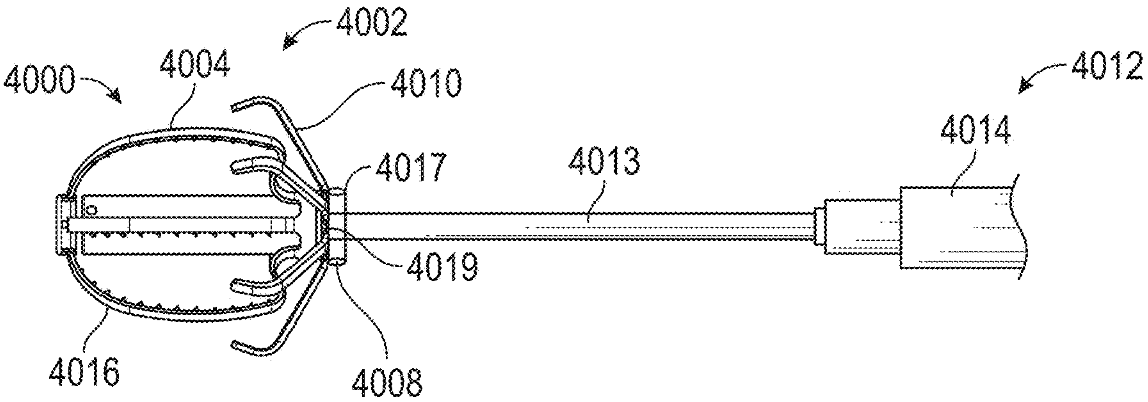
Figure 80H:
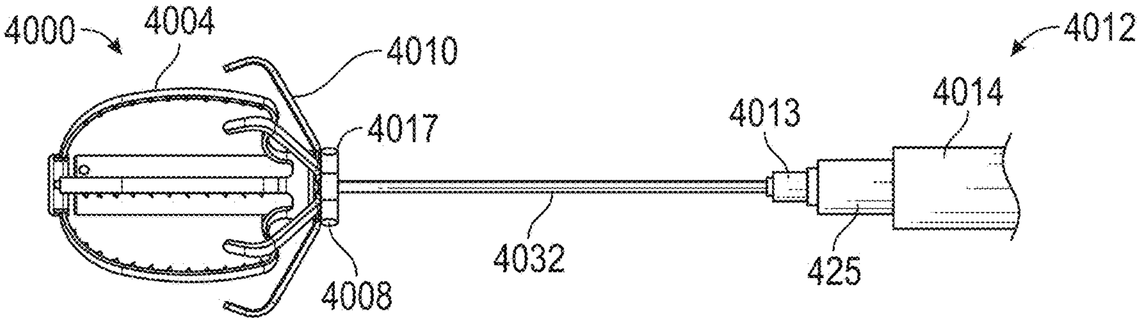
Figure 80I:
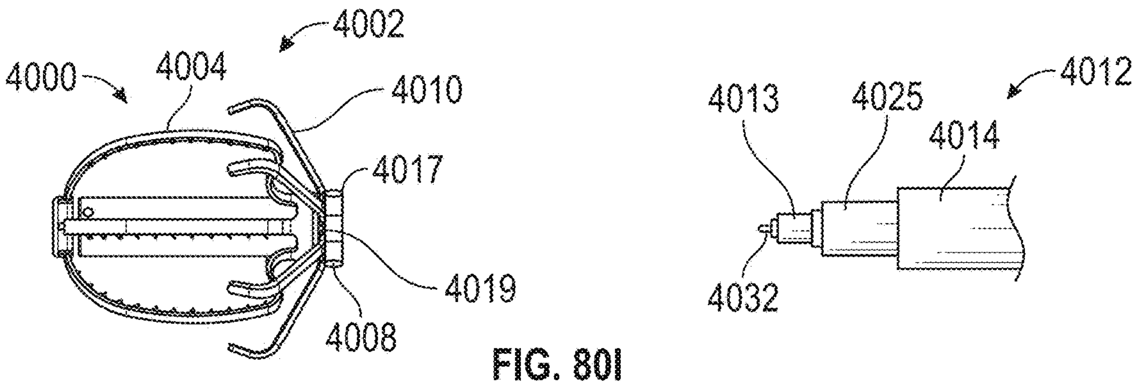
Figure 80J:
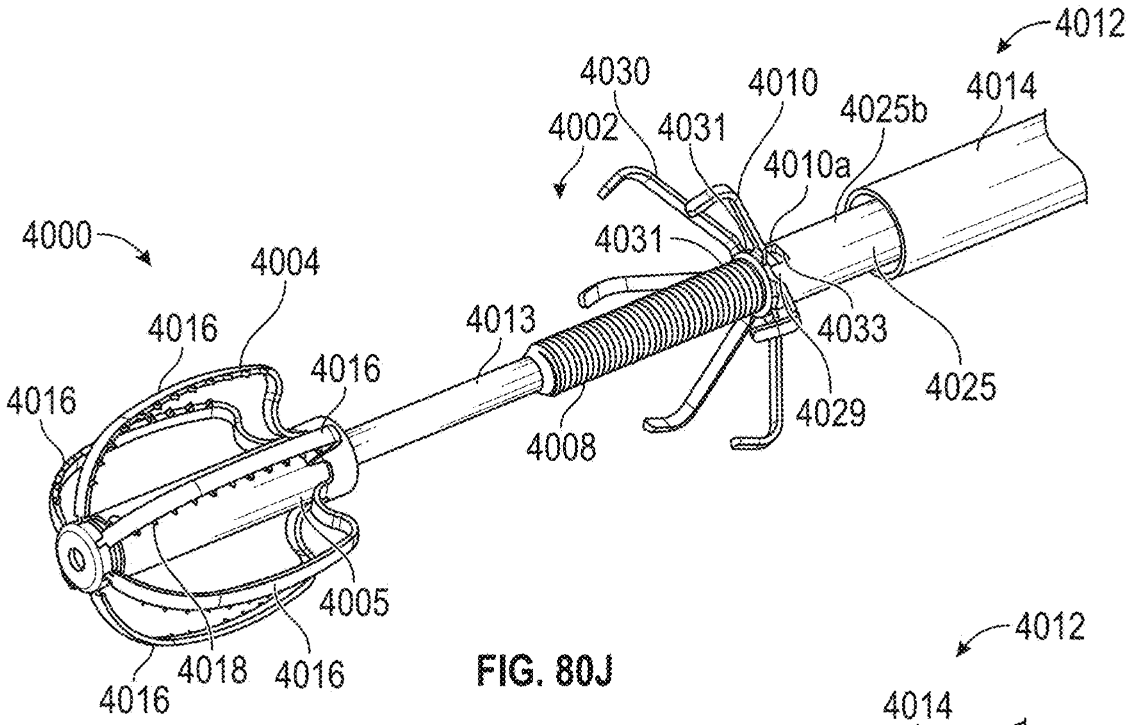
Figure 80K:
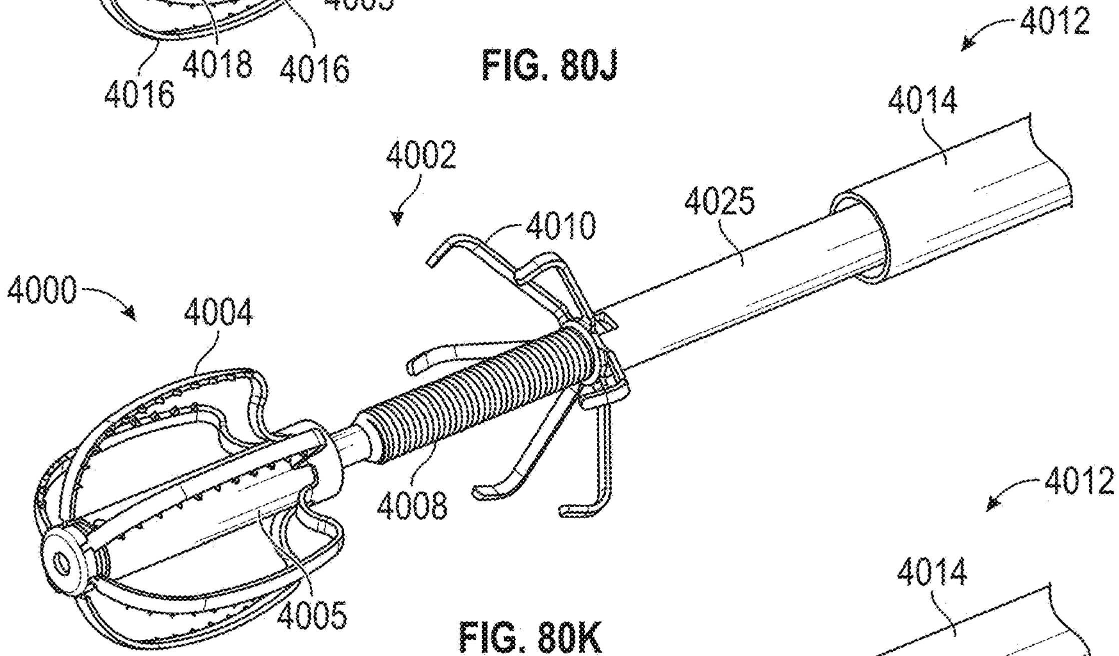
Figure 80L:
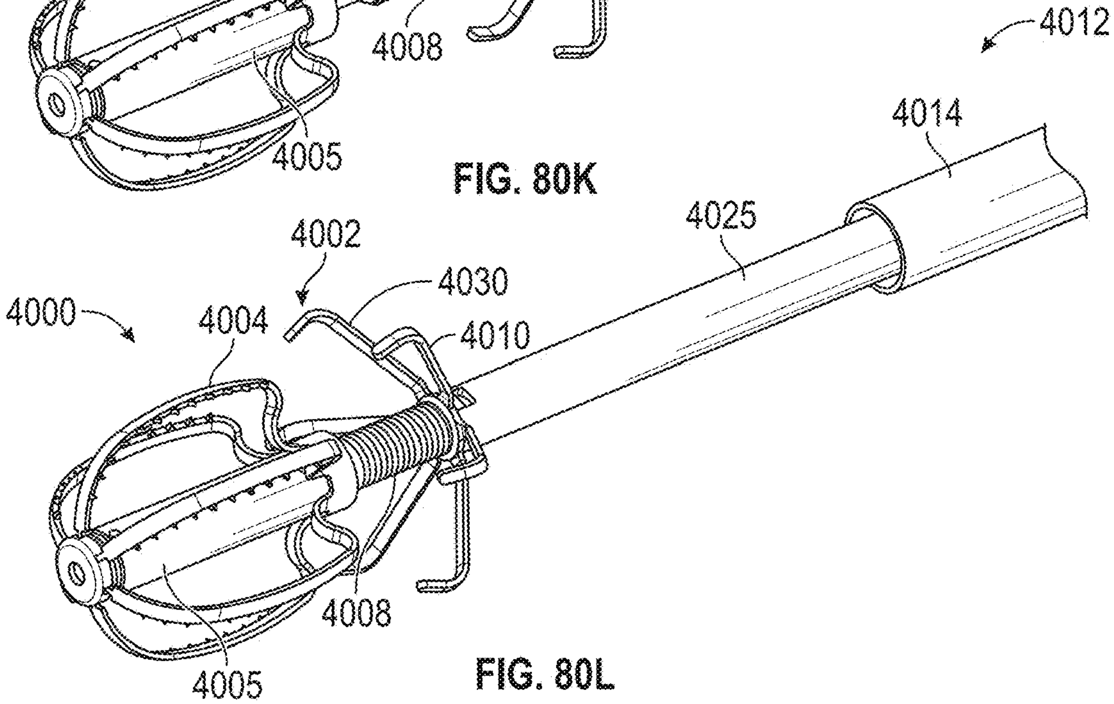
Figure 80M:
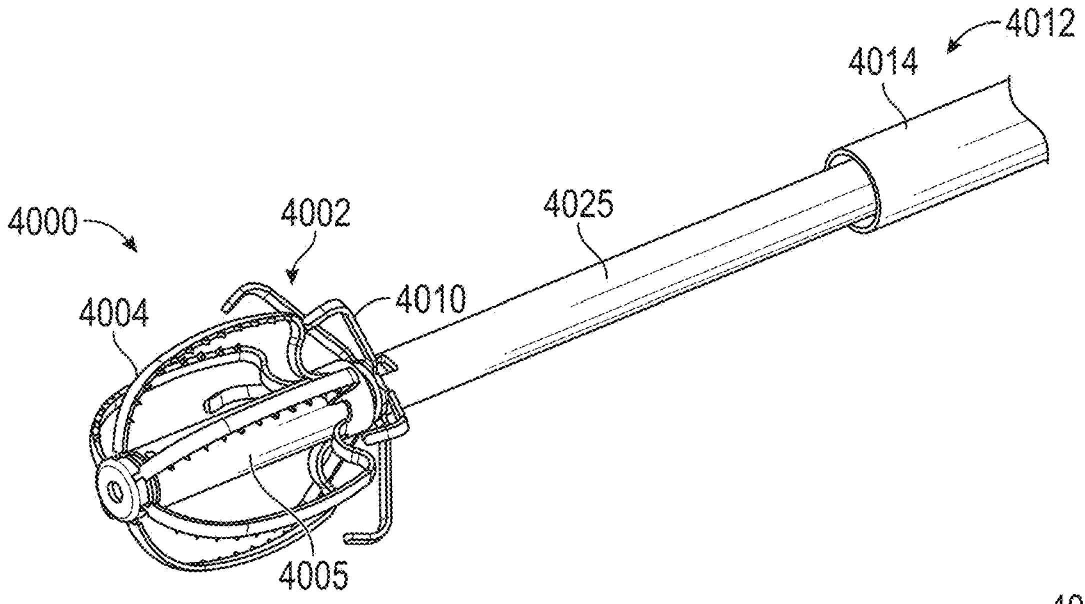
Figure 80N:
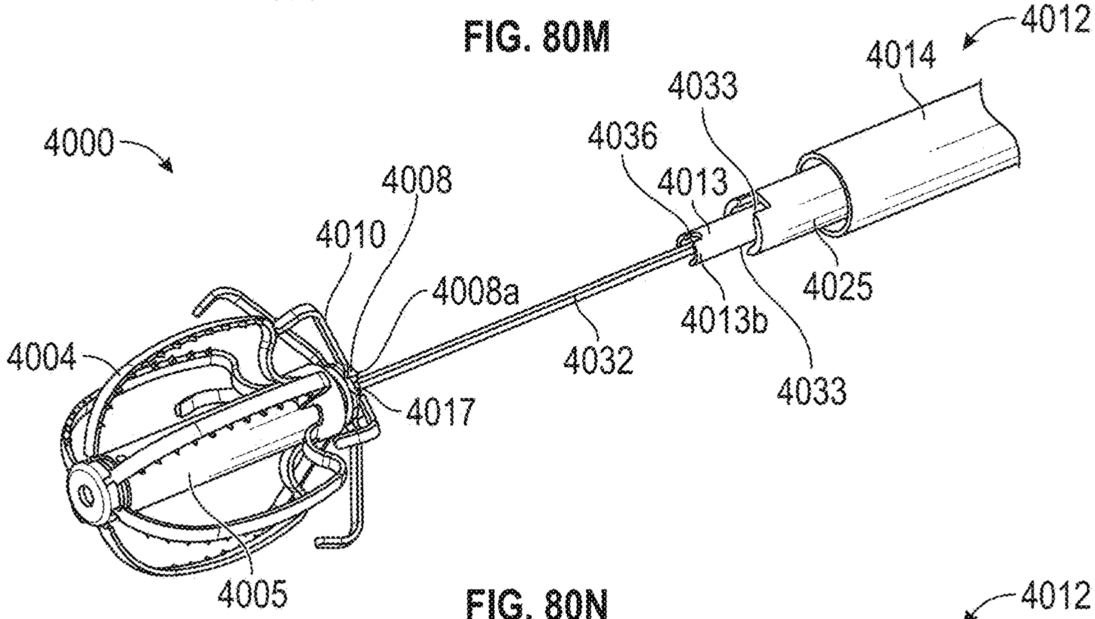
Figure 80O:
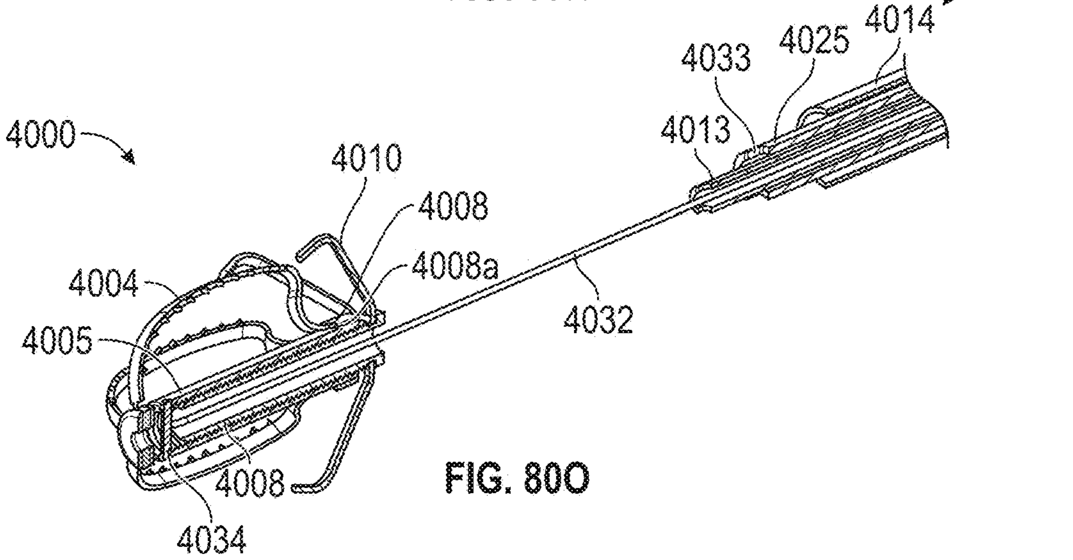
Figure 80P:
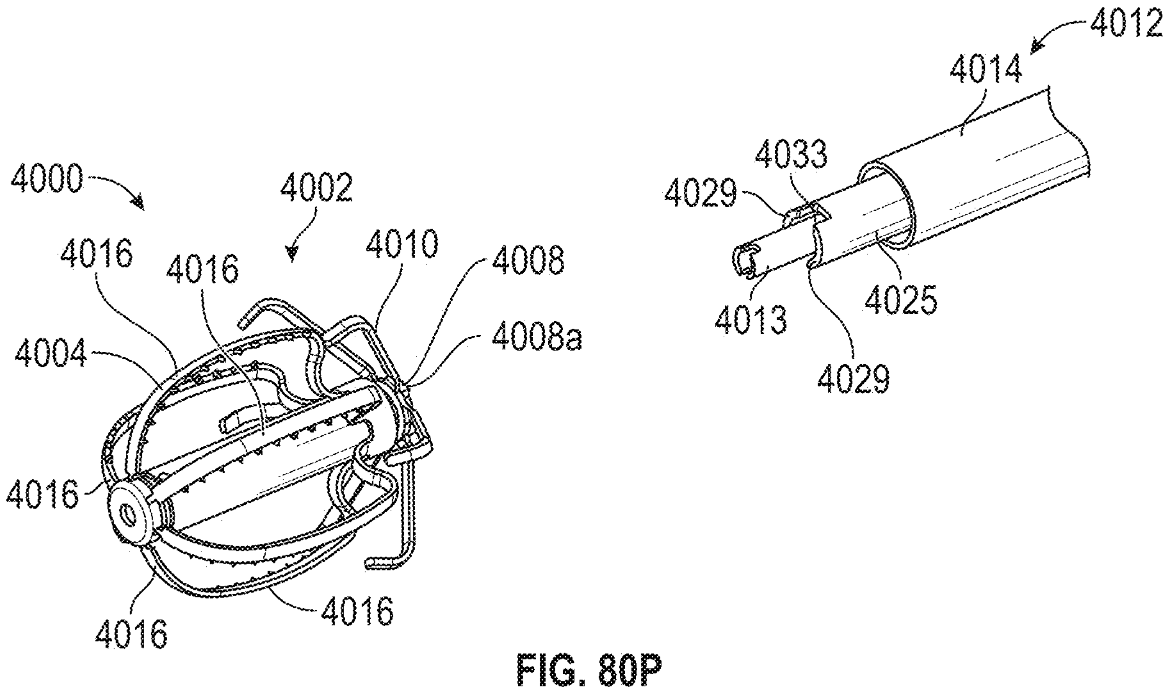
Figure 80Q:
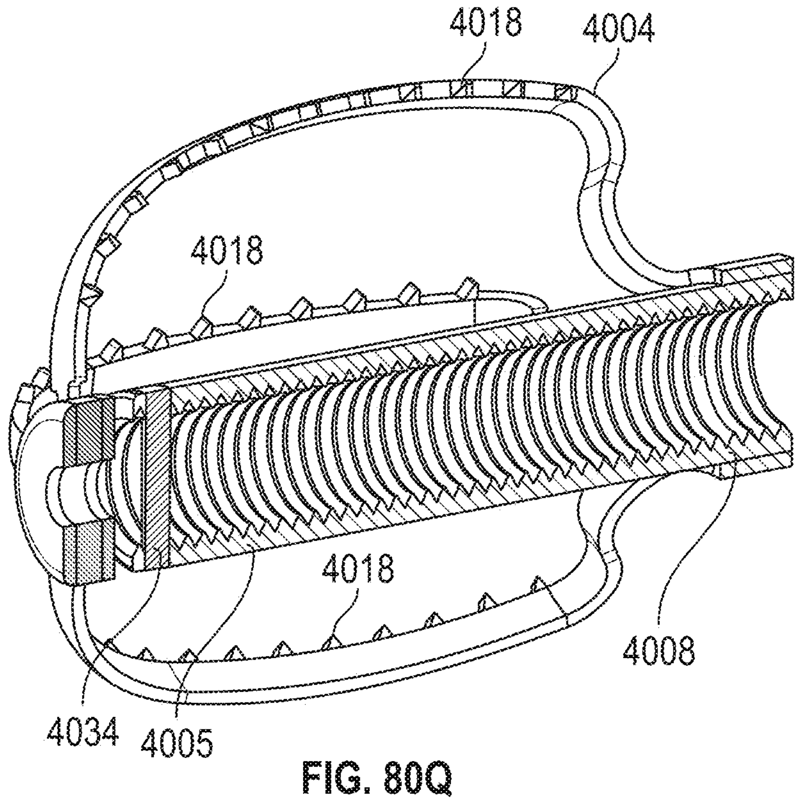
Figure 80R:
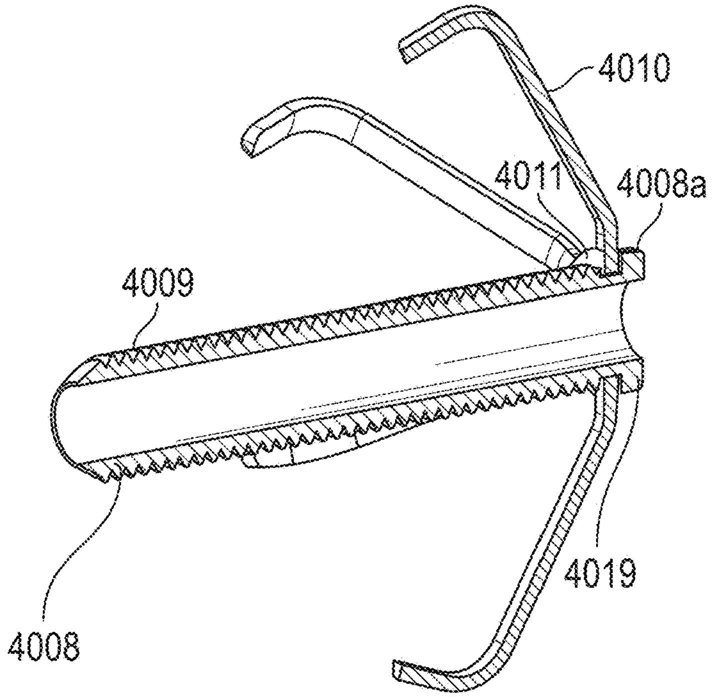
Figure 80S:
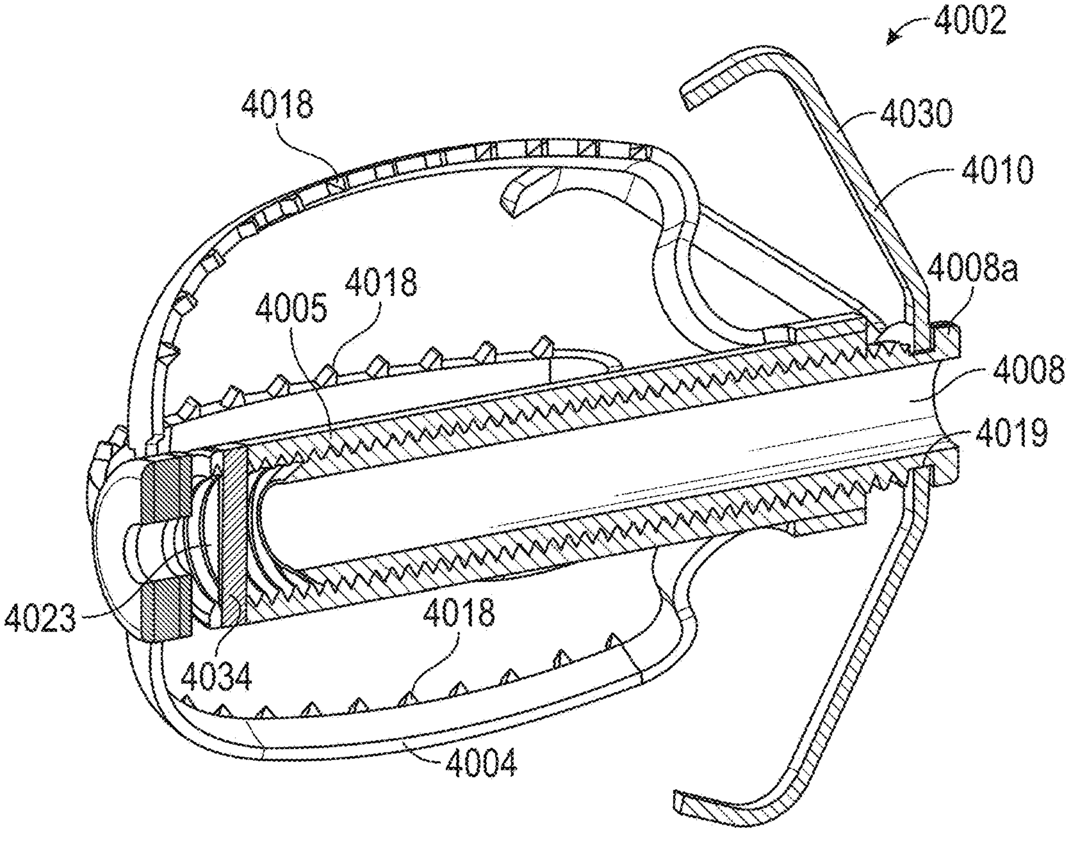
Figure 80T:
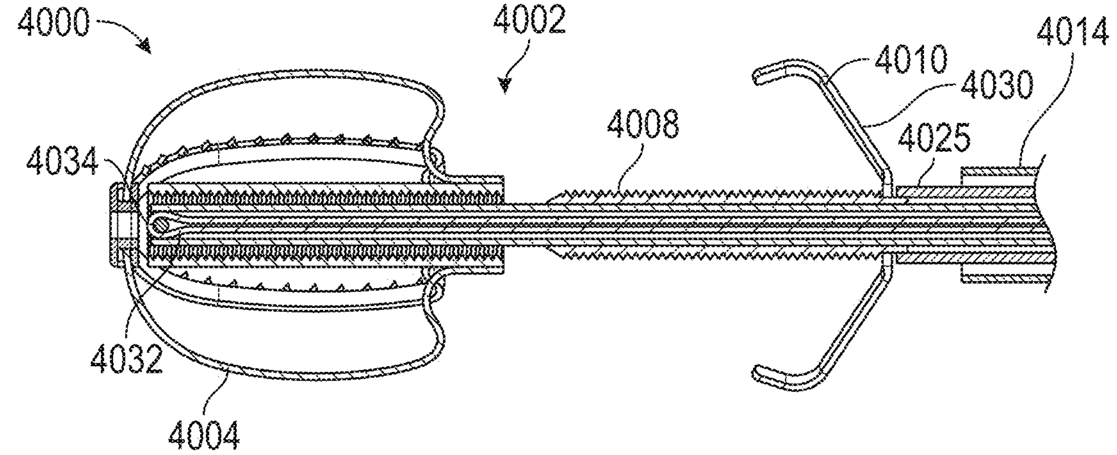
Figure 80U:
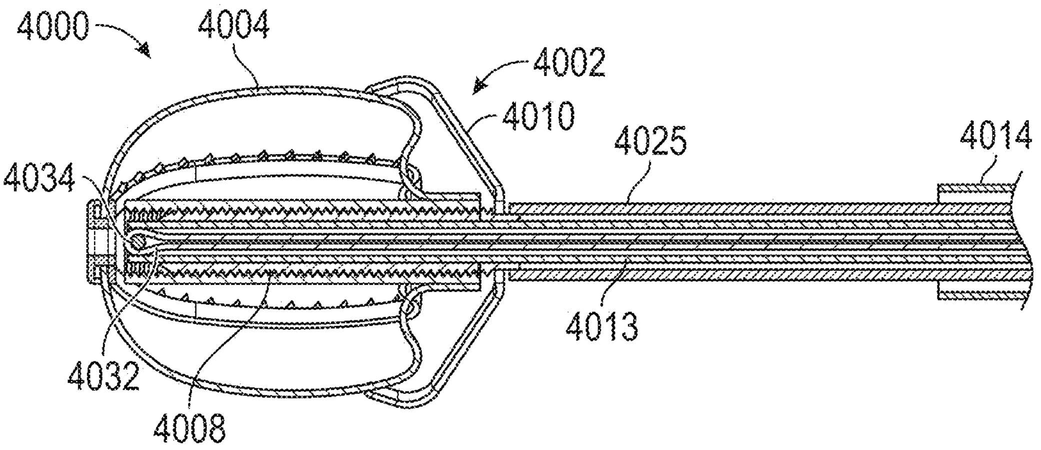
Figure 80V:
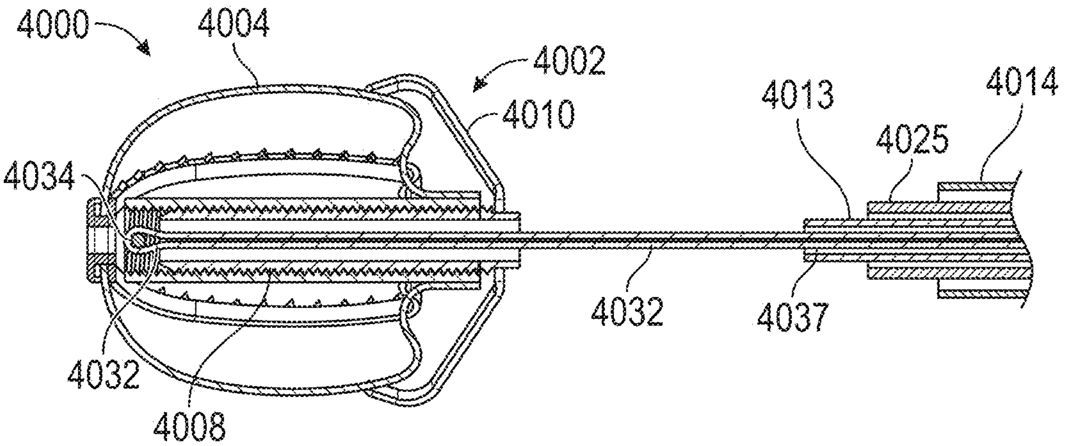
Figure 80W:
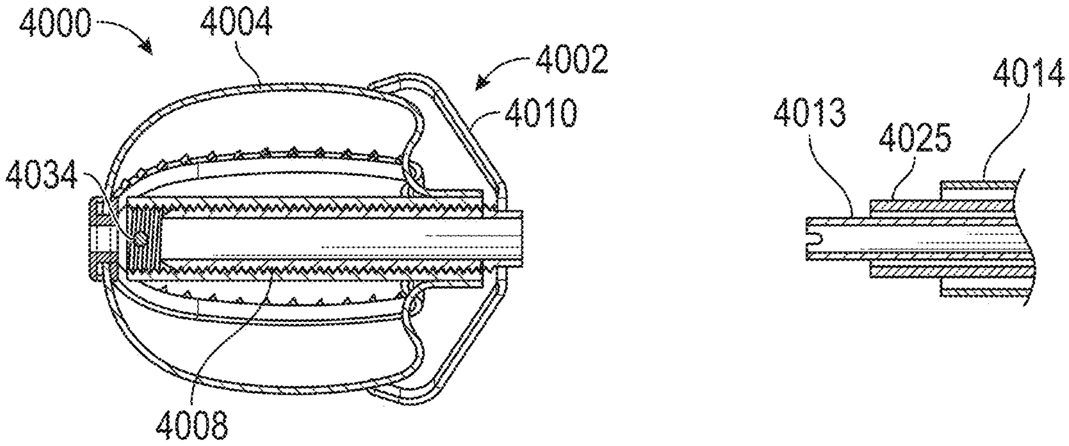

FIGS. 80A-80W show another embodiment of a treatment device for closing or occluding an LAA.

FIGS. 81A-81F an embodiment of a treatment of an LAA using the embodiment of the device shown in FIG. 80A.

FIGS. 82A-82E show another embodiment of a treatment device for closing or occluding an LAA.

FIGS. 83A-83J show another embodiment of a treatment device for closing or occluding an LAA.

Figure 84A:
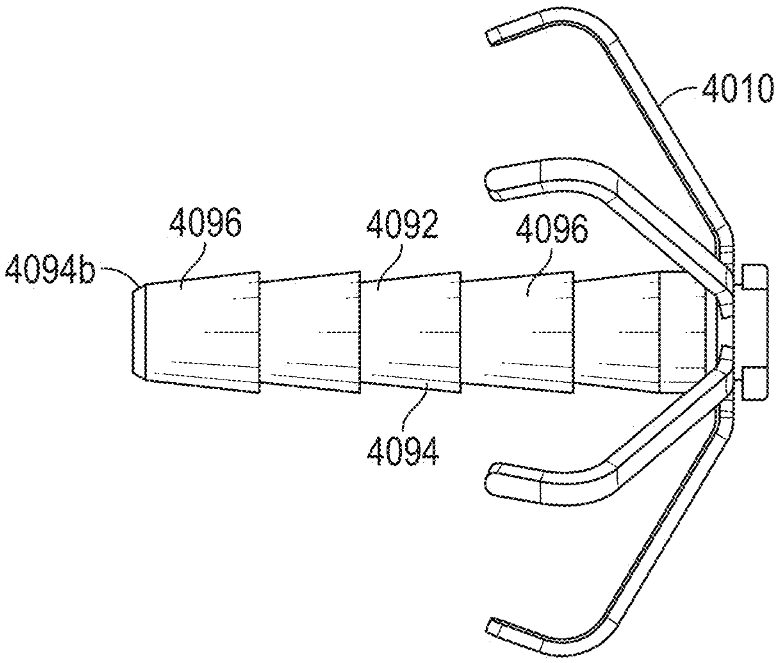
Figure 84B:
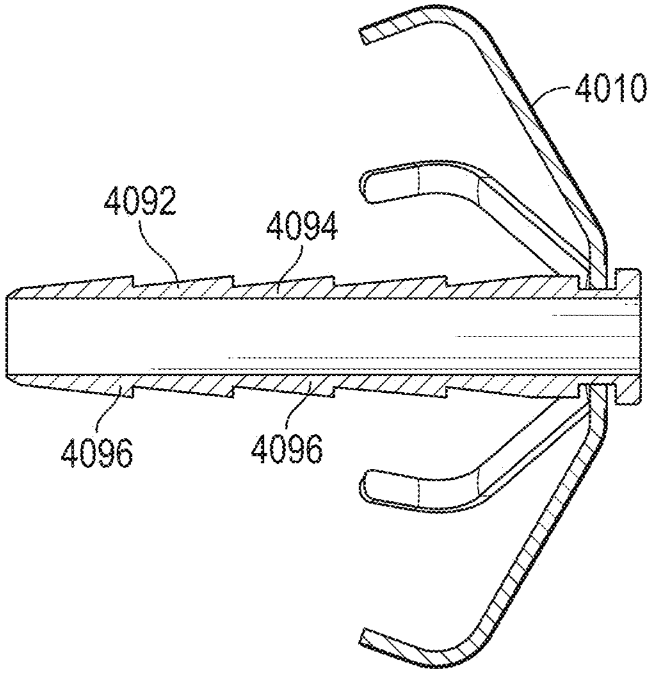

FIGS. 84A-84B show another embodiment of a retention element that can be used with any of the embodiments of the treatment device or the implant device disclosed herein.

FIGS. 85A-85I show another embodiment of a treatment device for closing or occluding an LAA.

FIGS. 86A-86I show another embodiment of a treatment device for closing or occluding an LAA.

Figure 86A:
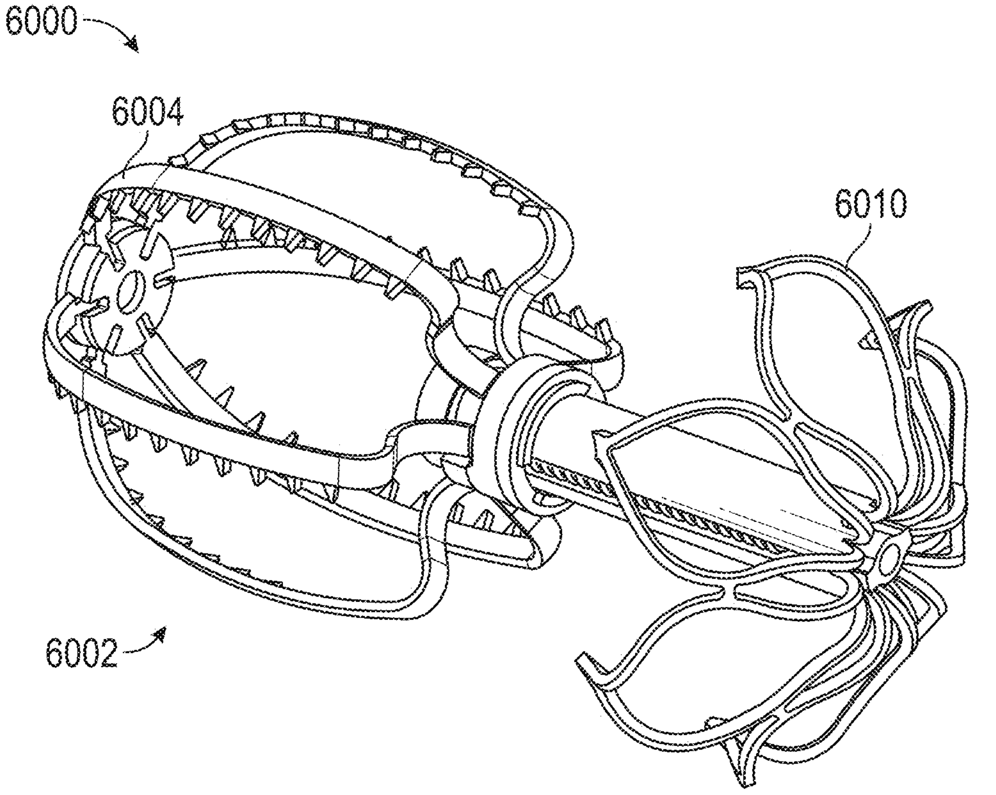
Figure 86B:
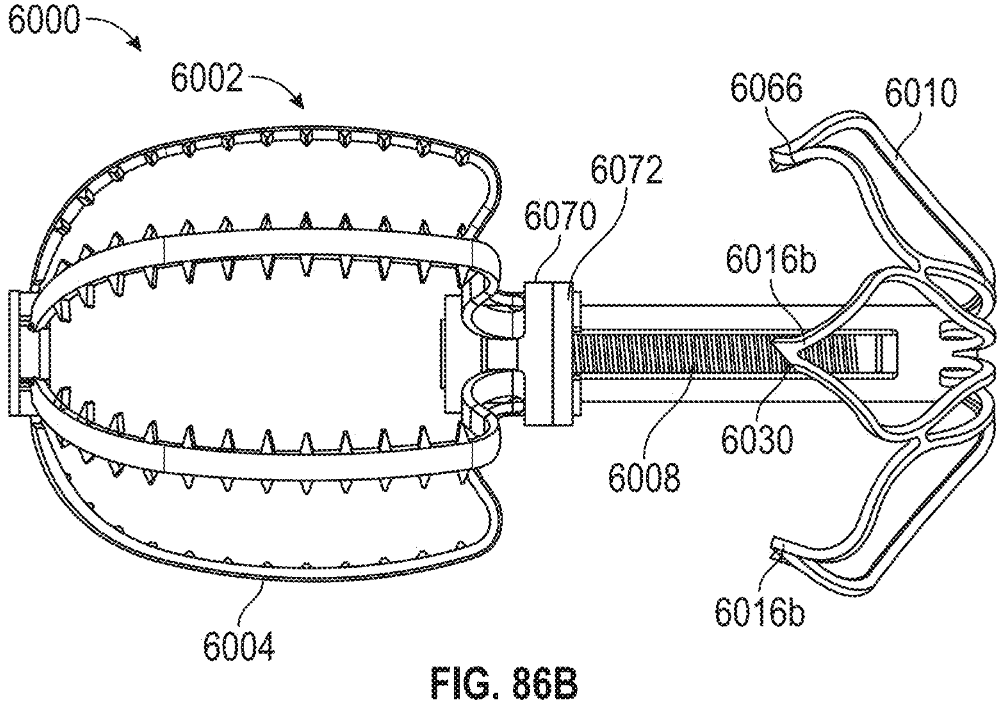
Figure 86C:
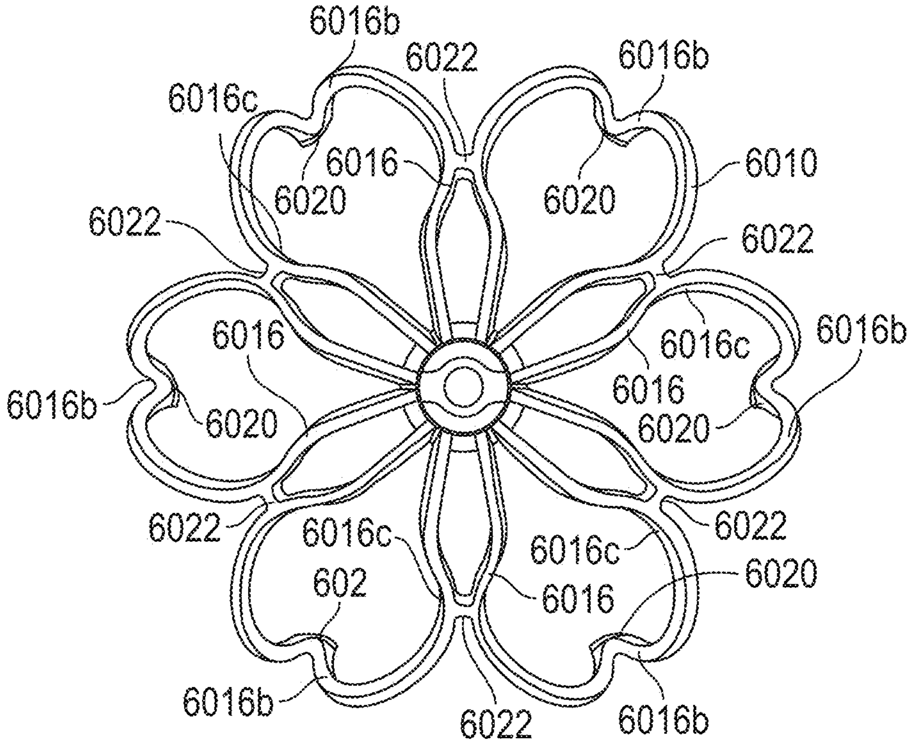
Figure 86D:
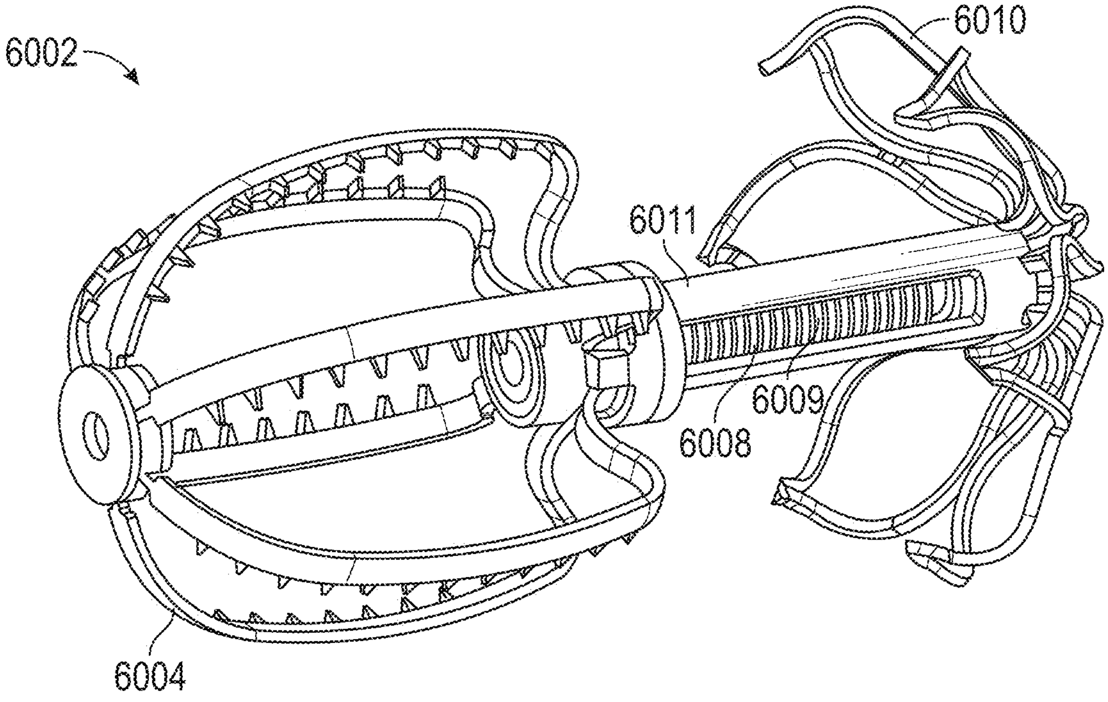
Figure 86E:
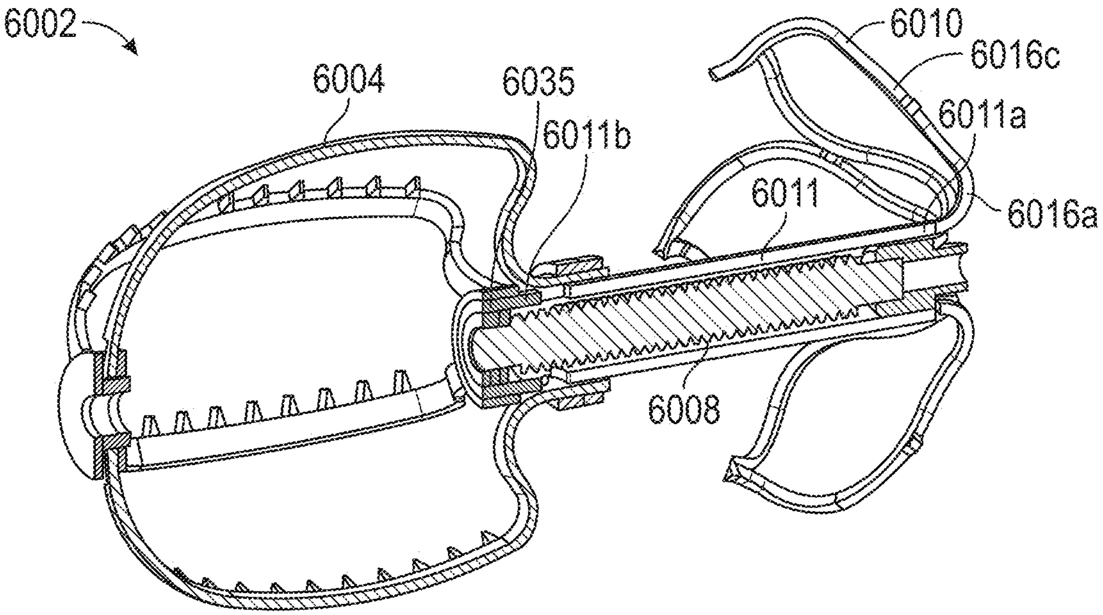
Figure 86F:
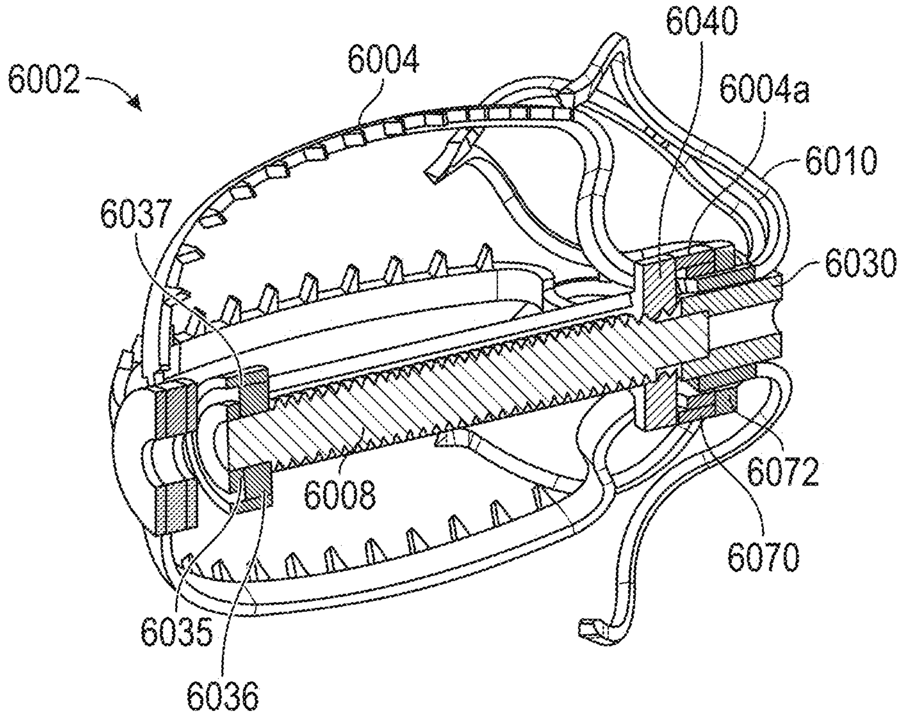
Figure 86G:
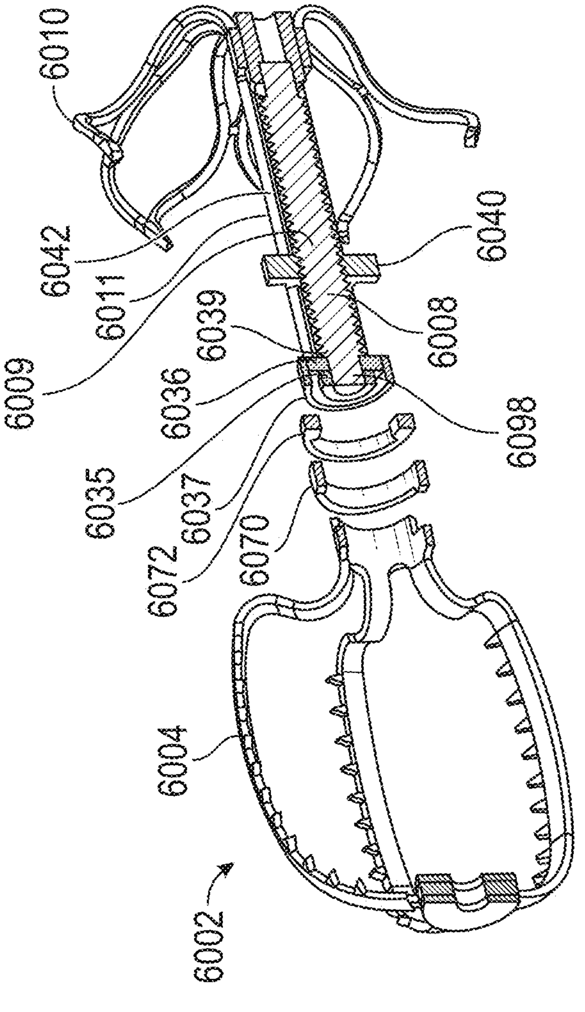
Figure 86H:
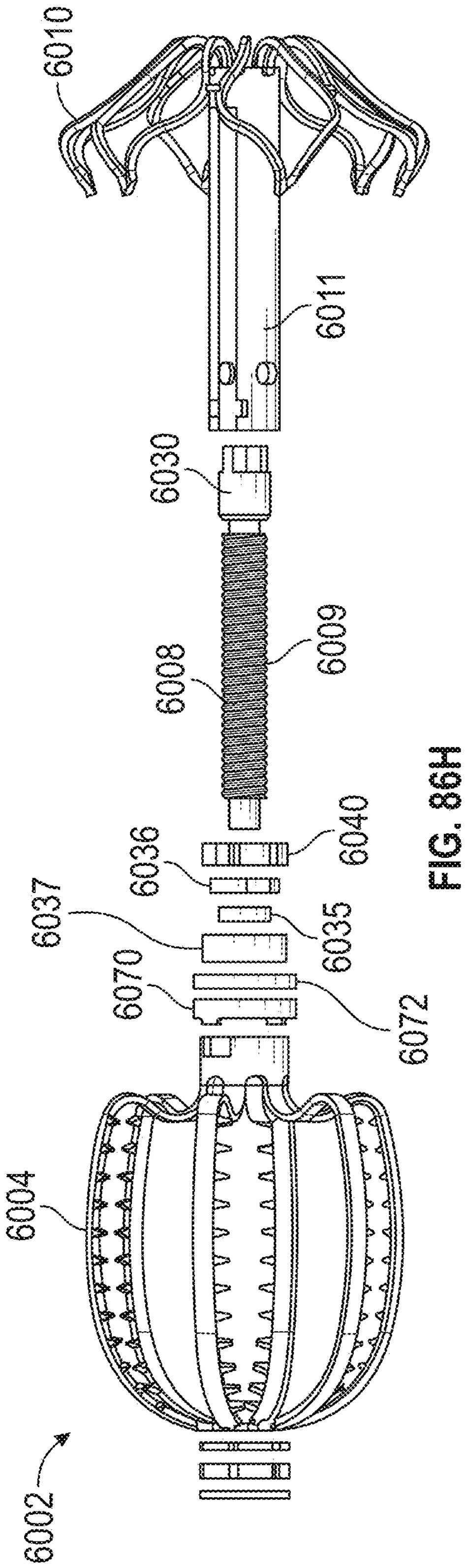
Figure 86I:
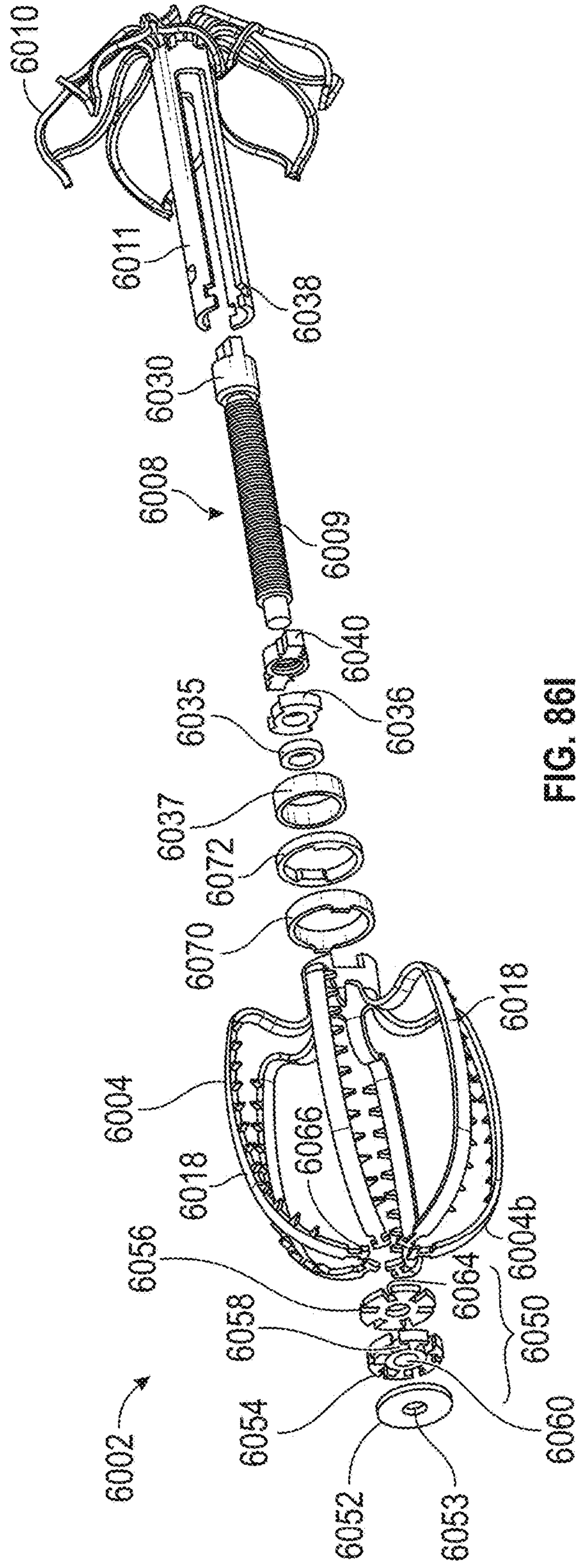
Figure 86J:
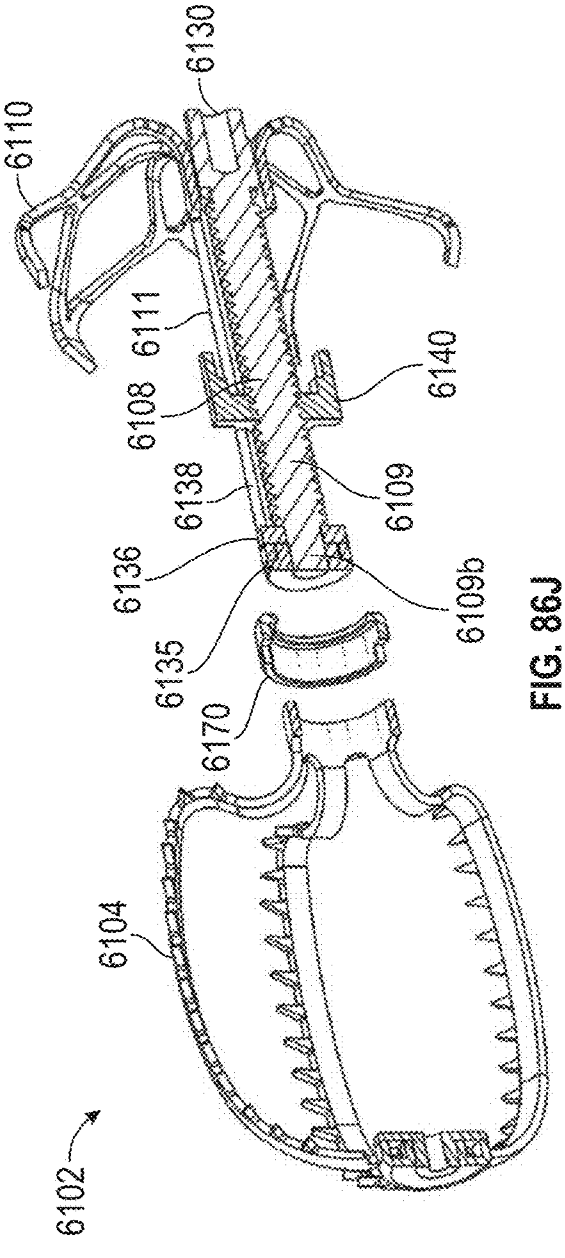
Figure 86K:
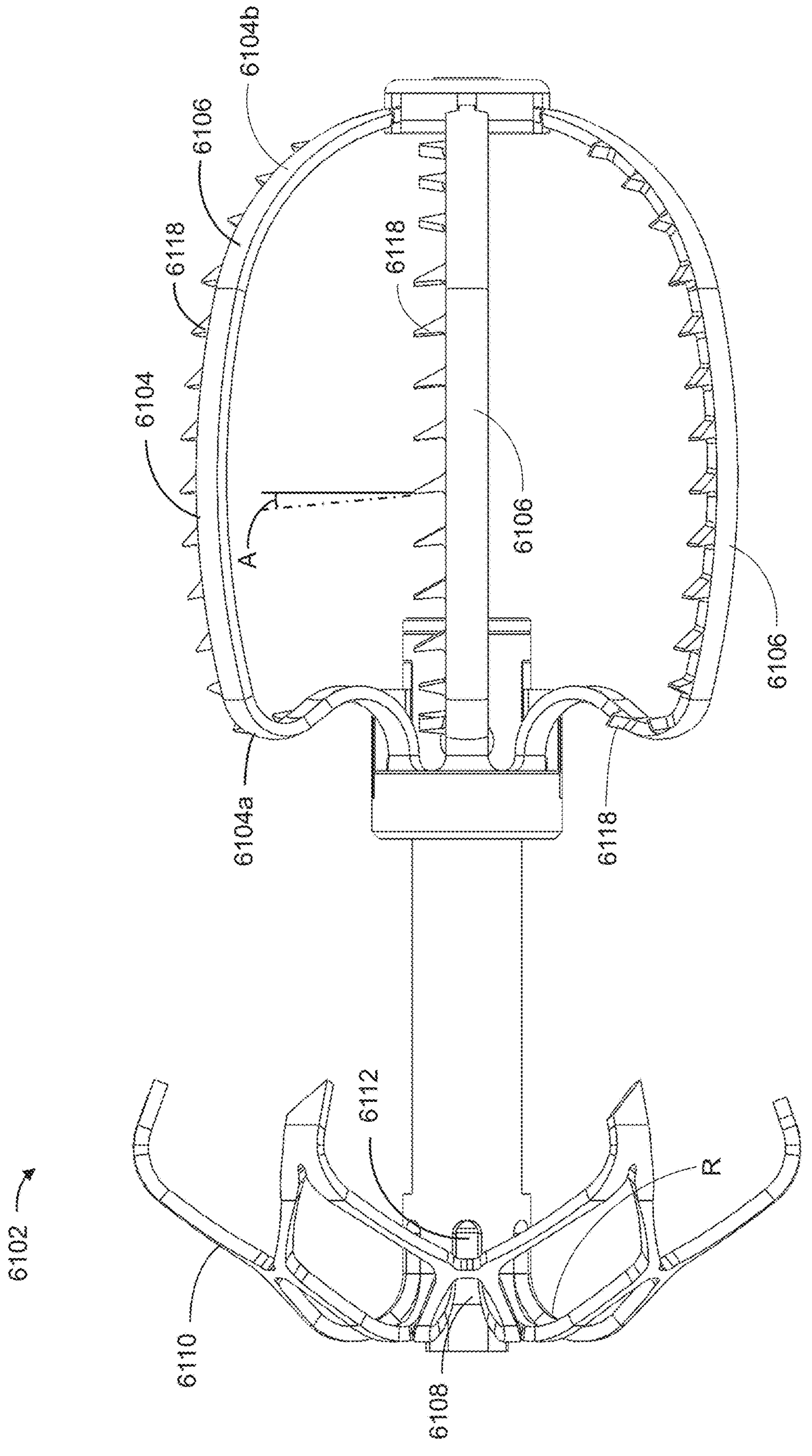
Figure 86L:
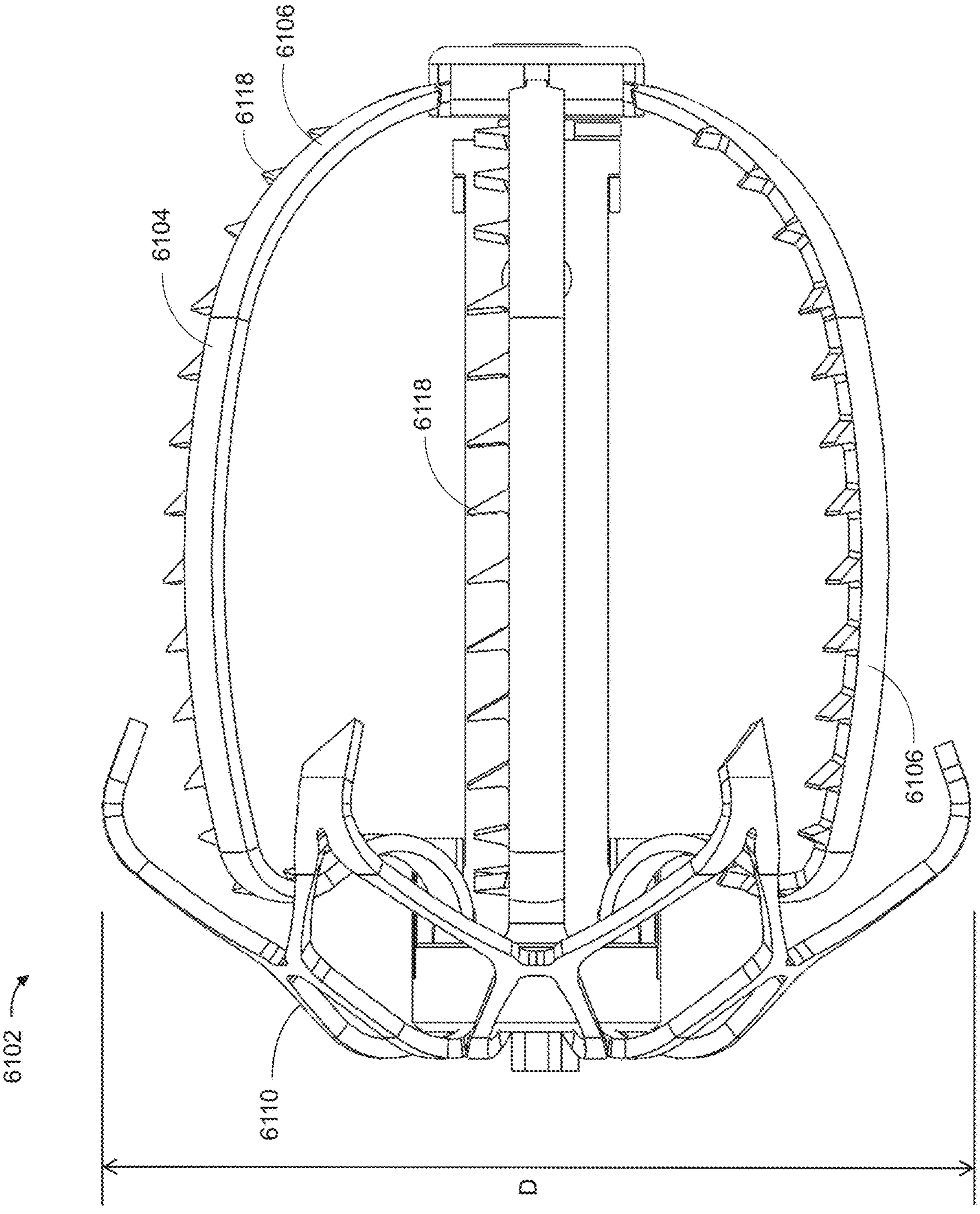

FIGS. 86J-86L show another embodiment of a treatment device for closing or occluding an LAA.

DETAILED DESCRIPTION OF THE SOME EXEMPLIFYING EMBODIMENTS

Described herein are novel devices, systems, and methods for closing or occluding an LAA. Some embodiments comprise a method that includes advancing a delivery system to the LAA, advancing and deploying an expandable element (which can be, in some embodiments, covered with barbs, texture, or other tissue engaging features or, alternatively, can be smooth) and which can have a generally spherical or orb shaped shape into the left atrial appendage, allowing the expandable element to engage distally and/or radially with inner wall surfaces of the LAA, applying a rotation to the inner catheter member connected to the expandable element to twist the LAA to close and/or occlude the LAA at or near the ostium. By occluding the LAA, some embodiments disclosed herein can effectively eliminate or significantly or nearly completely eliminate a communication of blood or other matter between the left atrium and the LAA. Any methods of deployment disclosed herein can also include deployment of a securing element (which is also referred to herein as a locking element or anchoring element) that is configured to inhibit or prevent the unwinding of the expandable element relative to the LAA and the LA ostial tissue, thereby inhibiting or preventing the untwisting of the LAA.

The devices, systems, and methods disclosed herein can be used, or can be adapted, for other applications within the body or on the surface of the body of any human, animal, reptile, or other living being. Other applications include, without limitation, closing openings in other tissues aside from the LAA, occluding or closing openings, passageways, and/or chambers within the heart or other organs, occluding or closing holes or other slits or openings in vessels and passageways, and/or treating other conditions.

The clinical benefit of some embodiments is a resultant implant which is not in direct blood contact with the left atrial blood or flow except a possible portion of the securing feature. The securing element of any embodiments can be configured to limit the exposure of the securing element to the blood within the left atrium (i.e., to limit the amount of the securing element that projects into the left atrium). In some embodiments, the entire implant can be surrounded by tissue of the LAA tissue so that no portion, or only a minimal portion (for example, less than 10% of the surface area, or less than 40% of the surface area) of the implant is exposed to blood flow within the left atrium. This can have clinical benefits to the patient as there should be post drug regiment required. Any of the devices used in any of the methods described here may be advanced under any of a variety of visualization techniques, e.g., fluoroscopic visualization, ultrasound, etc.

For any of the embodiments disclosed herein, access to the LAA can be gained by any number of suitable means or access points. For example and without limitation, access to the LAA for some embodiments can be gained by entering through the venous system via femoral vein and a transseptal puncture into the left atrium. Imaging could use both fluoroscopy and echo (TEE, ICE or transthoracic) to image the size, position, and location of the LAA for entry of the prosthesis or device for occlusion. FIGS. 1A-1D show a portion of an example of a path from an access site to the LAA.

Entering through the venous system via femoral vein and a transseptal puncture into the left atrium, access to the left atrial appendage (LAA) for any of the embodiments of the devices, systems, and methods disclosed herein can be gained. Imaging could use both fluoroscopy and echo (TEE, ICE or transthoracic), the size, position, and location of the LAA for entry of the prosthesis for closure. FIGS. 1A-1D show this example of a path from the access site to the LAA. Other access cites for any of the embodiments of the devices, systems, and methods disclosed herein can include access through the internal jugular (IJ) vein, as shown in FIG. 1E.

Further, any device, system, and method embodiments disclosed herein can be delivered to the LA/LAA or include delivery to the LA/LAA via a transfemoral arterial pathway. In some embodiments, the transfemoral arterial pathway can include advancing the delivery device through the femoral artery, up the aorta, down the aortic valve, up the mitral valve, and into the LAA. Similarly, any device, system, and method embodiments disclosed herein can be delivered to the LA/LAA or include delivery to the LA/LAA via a transradial pathway, which can include access through a radial artery in the wrist, for example and without limitation. This access pathway is also referred to as transradial access, the transradial approach, or transradial angioplasty.

The implant of any embodiments disclosed herein can have an expandable atraumatic shape with tissue gripping features located on the outer edges of the shape, coupled to a securing and or ratcheting feature which can hold the initial or final closed position of the implant. The implant of any embodiments disclosed herein can be configured to grip the internal tissue of the LAA with radial force as well. In some embodiments a vacuum or suction can be provided by the catheter or any component thereof to draw a tissue portion of the LAA or atrium toward the implant. The implant of any embodiments disclosed herein can have an atraumatic shape that can be spherical, dome shaped, or comprise a coil of wire in the shape of a disk, can have expanded cut pattern in the shape of a stent, or anything else which can have rounded edges. In some embodiments, the barbs (which can be tissue anchors) on the outer edges or surface of the implant can comprise metal hooks, plastic cleats, rough texture of some material or surface features, a coating or activated adhesive which grips the inside surface of the LAA. Additionally, in any embodiments disclosed herein, the tissue anchors can be positioned on or adjacent to an end portion of the implant to engage with an end portion of the LAA. In any embodiments, the barbs can be directional allowing for tissue engagement in one rotational direction and a disengagement in the opposite rotational direction for a possible repositioning, resizing, or removal from the LAA.

The rotation used to twist closed or occluded (completely or substantially) the LAA for any embodiments disclosed herein may be as little as a quarter of a turn (i.e., revolution), a half turn, a complete turn, up to as much as multiple turns for deeper or longer LAAs. The securing feature or element (also referred to herein as an anchoring element) in any embodiments disclosed herein can have a single arm or multiple arms which can be connected to the implant body that is positioned and rotated within the closed or substantially closed LAA. The securing feature or element can also be configured to engage tissue adjacent to the ostium of the LAA. In any embodiments, the securing element can have multiple arms or members, can have an annular ring, can have a disk, or any other suitable shaped surface anchor configured to couple non-twisted tissue to the twisted implant. In some embodiments, the securing element can also have a small diameter ring which can be configured to clamp to or engage with the tissue which contacts to the center hub of the implant (adjacent to the ostium of the LAA) or it can also have a clip which folds and clips the implant to the side of the wall of the left atrium (LA).

In some embodiments disclosed herein, the device can be configured to restrict an opening of the LAA by reducing a cross-sectional area of the opening of the LAA by at least 95%, or by at least 90%, or by from at least approximately 80% to approximately 100% as compared to a cross-sectional area of the opening of the LAA before the device was implanted (including a blockage effect from the device). Further, in some embodiments, the method can include rotating the implant from the first rotational position to the second rotational position to twist the LAA until an ostium of the LAA is at least 95% blocked and/or restricted, or at least 90% blocked and/or restricted, or at least 80% blocked and/or restricted, or from approximately 70% blocked and/or restricted to approximately 100% blocked and/or restricted. Additionally, any embodiments disclosed herein can include implanting two or more implants of any of the implant embodiments disclosed herein in the LAA. For example and without limitation, any of the implant embodiments disclosed herein can be configured to be deployed or implanted in the LAA to improve the occlusion of implants already implanted in the LAA, including any implants that fit within any of the foregoing ranges of less than complete occlusion. In some embodiments, one or more additional implants or devices can be implanted adjacent to, over, around, or otherwise with an existing implant to improve a level of occlusion of the LAA.

Alternatively, in any embodiments disclosed herein, the securing element can be configured to merely compress the tissue of the left atrium and/or the left atrial appendage that has constricted around an outer surface of a body portion of the implant between a distal surface of the securing element and the contact member to prevent rotation of the implant in the second direction, i.e., after the contact member has been rotated to the second rotational position, without penetrating into such tissue. For example and without limitation, in any embodiments disclosed herein, the securing element can have a body portion that is smooth an nonobtrusive or nonpenetrating, e.g., so that the securing element does not have any tissue penetrating features on it that extend toward the tissue surfaces. In other embodiments, the arms (or, at least, the portions of the arms that extend in the axial direction when the securing element is in the second state) or other tissue penetrating portions of the securing element can be short, such as from approximately 1 mm to approximately 5 mm in length, or from approximately 1 mm to approximately 3 mm in length, or from approximately 1 mm to approximately 2 mm in length, or of any values or ranges of values between any of the foregoing ranges.

Figure 1A:
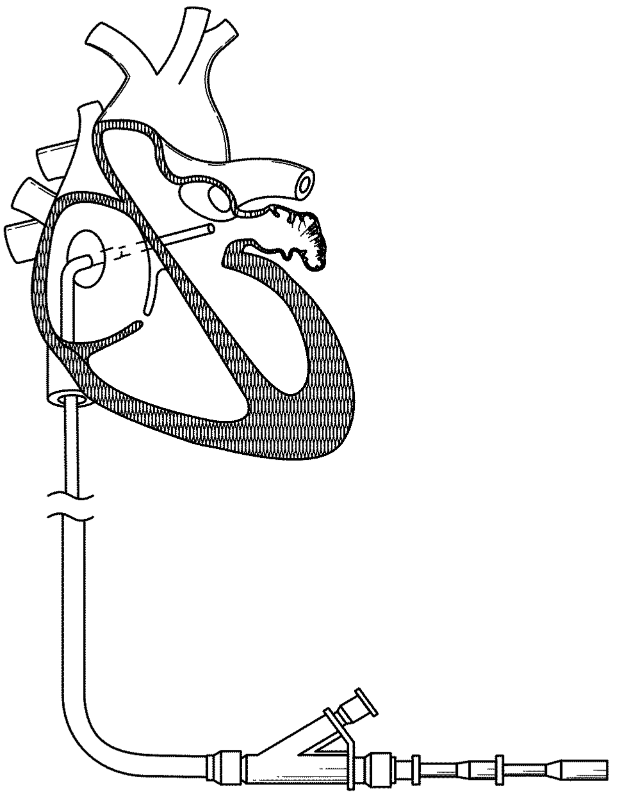
FIG. 1A illustrates a path through the venous system via femoral vein and a transseptal puncture into the left atrium that can be used to access the left atrial appendage (LAA).
Figure 1B:
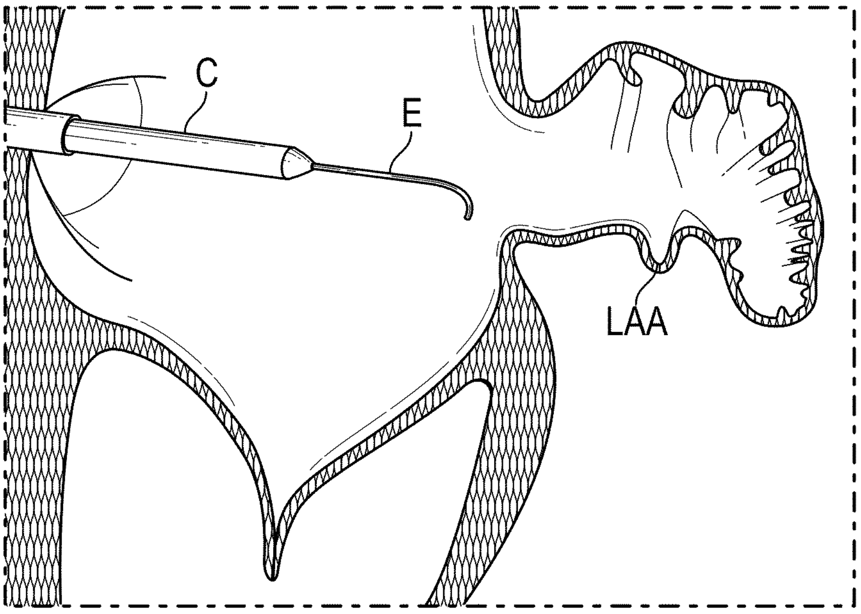
FIG. 1B shows a section view of a left atrium, showing a guidewire advancing toward the LAA.
Figure 1C:
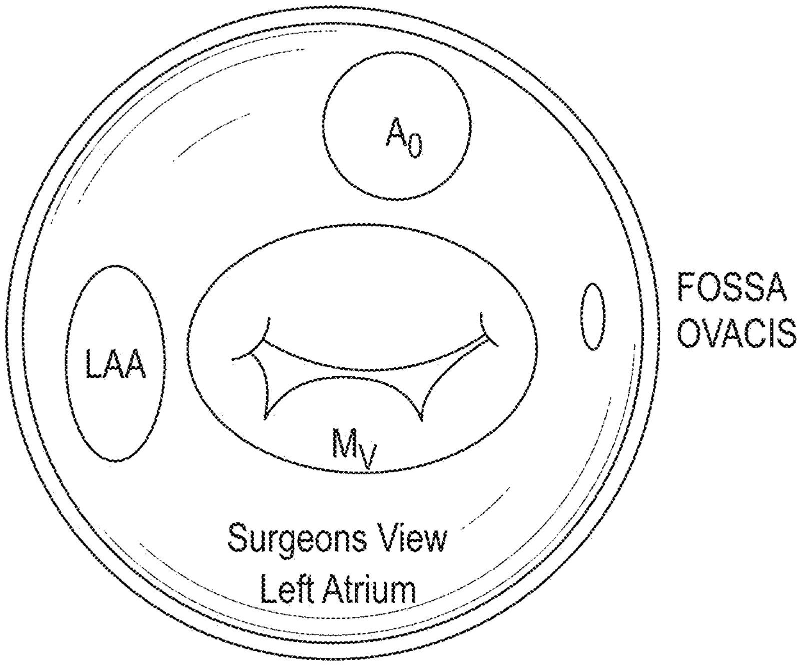
FIG. 1C shows a surgeon's left view of the left atrium.
Figure 1D:
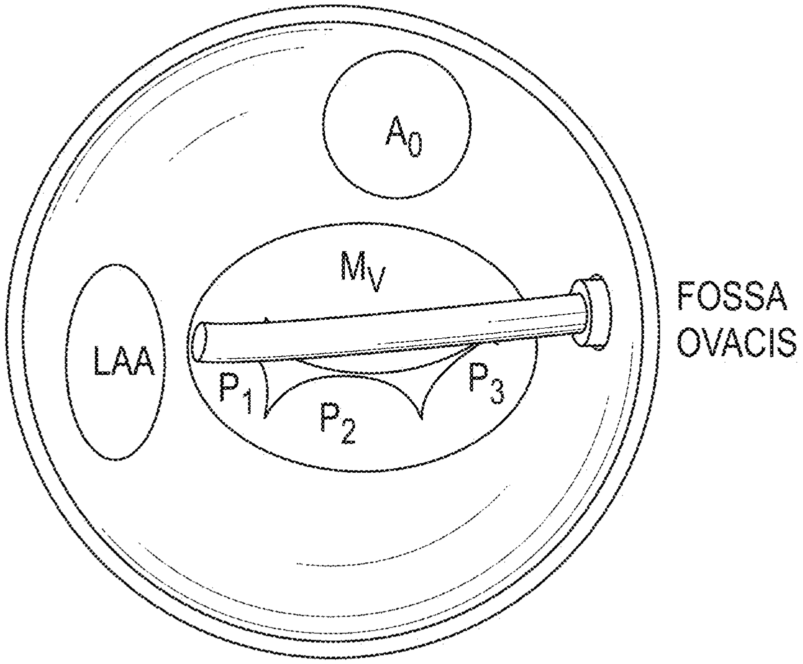
FIG. 1D shows a surgeon's left view of the left atrium, showing a delivery device advancing toward the LAA.
Figure 1E:
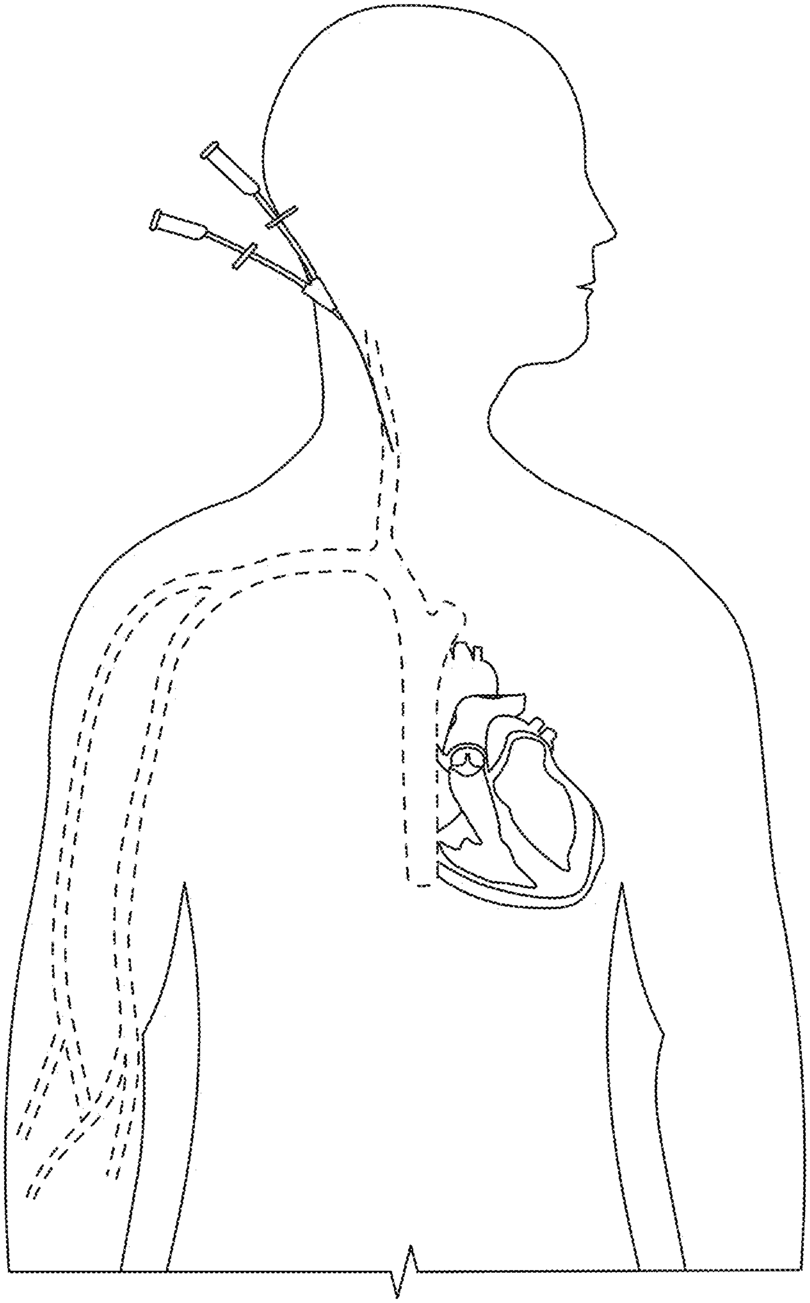
FIG. 1E shows an example of a device being advanced toward the heart of a patient through an access point in the internal jugular vein.
Figure 2A:
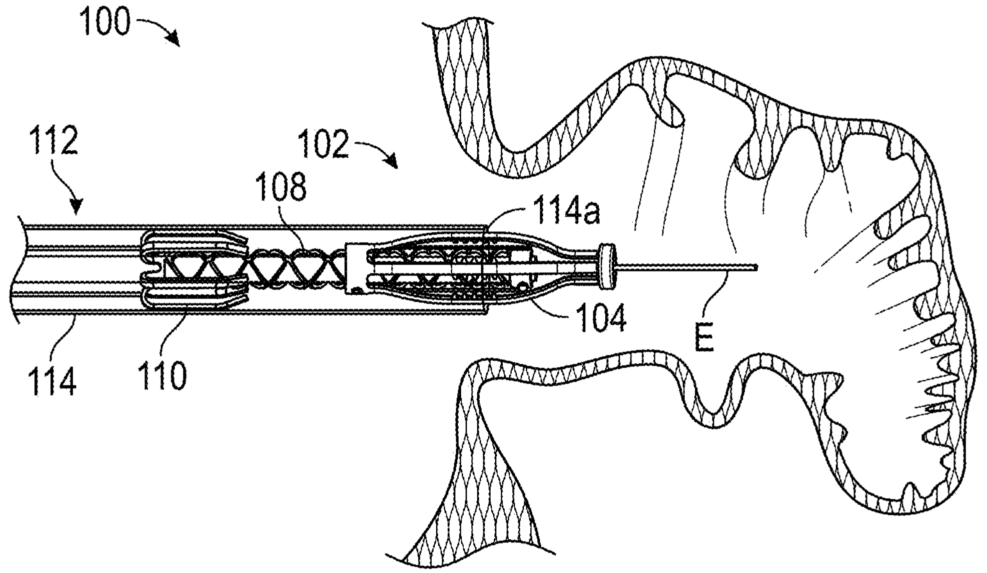
FIG. 2A shows an embodiment of treatment device having an implant device being advanced through a catheter into the LAA, the implant device being in a collapsed state and restrained within an outer tube of the catheter.

FIGS. 1A and 1B show a section view of a left atrium, showing a guidewire G advancing from a catheter C toward the left atrial appendage LAA. FIG. 2A shows an embodiment of a treatment device 100 for occluding or closing the opening of the LAA (also referred to herein as an occlusion device).

In any embodiments disclosed herein, a rotation of the contact member, implant device, and/or left atrial appendage can comprise rotating the contact member, implant device, and/or left atrial appendage about a longitudinal axis of the contact member and/or implant device. In some embodiments, the axis of rotation can be an axis that extends through the ostium of the LAA towards an internal wall of the LAA, or is an axis that is defined by an insertion path of the implant into the LAA. In some embodiments, the insertion path can be through the ostium of the LAA to a far wall of the LAA. In some embodiments, the axis of rotation can be an axis that extends through the ostium of the LAA towards an internal wall of the LAA and the LAA and/or the implant is rotated about the axis. In some embodiments, the axis of rotation can be an axis that extends through the ostium of the LAA towards an internal wall of the LAA and the LAA and/or the implant is rotated about the axis to twist the LAA.

In any embodiments disclosed herein, the treatment device (including the embodiment of the treatment device 100) can be configured to rotate and twist the LAA so as to cause a neck or a portion of the LAA adjacent to the opening of the LAA to constrict and substantially or fully close about an outside surface of a portion of the implant device, thereby causing the opening of the LAA to be occluded. In any embodiments of the treatment device, including the embodiment of the treatment device 100, the system can have an implant device 102 having a contact member 104 (also referred to in any embodiments disclosed herein as a contact element, a first portion of the implant, or an expandable implant member), a securing member or securing element 110 (also referred to in any embodiments herein as a securing member or a second portion of the implant), and a retention element 108 (also referred to as a retention member). The implant device 102 can be configured to be advanced through a catheter 112 into the LAA. The embodiment of the implant device 102 shown in FIG. 2A is shown in a collapsed state and restrained within an outer sleeve 114 of the catheter 112. As shown, the implant device 102 can be advanced distally out of the catheter 112 past a distal end 114*a* of the outer sleeve 114 by advancing a portion of or member of the catheter, such as without limitation a core member 113 of the catheter 112, so that the contact member 104 of the implant device 102 can be advanced into the LAA and/or deployed within the LAA.

Figure 2B:
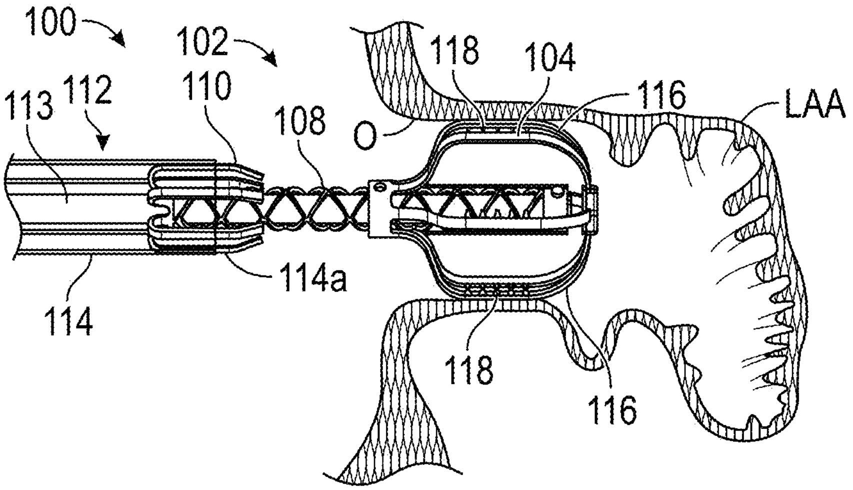
FIG. 2B shows the embodiment of the treatment device of FIG. 2A, showing the contact member being expanded within the LAA.

Alternatively, the catheter 112 having the implant device 102 therein can be advanced into a desired position within the LAA and, while holding the implant device 102 in a stationary axial position by maintaining the core member 113 of the catheter 112 in a stationary axial position, the outer sleeve 114 of the catheter 112 can be retracted or withdrawn so as to expose and/or unrestrain the contact member 104 of the implant device 102. In any embodiments disclosed herein, the contact member 104 can be self-expanding in a radial direction so that, when a restraint is removed from the contact member 104, the contact member 104 can expand against an inner surface or wall of the LAA automatically. In other embodiments, the contact member 104 can be mechanically expandable, such as by a balloon expander, so as to expand against inside surface or wall of the LAA. FIG. 2B illustrates the contact number 104 after it has been expanded against an inside wall of the LAA distal to an ostium or opening O of the LAA.

Alternatively, in any embodiments disclosed herein, the contact member can be configured to remain in a first state within the catheter, during the entire treatment procedure, and/or thereafter. For example and without limitation, in any embodiments disclosed herein, the contact member can be configured such that the contact member is deployed from the catheter and advanced into contact with a tissue surface of an inside wall of the LAA, engage the tissue surface of the inside wall of the LAA, and cause the LAA to twist when a torque and/or rotation is applied to the contact member, all without changing the state of the contact member. Alternatively, in any embodiments disclosed herein, a contact member can be configured to be advanced into the pericardial space around an outside of the LAA to engage an outside surface of the LAA and to and cause the LAA to twist when a torque and/or rotation is applied to the contact member.

In any embodiments disclosed herein, including the embodiment illustrated in FIG. 2B, the contact member 104 can have a plurality of arms or struts 116 that are each configured to self-expand in a radial direction when a restraint has been removed from an outside surface of the contact member 104. For example without limitation, any embodiments of the contact member disclosed herein can have six struts 116, or between six and ten struts, or from less than six to more than ten struts.

Further, in any embodiments, the contact member 104 can have a plurality of teeth, cleats, barbs, nubs, texture, studs, anchors or other tissue engaging features 118 or other similar features configured to penetrate or engage the tissue of the LAA that are configured to penetrate into a tissue within the LAA when the contact member 104 is expanded against the tissue of the LAA and/or when the contact member 104 is rotated or twisted within the LAA. Note that teeth, cleats, barbs, nubs, texture, studs, anchors and other tissue engaging features or features configured to grip or engage the tissue when torque is applied to the expanded contact member will be collectively referred to herein as tissue anchors, which use of this term is meant to describe and include any of the foregoing features individually and/or any combination of these features.

The tissue anchors 118 can be integrally formed with the struts, on the struts, added to the struts, or otherwise coupled with or supported by the struts. The tissue anchors 118 can be circumferentially facing (as shown, can be radially facing so as to penetrate or engage the tissue at an orthogonal angle relative to the tissue surface of the LAA, at an angle relative to the line that is tangential to the outer surface of the contact member 104, or otherwise. In some embodiments, each strut 116 can support a plurality of tapered tissue anchors facing in a circumferential direction, as illustrated in FIG. 2B. All of the tissue anchors can face in a similar orientation relative to each of the struts, such as in the circumferential direction relative to each strut. In the illustrated embodiment, each strut 104 has five tissue anchors 118. In this embodiment, when the contact member 104 is rotated in a first direction (indicated by arrow A1 in FIG. 2C, which can be in the clockwise or the counterclockwise direction), one or more or all of the struts 116 and one or more or all of the tissue anchors 118 can engage the tissue of the LAA and cause the LAA to twist or rotate in the first direction A1. The twisting or rotation of the LAA in the first direction from a first rotational position to a second rotational position results in the opening or ostium O of the LAA constricting in a radial direction (represented or identified by arrows A2 in FIG. 2C) so that the opening O of the LAA is caused to move or constrict around an outside surface of a proximal portion 104*a* of the contact member 104. An operator can twist or rotate the contact member 104 by twisting or rotating the core member 113 of the catheter 112. The tightening or constriction of the opening O of the LAA around an outside surface of the proximal portion 104*a* of the contact member 104 or other portion of the implant device can result in the occlusion, or substantial occlusion, or substantial closing off of the interior portion of the LAA from the remaining chambers within the heart, thereby substantially reducing the health risks associated with an open LAA.

In some embodiments, as in the illustrated embodiment, the securing element 110 can be maintained in a collapsed or first state such as by being restrained by the outer sleeve 114 of the catheter 112 while the contact member 104 is being deployed and rotated to prevent the securing element 110 from contacting tissue within the heart and potentially lacerating or otherwise damaging such tissue. An intermediary sleeve or tube 115 can be coupled with the securing element 110 and can be used to manipulate and control a position and/or an orientation of the securing element 110, including holding a proximal end portion 110*a* of the securing element in a fixed axial position while a distally directed force is exerted on the contact member 104 to maintain the retention element in the first, extended state. In any implant device embodiments disclosed herein, the securing element (including, for example and without limitation, securing element 110) can be keyed, indexed, or otherwise rotationally fixed to the contact member (including, for example and without limitation, contact member 104) so that the securing element cannot rotate relative to the contact member and the contact member cannot rotate relative to the securing element. In this configuration, the securing element can prevent or substantially prevent or inhibit the contact member and the LAA from rotating back toward the first rotational position.

Figure 2C:
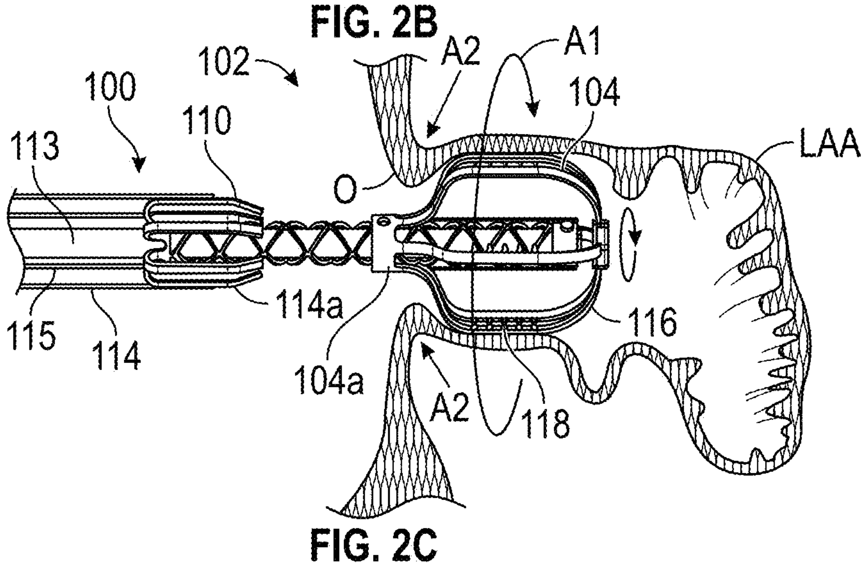
FIG. 2C shows the embodiment of the treatment device of FIG. 2A, showing the contact member being rotated to twist the LAA and cause a neck or opening of the LAA to constrict around a portion of the implant device.
Figure 2D:
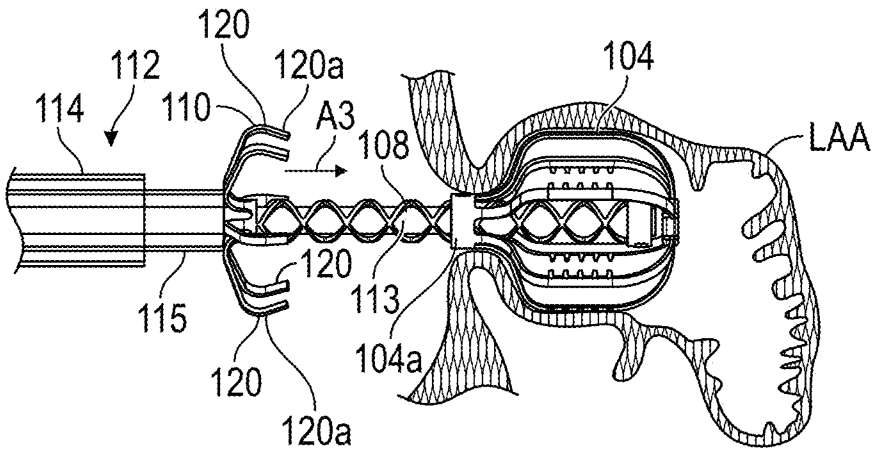
FIG. 2D shows the embodiment of the treatment device of FIG. 2A, showing the securing element of the embodiment of the implant device being advanced toward the contact member of the implant device.
Figure 2E:
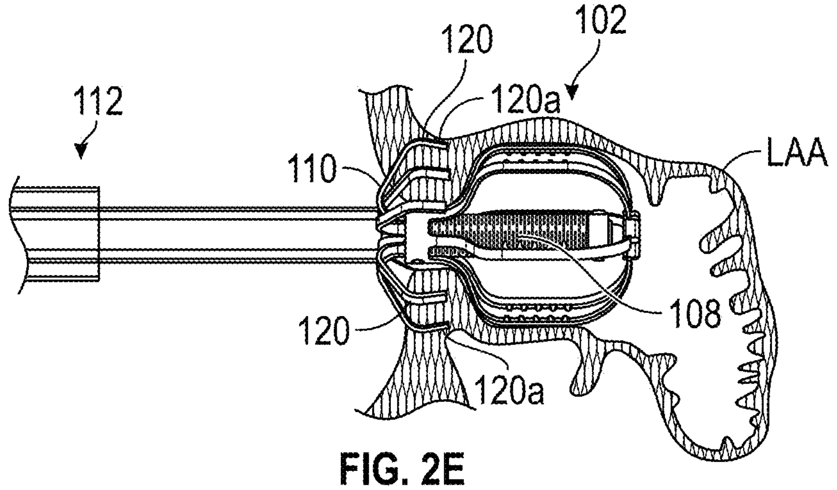
FIG. 2E shows the securing element of the treatment device of FIG. 2A engaged with the patient's tissue that has constricted as a result of the twisting of the LAA.
Figure 2F:
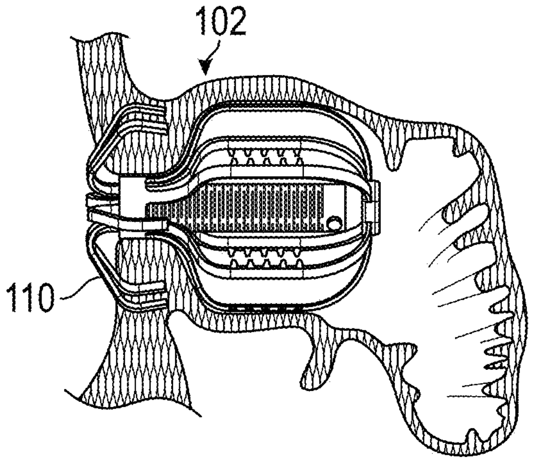
FIG. 2F shows the implant device of FIG. 2A disengaged and removed from the catheter.

With reference to FIG. 2D, with the contact member 104 having been rotated to the second rotational position and maintained in the second rotational position such that the opening O of the LAA remains constricted around a proximal portion 104*a* of the contact member 104 or other portion of the implant device and the LAA is generally occluded from the remainder of the heart chambers, the catheter tube member 115 can then be advanced in a distal direction (represented by arrow A3 as shown in FIG. 2D) or the outer sleeve 114 can be withdrawn in a proximal direction so that the securing element of 110 can be exposed so that it can self-expand from a first, collapsed state (as shown in FIG. 2C) to a second, expanded or open state (as shown in FIG. 2D). In the second state, a plurality of struts or members 120 of the securing element 110 can expand in a generally radial direction so as to open up to a larger overall diameter or profile. Additionally, because each of the one or more members 120 of the securing element 110 can have end portions 120*a* that extend in a generally distal axial direction (but can be slightly angled inwardly), as the securing element 110 is advanced in the axial direction, the distal portions 120*a* of each of the one or more members 120 can penetrate into and/or engage with a tissue portion of the heart, as shown in FIG. 2E. The tissue portion that the one or more members 120 can penetrate into or engage with can include portions of the tissue comprising the left atrium and/or portions of the tissue comprising the LAA. As mentioned above, the contact member 104 can be held in generally a stationary axial position using the core member 113 while the securing element 110 is advanced distally toward the contact member 104. The retention element 108 can thereafter be unrestrained so that it can maintain the securing element 110 in the second rotational position wherein the securing element 110 is engaged with the tissue of the heart, as shown in FIG. 2E. In some embodiments, the securing element can be biased toward a smaller size in the axial direction, such as with a spring member or similar. For example, the retention element 108 can be formed by laser cutting openings within a cylindrical tube, such as a hypo tube made of an elastic material, such as Nitinol. Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the LAA can be prevented from rotating to the first rotational position, which is the untwisted or relaxed position. In this configuration, the implant device 102 can secure and maintain the LAA in a substantially or completely occluded or substantially or completely closed state.

Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the LAA is prevented or, at least, inhibited or biased from rotating to the first rotational position, which is the untwisted or relaxed position. In this configuration, the implant device 102 can secure and maintain the LAA in a substantially or completely occluded or substantially or completely closed state.

Figure 2G:
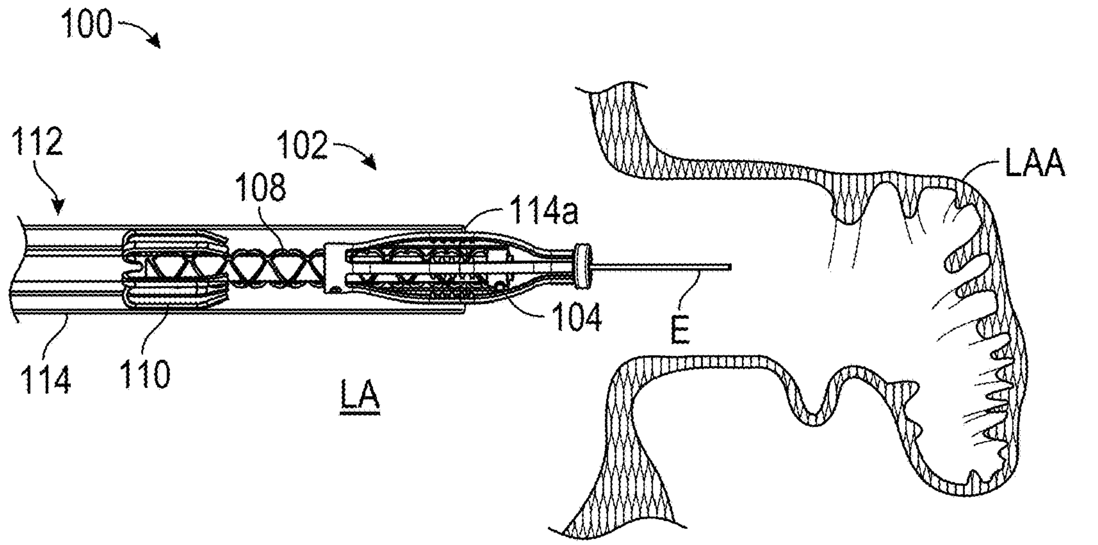
FIG. 2G shows the embodiment of treatment device of FIG. 2A advanced to the left atrium (LA), the implant device being in a collapsed state and restrained within an outer tube of the catheter.
Figure 2H:
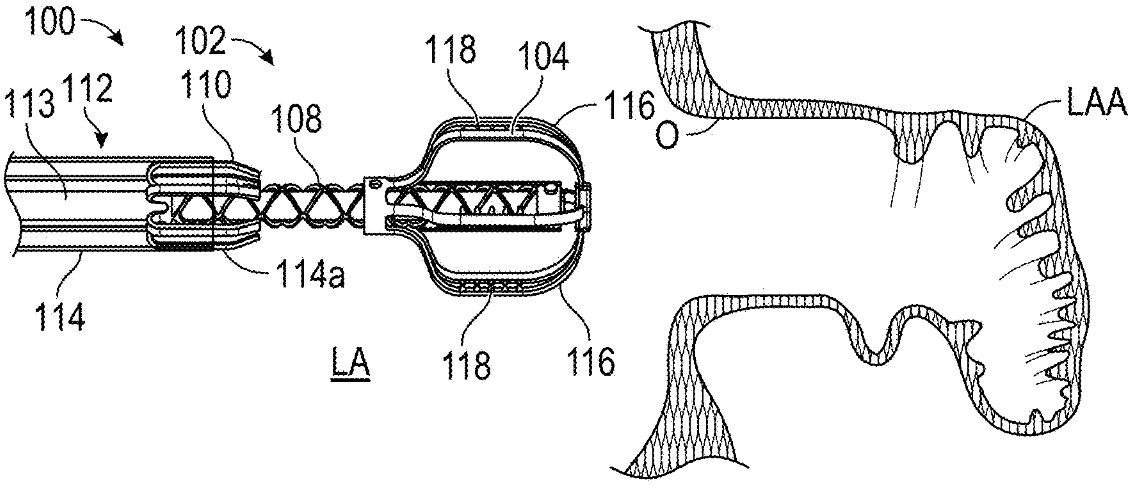
FIG. 2H shows the embodiment of the treatment device of FIG. 2A, showing the contact member being expanded within the LA before being advanced into the LAA.
Figure 2I:
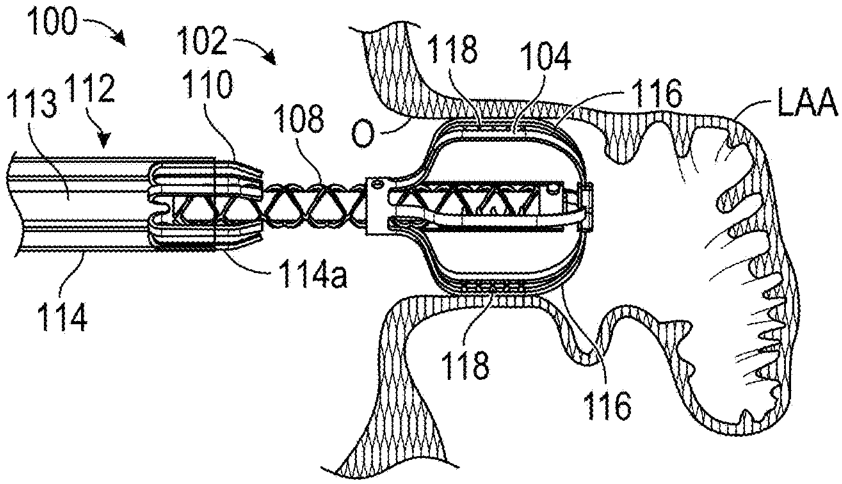
FIG. 2I shows the embodiment of the treatment device of FIG. 2A, showing the contact member being advanced into the LAA after the contact member has been expanded.
Figure 2J:
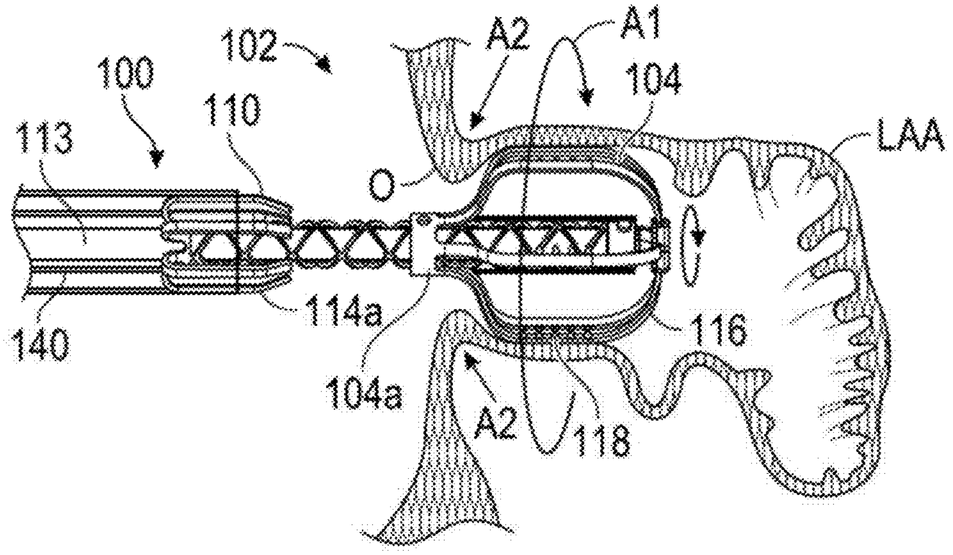
FIG. 2J shows the embodiment of the treatment device of FIG. 2A, showing the contact member being rotated to twist the LAA and cause a neck or opening of the LAA to constrict around a portion of the implant device.

Note that, in any embodiments of the methods and devices disclosed herein, including without limitation any of the methods of treating an LAA, the contact member can be partially or completely expanded in the left atrium (LA) before being advanced into the LAA. For example and without limitation, FIG. 2G shows the embodiment of treatment device 100 of FIG. 2A advanced the left atrium (LA), the implant device 102 being in a collapsed state and restrained within an outer tube of the catheter. FIG. 2H shows the contact member 104 being partially or completely expanded (or partially or completely moved to the second state) within the LA before being advanced into the LAA. As shown in FIG. 2I, the contact member 104 and other components of the treatment device 100 can be advanced into the LAA when the contact member is in an expanded or second state, or when the contact member is partially in an expanded state or is between the first state and the second state. As shown in FIG. 2J, the contact member can be rotated to twist the LAA and cause a neck or opening of the LAA to constrict around a portion of the implant device, just as described above. Other steps to complete the treatment can be as described above and in other methods disclosed herein. Note that, as mentioned above, any of the treatment device embodiments disclosed herein can be configured so that the contact member can be partially or completely expanded in the LA before the contact member is advanced into the LAA. Similarly, in any of the embodiments of the methods disclosed herein (for example and without limitation, the embodiments of treating and/or occluding the LAA), the contact member can be partially or completely expanded in the LA before the contact member is advanced into the LAA. In certain embodiments, the contact member is not further expanded once positioned within the LAA and, in certain embodiments, the contact member can be further expanded or constricted once positioned within the LAA. In certain embodiments, the contact member could be constricted in the LA before entering the LAA and then could remain in a constricted position within the LAA or could be further expanded or constricted once positioned within the LAA.

As noted above, the contact member can be rotated to twist the LAA so as to cause a neck or a portion of the LAA adjacent to the opening of the LAA to constrict and substantially or fully close about an outside surface of a portion of the implant device, thereby causing the opening of the LAA to be occluded. In the illustrated embodiment, the contact member 104 can be rotated about its longitudinal axis to cause the twisting of the LAA. In certain embodiments, the longitudinal axis that the contact member is rotated about can correspond to or be closely aligned with an insertion axis of the securing element 110 as it is advanced towards the contact member 104. Additionally, any of the embodiments of the methods and devices disclosed herein can be configured such that the implant or contact member can be advanced from the delivery catheter and engage a wall of the LAA without the implant or contact member completely or partially expanding, changing size, changing shape, or moving to or toward a second state. For example, in some embodiments, the implant or contact member can be configured to engage and, upon rotation of the implant or contact member, rotate the LAA without the implant or contact member completely or partially expanding, changing size, changing shape, or moving to or toward a second state.

Figure 2K:
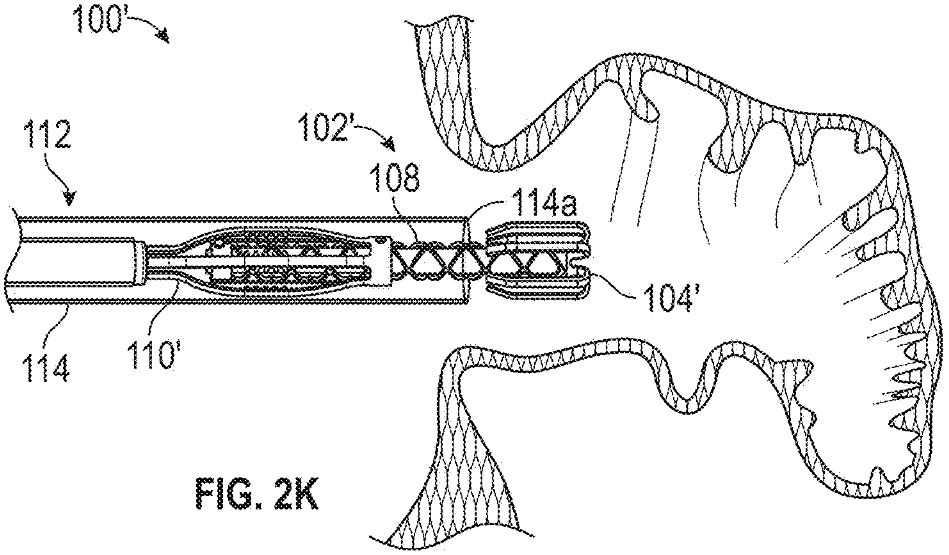
FIG. 2K shows another embodiment of treatment device having an implant device being advanced through a catheter into the LAA, the implant device being in a collapsed state and restrained within an outer tube of the catheter.
Figure 2L:
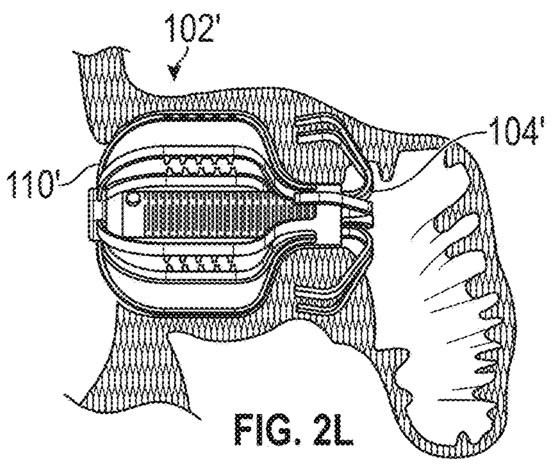
FIG. 2L shows the embodiment of the implant device of FIG. 2K engaged with the patient's tissue that has constricted as a result of the twisting of the LAA.

FIG. 2K shows another embodiment of treatment device 100' having an implant device 102' being advanced through a catheter into the LAA, the implant device 102' being in a collapsed state and restrained within an outer tube 114 of the catheter. FIG. 2L shows the embodiment of the implant device 102' of FIG. 2K engaged with the patient's tissue that has constricted as a result of the twisting of the LAA. In any embodiments, the implant device 102' can have a contact member 104', a securing element 110', and a retention element 108' extending between the contact member 104' and the securing element 110'. In some embodiments, the implant device 102' can be flipped as compared to the implant device 102 described above.

In some embodiments, the contact member 104' can be configured to treat the LAA the same as any other embodiments of the contact members disclosed herein. For example and without limitation, the contact member 104' can be configured to engage a tissue portion inside the LAA and twist the LAA so as to cause a portion of tissue of the LAA to constrict inwardly, just as other embodiments of the contact members disclosed herein. In the illustrated embodiment, the contact member 104' can have the same or a similar structure, functionality, components, and/or other details as any of the embodiments of the securing elements disclosed herein, for example and without limitation, the embodiments of the securing elements 110 disclosed herein, while being configured for engaging the tissue inside the LAA and twisting the LAA to constrict and/or occlude the ostium of the LAA.

Further, in some embodiments, the securing element 110' can be configured to treat the LAA the same as any other embodiments of the securing elements disclosed herein. For example and without limitation, the securing element 110' can be configured to engage the tissue that has constricted as a result of the twisting of the LAA so as to inhibit the constricted tissue from untwisting and/or so as to inhibit the constricted opening of the LAA from expanding. In the illustrated embodiment, the securing element 110' can have the same or a similar structure and functionality as any of the embodiments of the contact members disclosed herein, for example and without limitation, the embodiments of the contact members 104 disclosed herein.

In other embodiments, the implant device 110' can have a contact member that is similar to the embodiments of the contact member 104 disclosed herein or other embodiments of contact members disclosed herein (with the exception of the embodiments of the contact member 104') along with the embodiments of the securing element 110' disclosed herein, or a securing element that has a structure that is the same or similar to any other embodiments of contact members disclosed herein (with the exception of the embodiments of the contact member 104'). Alternatively, in other embodiments, the implant device 110' can have a contact member 104' as disclosed herein and can have a securing element that is similar to any of the other securing elements shown herein, such as any of the embodiments of the securing element 110 disclosed herein.

Any of the components of any of the implant embodiments disclosed herein can be made from Nitinol or any other elastic or super elastic material, including any other shape memory materials, or any mechanically expandable material such as stainless steel or otherwise. In any embodiments disclosed herein, the contact member (such as contact member 104) can have a spherical, cylindrical, or other shape, such as the shape of an elongated bullet, a stent, a mushroom, or other non-round or non-cylindrical shape or any of the shapes described or shown with respect to any of the embodiments disclosed herein. In any embodiments disclosed herein, the contact member may comprise a series of interconnected struts (that can, but are not required to, form a diamond shaped pattern across all or a portion of the surface of the contact member), or may be made from a series of ribs or paddles which form the expandable device.

Figure 3B:
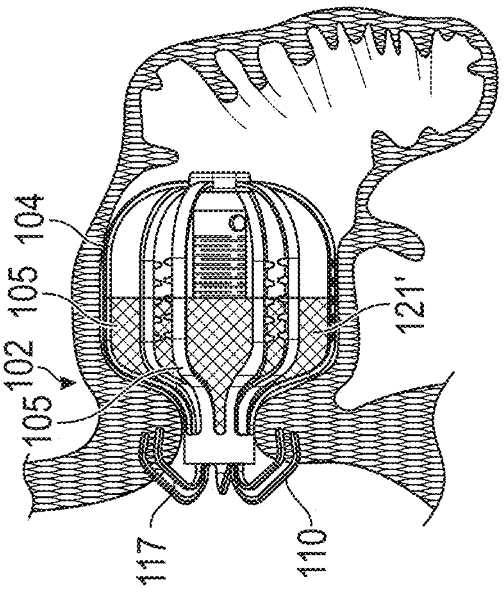
FIG. 3B shows an embodiment of an implant device having a cover member position against at least a portion of an inside surface of a portion of the implant device.
Figure 3C:
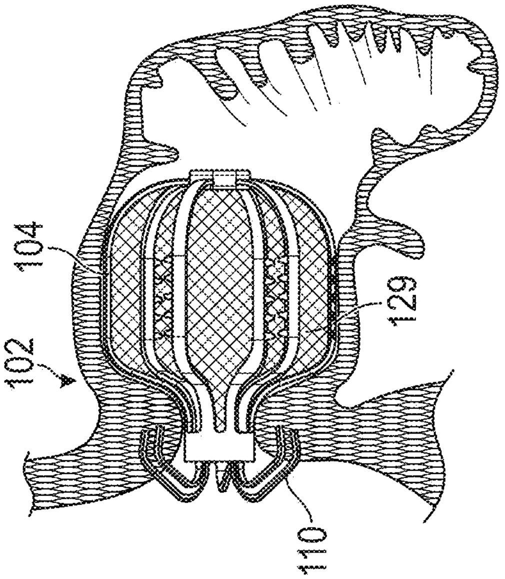
FIG. 3C shows another embodiment of an implant device having a foam material or other seal material inside a portion of the implant device.
Figure 3A:
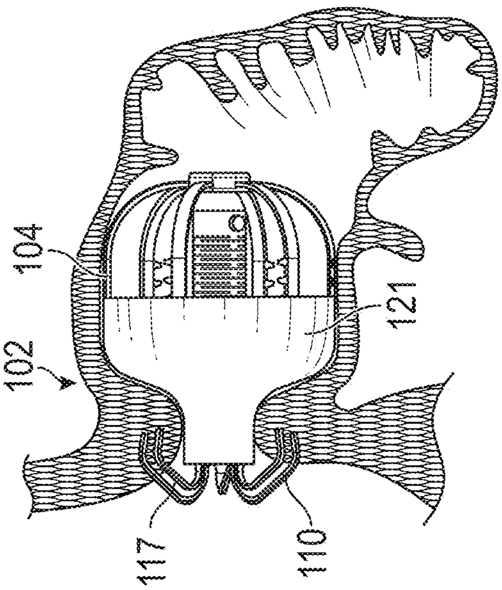
FIG. 3A shows an embodiment of an implant device having a cover member surrounding at least a portion of the implant device.

With reference to FIG. 3A, the securing element of any device embodiments disclosed herein, including without limitation the securing element 110, can have an outer size (such as an outer diameter of the arms 117 of the securing element 110) that is significantly smaller than an outer size (such as an outer diameter) of the contact member 104. For example and without limitation, the securing element of any device embodiments disclosed herein can have an outer size that is approximately one-half of an outer size of the contact member 104, or from approximately 30% to approximately 80% of an outer size of the contact member 104, or from approximately 50% to approximately 60% of an outer size of the contact member 104. In any embodiments, the outer size of the securing element can be similar to or approximately the same as, or even larger than, the outer size of the contact member 104.

As also shown in FIG. 3A, any embodiments of the implant device 102 or embodiments of the contact member disclosed herein can have a cover member 121 that can provide an additional seal or barrier around an outside surface of the contact member 104 and/other portions of the implant device 102 to provide an additional barrier to the implant device 102. In some embodiments, the cover can be located or positioned on or against an inside surface or portion of the contact member of the implant, as is shown in FIG. 3B wherein the cover member 121' is coupled against an inside surface of the contact member 104. This can improve the seal or occlusion that the implant device 102 creates in the LAA. In some embodiments, the cover member 121 or 121' can cover substantially or completely all of the contact member 104 of the implant device.

In any embodiments disclosed herein, the cover member 121 or 121' can be coupled with the contact member 104 using one or more loops 105 (that can be sutures or made from suture material) that pass around each of the arms or struts of the contact member 104 and are coupled with the cover member 121 or 121'. In some embodiments, the cover member 121 or 121' can be coupled with the contact member 104 using adhesive, loops of the cover material, or any other suitable fasteners, connectors, or otherwise.

Additionally, with reference to FIG. 3C, any embodiments disclosed herein can be configured to have a foam material or other seal material 129 inside the contact member 104. For example and without limitation, the seal material 129 can be self-expanding upon actuation by a surgeon or other user, or upon expansion of the contact member 104, or upon occurrence of another actuation or deployment step, such as when the securing element 110 is advanced toward the contact member 104. In other embodiments, the seal material 129 can be in a compressed state when the contact member 104 is in the first or collapsed state, and to expand to an expanded state when the contact member 104 is unrestrained. In some embodiments, the seal material 129 can be self-expanding or expanded by actuation from the surgeon and can cause the contact member 104 to expand to the second or expanded state. In other embodiments, for example, wherein the contact member 104 is configured to remain in a similar or the same size and shape during the entire procedure and/or thereafter, the seal material 129 can be fully expanded within the contact member 104 prior to deployment of the contact member 104.

Figure 4:
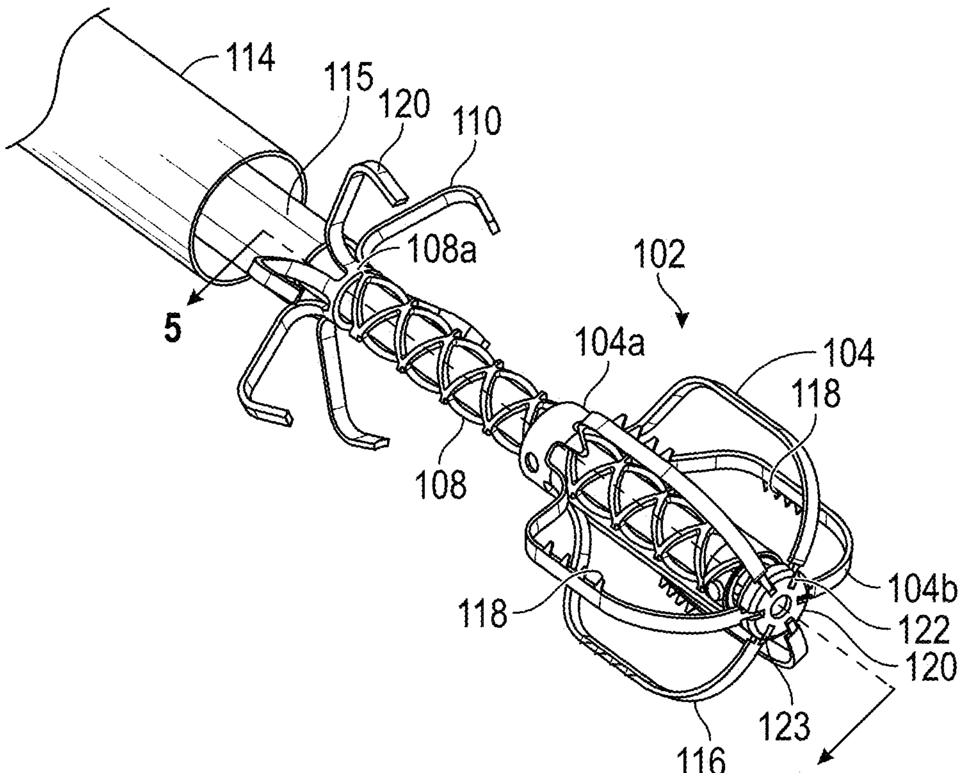
FIG. 4 shows the implant device of FIG. 2A wherein the contact member is in a second, expanded state, the retention element is in a first, extended state, and the securing element is in a second, open state.
Figure 5:
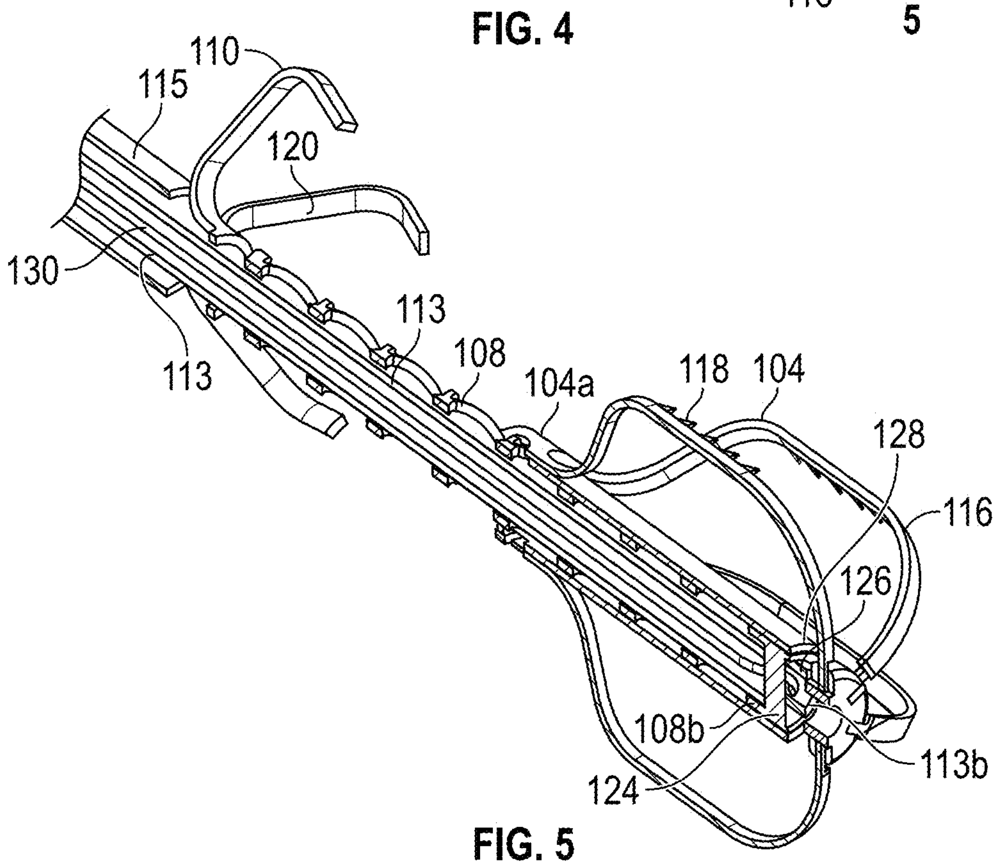
FIG. 5 is a section view of the implant device shown in FIG. 2A, taken through line 5-5 of FIG. 4.
Figure 6:
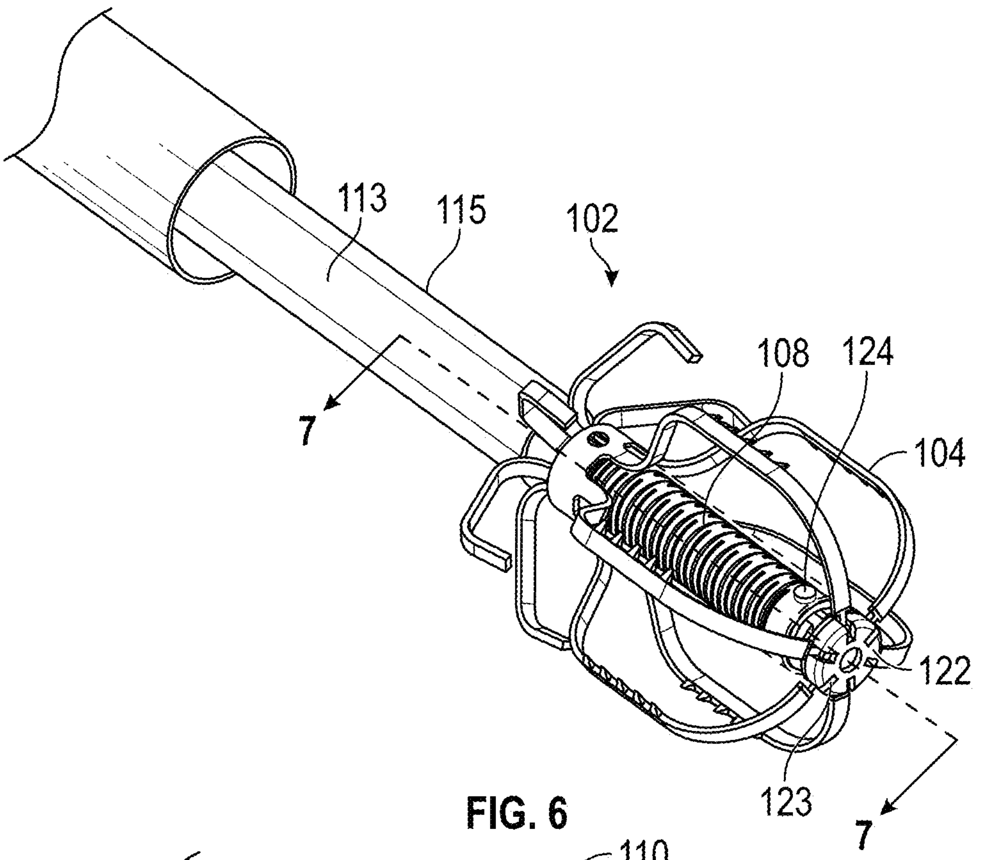
FIG. 6 shows the implant device of FIG. 2A wherein the contact member is in a second, open state, the retention element is in a second, contracted state, and the securing element is in a second, open state.

Further details regarding the implant system 100 will now be described, with reference to FIGS. 4-7. FIG. 4 shows the contact member 104 in the second, expanded state, the retention element 108 (also referred to herein as a biasing member) in the first, extended state, and the securing element 110 in the second, open state. In any embodiments disclosed herein, the retention element can be an axial spring-like member or other axially resilient member. In some embodiments, the contact member 104 can have a continuous and uninterrupted circumference at a proximal end 104*a* that each of the strut members 116 extend distally away from. Each of the strut members 116 can be preformed into a curved shape such that the strut members 116 are biased to expand to the second state when no external restraint or constraint is applied to the outside surface of the contact member 104 (for example, when in a relaxed state). At a distal end, each of the strut members 116 can, but are not required to, couple with a hub member 122. With reference to FIGS. 5-6, the hub member 122 can have a plurality of receptacles 123 configured to receive and constrain distal end portions 116*b* of each of the strut members 116. Additionally, each of the receptacles 123 can be configured to permit the distal end portions 116*b* of each of the strut members 116 to rotate relative to the hub member 122 so that the distal end portions 116*b* of the strut members 116 can extend generally radially away from the hub member 123 when the contact member 104 is in the second, expanded state. The hub member 123 can be configured to permit the distal end portions 116*b* of each of the strut members 116 to rotate relative to the hub member 122 without resistance or significant resistance. The distal ends of each of the strut members 116 can have a tab or other feature (such as a T shaped termination or other increased width) 119 that locks into, is secured by, or is otherwise engaged by each of the receptacles 123 so as to axially constrain the end portion of each of the strut members 116, while allow rotation about the end portion.

Figure 7:
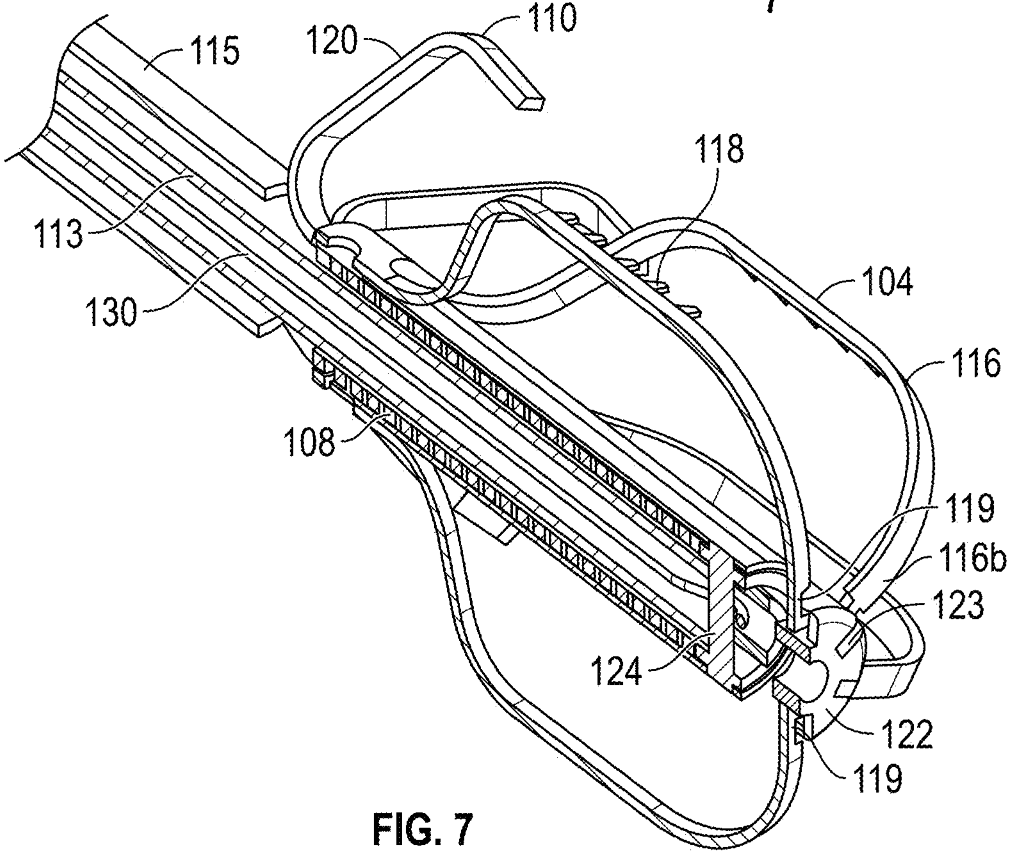
FIG. 7 is a section view of the implant device shown in FIG. 2A, taken through line 7-7 of FIG. 6.

In some embodiments, as in the embodiment illustrated in FIG. 4, the retention element 108 and the securing element 110 can be integrally formed. For example and without limitation, the retention element 108 and the securing element can be laser cut from a single length of tube material, for example, from an elastic or shape memory material, and thereafter formed into the desired shape using conventional or suitable processes. In other embodiments, the securing element 110 can be formed separately and coupled with a proximal end 108*a* of the retention element 108. In the relaxed state (i.e., the state where no external forces are acting thereon), some embodiments of the retention element 108 can be biased to move to the second or collapsed state, as shown in FIGS. 2E, 6, and 7, for example. Further, in the relaxed state, the retention element 110 can be in the second, or open position as also shown in FIG. 2E. Additionally, with reference to FIG. 5, which is an enlarged section view through line 5-5 of FIG. 4, a pin or cross member 124 can be coupled with a distal end 108*b* of the retention element 108 and can be configured to fit within a slot 126 formed within a distal end 113*b* of the core member 113. In this embodiment, the core member 113 can be advanced in a distal direction resulting in the advancement of the contact member 104 in a distal direction. Further, a core tube 128 can extend proximally from a distal end 113*b* of the core member 113 and couple with a proximal end 104*a* of the contact member 104. The pin 124 can extend through a pair of openings formed in the core tube 128 to secure the core tube 128 to the pin 124 and, hence, the distal end 108*b* of the retention element 108. The core tube 128 can, therefore, be used to couple the contact member 104 to the retention element 108. Pins, tabs, sutures, ties, protrusions, clips, depressions, detents, or other features can be used to couple a proximal end 104*a* of the contact member 104 with a proximal end of the core tube 128. Note that the core tube 128 has been omitted from some of the figures for clarity.

Additionally, in any embodiments, the system 100 can be configured so that the implant device 102 is biased or selectively secured in the proximal direction relative to the core member 113. For example and without limitation, as shown in FIG. 5, some embodiments of the implant device 102 can have a suture or thread 130 that extends through an inside of the core member 113 (such as through a lumen of the core member 113) and loops around the pin 124, thereby permitting a user to retract or withdraw the suture to pull the implant device 102 proximally relative to the core member 113. In this configuration, both ends of the suture 130 can extend from a proximal end of the device 100 such that a practitioner can grasp both ends of the suture 130 to exert the biasing force around the pin 124 to maintain the pin against a proximal end of the slot 126 formed within the distal end 113*b* of the core member 113. When the implant device 102 is ready to be released from the core member 113, the practitioner can simply release one end of the suture and withdraw the other end of the suture until the suture no longer forms a loop and/or no longer wraps around the pin 124. After removing the biasing force or retaining force from the suture 130 and/or removing the proximally directed force from the contact member, the core member 124 can be withdrawn relative to the implant device 102, while the contact member remains stationary within the LAA. This may be done after the contact member and the securing element have been fully deployed or implanted into the LAA and/or tissue adjacent to the LAA.

Further, in any embodiments disclosed herein, the pin or cross member 124 can be configured to permit a guidewire to pass through a distal end portion of the implant device 102 without obstruction. For example without limitation, an opening larger than an outside diameter of a guidewire can be formed in the pin 124 to permit a guidewire to pass therethrough, or the pin 124 can be formed in two parts, with a sufficiently large space therebetween.

Figure 8A:
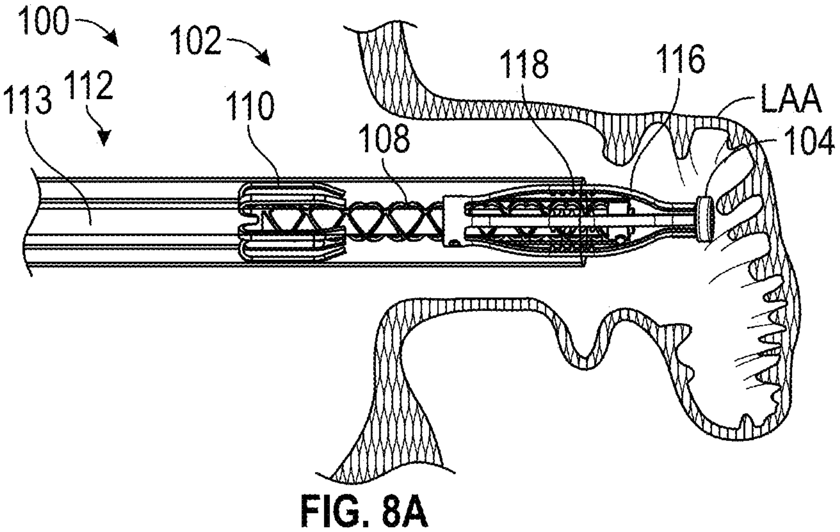
FIG. 8A shows the embodiment of the implant device of FIG. 2A, showing the contact member being advanced further distally into the LAA.
Figure 8B:
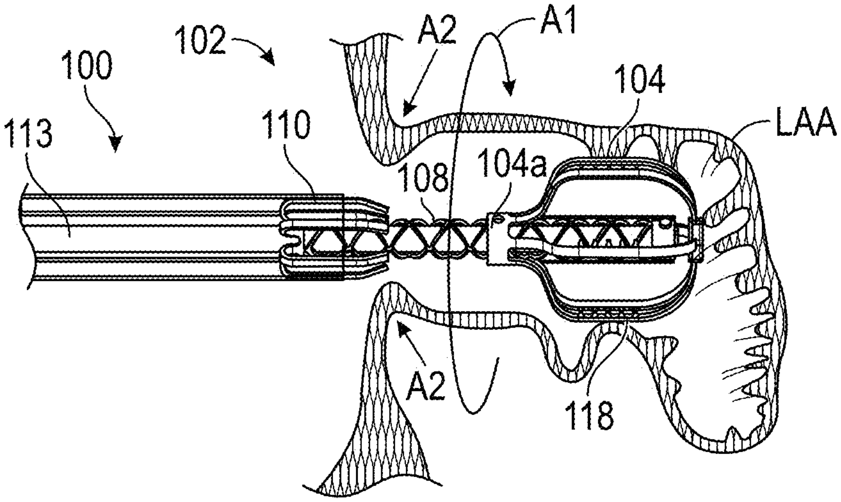
FIG. 8B shows the embodiment of the implant device of FIG. 2A, showing the contact member being rotated to twist the LAA and cause a neck or opening of the LAA to constrict around a portion of the implant device.
Figure 8C:
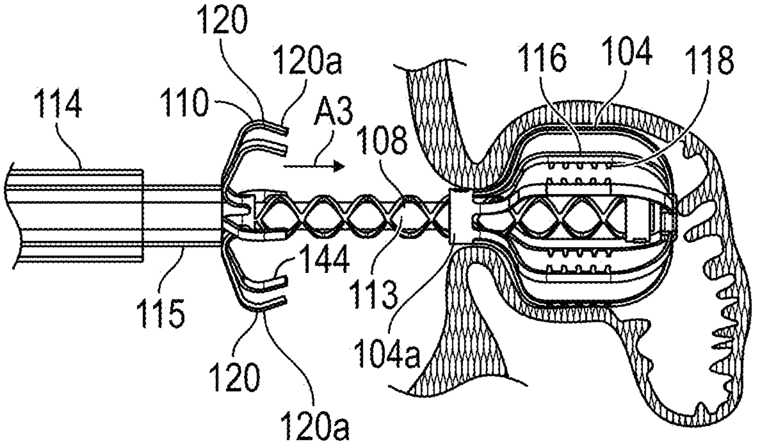
FIG. 8C shows the embodiment of the implant device of FIG. 2A, showing the securing element of the embodiment of the implant device being advanced toward the contact member of the implant device.

With reference to FIGS. 8A-8C, in any embodiments, the contact member 104 of the implant device 102 can be advanced as far into the LAA is desired by the surgeon, or as is appropriate. For example and without limitation, as shown in FIGS. 8A-8C, the contact member 104 can be advanced into contact with, adjacent to, or near to a distal end of the LAA before the contact member 104 is rotated. This will permit more of the implant to be positioned within the LAA and, in some embodiments, more of the tissue of the LAA to constrict around a body portion or other portion of the implant device 102. This can, in some embodiments, permit the user to rotate the contact member 104 of the implant device 102 to a greater extent, and can also result in less stress on the tissue of the LAA. Any implant device embodiments disclosed herein can be configured to be advanced to any extent within the LAA, including being advanced just past the ostium of the LAA, in the middle portion of the LAA, advanced further into the LAA so as to be into contact with, adjacent to, or near to a distal end of the LAA, before the contact member 104 is rotated.

FIGS. 9A-9I show another embodiment of treatment device 140 (also referred to herein as a treatment system) for closing or occluding an LAA. In any embodiments disclosed herein, any components, features, or other details of the treatment device 140 or implant device 142 shown in FIGS. 9A-9I can have any of the components, features, or other details of any other treatment device embodiments or implant device embodiments disclosed herein, including without limitation any of the embodiments of the treatment device 100 or implant device 102 described above, in any combination with any of the components, features, or details of the treatment device 140 or implant device 142 disclosed below. Similarly, any components, features, or other details of any of the other treatment device embodiments or implant device embodiments disclosed herein can have any of the components, features, or other details of any embodiments of the treatment device 140 or implant device 142 disclosed herein in any combination with any of the components, features, or details of the treatment device and/or implant device.

Figure 9A:
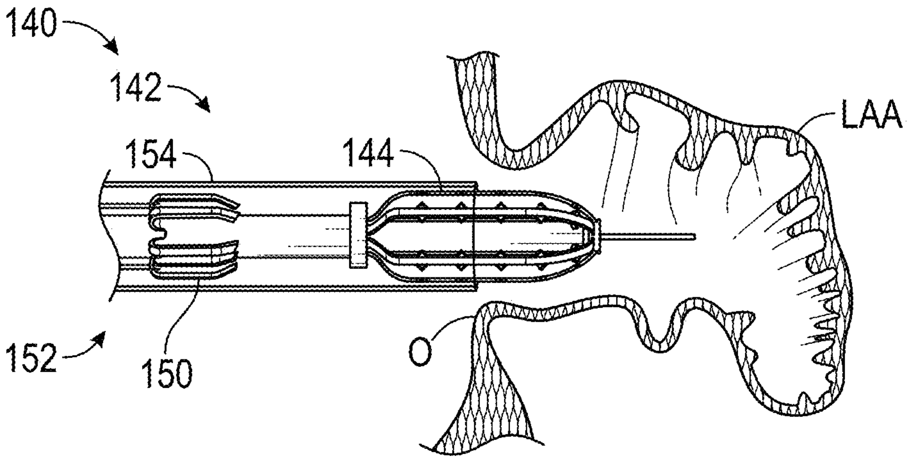
FIG. 9A shows another embodiment of treatment device having an implant device being advanced through a catheter into the LAA, the implant device being in a collapsed state and restrained within an outer tube of the catheter.
Figure 9B:
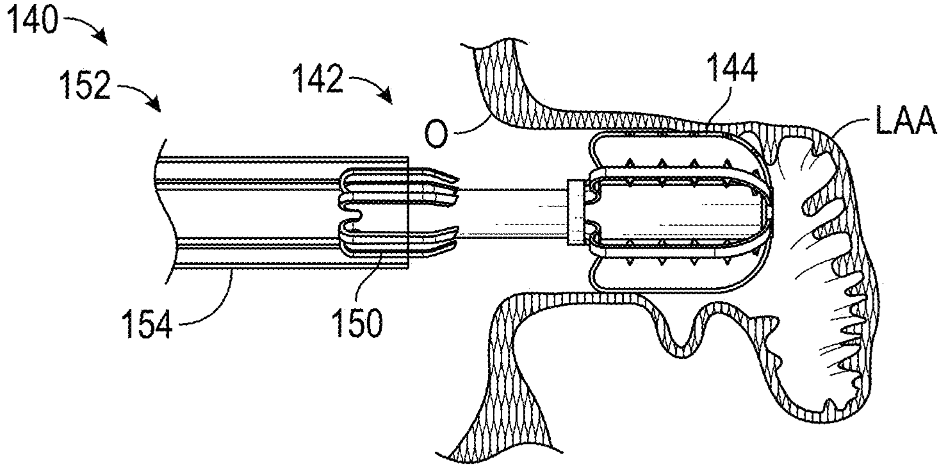
FIG. 9B shows the embodiment of the treatment device of FIG. 9A, showing the contact member being expanded within the LAA.
Figure 9C:
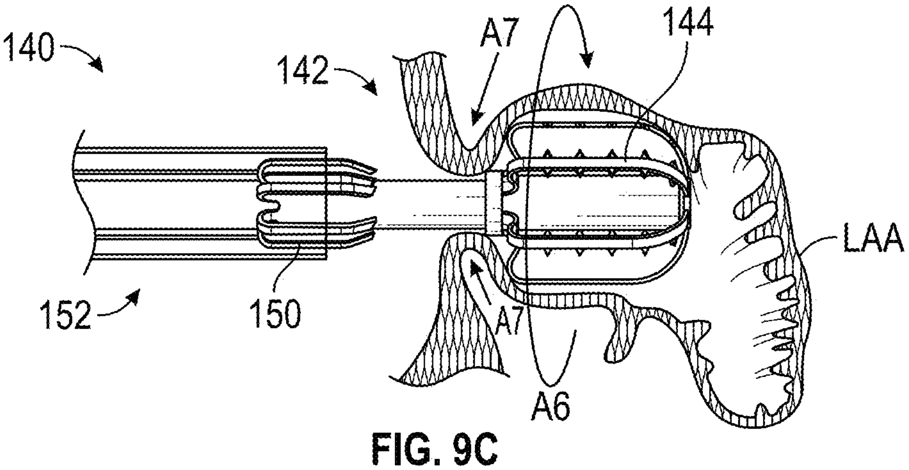
FIG. 9C shows the embodiment of the treatment device of FIG. 9A, showing the contact member being rotated to twist the LAA and cause a neck or opening of the LAA to constrict around a portion of the implant device.
Figure 9D:
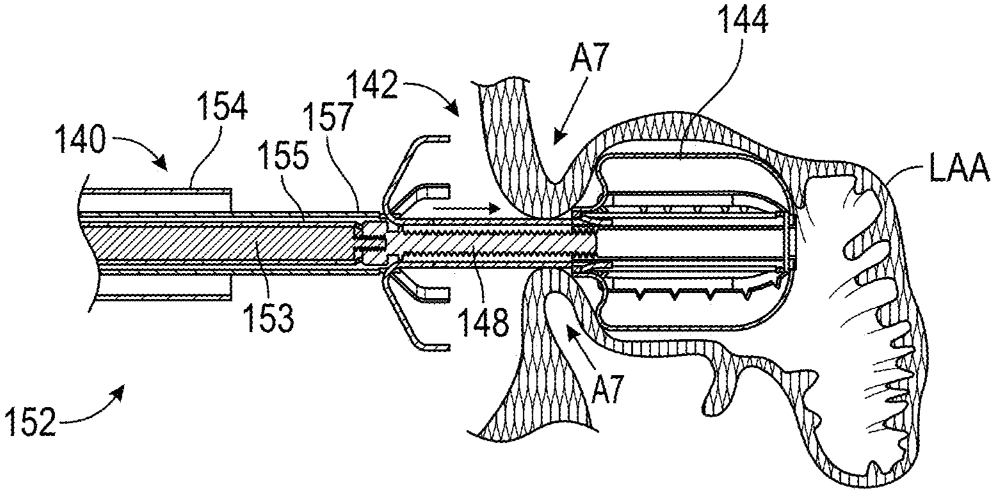
FIG. 9D shows the embodiment of the treatment device of FIG. 9A, showing the securing element of the embodiment of the implant device being advanced toward the contact member of the implant device.

In any embodiments of the treatment device 140, including the embodiment of the treatment device 140, the system can have an implant device 142 having a contact member 144 (also referred to herein as a contact element or an expandable implant member), a securing element 150 (also referred to as a securing member), and a retention element 148. FIG. 9A shows the contact member 144 and the securing element 150 both in a first, contracted or restrained state within an outer sleeve 154 of the catheter 152. The implant device 142 can be advanced distally out of the catheter 152 past a distal end 154*a* of the outer sleeve 154 by advancing a core member 153 of the catheter 152 so that the contact member 144 of the implant device 142 can be deployed within the LAA at any desired depth within the LAA, including near or in contact with a distal wall of the LAA, the middle portion of the LAA, or otherwise by, for example and without limitation, holding the implant device 142 in a stationary axial position by maintaining the core member 153 of the catheter 152 in a stationary axial position and retracting the outer sleeve 154 of the catheter 152. In any embodiments disclosed herein, the contact member 144 can be self-expanding in a radial direction so that, when a restraint is removed from the contact member 144, the contact member 144 can expand against an inner surface or wall of the LAA automatically. In other embodiments, the contact member 144 can be mechanically expandable, such as by a balloon expander, so as to expand against inside surface or wall of the LAA.

In any embodiments, the contact member 144 can have a plurality of arms or struts 156 that are each configured to self-expand in a radial direction when a restraint has been removed from an outside surface of the contact member 144. For example without limitation, any embodiments of the contact member disclosed herein can have six struts 156, or between six and ten struts, or from less than six to more than ten struts. Further, in any embodiments, the contact member 144 can have a plurality of tissue anchors 158 or other similar features configured to penetrate or engage the tissue of the LAA that are configured to penetrate into a tissue within the LAA when the contact member 144 is expanded against the tissue of the LAA and/or when the contact member 144 is rotated or twisted within the LAA.

In this configuration, when the contact member 144 is rotated in a first direction (indicated by arrow A6 in FIG. 9C, which can be in the clockwise or the counterclockwise direction), one or more or all of the struts 156 and one or more or all of the tissue anchors 158 can engage the tissue of the LAA and cause the LAA to twist or rotate the LAA in the first direction A6. The twisting or rotation of the LAA in the first direction from a first rotational position to a second rotational position results in the opening or ostium O of the LAA constricting in a radial direction (identified by arrows A7 in FIG. 9C) so that the opening O of the LAA is caused to move or constrict around an outside surface of the implant device 142. An operator can twist or rotate the contact member 144 by twisting or rotating the core member 153 of the catheter 152. The tightening or constriction of the opening O of the LAA around an outside surface of the proximal portion 144*a* of the contact member 144 or other portion of the implant device can result in the occlusion, or substantial occlusion, or substantial closing off of the interior portion of the LAA from the remaining chambers within the heart, thereby substantially reducing the health risks associated with an open LAA. In any embodiments disclosed herein, the implant 142 can be configured to be removed after the securing element is applied to the tissue that has been constricted by the twisting of the contact member so that the only portion of the implant device 142 left in the LAA or the heart is the securing element 150.

Figure 9E:
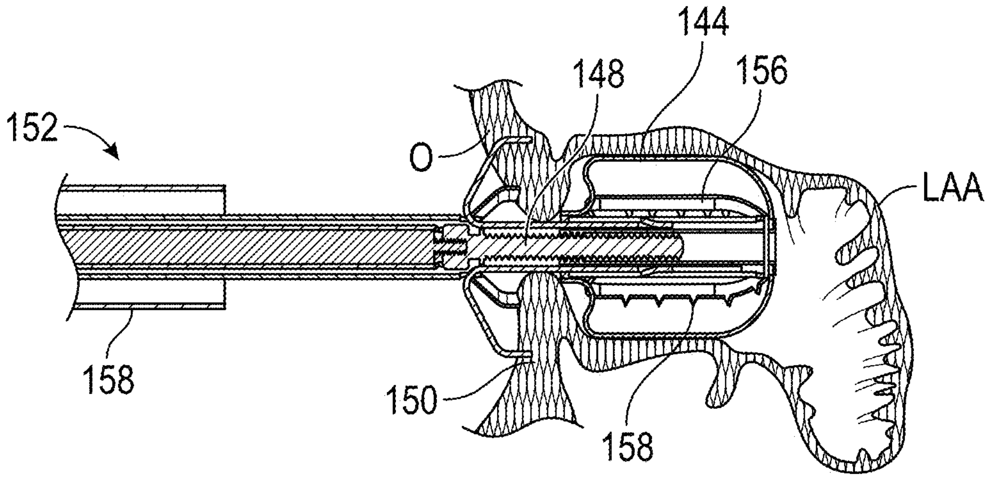
FIG. 9E shows the securing element of the treatment device of FIG. 9A engaged with the patient's tissue that has constricted as a result of the twisting of the LAA.
Figure 9F:
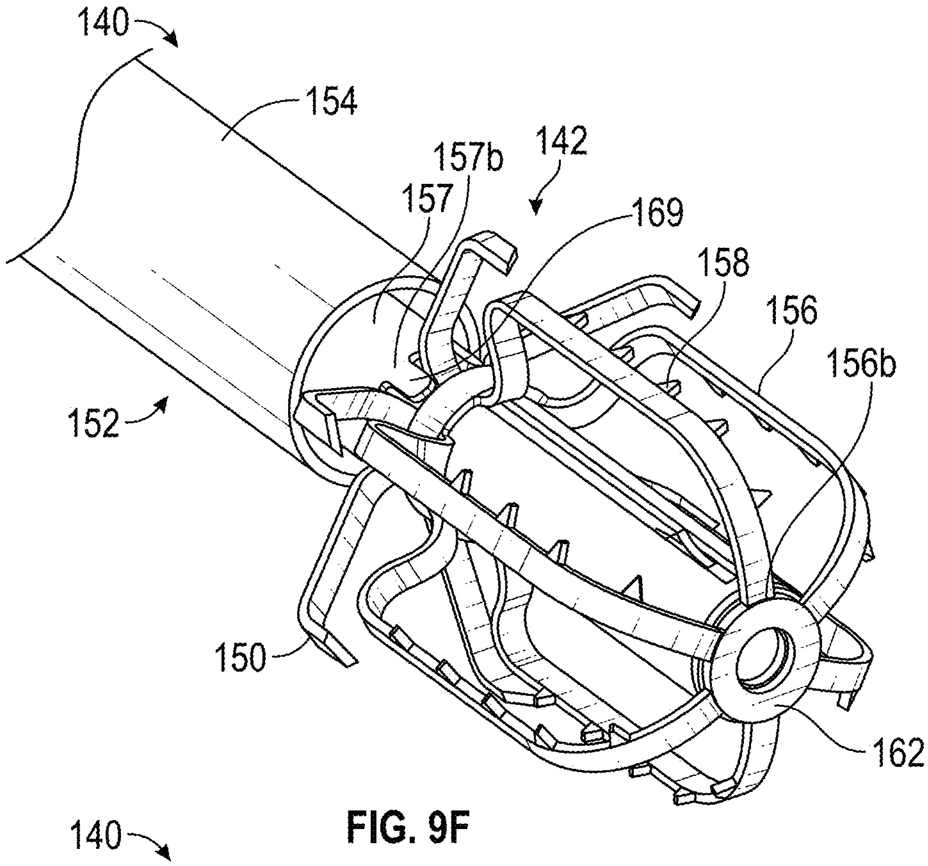
FIG. 9F shows the treatment device of FIG. 9A wherein the contact member is in a second, expanded state, the retention element is in a second, contracted state, and the securing element is in a second, open state.
Figure 9G:
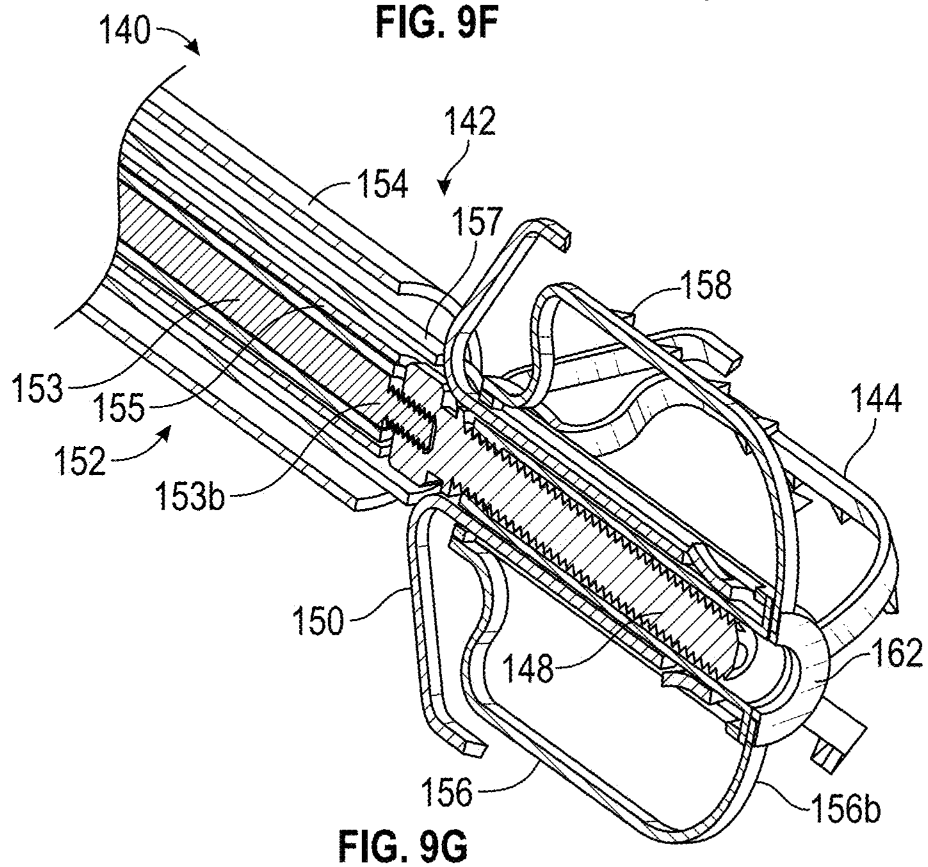
FIG. 9G is a section view of the treatment device shown in FIG. 9A, taken through line 9G-9G of FIG. 9F.
Figure 9H:
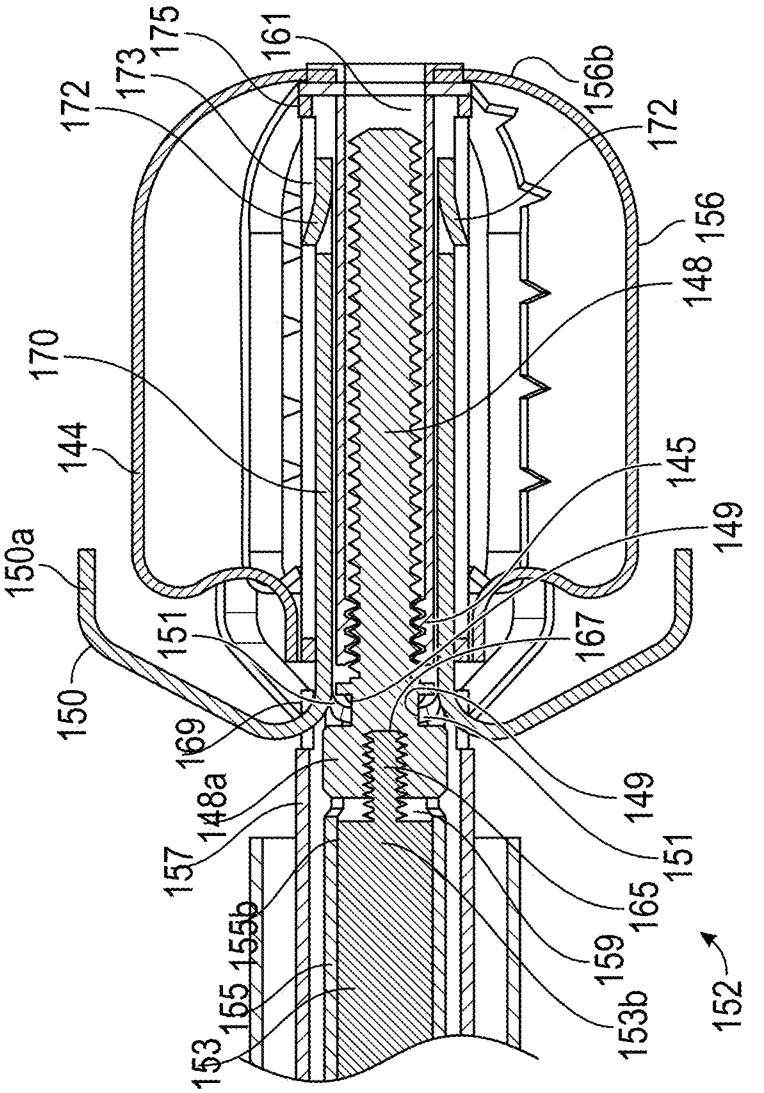
FIG. 9H shows an enlarged side view of the treatment device of FIG. 9A.
Figure 9I:
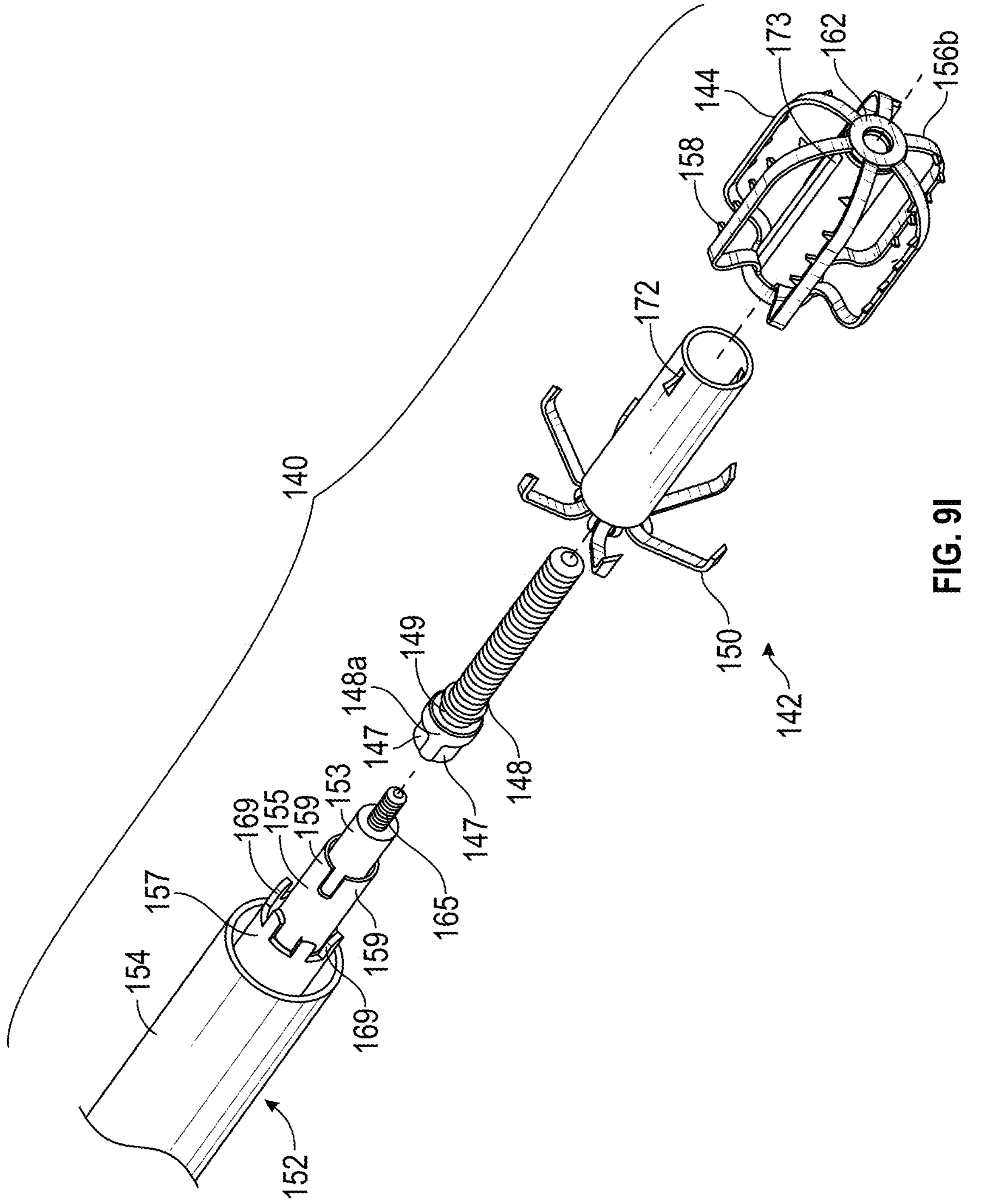
FIG. 9I shows an exploded view of the treatment device of FIG. 9A.

The retention element 148 can be used to couple the securing element 150 to the contact member 144 and to also allow a user (such as a surgeon) to move the securing element 150 toward and away from the contact member 144. In any embodiments, the retention element 148 can have helical threads on an outer surface thereof. In any embodiments, the retention element 148 can comprise a threaded shaft. In this configuration, the retention element 148 can be rotated in a first direction to advance the securing element 150 toward the contact member 144, and rotated in a second, opposite direction to move the securing element 150 away from the contact member 144. The retention element 148 can be configured to engage the securing element 150 such that, when the retention element 148 rotates, the securing element 150 moves in an axial direction corresponding to the rotation of the retention element 148. For example and without limitation, the retention element 148 can have an annular recess 149 near a proximal end 148*a* thereof that is configured to engage or couple with a tab or projection 151 of the securing element 150. In some embodiments, the projection 151 can extend into the annular recess 149 so as to axially lock or engage the securing element 150 with the retention element 148. The interaction of the projection 151 with the annular recess 149, wherein the walls of the annular recess contact and push the projection 151, causes the retention element 148 to move the securing element 150 when the retention element 148 is rotated. In some embodiments, as in the illustrated embodiment, the securing element 150 can have two tabs 151, both engaged with the annular recess 149. The contact member 144 can have a threaded neck portion 145 that threadedly engages the threads of the retention element 148 so that the retention element 148 threads into and out of the threaded neck portion 145. In this configuration, the retention element 148 threads into and out of the contact member 144 to cause the securing element 150 to move relative to the contact member. As shown in FIG. 9H, the retention element 148 is nearly completely threaded into the contact member 144 and into the cavity or space 161 within the contact member 144 such that the securing element 150 is moved toward the contact member 144 about as much as the securing element 150 can be. As the retention element 148 is rotated in the second direction, the retention element 148 will move out of the space 161 within the contact member 144 and move the securing element 150 away from the contact member 144.

With reference to FIG. 9H, an intermediate sleeve 155 can be advanced distally into contact with and engage a proximal end portion 148*a* of the retention element 148. The intermediate sleeve 155 can be configured such that, when the intermediate sleeve 155 is engaged with the proximal end portion 148*a* of the retention element 148, the retention element 148 can be rotated in the first or second direction by rotating the intermediate sleeve 155 in the first or second direction. In some embodiments, the intermediate sleeve 155 can be moved axially and rotated independently of the other tubes or sleeves of the catheter 152. For example and without limitation, as shown in FIG. 9H, projections or tabs 159 on a distal end portion 155*b* of the intermediate sleeve 155 can selectively couple with or be advanced into recesses or depressions 147 formed in the proximal end portion 148*a* of the retention element 148 that can selectively key or index the intermediate tube 155 with the retention element 148.

Further, in any embodiments, retention element 148 can be used to couple the implant 142 to the delivery catheter 152. For example and without limitation, the core member 153 of the delivery catheter 152 can be coupled with the retention element 148 via a threaded projection 165 at a distal end 153*b* of the core member 153 that threadedly engages a threaded recess 167 formed in a proximal end portion 148*a* of the retention element 148. The threaded projection 165 can be formed separately from and coupled with a distal end of the core member 153, or can be formed monolithically therewith. In this configuration, the implant 142 can be removed from the catheter by disengaging the threaded projection 165 from the retention element 148. This can be performed by preventing a rotation of the retention element 148 using the intermediate tube 155 while the core member 153 is being rotated in a second direction so as to withdraw the threaded projection 165 from the recess 167 of the retention element 148.

Further, a second intermediate tube or sleeve 157 can be advanced distally into contact with and engage a proximal end portion 150*a* of the securing element 150. The second intermediate sleeve 157 can be configured such that, when the second intermediate sleeve 157 is engaged with the proximal end portion 150*a* of the securing element 150, the securing element 150 can be rotated in the first or second direction by rotating the second intermediate sleeve 157 in the first or second direction. In some embodiments, the second intermediate sleeve 157 can be moved axially and rotated independently of the other tubes or sleeves of the catheter 152. For example and without limitation, as shown in FIG. 9H, projections or tabs 169 on a distal end portion 157*b* of the second intermediate sleeve 157 can selectively couple with the struts or arms of the securing element 150 so that the second intermediate sleeve 157 can be keyed or indexed to the securing element 150.

Further, in some embodiments, the securing element 150 can be keyed or indexed to the contact member 144 so that the securing element 150 and the contact member 144 rotate dependently and simultaneously. For example, in some embodiments, the securing element 150 can have a body portion 170 having one or more tabs or projections 172 that are configured to extend into a channel or recess 173 formed in a body portion 175 of the contact member 144. One or more channels 173 can be formed in an axial orientation such that the projection(s) 172 of the securing element 150 and the securing element 150 can freely move in an axial direction relative to the contact member 144. However, a narrow width of the channel(s) 173 relative to the projection(s) 172 can prevent the projection(s) 172 and, hence, the securing element 150 from rotating relative to the contact member 144.

In this configuration, the second intermediate sleeve 155 can be coupled with the securing element 150 and can be used to at least rotate the implant 142 in the first or second direction. For example and without limitation, the second intermediate sleeve 155 can be rotated to rotate the contact member 144 to twist the LAA to the desired level of rotation and/or torque. Thereafter, the second intermediate sleeve 155 can be used to maintain the desired position (e.g., rotational position) of the contact member 144 by maintaining the second intermediate sleeve 155 in contact with the securing element 150 and in a fixed rotational position, hence holding the contact member 144 in a fixed rotational position while the retention element 148 is rotated in the first direction to advance the securing element 150 toward the contact member 144. Once the securing element 150 is in the desired axial position (for example, engaged with the tissue of the LA/LAA that has constricted as a result of the twisting of the contact member 144), the implant 142 can be removed from the catheter 152 by disengaging the threaded projection 165 from the retention element 148 as described above, and the catheter can be removed from the LA. With the securing element 150 engaged with the patient's tissue, as illustrated in FIG. 9E, the LAA can be prevented from rotating to the first rotational position, which is the untwisted or relaxed position. In this configuration, the implant device 142 can secure and maintain the LAA in a substantially or completely occluded or substantially or completely closed state.

Figure 11:
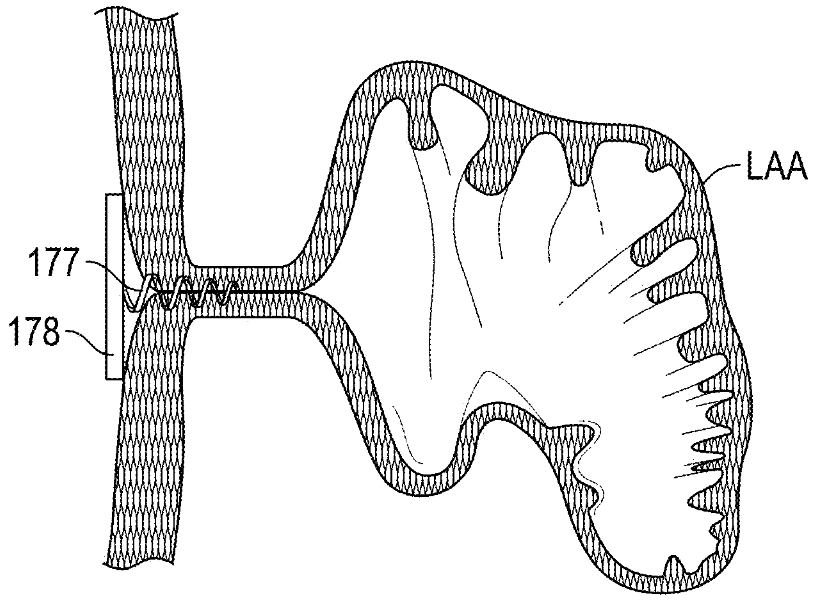
FIG. 11 shows an embodiment of a securing element implanted adjacent to an occluded opening of the LAA.
Figure 12:
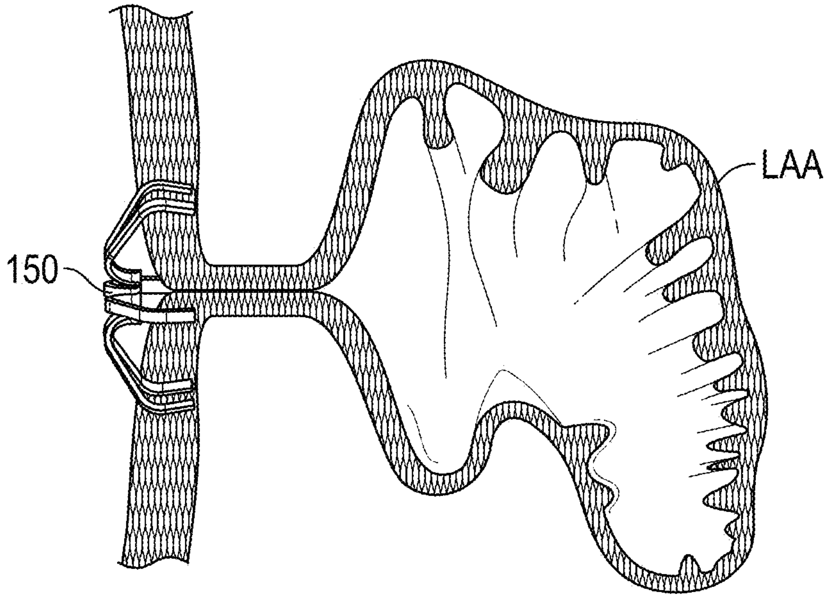
FIG. 12 shows another embodiment of a securing element implanted adjacent to an occluded opening of the LAA.

Further, in any embodiments, the device can be configured such that the contact member 144 can be removed from the patient's LAA after the securing element 150 is engaged with the tissue sufficiently to hold the tissue in a closed or occluded state, for example as shown in FIGS. 11-12, wherein the securing element 177 and the securing element 150 are the only components remaining within the body following the completion of the implant procedure. In this configuration, the implant can have a plug or cover (such as cover 178 coupled with the securing member 177) that can cover the opening in the implant that the contact member (such as contact member 180 or contact member 144) is withdrawn through, or be otherwise configured to plug or cover the opening in the implant that the contact member 144 is withdrawn through. For example and without limitation, a cover member such as cover member 121 can be coupled with the securing element 150 to substantially cover any openings in the implant, or can be coupled with the contact member 144 so as to cover the contact member 144 inside the LAA, in configurations where the contact member 144 remains in the LAA after the securing element 150 has been implanted.

Additionally, in some embodiments, the contact member 144 can have a continuous and uninterrupted circumference at a proximal end 144*a* that each of the strut members 156 extend distally away from. Each of the strut members 156 can be preformed into a curved shape such that the strut members 156 are biased to expand to the second state when no external restraint or constraint is applied to the outside surface of the contact member 144 (for example, when in a relaxed state). At a distal end, each of the strut members 156 can, but are not required to, couple with a hub member 162. Similar to the hub member 122 described above, the hub member 162 can have a plurality of receptacles (not shown) configured to receive and constrain distal end portions 156*b* of each of the strut members 156. Additionally, each of the receptacles 163 can be configured to permit the distal end portions 156*b* of each of the strut members 156 to rotate relative to the hub member 162 so that the distal end portions 156*b* of the strut members 156 can extend generally radially away from the hub member 163 when the contact member 144 is in the second, expanded state. The hub member 163 can be configured to permit the distal end portions 156*b* of each of the strut members 156 to rotate relative to the hub member 162 without resistance or significant resistance. In any embodiments, the distal ends of each of the strut members 156 can have a tab or other feature (such as a T shaped termination or other increased width) (not shown) that locks into, is secured by, or is otherwise engaged by each of the receptacles 163 so as to axially constrain the end portion of each of the strut members 156, while allow rotation about the end portion.

Figure 9J:
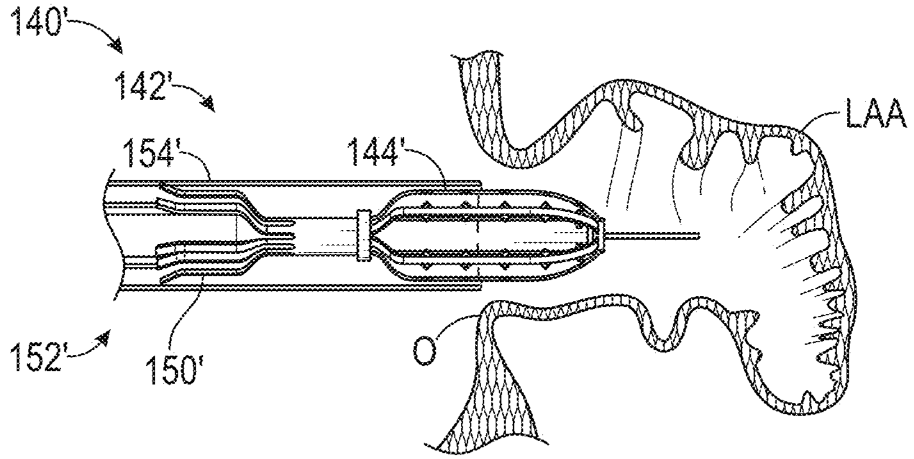
FIG. 9J shows another embodiment of a treatment device for treating the LAA, showing the contact member being advanced into the LAA before being expanded.
Figure 9K:
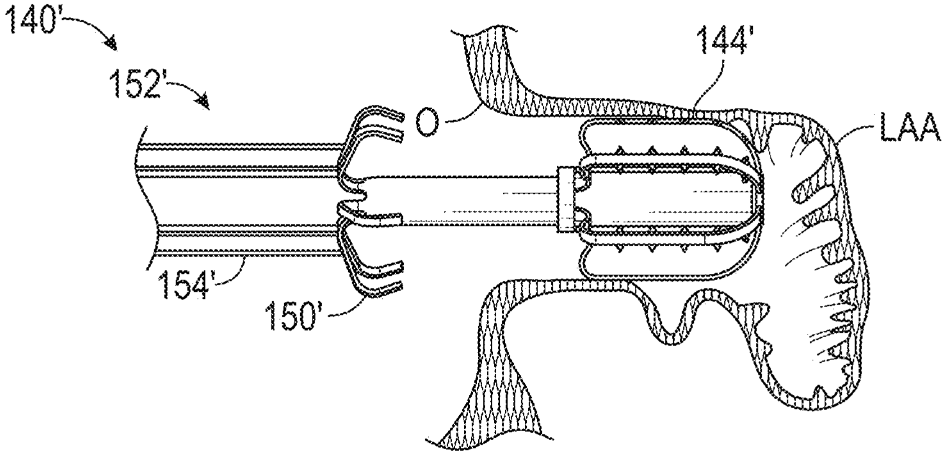
FIG. 9K shows the embodiment of the treatment device of FIG. 9J, showing the contact member engaging a wall of the LAA.

In any embodiments of the devices and methods disclosed herein, the securing element can be configured such that the arms or struts of the securing element extend in a proximal direction when the securing element is in a first or collapsed state. In some embodiments, the securing element can be in a first or collapsed state within the delivery catheter, within a restraint, and/or wherein just the struts of the securing element are restrained or secured in a collapsed position, such as with a retaining element that slides or moves over the struts in an axial direction. FIGS. 9J-9K show another embodiment of a treatment device 140'. In any embodiments disclosed herein, any components, features, or other details of the treatment device 140' or implant device 142' can have any of the components, features, or other details of any other treatment device embodiments or implant device embodiments disclosed herein, including without limitation any of the embodiments of the treatment device 140 or implant device 142, or treatment device 100 or implant device 102 described above, in any combination with any of the components, features, or details of the treatment device 140' or implant device 142' disclosed below. Similarly, any components, features, or other details of any of the other treatment device embodiments or implant device embodiments disclosed herein can have any of the components, features, or other details of any embodiments of the treatment device 140' or implant device 142' disclosed herein in any combination with any of the components, features, or details of the treatment device and/or implant device.

With reference to FIGS. 9J-9K, some embodiments of the delivery device 140' can have a securing element 150' having one or more struts or arms that can extend in a proximal direction when the securing element is in a first or collapsed state. In some embodiments, the arms can reverse direction as the arms expand or are expanded to the second state so that the distal ends of the arms extend toward the contact member 144', as shown in FIG. 9K. For example, in some embodiments, an outer sleeve 154' of the treatment device 140' can be retracted to expose and/or unrestrain the securing element 150'. As restraint is removed from the securing element 150', the arms of the securing element 150' can unfold or rotate in the distal direction—for example, toward the contact member 144'. The securing element 150' can thereafter be advanced distally so that at least the distal points or portions the arms of the securing element 150' penetrate into the tissue of the LAA and/or LA that has gathered constricted as a result of the twisting of the LAA. The securing element 150' can be held or biased in the second rotational position wherein the securing element 150' is engaged with the tissue of the heart, such as is shown in FIG. 9E.

FIGS. 9L-9P show another embodiment of a treatment device 140" treating the LAA. In any embodiments disclosed herein, any components, features, or other details of the treatment device 140" or implant device 142" thereof can have any of the components, features, or other details of any other treatment device embodiments or implant device embodiments disclosed herein, including without limitation any of the embodiments of the treatment device 140 or implant device 142, or treatment device 100 or implant device 102 described above, in any combination with any of the components, features, or details of the treatment device 140" or implant device 142" disclosed below. Similarly, any components, features, or other details of any of the other treatment device embodiments or implant device embodiments disclosed herein can have any of the components, features, or other details of any embodiments of the treatment device 140" or implant device 142" disclosed herein in any combination with any of the components, features, or details of the treatment device and/or implant device.

Figure 9L:
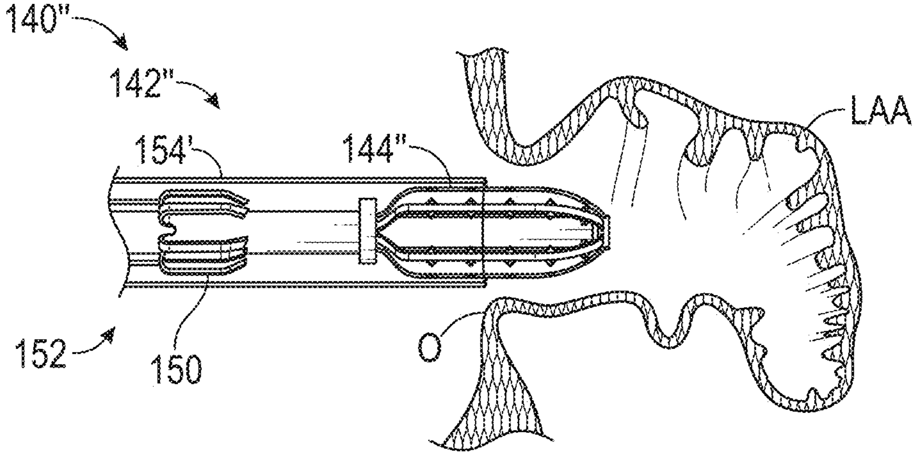
FIG. 9L shows another embodiment of a treatment device for treating the LAA, showing the contact member being advanced into the LAA without being expanded.
Figure 9M:
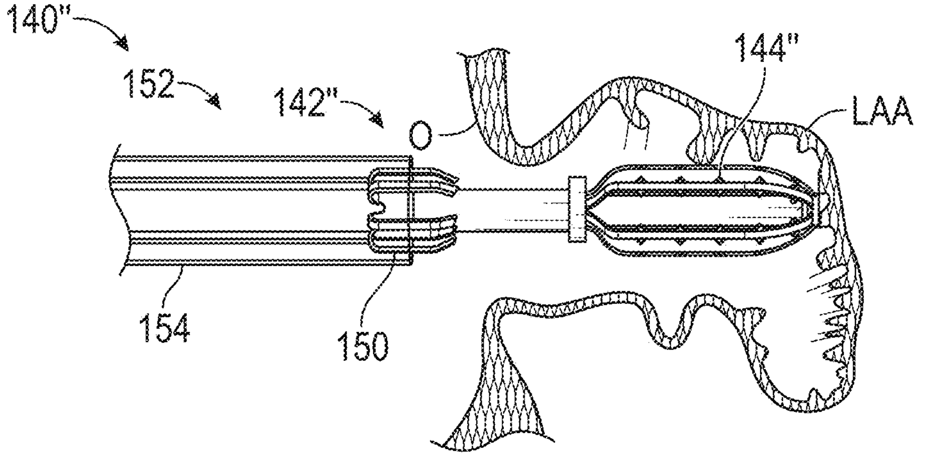
FIG. 9M shows the embodiment of the treatment device of FIG. 9L, showing the contact member being advanced into contact with an inner wall surface of the LAA.
Figure 9N:
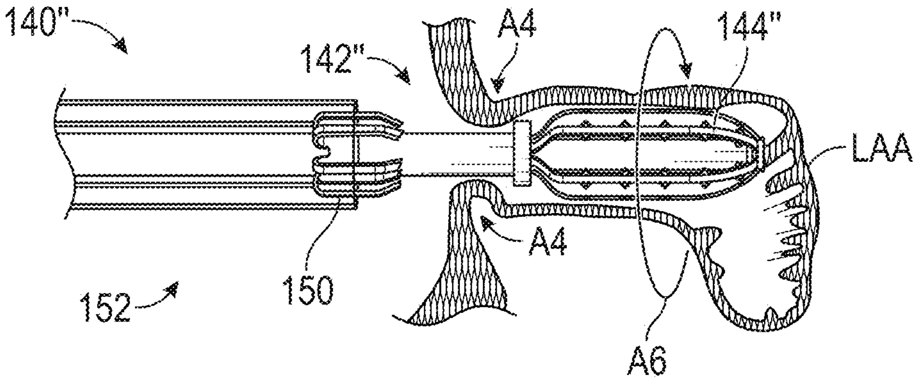
FIG. 9N shows the embodiment of the treatment device of FIG. 9L, showing the contact member being rotated to twist the LAA and cause a neck or opening of the LAA to occlude and/or constrict around a portion of the implant device.
Figure 9O:
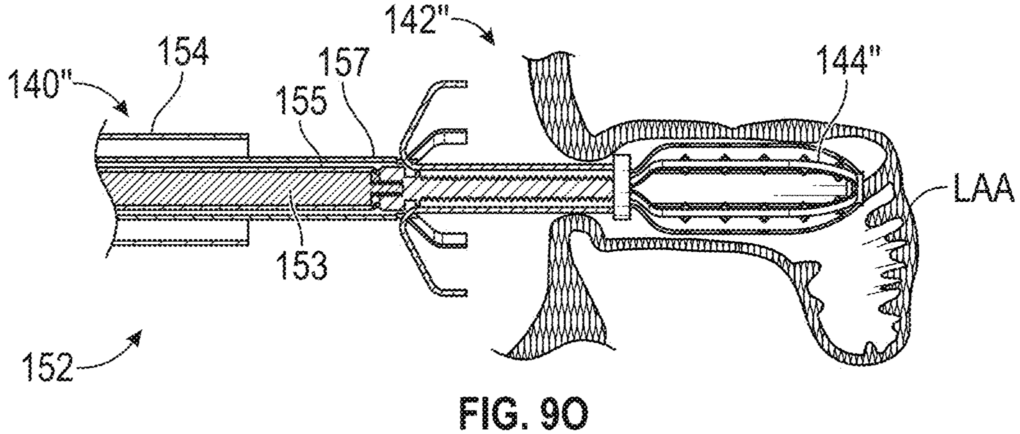
FIG. 9O shows the embodiment of the treatment device of FIG. 9L, showing the securing element of the embodiment of the implant device being advanced toward the contact member of the implant device.
Figure 9P:
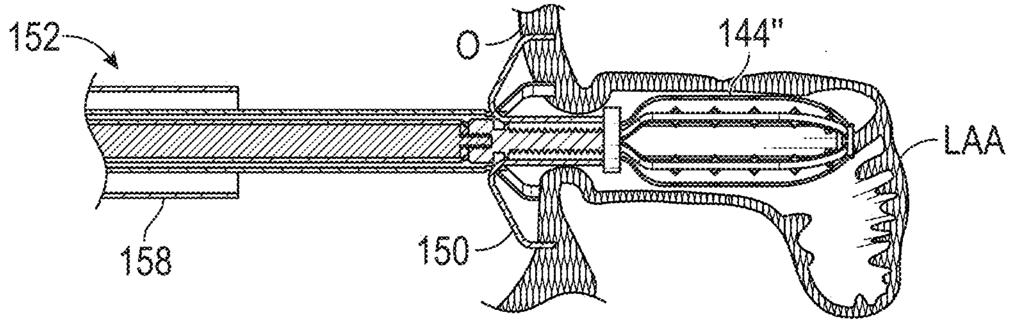
FIG. 9P shows the securing element of the treatment device of FIG. 9L engaged with the patient's tissue has constricted as a result of the twisting of the LAA.

In any embodiments of the devices and methods disclosed herein, the contact member 144" can be non-expandable or otherwise be configured to not expand or not change size or shape during the entire treatment procedure. For example and without limitation, the contact member 144" can remain in the same or a similar size and/or shape or can maintain the same or a similar size and/or shape during the entire treatment procedure. In this configuration, the contact member 144" can have the same or a similar size and/or shape when the contact member 144" is positioned within the delivery catheter 152 (as shown in FIG. 9L) as when the contact member 144" has been extended past a distal end of the delivery catheter 152 and is in engagement with a tissue surface on any inside of the LAA (as shown in FIG. 9M). Further, in any embodiments, the contact member 144" can have the same or a similar size and/or shape when the contact member 144" is rotating to a second rotational position or is twisting the LAA to a second rotational position (as shown in FIG. 9N) and when the contact member 144" has been rotated to a second rotational position or has twisted the LAA to a second rotational position (as shown in FIGS. 9O and 9P).

Figure 10A:
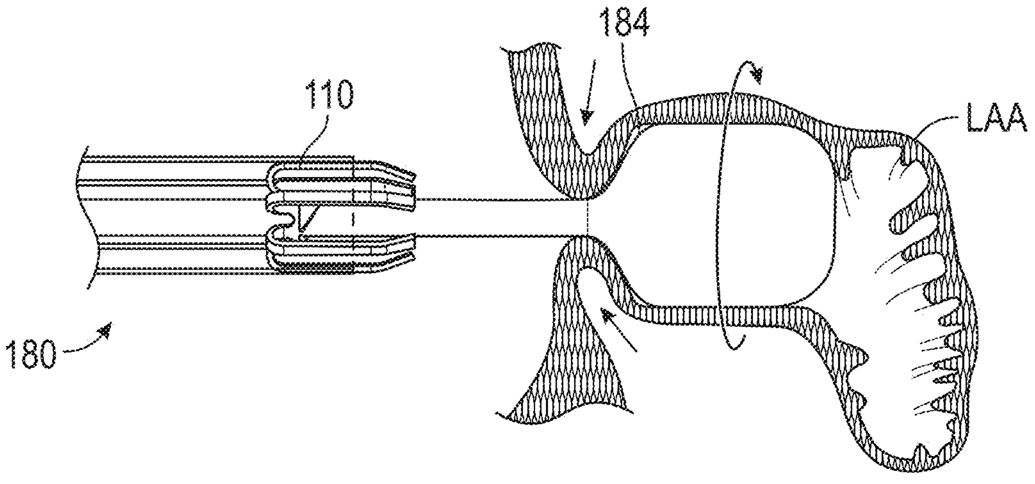
FIG. 10A shows another embodiment of a treatment device for treating the LAA, showing the contact member of the treatment device being expanded within the LAA.

Additionally, as described above, in any embodiments disclosed herein, the implant device can be configured such that the contact member can be removed from the patient's LAA after the securing element engages the tissue to hold the ostium of the LAA in a closed state. For example, with reference to FIG. 10A, in any embodiments disclosed herein, the contact member can be an expansion balloon such as expansion balloon 184. The balloon can have a smooth outside surface, or can have dimples, projections, rough texture, tissue anchors, or otherwise to engage the inside surface of the LAA. In some embodiments, the balloon can be a typical expansion balloon such as a balloon used in angioplasty procedures, and can be sized and configured for use in LAA. With reference to FIG. 10A, the distal end portion of the expansion balloon can have an atraumatic surface to reduce the risk of any injury to the tissue of the LAA or otherwise. In any embodiments of the implant devices or contact members disclosed herein, the contact member can be configured to have an atraumatic distal tip, such as a distal tip made from or covered by a rubber material or other soft or atraumatic material.

Further, any embodiments of the balloons or implant members disclosed herein can have any of the features, components, shapes, sizes, or other details of any of the expansion members shown in FIGS. 10E-10L, and any of the treatment device embodiments disclosed herein can use any of the embodiments of the expansion members disclosed in FIGS. 10E-10L in place of or in combination with the contact members of such treatment device embodiments. Further, any of the expansion members shown in FIGS. 10E-10L can have an atraumatic distal tip. For example and without limitation, the expansion members shown in FIGS. 10E-10L can extend to the distal end of the device so that the distal portions of the expansion members shown in FIGS. 10E-10L are atraumatic. Additionally, in any embodiments disclosed herein, the expansions members and/or contact members can include a compliant or adjustable balloon in which the diameter of the balloon can be adjusted by the surgeon or user based on pressure of inflation, thereby customizing the size of the contact member at the point of use to achieve the best closure in varied LAA shapes and sized.

With reference to the figures, some expansion members can have points, protrusions, linearly arranged ridges, wire mesh structures, wire frame structures, channels, and other features to improve the engagement of the expansion members with the tissue of the LAA. In any of these configurations, after the LAA has been rotated and/or torqued to the desired degree and the securing element implanted to hold the opening of the LAA sufficiently closed or constricted, the balloon can be deflated and removed from the LAA, leaving only the securing element to maintain the LAA in the occluded state, as shown in the nonlimiting examples of FIGS. 11-12.

Figure 10B:
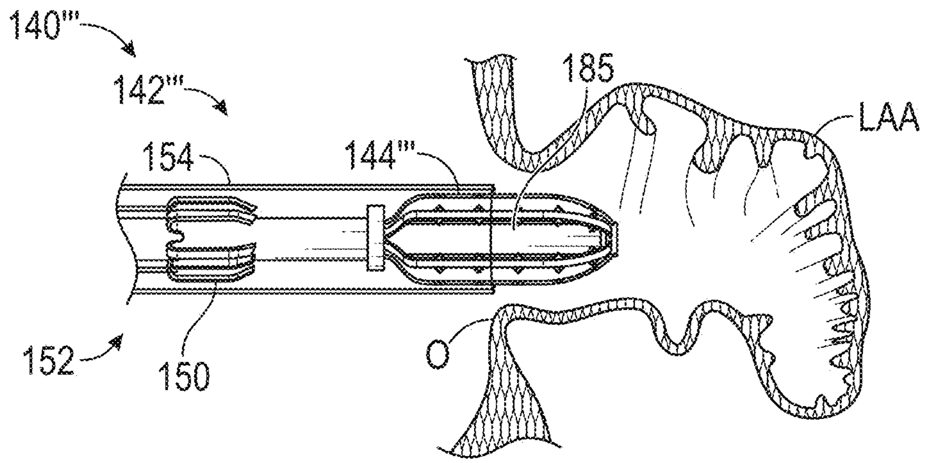
FIG. 10B shows another embodiment of a treatment device for treating the LAA, showing the contact member of the treatment device being advanced into the LAA.
Figure 10C:
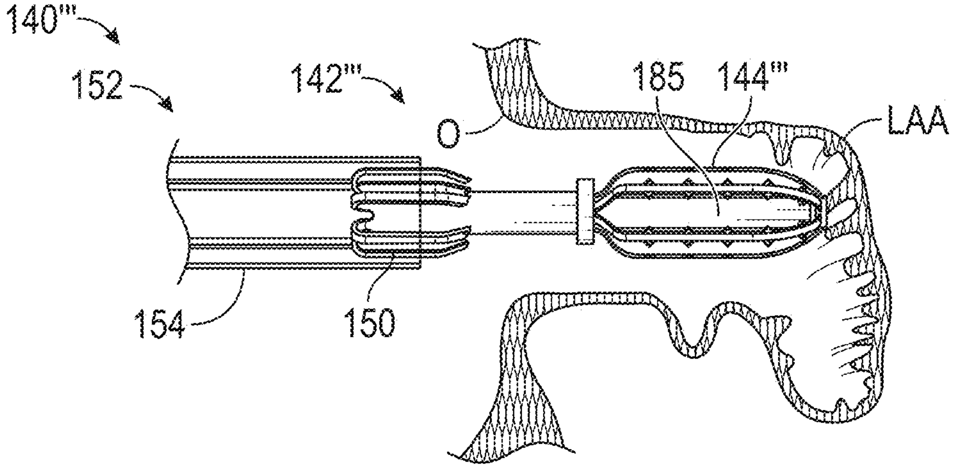
FIG. 10C shows the embodiment of the treatment device shown in FIG. 10B, showing the contact member advanced into the LAA in a pre-expanded state.
Figure 10D:
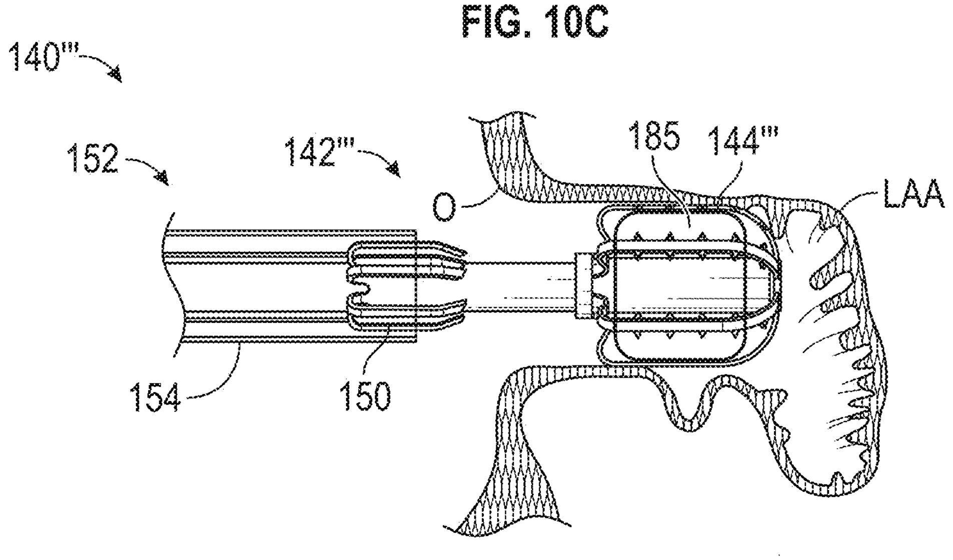
FIG. 10D shows the embodiment of the treatment device shown in FIG. 10B, showing the contact member being expanded so as to engage an inside surface of the tissue of the LAA.
Figure 10E:
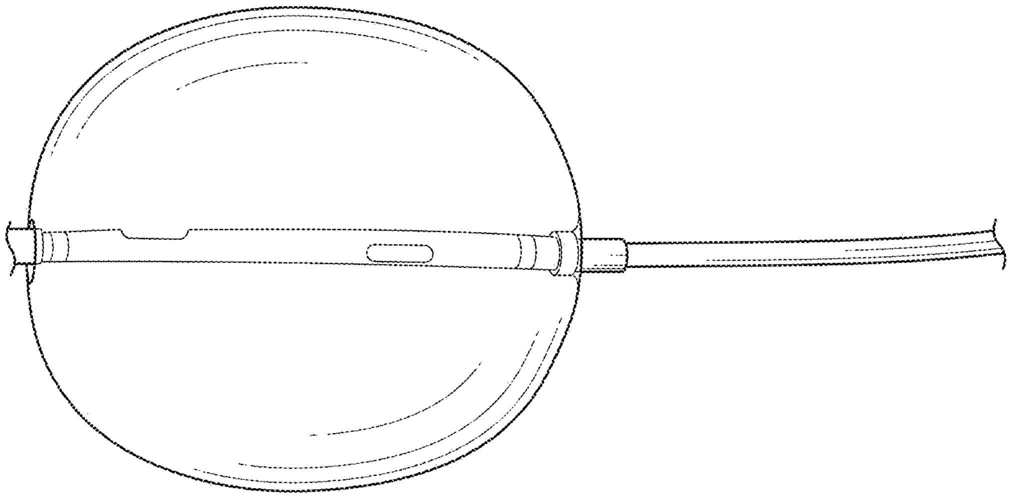
FIGS. 10E-10L show different embodiments of expandable members that can be used with any of the treatment devices or implant devices disclosed herein.
Figure 10F:
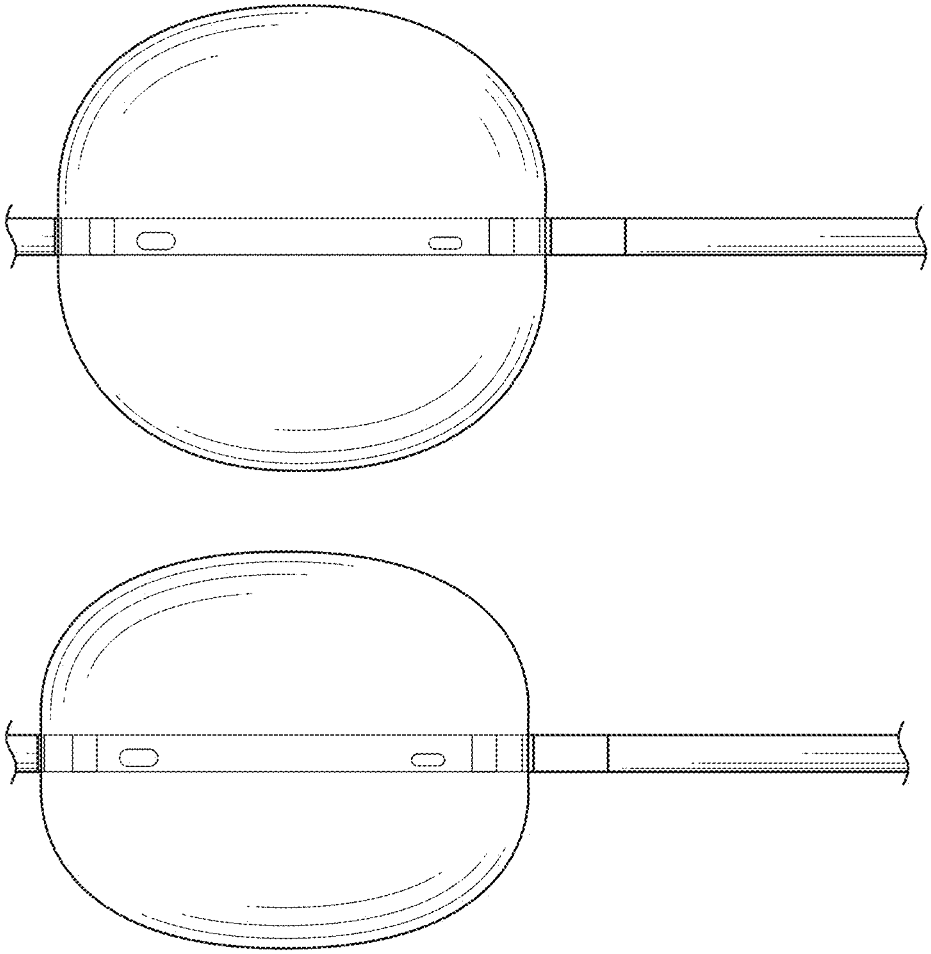
Figure 10G:
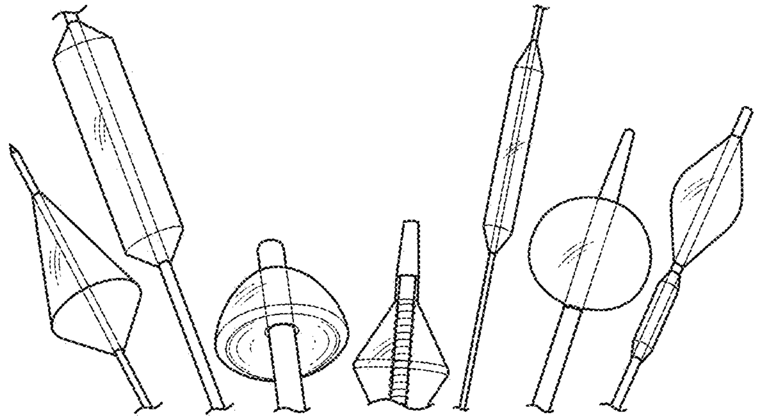
Figure 10H:
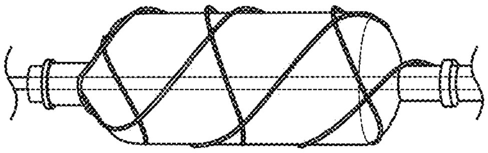
Figure 10I:
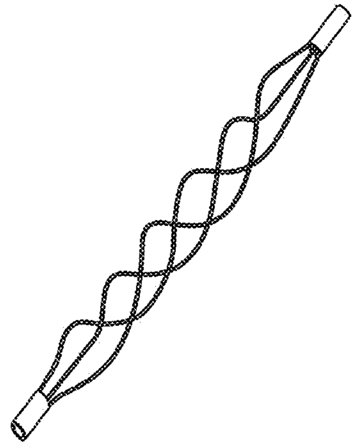
Figure 10J:
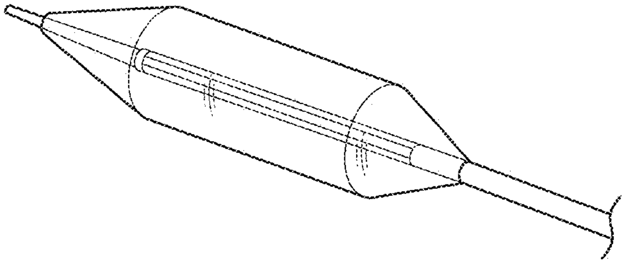
Figure 10K:
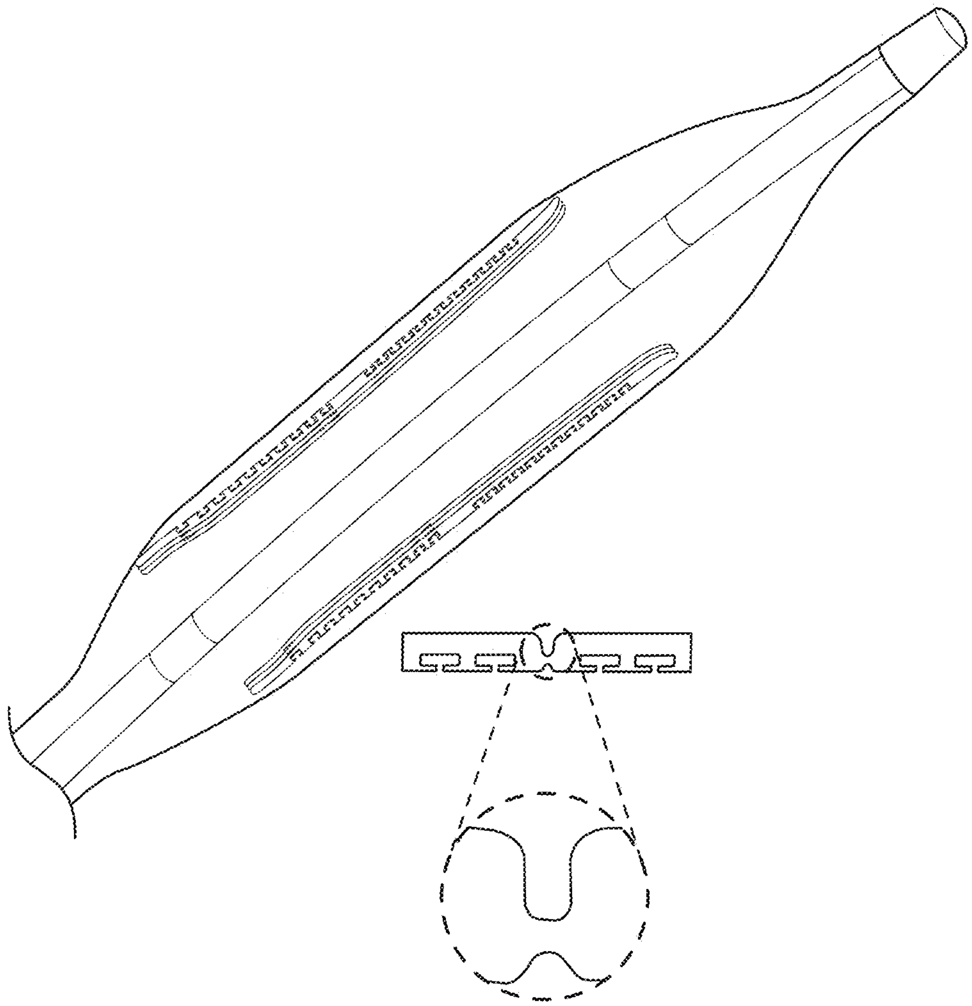
Figure 10L:
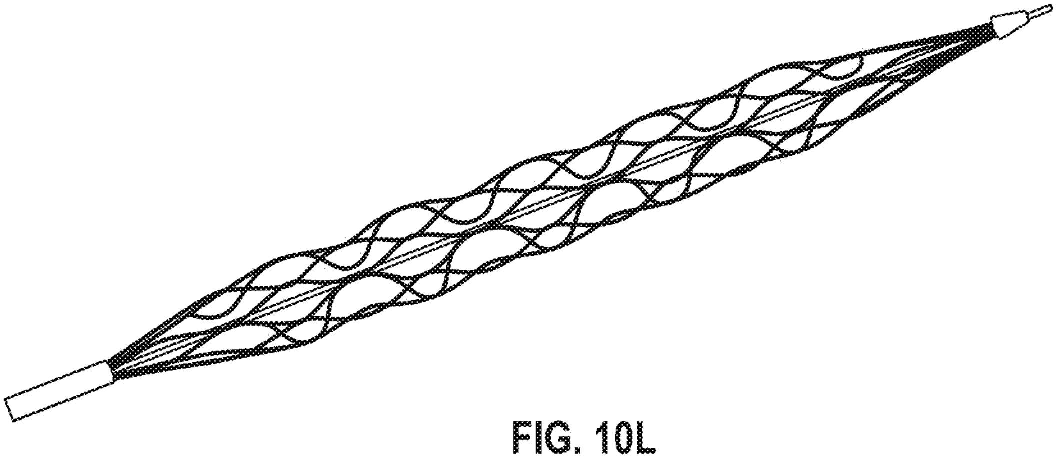

FIG. 10B shows another embodiment of a treatment device 140''' for treating the LAA, showing the contact member 144''' of the treatment device 140''' being advanced into the LAA. FIG. 10C shows the contact member 144''' advanced into the LAA in a pre-expanded state. However, in other embodiments, the contact member 144''' can be expanded in the LA and advanced into the LAA in an expanded state. FIG. 10D shows the contact member 144''' expanded so as to be engaged with an inside surface of the tissue of the LAA.

In some embodiments, as with other embodiments disclosed herein, the contact member 144''' can be configured to be expandable, for example and without limitation, mechanically expandable such as using an expandable or inflatable balloon. Further, any embodiment of the treatment device 140''' and/or the contact member 144''' can have any of the features, components, or details of any other treatment device or contact member embodiments disclosed herein in place of or in combination with any of the features, components, or other details of the embodiments of the treatment device 140''' and/or the contact member 144''' disclosed herein. Similarly, any of the other embodiments of the treatment devices and/or contact members disclosed herein can have any of the features, components, or details of the treatment device 140''' and/or the contact member 144''' disclosed herein, including a mechanically or balloon expanded contact member.

In some embodiments, the contact member 144''' can be expanded to an approximately spherical or elongated spherical shape. In other embodiments, the contact member 144''' can be expanded to an approximately cylindrical shape, a stent-like shape, or any other suitable or desired shape, including one which matches a shape of an inside of the LAA.

For example and without limitation, any embodiments of the contact member 144''' can have a plurality of struts or arms having a plurality of tissue anchors or barbs thereon configured to engage the tissue of the LAA. In other embodiments, the contact member 144''' can be barbless and/or have any other desired shape, such as any of the shapes of any other contact member or implant embodiments disclosed herein.

With reference to FIGS. 10B-10D, the contact member 144''' or any other contact member disclosed herein can have an inflatable or expandable balloon 185 in an interior space of the contact member 144''', the balloon being selectively actuatable to expand the contact member 144''' so that the contact member 144''' can be expanded against an inside surface of the LAA. Any embodiments of the treatment device 140''' can be configured such that the contact member 144''' can be expanded to any desired desire size and/or shape. In some embodiments, a surgeon or other user of the treatment device 140''' can control a level of inflation of the balloon 185 within the contact member 144''' through controlled inflation and/or deflation of the balloon 185 so that the contact member 144''' can be expanded to any of a range of sizes. For example and without limitation, the balloon 185 and the contact member 144''' can be partially expanded for smaller LAA anatomy, or more fully expanded for larger LAA anatomy. In some embodiments, any of the balloons or expandable members disclosed herein can have an outer diameter or size that can range from 4 mm (or approximately 4 mm) or less to 16 mm (or approximately 16 mm) or more in a deflated or first state, or from 4 mm (or approximately 4 mm) to 10 mm (or approximately 10 mm) in the deflated or first state, and/or from 10 mm (or approximately 10 mm) or less to 40 mm (or approximately 40 mm) or more in an expanded or second state, or from 15 mm (or approximately 15 mm) to approximately 35 mm (or approximately 35 mm) in the expanded or second state.

In any embodiments, the balloon 185 can be removed from the contact member 144''' after the desired level of expansion of the contact member 144''' is reached by deflating and withdrawing the balloon 185 through an axial opening in the contact member 144'''. In other embodiments, the treatment device 140''' can be configured such that the balloon 185 can remain in the contact member 144''', even after the procedure has been completed and the LAA has been occluded. The balloon 185 can remain in the contact member 144''' in an inflated state, a deflated state, or a partially inflated state.

Figure 13:
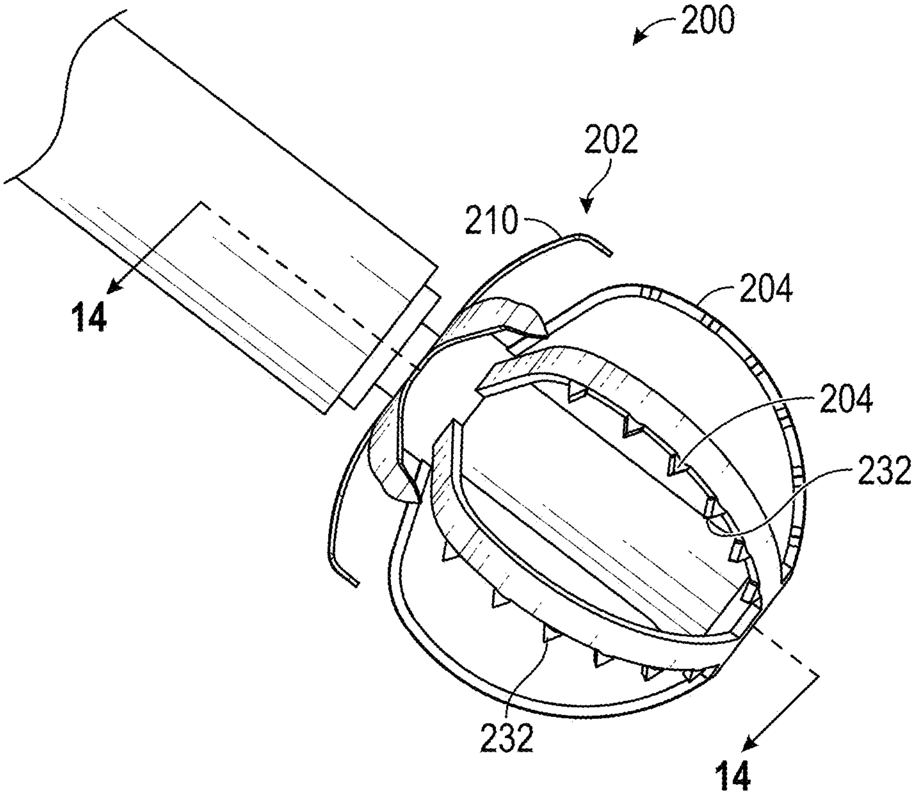
FIG. 13 shows another embodiment of treatment device having an implant device wherein the contact member is in a second, expanded state, the retention element is in a second, contracted state, and the securing element is in a second, open state.
Figure 14:
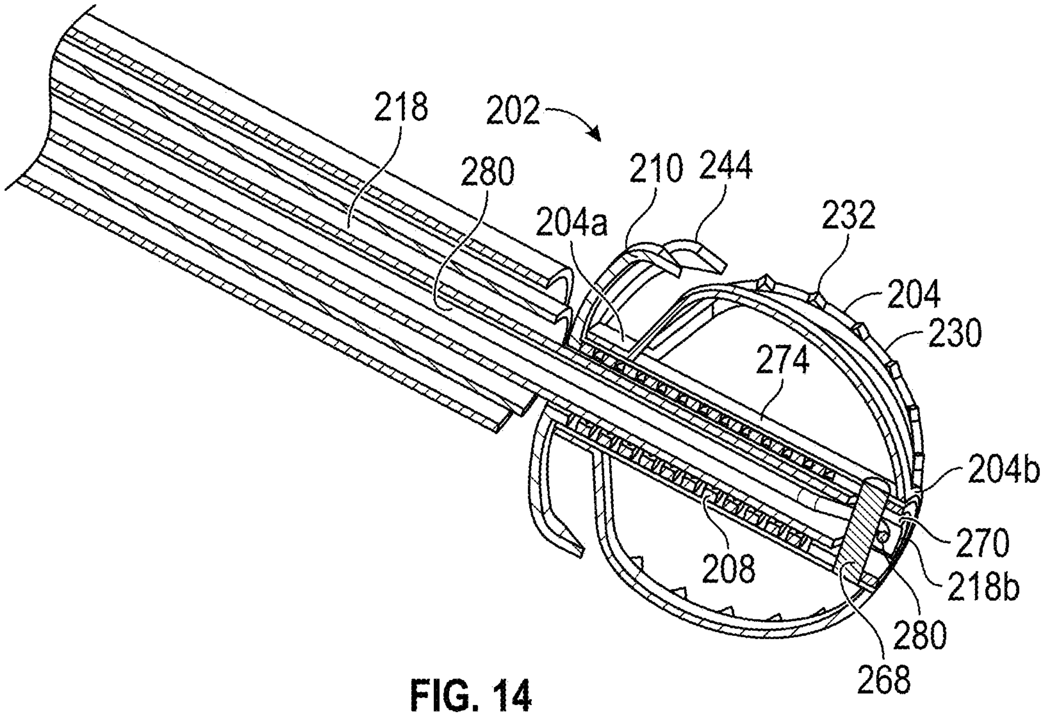
FIG. 14 is a section view of the treatment device shown in FIG. 13, taken through line 14-14 of FIG. 13.

FIG. 13 shows another embodiment of treatment device 200 having an implant device 202, wherein the contact member 204 of the implant device 202 is in a second, expanded state, the retention element 208 is in a second, contracted state, and the securing element 210 is in a second, open state. FIG. 14 is a section view of the embodiment of the treatment device 200 shown in FIG. 13, taken through line 14-14 of FIG. 13. In any embodiments disclosed herein, any components, features, or other details of the treatment device 200 or implant device 202 can have any of the components, features, or other details of any other treatment device embodiments or implant device embodiments disclosed herein, including without limitation any of the embodiments of the treatment device 100 or implant device 102 described above, in any combination with any of the components, features, or details of the treatment device 200 or implant device 202 disclosed below. Similarly, any components, features, or other details of any of the other treatment device embodiments or implant device embodiments disclosed herein can have any of the components, features, or other details of any embodiments of the treatment device 200 or implant device 202 disclosed herein in any combination with any of the components, features, or details of the treatment device and/or implant device.

With reference to FIGS. 13-14, in some embodiments, the contact member 204 can have an annular proximal end portion 204*a* wherein all of the arms or struts 230 (six being shown) of the contact member 204 extend distally away from the proximal end portion 204*a*. The struts 230 can have any form of tissue anchors 232 on the struts or attached to the struts, such as any of the tissue anchors 118 described above.

Additionally, in some embodiments, the contact member 204 can have an annular distal end portion 204*b* wherein all of the arms or struts 230 can be coupled with the annular distal end portion 204*b*. The contact member 204 can have a bulbous shape, cylindrical shape with a curved distal portion, an elongated spherical shape, or otherwise. In some embodiments, the contact member 204 can be laser cut from a hypotube, or can be formed from different components and welded, brazed, or otherwise coupled together. Each of the strut members 230 can be preformed into a curved shape (which can have a spherical or bulbous shape) and formed such that the strut members 230 are biased to expand to the second state when no external restraint or constraint is applied to the outside surface of the contact member 204.

In some embodiments, as in the illustrated embodiment, the retention element 208 and the securing element 210 can be integrally formed. For example and without limitation, the retention element 208 and the securing element can be laser cut from a single length of tube material, for example, from an elastic or shape memory material such as Nitinol, and thereafter formed into the desired shape. In other embodiments, the securing element 210 can be coupled with a proximal end 208*a* of the retention element 208. In the relaxed state (i.e., the state where no external forces are acting thereon), some embodiments of the retention element 208 can be biased to move to the second or collapsed state, for example, and the securing element 210 can be in the second, or open state.

Additionally, with reference to FIG. 14, a pin or cross member 268 can be coupled with a distal end 208*b* of the retention element 208 and can be configured to fit within a slot 270 formed within a distal end 218*b* of the core member 218. In this embodiment, the core member 218 can be advanced in a distal direction resulting in the advancement of the contact member 204 in a distal direction. Further, a core tube 274 can extend proximally from a distal end 218*b* of the core member 218 and couple with a proximal end 204*a* of the contact member 204. The pin 268 can extend through a pair of openings formed in the core tube 274 to secure the core tube 274 to the pin 268 and, hence, the distal end 208*b* of the retention element 208. The core tube 274 can be, therefore, be used to couple the contact member 204 with the retention element 208. Pins, tabs, sutures, ties, protrusions, clips, depressions, detents, or other features can be used to couple a proximal end 204*a* of the contact member 204 with a proximal end of the core tube 274.

Additionally, in any embodiments, the system 200 can be configured so that the implant device 202 is biased in the proximal direction relative to the core member 218. For example and without limitation, as shown in FIG. 14, some embodiments of the implant device 202 can have a suture or thread 280 that extends through an inside of the core member 218 (such as through a lumen of the core member 218) and loops around the pin 268, thereby permitting a user to retract or withdraw the suture to pull the implant device 202 proximally relative to the core member 218. In this configuration, both ends of the suture 280 can extend from a proximal end of the device 200 such that a practitioner can grasp both ends of the suture 280 to exert the biasing force around the pin 268 to maintain the pin against a proximal end of the slot 270. When the implant device 202 is ready to be released from the core member 218, the practitioner can simply release one end of the suture and withdraw the other end of the suture until the suture no longer forms a loop or wraps around the pin 268. After removing the biasing force from the suture 280, the core member 268 can be withdrawn relative to the implant device 202. This may be done after the contact member and its securing element have been fully deployed.

Figure 15:
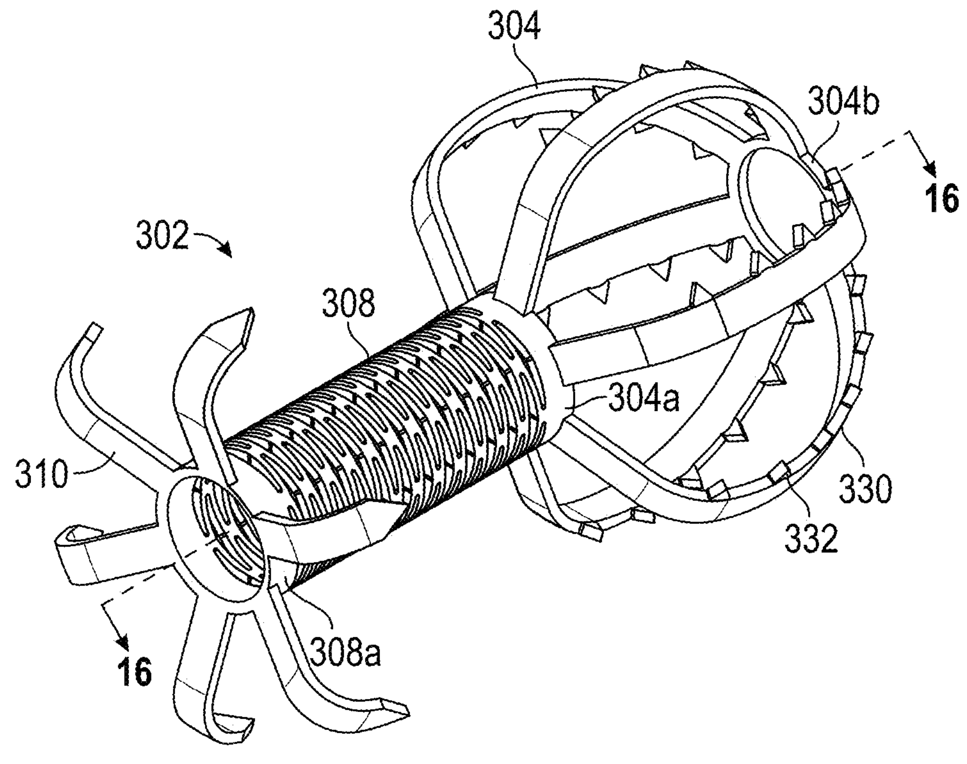
FIG. 15 shows another embodiment of an implant device wherein the contact member is in a second, expanded state, the retention element is in a second, contracted state, and the securing element is in a second, open state.
Figure 16:
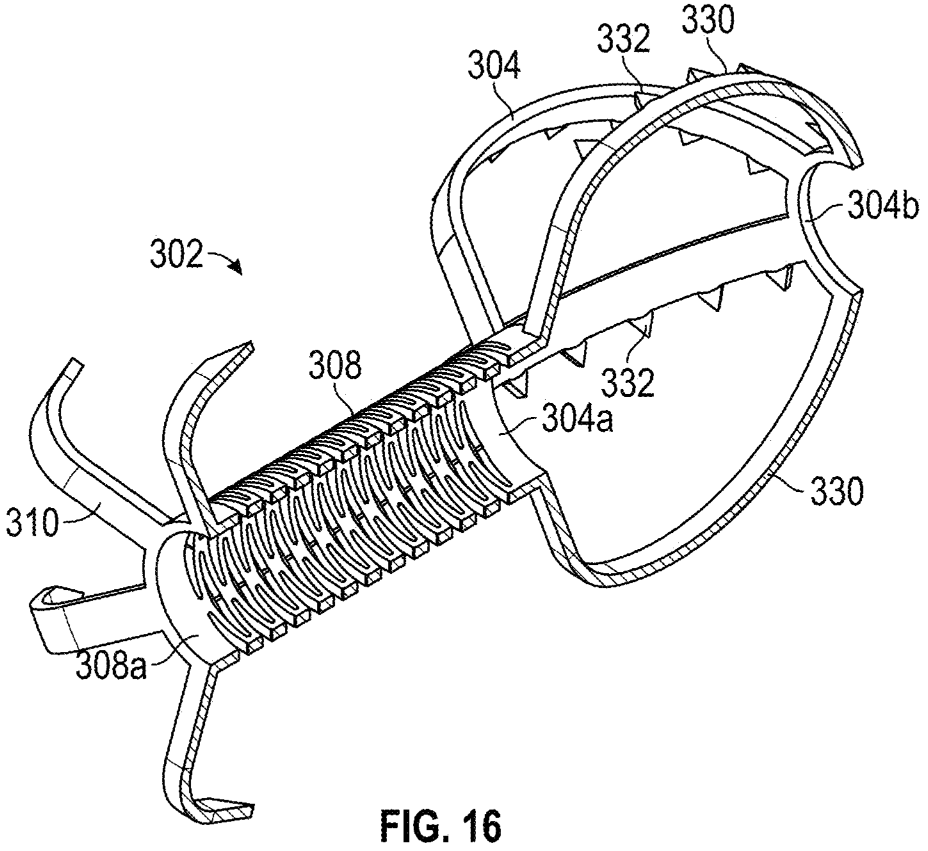
FIG. 16 is a section view of the treatment device shown in FIG. 15, taken through line 16-16 of FIG. 15.

FIG. 15 shows another embodiment of an implant device 302 wherein the contact member 304 is in a second, expanded state, the retention element 308 is in a second, contracted state, and the securing element 310 is in a second, open state. In any embodiments disclosed herein, any components, features, or other details of the treatment device 300 or implant device 302 can have any of the components, features, or other details of any other treatment device or implant device embodiments disclosed herein, including without limitation any of the embodiments of the treatment device 100, 200 or implant device 102, 202 described above, in any combination with any of the components, features, or details of the treatment device 300 or implant device 302 disclosed below. Similarly, any components, features, or other details of any of the other treatment device or implant device embodiments disclosed herein can have any of the components, features, or other details of any embodiments of the treatment device 300 or implant device 302 disclosed herein in any combination with any of the components, features, or details of the treatment device and/or implant device.

In any embodiments, a length of the retention element (including retention element 308) and/or a distance between the securing element and the contact member can be adjusted or varied beyond what is shown and described, for example to accommodate differing anatomy sizes and characteristics of the LA and/or LAA, or to accommodate differing amounts or thicknesses of LAA tissue that has been gathered or twisted up. For example and without limitation, in some embodiments, the length of the retention element, or the distance between the securing element and the contact member, can be approximately the same as a length of the contact member when the retention element is in a relaxed or collapsed state (e.g., in the second state), or can be approximately one-half of the length of the contact member when the retention element is in the second state, or between one-quarter and one-half of the length of the contact member when the retention element is in the second state, or otherwise.

In some embodiments, the contact member 304 can have an annular proximal end portion 304*a* wherein all of the arms or struts 330 (six being shown) of the contact member 304 extend distally away from the proximal end portion 304*a*. Additionally, in some embodiments, the contact member 304 can have an annular distal end portion 304*b* wherein all of the arms or struts 330 can be coupled with the annular distal end portion 304*b*. In some embodiments, the contact member 304 can be laser cut from a hypotube, or can be formed from different components and welded, brazed, or otherwise coupled together. Each of the strut members 330 can be preformed into a curved shape (which can have a rounded or bulbous shape) and formed such that the strut members 330 are biased to expand to the second state when no external restraint or constraint is applied to the outside surface of the contact member 304. The struts 330 can have any form of tissue anchors 332 on the struts or attached to the struts, such as any of the tissue anchors 118 described above.

In some embodiments, the contact member 304, the retention element 308, and the securing element 310 can be integrally formed, such as being cut from a single length of hypotube, or otherwise. For example and without limitation, the retention element 308 and the securing element can be laser cut from a single length of tube material, for example, from an elastic or shape memory material, and thereafter formed into the desired shape. In other embodiments, the contact member 304, the retention element 308, and/or the securing element 310 can be separately formed and welded, brazed, or otherwise joined together to form a single, unitary component. Because, in some embodiments, a distance between the contact member 304 and the securing element 310 can be large, for example and without limitation, greater than a length of the contact member when the contact member is in the second, expanded state, the contact member 304 can be advanced further distally into the LAA and then rotated so as to twist the opening of the LAA to cause the opening of the LAA to constrict around an outside surface of the retention element. The greater length of the retention element 310 can also accommodate a greater degree of twisting or rotation, or a greater number of rotations or twists of the LAA before the securing element is engaged.

An intermediary sleeve or tube (not shown) can be coupled with the securing element 310 and can be used to manipulate and control a position and/or an orientation of the securing element 310, including holding a proximal end portion 310*a* of the securing element in a fixed axial position while a distally directed force is exerted on the contact member 304 to maintain the retention element 310 in the first, extended state. Additionally, a core member (not shown) can engage a distal end portion 304*b* of the contact member 304*b* to allow a distally directed force to be exerted on the contact member 304. Pins, tabs, sutures, ties, protrusions, clips, depressions, detents, or other features can be used to selectively (i.e., reversibly) couple the contact member 304 to the core member.

After the desired degree of twisting of the LAA has been performed, the securing element 310 can be moved to the second, expanded state by, for example, advancing the securing element 310 out of a distal end of a tube of the delivery catheter and allowed to expand to the second state of the securing element. Thereafter, while maintaining the contact member 304 in the desired axial and rotational position (for example, the second rotational position), the securing element 310 can be advanced into the tissue that has constricted around an outside surface of the implant so as to secure the tissue in the twisted and/or constricted state. In some embodiments, this can be achieved or performed simply by holding the contact member in the desired position and allowing the retention element 308 to retract to its retracted or relaxed state, thereby causing the securing element 310 to advance into the tissue. When the deployment is complete, a user may disengage the core member from the contact member 304 so that the core member may be withdrawn. As with the other embodiments, the implant device 304 can be selectively biased or secured in the proximal direction relative to a delivery catheter, such as with a suture or thread 380 that extends through an inside of the catheter and loops around a pin, tab, or other feature of the implant device and released by disengaging or removing the suture or other retaining device.

Figure 17:
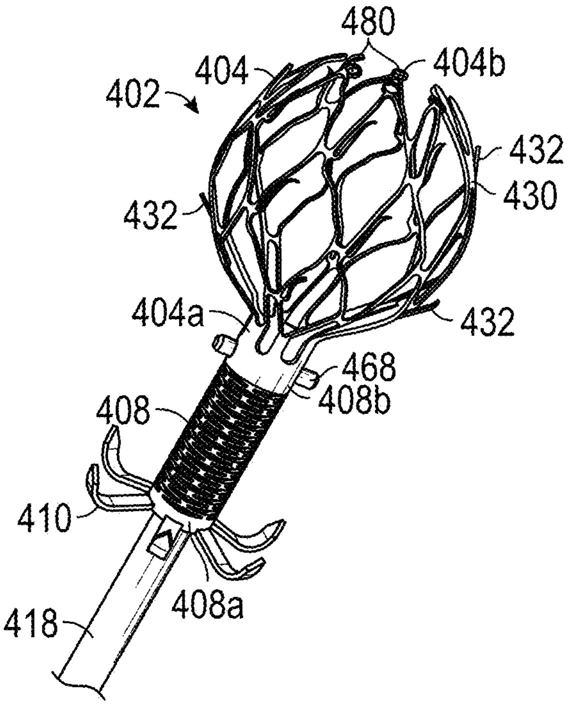
FIG. 17 shows another embodiment of a treatment device wherein the contact member is in a second, expanded state, the retention element is in a second, contracted state, and the securing element is in a second, open state.
Figure 18:
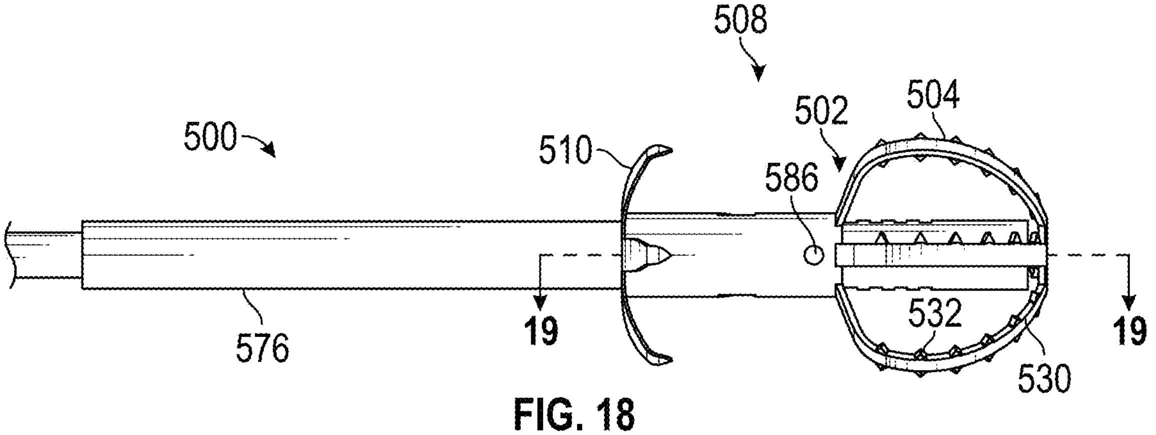
FIG. 18 shows a side view of another embodiment of a treatment device wherein the contact member is in a second, expanded state, the retention element is in a second, contracted state, and the securing element is in a second, open state.

FIG. 17 shows another embodiment of an implant device 402 wherein the contact member 404 is in a second, expanded state, the retention element 408 is in a second, contracted state (or in at least partially contracted or retracted state), and the securing element 410 is in a second, open state. Any embodiments of the treatment device 400 or implant device 402 can have any of the components, features, or other details of any other treatment device or implant device embodiments disclosed herein, including without limitation any of the embodiments of the treatment device 100, 200, 300 or implant device 102, 202, 302 described above, in any combination with any of the components, features, or details of the treatment device 400 or implant device 402 disclosed below. Similarly, any components, features, or other details of any of the other treatment device or implant device embodiments disclosed herein can have any of the components, features, or other details of any embodiments of the treatment device 400 or implant device 402 disclosed herein, in any combination, with any of the components, features, or details of the treatment device or implant device embodiments disclosed herein.

The contact member 404 can have an annular proximal end portion 404*a* and a distal portion 404*b* having a plurality of openings or rings 480. The struts or links 430 of the contact member 404 can form a web-like pattern so as to form a curved, bulbous, elongated bulbous, spherical or other shaped contact member. The struts 430 can have a plurality of tissue anchors or protrusions 432 coupled with the struts or links 430 at a plurality of locations about the contact member 404, such as any of the tissue anchors 118 described above. As in any of the embodiments disclosed herein, the tissue anchors 432 can be, but are not required to be, integrally formed with the struts 430. The struts or links 430 can form a generally diamond shaped pattern about the surface of the contact member. The contact member 404 can have a generally spherical or bulbous shape.

Additionally, with reference to FIG. 17, a pin or cross member 468 can be coupled with the implant device 402, for example and without limitation, at a distal end 408*b* of the retention element 408, or between the retention element 410 and the contact member 404. The pin 468 can be configured to engage an end portion of a core member 418 of the catheter, or a feature formed within a distal end portion of the core member of the catheter to selectively couple the implant device 402 with the core member of the catheter, just as with the other embodiments disclosed herein.

Additionally, similar to the other embodiments of the system disclosed above, some embodiments of the implant device 402 can have a suture or thread 480 that loops around or otherwise engages the pin 468, thereby permitting a user to retract or withdraw the suture to pull the implant device 402 proximally relative to the core member 418. After removing the biasing force from the suture 480, the core member 468 can be withdrawn relative to the implant device 402. This may be done after the implant and its securing element have been fully deployed.

In some embodiments, the contact member 404, the retention element 408, and/or the securing element 410 can be integrally formed, such as being laser cut from a single length of hypotube, or otherwise. For example and without limitation, the retention element 408 and the securing element can be laser cut from a single length of tube material, for example, from an elastic or shape memory material, and thereafter formed into the desired shape. In other embodiments, the contact member 404, the retention element 408, and/or the securing element 410 can be separately formed and welded, brazed, or otherwise joined together to form a single, unitary component. Because, in some embodiments, a distance between the contact member 404 and the securing element 410 can be large, the contact member 404 can be advanced further distally into the LAA and then rotated so as to twist the opening of the LAA to cause the opening of the LAA to constrict around an outside surface of the retention element. The greater length of the retention element 410 can also accommodate a greater number of rotations or twists of the LAA before the securing element is engaged.

An intermediary sleeve or tube (not shown) can be coupled with the securing element 410 and can be used to manipulate and control a position and/or an orientation of the securing element 410, including holding a proximal end portion 410*a* of the securing element in a fixed axial position while a distally directed force is exerted on the contact member 404 to maintain the retention element 410 in the first, extended state. Deployment of the device 402 can include any combination of the steps described with respect to any of the other embodiments disclosed herein.

FIGS. 18-21 show another embodiment of a treatment device 500 having an implant device 502 wherein the contact member 504 is in a second, expanded state, the retention element 508 is in a second, contracted state, and the securing element 510 is in a second, open state. Any embodiments of the treatment device 500 or implant device 502 can have any of the components, features, or other details of any other treatment device or implant device embodiments disclosed herein, including without limitation any of the embodiments of the treatment device 100, 200, 300, 400 or implant device 102, 202, 302, 402 described above, in any combination with any of the components, features, or details of the treatment device 500 or implant device 502 disclosed herein. Similarly, any components, features, or other details of any of the other treatment device or implant device embodiments disclosed herein can have any of the components, features, or other details of any embodiments of the treatment device 500 or implant device 502 disclosed herein, in any combination, with any of the components, features, or details of the treatment device or implant device embodiments disclosed herein.

The contact member 504 can have a plurality of struts or links 530 that can have a plurality of tissue anchors 532 thereon at a plurality of locations about the contact member 504, such as any of the tissue anchors 118 described above. As in any of the embodiments disclosed herein, the tissue anchors 532 can be, but are not required to be, integrally formed with the struts 530. The contact member 504 can have a generally spherical or bulbous shape, or the shape of any of the other embodiments disclosed herein.

Similar to other embodiments described above, any embodiments of the treatment device 500 can have a suture or thread 580 that extends through an inside of the core member 518 (such as through a lumen of the core member 518) and loops around a pin 568 or other retention element that is coupled with the contact member 504, thereby permitting a user to retract or withdraw the suture 580 to pull the contact member 504 proximally relative to the securing element 510 and to keep the implant 502 engaged with the delivery catheter. In this configuration, both ends of the suture 580 can extend from a proximal end of the device 500 such that a practitioner can grasp both ends of the suture 580 to exert a proximally directed force around the pin 568 to pull the contact member 504 toward the securing element 510 and to keep the pin 568 positioned within a slot 570 of the core member 518. Additionally, a slot 574 formed in the cylindrical body portion 572 of the securing element 510 can be sized so that the cylindrical body portion 572 of the securing element 510 can be moved axially in a proximal and distal direction relative to the pin 568, between a proximal end 574*a* of the slot 574 and a distal end 574*b* of the slot 574. Thus, the pin 568 and suture 580 can be used to bias or force the implant 502 to remain in contact with the catheter (for example, in contact with the core member 518 or the slot 570 formed in the core member) and to permit the user to move the securing element 510 from the first rotational position to the second, engaged position (as shown in FIGS. 18-21).

Figure 19:
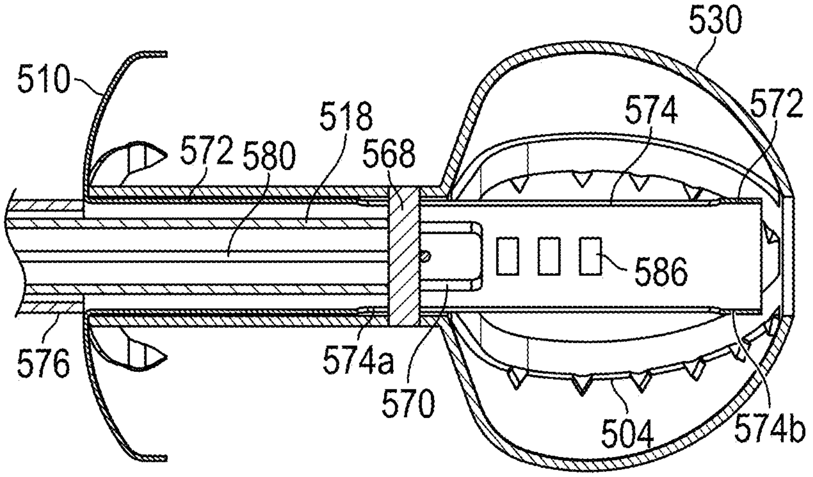
FIG. 19 is a section view of the treatment device shown in FIG. 18, taken through line 19-19 of FIG. 18.
Figure 20:
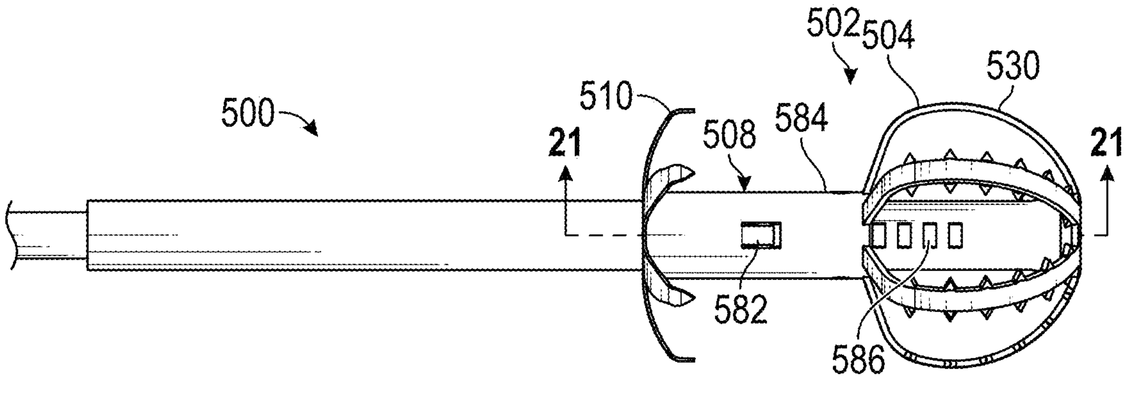
FIG. 20 is another side view of the treatment device shown in FIG. 18.
Figure 21:
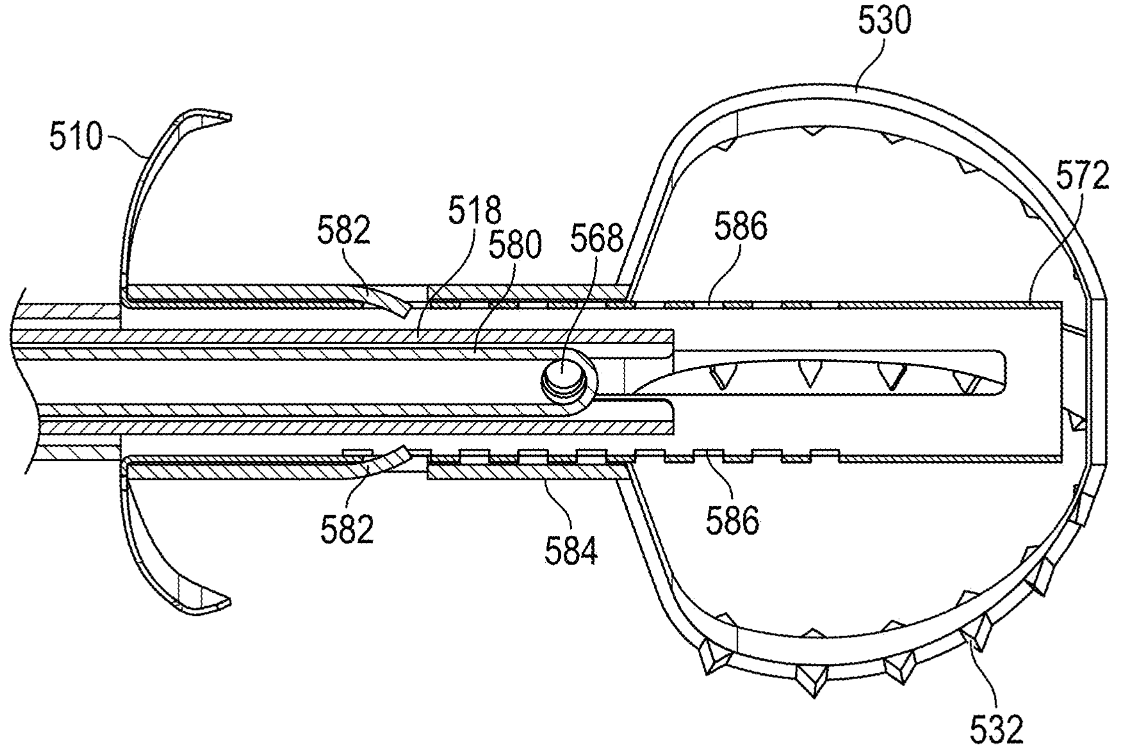
FIG. 21 is a section view of the treatment device shown in FIG. 18, taken through line 21-21 of FIG. 20.

In some embodiments, if the contact member 504 is maintained in a fixed position using the catheter or the core member 518, the user can move the securing element 510 from the first rotational position to the second rotational position by pulling back on or withdrawing the suture 580 (again, while the contact member 504 is held in a fixed position within the LAA) and advancing an outer tube 576 of the deliver catheter in a distal direction so as to push the securing element 576 distally. This would be done after the desired level of twisting of the LAA has been achieved by torqueing or twisting the core member 518 or other portion of the catheter. With reference to FIG. 19, this can, in some embodiments, cause the securing element 510 and body portion 572 of the securing element to advance distally relative to the contact member 504, thereby forcing the securing element into the tissue of the LAA or LA so as to hold the tissue in the closed or contracted position.

Additionally, any embodiments of the device can be configured such that, as the securing element 510 is advanced into the second rotational position, wherein the securing element 510 engages with the tissue and holds the LAA in an occluded or closed position, a retention element can be used to prevent the securing element from moving away from the second rotational position toward the first rotational position, thereby maintaining the position of the securing element and maintaining the occlusion in the LAA. For example and without limitation, one or more tabs 582 formed on or coupled with a body portion 584 of the contact member 504 can be biased to deflect into or engage with a respective depression or opening 586 of a plurality of depressions or openings 586 so as to prevent or inhibit the securing element 510 from moving back toward the first rotational position relative to the contact member 504. The tabs 582 (which can be any other type of securing feature, such as ball and detent, or a zip tie type securing feature, or otherwise) can be configured such that the securing element 510 can freely move from the first, expanded position to the second, collapsed position, and to selectively prevent or inhibit movement from the second rotational position to the first rotational position, thereby essentially securing the securing element in the second rotational position. Further, in any embodiments disclosed herein, the securing element and contact member can be held together using one or more sutures, wires, pins, or other components or fasteners, including, for example and without limitation, a suture with a slip knot which can be cinched during deployment. The suture can then be trimmed to length during final deployment, holding the securing element and contact member together to maintain the LAA in a closed or constricted state. Thereafter, the suture 580 can be removed, and the remaining components of the deployment device can be withdrawn from the patient's body, leaving the implant 502 in place.

In some embodiments, the implant device 502 can be configured such that the ratchet or retention mechanism formed by engagement of the tabs 582 and openings 586 is reversible or releasable, so that the securing element can be moved from the second to or toward the first rotational position, for example, to disengage the securing element from the tissue for repositioning, for re-twisting the LAA, or otherwise. For example, some embodiments of the implant device 502 can be configured such that rotating or twisting the securing element (and, hence, the one or more tabs 582) relative to the body portion 584 of the contact member 504 so that the tabs 582 disengage the openings 586. Additionally, in some embodiments, the tabs can be positioned on the body portion 584 of the contact member 504 and the openings can be formed in a body portion of the securing element 510. Further, tabs can be formed in both directions so that the securing element can ratchet or be selectively securable in both axial movement directions. Further, in any embodiments disclosed herein, the tabs can be formed and configured so that the tabs can be moveable from a securing position or state to a non-securing (or sliding) state. Examples of these embodiments will be described below.

Figure 22A:
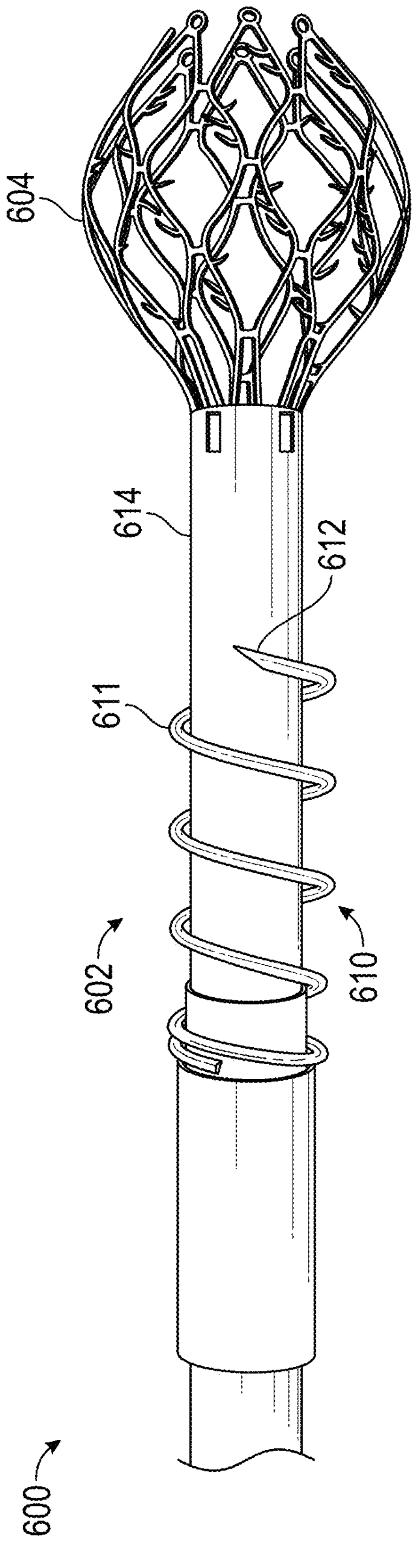
FIG. 22A shows a side view of another embodiment of a treatment device wherein the contact member is in a second, expanded state and the retention element is in a first, retracted state.

FIG. 22A shows another embodiment of a treatment device 600 having an implant device 602 wherein a contact member 604 is in a second, expanded state and a securing element 610 is in a first, retracted or pre-deployment state. FIG. 23 shows the embodiment of the implant device 602 wherein the securing element 610 has been moved to the second, deployed or locked state. FIGS. 24-35 illustrate an embodiment of a deployment method for the embodiment of the treatment device 600 illustrated in FIGS. 22-23. Any embodiments of the treatment device 600 or implant device 602 can have any of the components, features, or other details of any other implant device embodiments disclosed herein, including without limitation any of the embodiments of the implant device 100, 200, 300, 400, 500 described above, in any combination with any of the components, features, or details of the treatment device 600 or implant device 602 disclosed below. Similarly, any components, features, or other details of any of the other treatment device or implant device embodiments disclosed herein can have any of the components, features, or other details of any embodiments of the treatment device 600 or implant device 602 disclosed herein, in any combination, with any of the components, features, or details of the treatment device or implant device embodiments disclosed herein.

Figure 22B:
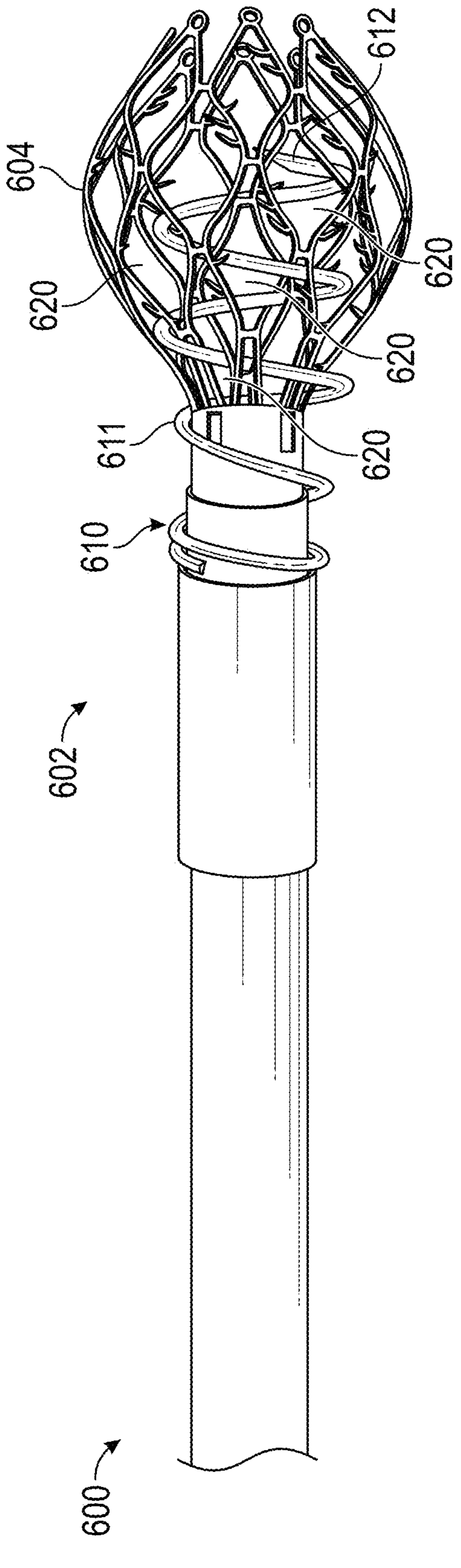
FIG. 22B shows a side view of the treatment device of FIG. 22 wherein the contact member is in the second state and the retention element is in a second, deployed state.

With reference to FIGS. 22A-22B, the securing element 610 can have a body portion 611 that can have a curved or helical (or corkscrew) shape that can extent from a proximal end portion 610*a* of the securing element 610 to a distal end portion 610*b* of the securing element 610, and can have a pointed distal tip 612 at the distal end portion 610*b* of the securing element 610 that can engage with (or, in some embodiments, penetrate at least partially through) the tissue of the LA and/or the LAA after the contact member 604 has been rotated to the second rotational position, thereby securing the tissue and closing or occluding the opening of LAA about the implant device, such as about a body portion 614 that is integral with or coupled with the contact member 604 or other portion of the implant device.

The securing element 610 can define an axial opening 615 therethrough. In some embodiments, the opening 615 can be larger than a distal portion of an inner core member of the catheter and/or a body portion 614 of the implant, so that a body portion 611 of the securing element 610 wraps around or curves around (helically or otherwise) and/or is rotatable around the inner core member of the catheter and/or the body portion 614 of the implant.

Figure 23A:
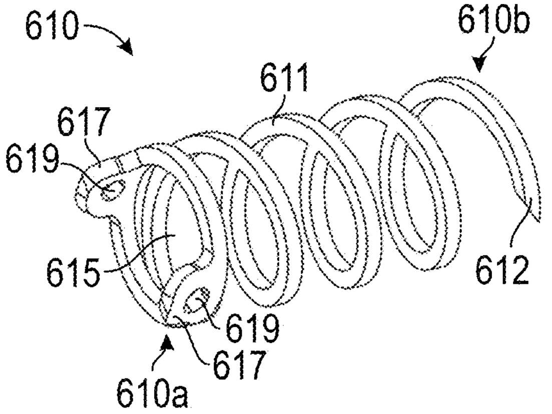
FIG. 23A shows an isometric view of another embodiment of a securing element.
Figure 23B:
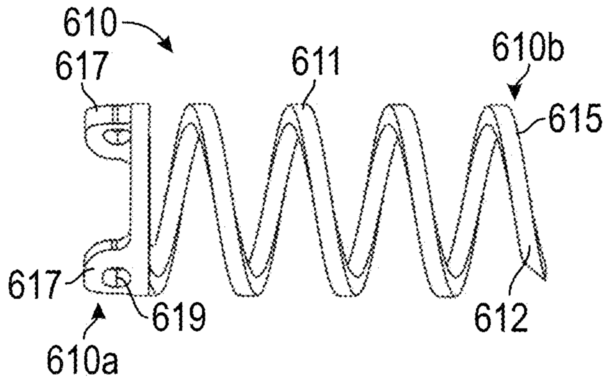
FIG. 23B shows a side view of the embodiment of the securing element shown in FIG. 23A.
Figure 23C:
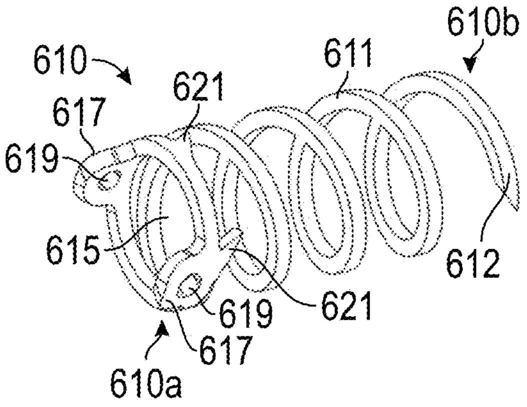
FIG. 23C shows an isometric view of another embodiment of a securing element.
Figure 23D:
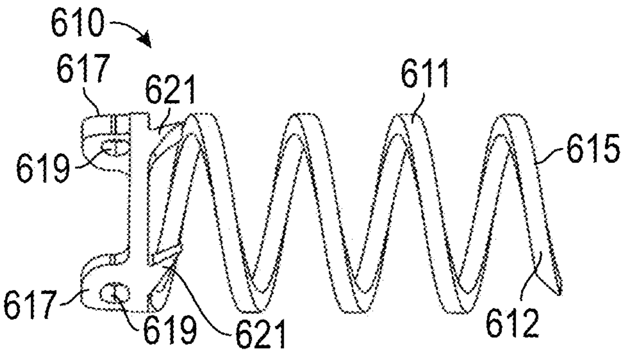
FIG. 23D shows a side view of the embodiment of the securing element shown in FIG. 23C.

FIGS. 23A-23B show another embodiment of a securing element 610 that can be used with any implant or delivery system embodiments and/or treatment methods disclosed herein. In any embodiments, a cross-section of the body portion 611 can be round, square (as shown), ovular, or have any other desired shape. In any embodiments, the body portion 611 can have from 2 to 15 or more coils (i.e., complete revolutions), or from 3 to 10 coils, or from 4 to 6 coils and can terminate at a distal end portion 610*b* of the securing element 610 in a sharp point, a blunt end, one or more tissue anchors or barbs, or otherwise. Additionally, any embodiments of the securing elements disclosed herein can have tissue anchors or barbs (not shown) along a length of the body portion 611 or body portions 611, in the embodiments having two or more body portions, such as described below, to engage with the tissue and prevent or inhibit the securing member 610 from backing out of the tissue after the securing element 610 has been advanced into such tissue. A proximal end portion 610*a* of the securing element 610 can have flanges 617, openings 619, and/or other features configured to connect the securing element 610 to the other portions of the implant 602.

Additionally, in any embodiments disclosed herein, the securing element 610 can also have rotational or axial lock features that can secure the securing element in a desired rotational position and/or desired axial position and/or inhibit the counter rotation of the securing element. The rotational or axial lock can be selectively reversible so that a user to return the securing element to a freely movable state, as desired. For example and without limitation, with reference to FIGS. 23C-23D, any embodiments of the securing elements disclosed herein can have one or more or a plurality of tissue anchors or barbs 621 extending away from a proximal end 610*a* of the securing element 610 that can improve the grip of the securing element in the target tissue, and/or prevent or inhibit the securing member 610 from backing out of the tissue after the securing element 610 has been advanced into such tissue. In any embodiments, the tissue anchors or barbs 621 can be axial facing, radially facing, or at an angle relative to the axial direction of the securing element 610. The tissue anchors or barbs 621 can be angled or otherwise configured to easily enter the tissue, and have a perpendicular face or otherwise be configured to engage with and/or lock with the tissue to prevent the counter-rotation of the securing element 610.

Figure 23E:
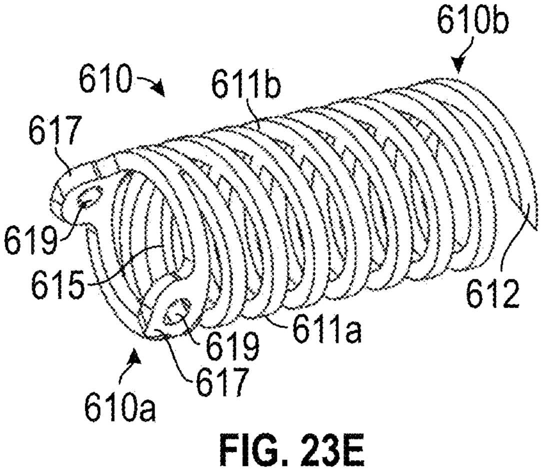
FIG. 23E shows an isometric view of another embodiment of a securing element.
Figure 23F:
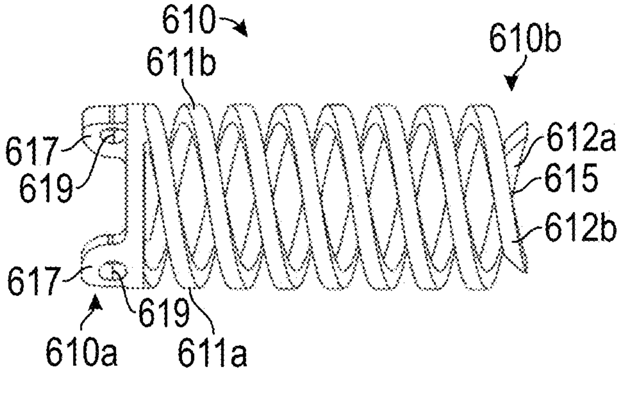
FIG. 23F shows a side view of the embodiment of the securing element shown in FIG. 23E.
Figure 24:
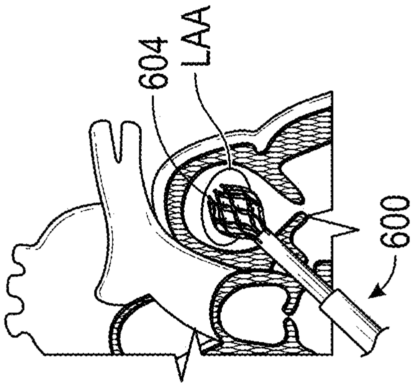
FIGS. 24-35 illustrate an embodiment of a deployment method for the embodiment of the treatment device illustrated in FIG. 22A.
Figure 25:
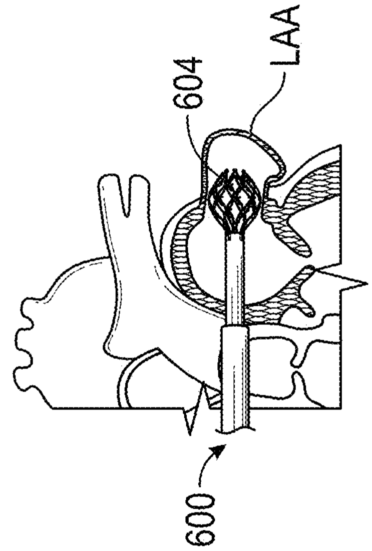
Figure 26:
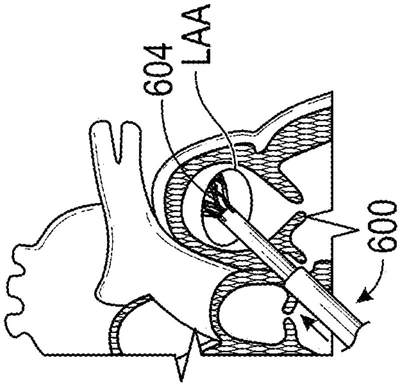

Further, with reference to FIGS. 23E-23F, any embodiments of the securing elements disclosed herein can have two or more or a plurality of body portions 611 extending away from a proximal end 610*a* of the securing element. The embodiment of the securing element 610 shown in FIGS. 23E-23F has a first body portion 611*a* and a second body portion 611*b* that are both helically shaped, have the same or similar pitch, and can both extend a full length of the securing element 610. In other embodiments, one of the body portions 611 can have a different length (e.g., be shorter) than the other body portion 611. Additionally, in any embodiments disclosed herein, the one or more body portions 611 can have a pitch that changes (increases or decreases) along a length thereof from a proximal portion to a distal portion of the securing element. A body portion 611 having a pitch that decreases along a length of the securing element (such that the spacing increases along a length of the body portion) can result in the tissue between the coils being compressed more near a proximal end portion of the securing element than near a distal end portion of the securing element. In some embodiments, this may increase the retaining force of the securing element in the tissue. The first body portion 611*a* can have a distal end portion 612*a* and the second body portion 611*b* can have a distal end portion 612*b*.

As mentioned, in some embodiments, the securing element 610 can have two or more curved or helical (or corkscrew) shaped body portions 611, each of which can have a pointed distal tip that can engage with (or, in some embodiments, penetrate at least partially through) the tissue of the LA and/or the LAA after the contact member has been rotated to the second rotational position. In any embodiments disclosed herein, the securing element having a helical shape (such as the embodiment of the securing element 610 shown in FIGS. 22A-22B) can have two helically shaped body portions 611 that can be each configured to penetrate and engage the tissue that has constricted around a portion of the implant. In any embodiments, including the single and double helical securing element embodiments, the body portion or portions 611 can be long enough to engage contact member, or shorter and just engage all or just a proximal portion of the LA wall/LAA tissue, such as from approximately 1 mm to approximately 2 mm of the LA wall/LAA tissue, or from approximately 2 mm to approximately 5 mm or more of the LA wall/LAA tissue.

Further, in any embodiments, the one or more body portions 611 may define a cylindrical shape along a length of the securing member 610, as shown, define a conical shape along a length of the securing member 610, or otherwise. For example and without limitation, in any embodiments, the one or more body portions 611 may define a conical shape that increases along a length of the securing member 610 so that the opening 615 is larger at the distal end portion 610*b* of the securing element 610. The conical shape can result in the tissue being gathered wide and brought together (i.e., radially inwardly) as the securing element 610 is advanced into the LA wall/LAA tissue.

With reference to FIG. 22B, the securing element 610 (which can be any of the securing element embodiments or have any combination of any of the features of the securing element embodiments disclosed herein) can be rotated (such as in a corkscrew fashion) and advanced so as to penetrate into and/or pass through the tissue of the LA and/or LAA that has gathered and/or constricted about the body portion 614 or other portion of the implant device 602. In this configuration, the securing element 610 is configured to be rotatable relative to the contact member 604 so that the securing element 610 can be rotated and passed through the tissue of the LA and/or LAA while the LAA is held generally stationary in the second rotational position by holding the contact member 604 in the stationary position. In any embodiments, a sleeve or other component of the catheter or delivery system can be coupled with the securing element (including, without limitation, securing element 610) to enable a user to move the securing element between a first state and a second state (which should be interpreted to also include moving from the second state to the first state), to rotate the securing element in either direction, to move the securing element between a first rotational position and a second rotational position, and/or to otherwise manipulate the securing element. In some embodiments, the catheter or delivery system can be configured to perform these operations independently of any other movements or operations of the catheter so that, for example, the securing element can be axially advanced toward the contact member while the contact member is held in a fixed position by the catheter.

The securing element 610 can thereby hold the tissue of the LA and/or LAA to hold the tissue of the LA and/or LAA in the constricted state about the implant device, so as occlude the LAA. Additionally, in some embodiments, as shown, the securing element 610 can be configured to also pass through one or more of the openings 620 that can be formed in or result in the contact member 604 when the contact member 604 is in the second, expanded state, thereby further securing the securing element 610 to the contact member 604 and preventing or inhibiting the contact member 604 from rotating toward the first rotational position. In any embodiments, the securing element 610 and/or the contact member 604 can have one or a plurality of teeth, cleats, barbs, nubs, texture, studs, anchors or other tissue engaging features or anchor members about an outside surface of the securing element 610 to prevent or inhibit the securing element 610 from disengaging from the tissue of the LA and/or LAA when in the second state. Further, in any embodiments, the securing element can be biased to the second rotational positioned by a biasing member (not shown) such as an axially resilient member, or using one or more sutures, wires, ratchets, tabs and openings, or other securing features. However, in some embodiments, the engagement of the securing element 610 into the tissue of the LA and/or LAA can be sufficient to secure the securing element 610 in the second rotational position and maintain the LAA in the occluded state.

Figure 27:
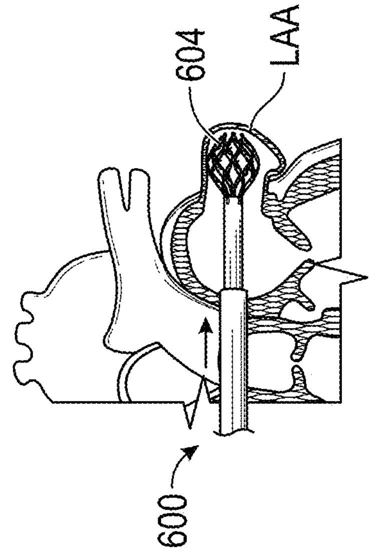
Figure 28:
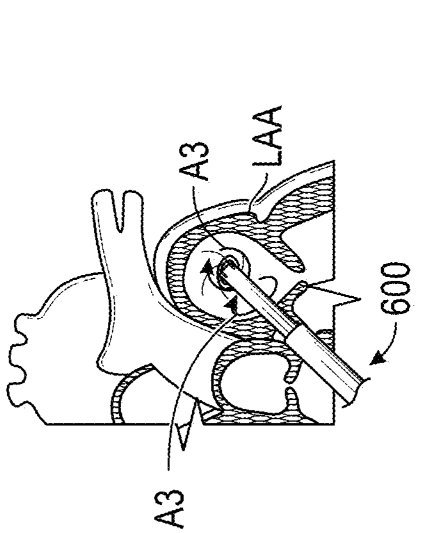
Figure 29:
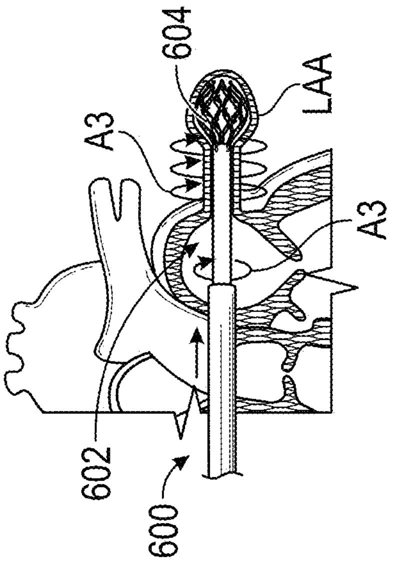

With respect to FIGS. 24-35, an embodiment of a deployment sequence will now be described. FIGS. 24-27 show the contact member 604 being advanced into the LAA. With reference to FIG. 27, the contact member 604 can be advanced to any desired depth, including to an end portion, of the LAA. In some embodiments, the contact member 610 can be advanced to the desired position relative to the LAA and then expanded to the second state so as to contact an inside surface or tissue of the LAA. Thereafter, the contact member 604 can be rotated in a first direction (represented by arrow A3 in FIGS. 28-29, which can be either the clockwise or counter-clockwise direction) toward the second rotational position so as to twist the LAA in the first direction, as also indicated by arrow A3 in FIGS. 28-29, toward the second state. As described, the twisting can cause the ostium of the LAA to constrict around a portion of a body of the implant device 602, so as to occlude the LAA from the LA, as shown in FIGS. 28-29.

Figure 30:
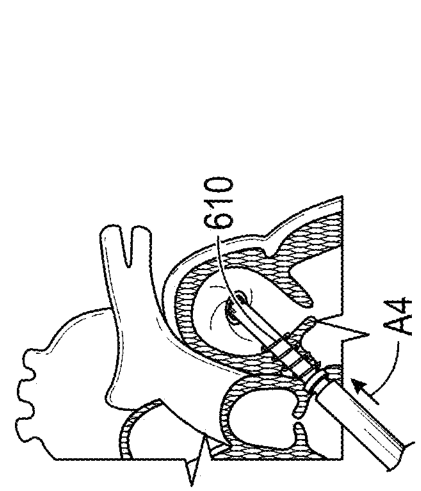
Figure 31:
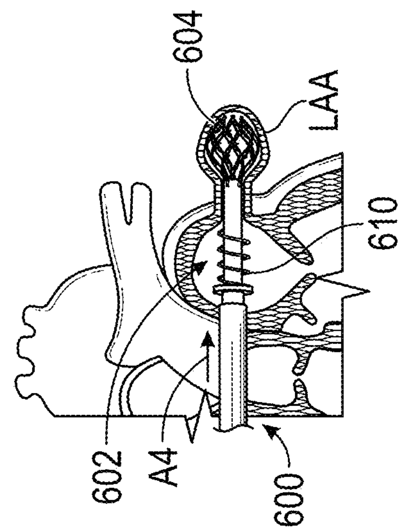
Figure 32:
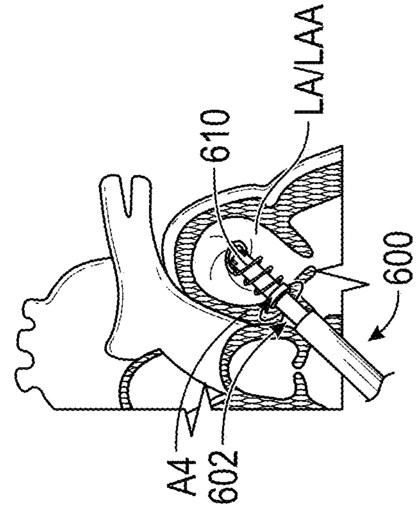
Figure 33:
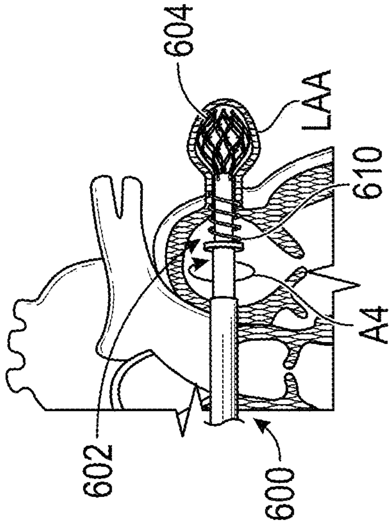
Figure 34:
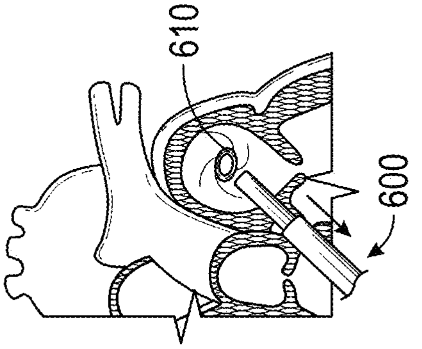
Figure 35:
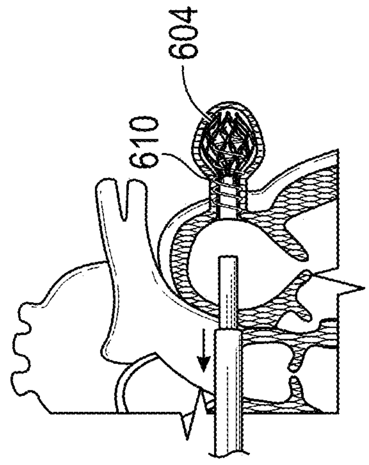

Thereafter, with reference to FIGS. 30-31, while maintaining the contact member 604 in the second rotational position and/or maintaining the tissue of the LA and/or LAA in the occluded or constricted state and the LAA in the twisted position, the securing element 610 can be advanced distally (as indicated by arrow A4 in FIGS. 30-31) toward the tissue of the LA and/or LAA that has constricted around the body of the implant device. Before a distal end of the securing element 610 reaches the tissue of the LA and/or LAA, the securing element 610 can be rotated in a first direction (such as the rotational direction indicated by arrow A5 shown in FIGS. 32-33) while the securing element 610 is being advanced distally to cause the securing element 610 to penetrate into and/or engage with the tissue of the LA and/or LAA that has constricted around the body portion of the implant device 602. In some embodiments, the securing element 610 can be advanced so as to penetrate completely through the tissue of the LA and/or LAA, as shown in FIGS. 34-35. In some embodiments, the securing element 610 can be configured so as to engage and/or only partially penetrate into the tissue of the LA and/or LAA. Thereafter, the implant device 602 can be released from the delivery catheter and the delivery catheter can be withdrawn from the patient's heart, as shown in FIGS. 34-35, leaving the LAA in the occluded position.

Figure 36:
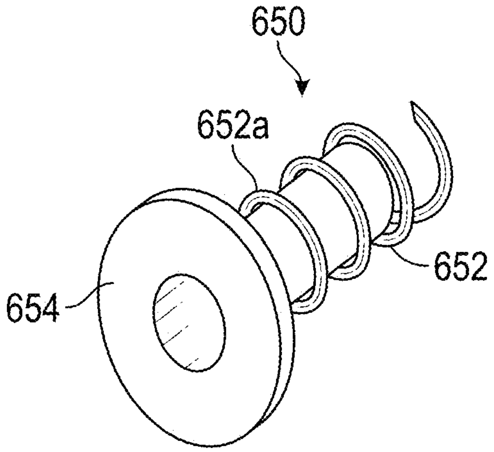
FIG. 36 shows another embodiment of an implant device wherein the retention element is engaging with a tissue surface surrounding an opening of the LAA.

FIG. 36 shows another embodiment of an implant device 650 having a different embodiment of a securing element 652 that can be used with any of the embodiments of the implant devices disclosed herein. As shown in FIG. 36, the securing element 650 can have a backing member 654 coupled with a proximal end 652*a* of the securing element 652 that can provide an additional seal against the tissue of the LA and/or LAA when the securing element is in the second or deployed position.

Figure 37:
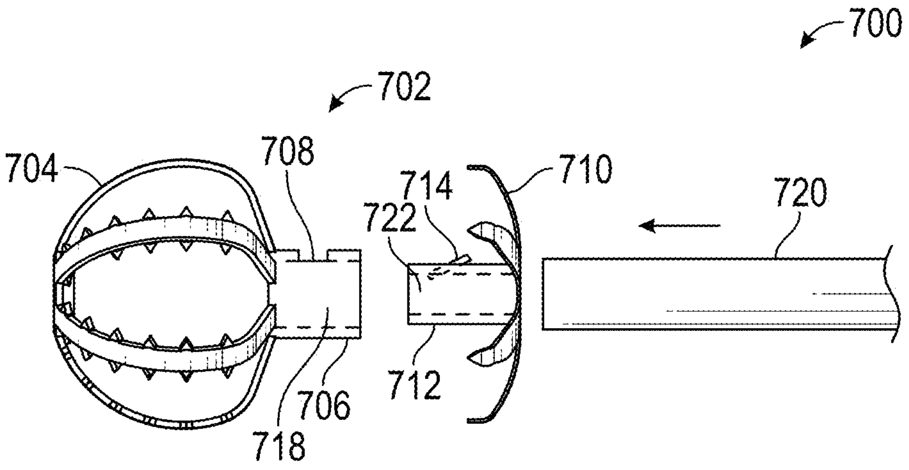
FIG. 37 shows another embodiment of a treatment device wherein a tab member of the securing element is in a first, engaged state.
Figure 38:
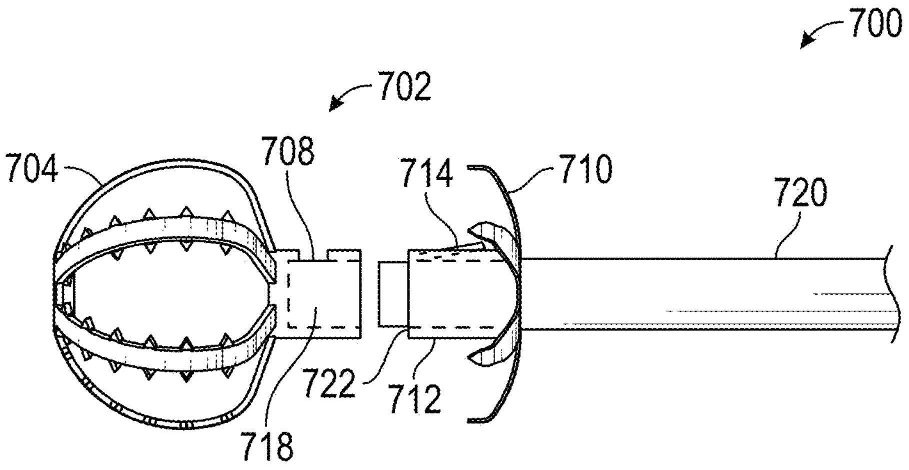
FIG. 38 shows the treatment device of FIG. 37, wherein the tab member is in a second, disengaged state.

FIGS. 37-38 show another embodiment of a treatment device 700 having an implant device 702 wherein the contact member 704 is in a second, expanded state, and the securing element 710 is in a second, open state. Any embodiments of the treatment device 700 or implant device 702 can have any of the components, features, or other details of any other treatment device or implant device embodiments disclosed herein, including without limitation any of the embodiments of the treatment device 100, 200, 300, 400, 500, 600 or implant device 102, 202, 302, 402, 502, 602 described above, in any combination with any of the components, features, or details of the treatment device 700 or implant device 702 disclosed below. Similarly, any components, features, or other details of any of the other treatment device or implant device embodiments disclosed herein can have any of the components, features, or other details of any embodiments of the treatment device 700 or implant device 702 disclosed herein, in any combination, with any of the components, features, or details of the treatment device or implant device embodiments disclosed herein.

In any embodiments, the contact member 704 can have a body portion 706 that can, but is not required to have, a cylindrical shape. An opening or recess 708 can be formed in the body portion 706 as part of a retaining element to retain the securing element 710 in a desired axial position relative to, or locked to, the coupling member 704. The securing element 710 can also have a body portion 712 that can, but is not required to have, a cylindrical shape. In some embodiments, the body portion 712 can extend into the body portion 706 of the contact member 704 even when the securing element 710 is in a first, retracted state. The body portion 706 can have an opening 708 extending therethrough, sized and configured to selectively receive the body portion 712 of the securing element 710. The body portion 712 can have an opening 722 extending therethrough, sized and configured to selectively receive a core member 720 of the delivery catheter of the treatment device 700.

Figure 39:
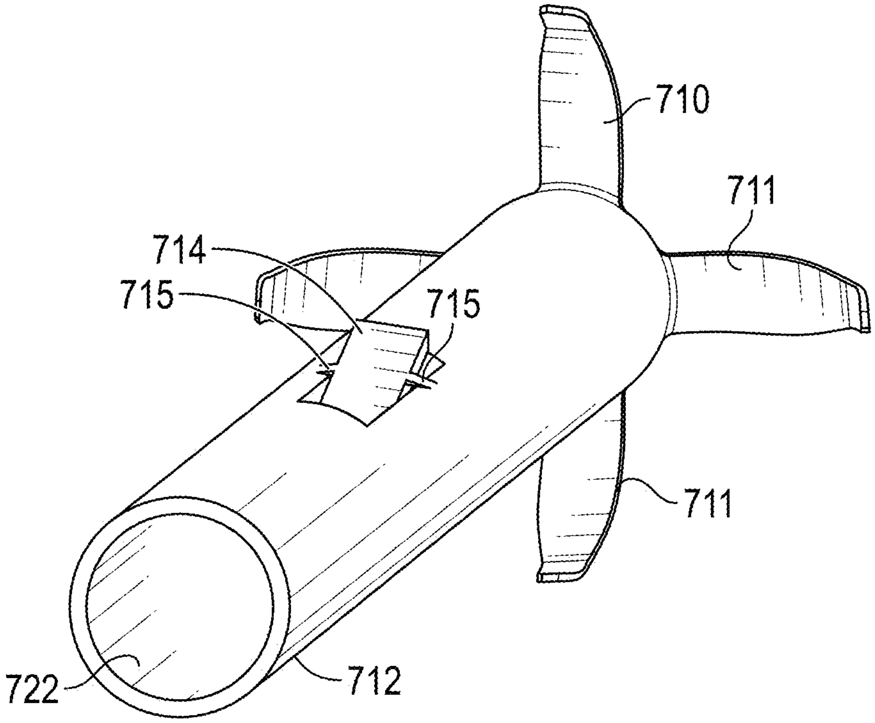
FIG. 39 shows the securing element of the treatment device of FIG. 37.

Additionally, with reference to FIG. 39, the securing element 710 can have a deflectable tab member 714 that can be movable or moved from a first, engaged position (as shown in FIG. 37) to a second, disengaged position (as shown in FIG. 38). The tab member 714 can be configured to rotate about a pin that can be coupled with the tab member 714 and the body portion 712, or can be configured to rotate about a thin strip of the material (referred to herein as a material strip 715) used to form the body portion 712 and/or the tab member 714. For example and without limitation, the body portion 712, the tab member 714, and the one or more material strips 715 (two being shown) can be integrally formed. Additionally, in some embodiments, the one or more arms 711 of the securing element 710 (four being shown) can also be integrally formed with the other features of the securing element 710. In some embodiments, the tab 714 can be biased toward the first, engaged position (as shown in FIGS. 37 and 39), but be physically deflectable or rotatable toward the second, disengaged position (as shown in FIG. 38) by advancing a core member 720 or other component through the opening 722 extending through the body portion 712 of the securing element 710. For example and without limitation, as shown in FIG. 38, the core member 720 can be advanced distally through the opening 722 of the securing element 710 to deflect or rotate the tab member 714, thereby moving the tab member 714 from the first, engaged position to the second, disengaged position.

When the tab member 714 is in the engaged position, the tab member 714 can engage with the opening 708 formed in the body portion 706 of the contact member to axially lock or couple the securing element 710 with the contact member 704, for example, after the contact member has twisted the LAA to a closed or occluded position or state, as described above. However, in some embodiments, if a user wishes to disengage or decouple the securing element 710 from the contact member 704, the user can achieve this by moving the tab member 714 to the second, disengaged position, such as, for example and without limitation, as described above, thereby disengaging the tab member 714 from the opening 708. Thereafter, the user can axially withdraw the securing element 710.

FIGS. 40-43 illustrate another embodiment of an implant device 732. Any embodiments of the implant device 732 can have any of the components, features, or other details of any other treatment device or implant device embodiments disclosed herein, including without limitation any of the embodiments of the treatment device 100, 200, 300, 400, 500, 600, 700 or implant device 102, 202, 302, 402, 502, 602 described above, in any combination with any of the components, features, or details of the implant device 732 disclosed below. Similarly, any components, features, or other details of any of the other treatment device or implant device embodiments disclosed herein can have any of the components, features, or other details of any embodiments of the implant device 732 disclosed herein, in any combination, with any of the components, features, or details of the treatment device or implant device embodiments disclosed herein.

Figure 40:
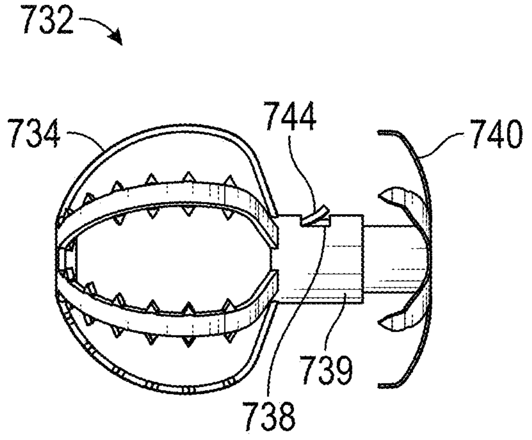
FIG. 40 shows the treatment device of FIG. 37, wherein the securing element is engaged with the contact member and the tab member of the securing element is in the first, engaged state.
Figure 41:
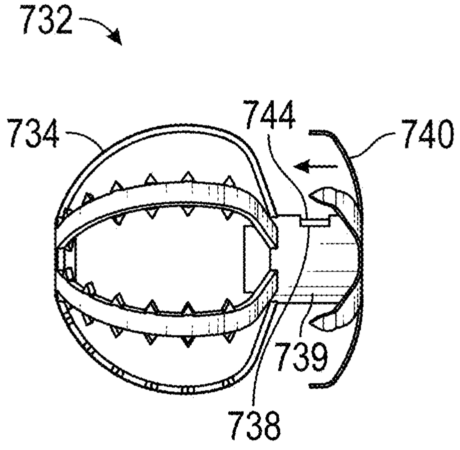
FIG. 41 shows the treatment device of FIG. 37, wherein the tab member of the securing element has been moved to the second, disengaged state by the axial advancement of a core member of the delivery system.
Figure 42:
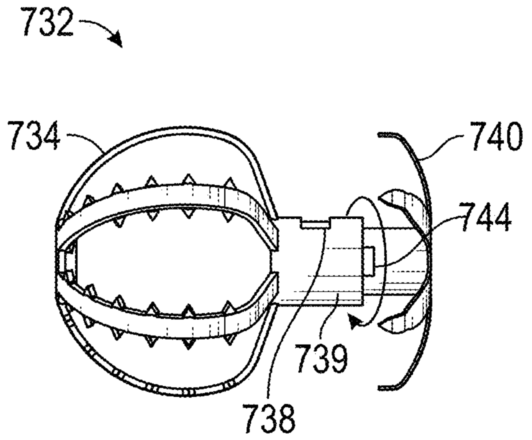
FIG. 42 shows the treatment device of FIG. 37, wherein the securing element has been rotated to misalign the tab member relative to the opening of the contact member and permit the withdrawal of the securing element from the contact member.
Figure 43:
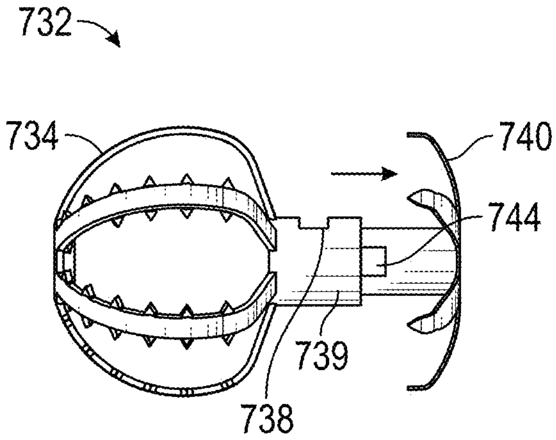
FIG. 43 shows the treatment device of FIG. 37, wherein the securing element has been withdrawn from the contact member.

As shown in FIG. 40, a deflectable tab member 744 of the implant device 732 is engaged with an opening 738 of the contact member 734, thereby causing the securing element 740 to be engaged with the contact member 734. In any embodiments, the deflectable tab member 744 can be movable or moved from a first, engaged position (as shown in FIG. 40) to a second, disengaged position (as shown in FIG. 41) by advancing the securing element 710 distally so that a body portion 739 of the contact member 734 causes the tab member 744 to deflect and move to the second, disengaged position, as shown in FIG. 41. Thereafter, the securing element 740 can be rotated in either direction (such as by 90 degrees) to a position in which the tab member 744 is not aligned with and therefore cannot engage with the opening 738, as shown in FIG. 42. The body portion 739 of the contact member 734 can hold the tab member 744 in the second, disengaged position while the securing element 740 is withdrawn away from or disengaged from the contact member, as shown in FIG. 43.

Figure 44A:
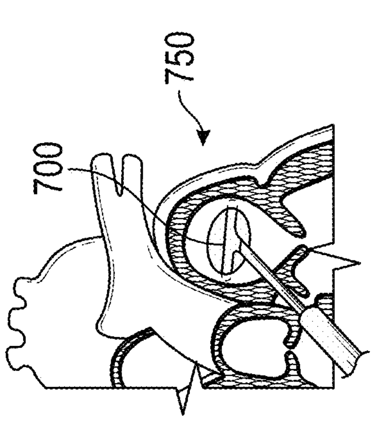
FIGS. 44A and 44B are a front view and a side view, respectively, of another embodiment of a treatment device configured to twist and close or occlude the LAA at the ostium of the LAA.
Figure 44B:
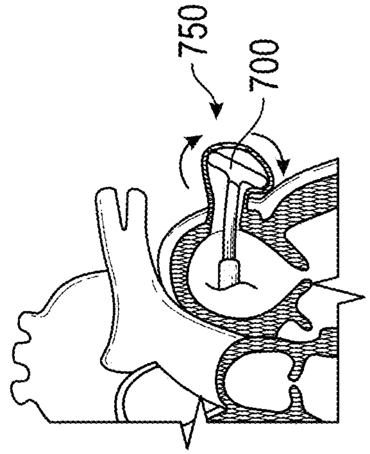
Figure 45A:
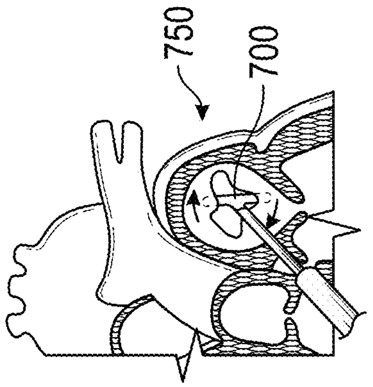
FIGS. 45A and 45B are a front view and a side view, respectively, of the treatment device of FIG. 44, showing the implant being used to twist the LAA to close or occlude the LAA at the ostium.
Figure 45B:
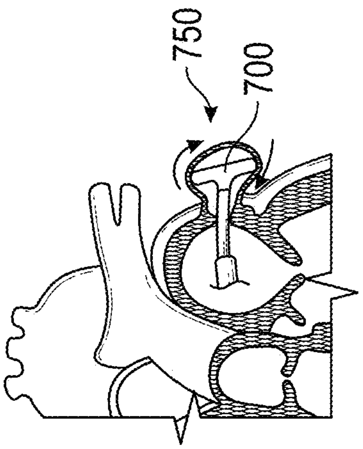
Figure 46A:
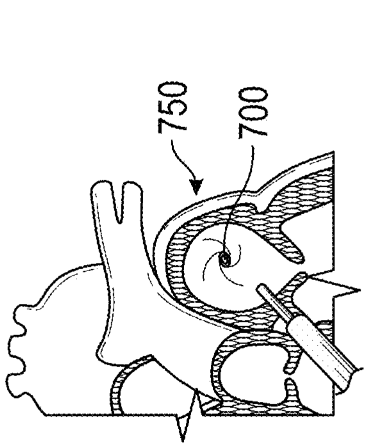
FIGS. 46A and 46B are a front view and a side view, respectively, of the treatment device of FIG. 44, showing the delivery device being removed from the implant device after the LAA has been occluded.
Figure 46B:
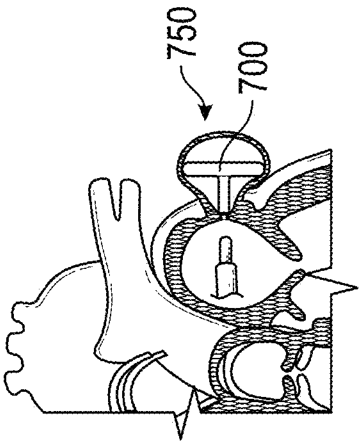
Figure 47A:
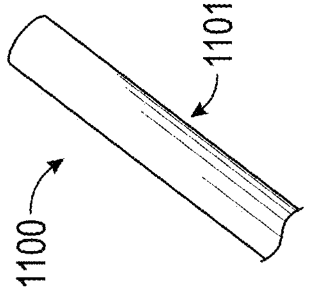
FIGS. 47A-47F show another embodiment of a treatment device for closing or occluding an LAA.
Figure 47B:
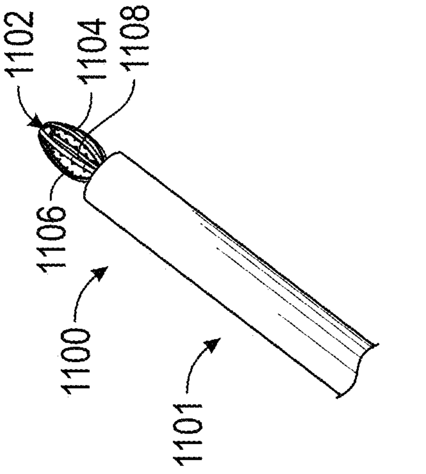
Figure 47C:
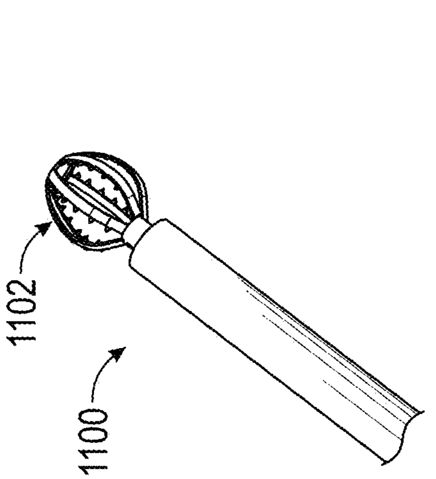
Figure 47D:
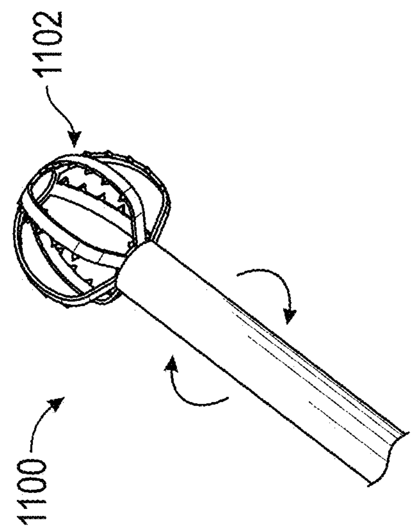
Figure 47E:
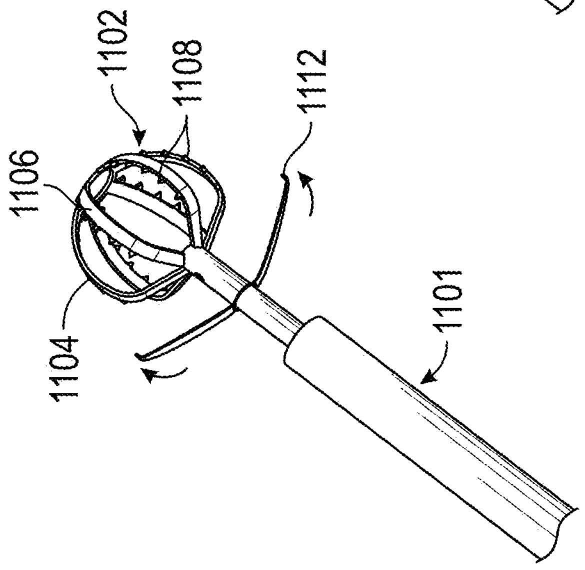
Figure 47F:
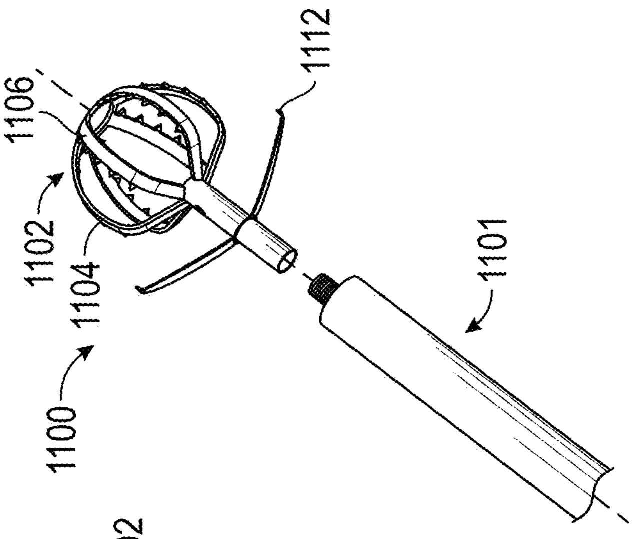
Figure 48A:
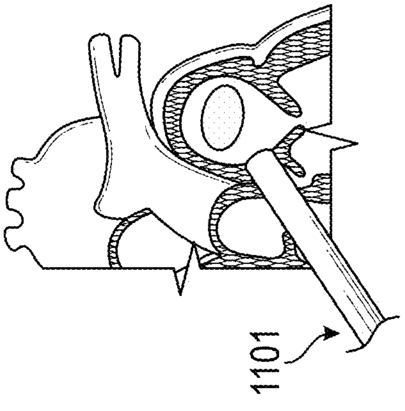
FIGS. 48A-48F show some stages or steps of an exemplifying deployment procedure of the expandable implant of FIGS. 47A-47F for treatment of an LAA.
Figure 48B:
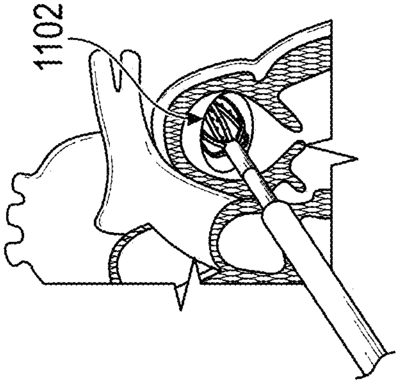
Figure 48C:
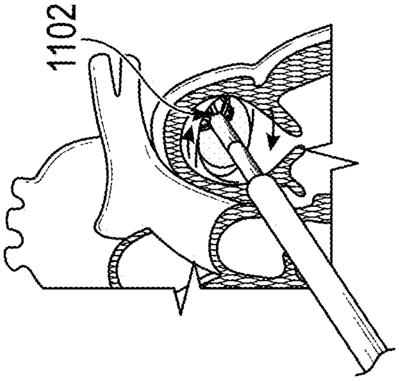
Figure 48D:
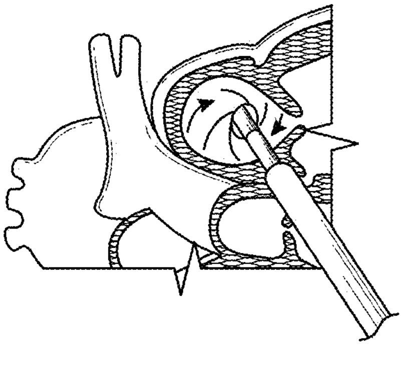
Figure 48E:
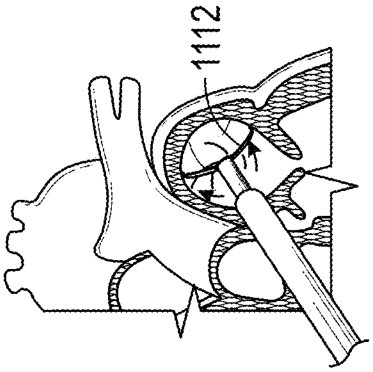
Figure 48F:
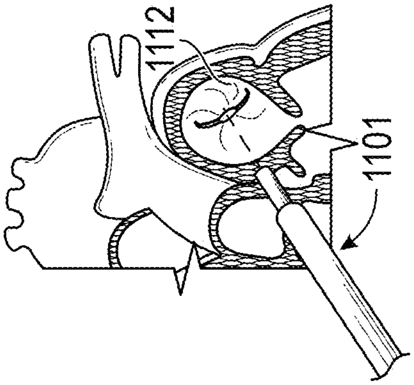
Figure 48G:
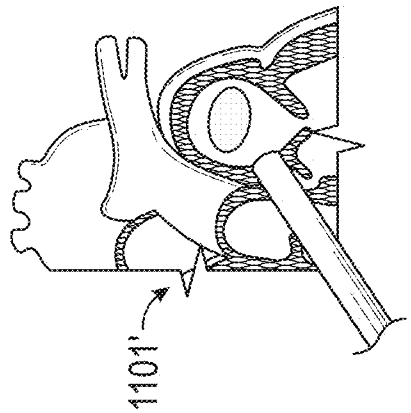
FIGS. 48G-48O show some stages or steps of an exemplifying treatment procedure of another treatment device.
Figure 48H:
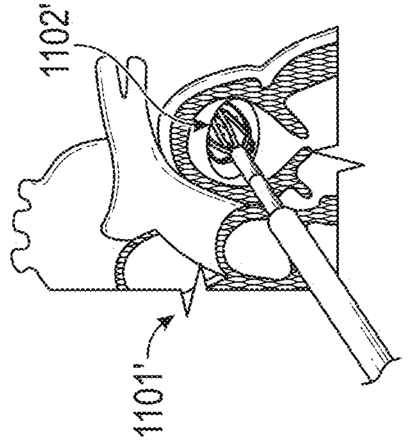
Figure 48I:
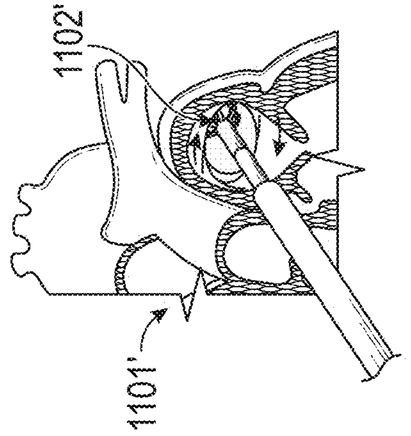
Figure 48J:
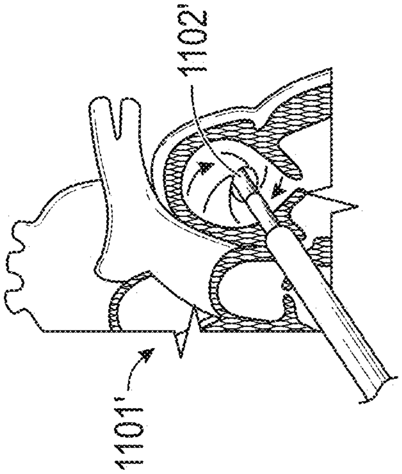
Figure 48K:
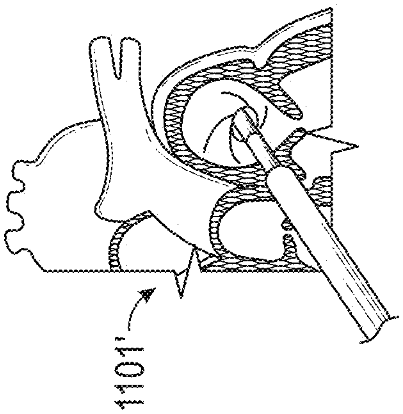
Figure 48L:
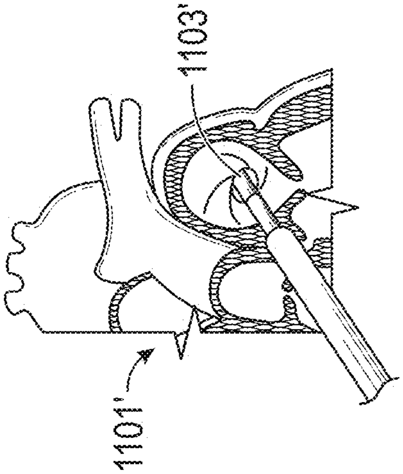
Figure 48M:
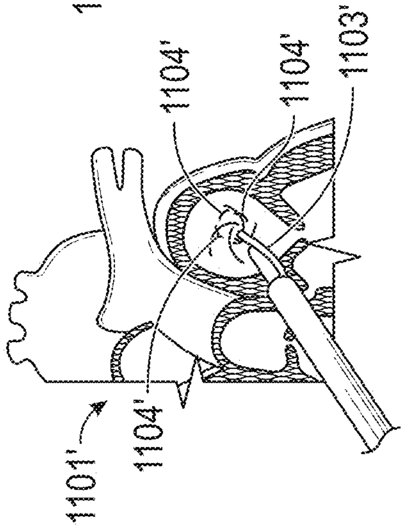
Figure 48N:
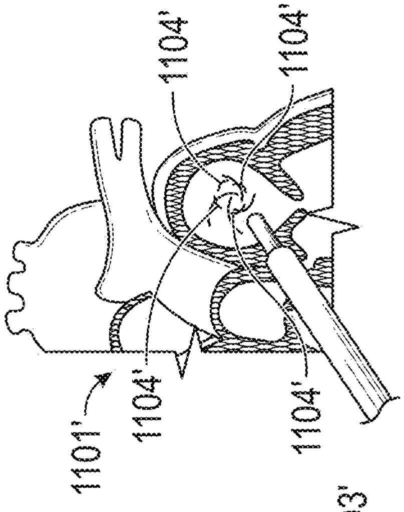
Figure 48O:
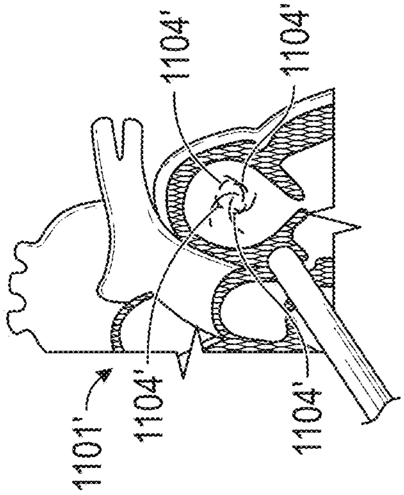

FIGS. 44A and 44B are a front view and a side view, respectively, of another embodiment of a treatment device 750 configured to twist and close or occlude the LAA at the ostium of the LAA. FIGS. 45A and 45B are a front view and a side view, respectively, of the treatment device 750 of FIG. 44, showing the implant being used to twist the LAA to close or occlude the LAA at the ostium. The ostium of the LAA or the material of the LA or LAA that has constricted around the implant device can then be clipped or locked in the constricted state, as in any embodiments disclosed herein and using any securing features or components disclosed herein. FIGS. 46A and 46B are a front view and a side view, respectively, of the treatment device of FIG. 44, showing the delivery device being removed from the implant device after the LAA has been occluded.

In some embodiments, the steps of deployment and implantation can include, in any combination and in any combination with any other steps: (a) inserting catheter and implant device through an ostium of the LAA; (b) rotating a contact member or other engaging component of the implant to twist the LAA, causing at least the ostium of the LAA to collapse on itself, thereby closing or occluding the ostium of the LAA; (c) clipping, holding, or securing the LA and/or LAA tissue in the occluded or closed state; and/or (d) releasing and withdrawing the delivery catheter from the implant. As illustrated, the treatment device twists and closes the LAA at the ostium, and then clip and hold that position, effectively closing the LAA. In some embodiments, the steps of deployment and implantation can include: Inserting catheter into middle of LAA ostium, rotating the paddle of the implant to twist LAA and self-collapsing the LAA on itself, clipping and holding position to atrial wall, and releasing the delivery catheter from the implant.

FIGS. 47A-47F show another embodiment of a treatment device 1100 for closing or occluding an LAA having an embodiment of a delivery device 1101 and an embodiment of an expandable implant or implant 1102 for the left atrial appendage, in particular, showing the implant 1102 in a plurality of exemplifying expansion and deployment stages. The implant 1102 can have a body portion 1104 having a plurality of struts or arms 1106 that are expandable. The body portion 1104 can, in some embodiments, expand to an approximately spherical shape, or elongated spherical shape. The struts 1106 can each have a plurality of barbs or tissue anchors 1108 thereon (which can be or comprise any of the tissue anchors disclosed herein). Any embodiments of the implant disclosed herein can have a laser cut Nitinol body portion that is self-expanding and which is covered with micro-barbs.

The barbs 1108 can be configured to engage the tissue upon the twisting movement or motion of the body portion 1104 relative to an internal wall of the LAA after the body portion 1104 has been expanded from the first state to the second state, wherein, in the second state, the struts 1106 and barbs 1108 can be engaged with or in contact with the tissue on an inside wall of the LAA. Additionally, any embodiments of the implant 1102 can have one or more anchoring elements 1112 configured to engage with the tissue adjacent to or surrounding the LAA to prevent the implant 1102 from rotating back to the first rotational position after the implant 1102 has been rotated within the LAA to the second rotational position. In any embodiments, the anchoring elements 1112 can comprise two arms or members that can each engage a tissue surface and can each have a plurality of barbs thereon, configured to prevent the implant from rotating back to a first rotational position. FIGS. 48A-48E show some stages or steps of an exemplifying deployment procedure of the expandable implant 1102 of FIGS. 47A-47F as the implant 1102 is being deployed into an LAA.

Any of the embodiments of the treatment systems or implant devices disclosed herein can be configured to use one or more sutures, or a plurality of sutures, to maintain the LAA in an occluded state. For example and without limitation, any embodiments disclosed here can be configured such that, after the LAA has been twisted and the ostium of the LAA has been constricted or occluded, one or more sutures or a plurality of sutures can be advanced into the tissue of the ostium of the LAA and/or adjacent to the ostium of the LAA to secure the tissue in the twisted, constricted, and/or occluded state, or inhibit the ostium of the LAA from expanding after the sutures are implanted.

FIGS. 48G-48O show some stages or steps of an exemplifying treatment procedure of another embodiment of a treatment device 1101' that can have any of the components, features, or details of any other embodiments disclosed herein. The treatment device 1101' can have an expandable implant 1102' that can be used to engage the tissue of the LAA and cause the LAA to be twisted upon a rotation of the LAA, and a suture device 1103' configured to implant one or more sutures 1104' in the tissue of the ostium and/or the tissue adjacent to the ostium to inhibit the ostium from expanding, as shown in FIGS. 48L-48O. For example and without limitation, one or more suture loops can be applied to the tissue of and/or adjacent to the LAA ostium in a circular or cross-like intersecting fashion to provide a secure closure. In any embodiments, the sutures can be implanted using a circular purse-string technique, a cross-stitch technique, interrupted or continuous suture techniques, vertical or horizontal mattress techniques, running subcuticular suture techniques, or other suitable technique or any combination of techniques.

Therefore, in some embodiments disclosed herein, the securing element can include one or more sutures. Thereafter, a portion of the implant 1102' can be decoupled from the treatment device 1101' and left in the LAA, or it the entire implant 1102' can be removed, for example and without limitation, before the sutures are pulled tight and tied off. The sutures of any embodiments disclosed herein can be of any suitable material, including nylon, polyester, PTFE, stainless steel, PVDF, polypropylene, and/or any other biocompatible and suitable material.

FIGS. 49A-49G show an embodiment of an implant 1202 that can be used to close or substantially close an LAA. In some embodiments, the implant 1202 can be formed by laser cutting a tube of elastic material, such as Nitinol. The implant 1202 and any other implant embodiment disclosed herein can be self-expanding or mechanically expandable, such as using balloon expansion techniques. Further, any embodiment of the implant 1202 can have any of the same features, components, or details of any other implant embodiments disclosed herein in place of or in combination with any of the features, components, or other details of the embodiments of the implant 1202 disclosed herein. In some embodiments, the implant 1202 can have a contact member 1204 that can be covered with a plurality of micro-barbs or other tissue anchors 1208 and have a securing element 1212 (also referred to herein as an anchoring element) that can include a single folding clip anchor. The securing element 1212 can be configured to lock the implant 1202 in a fixed rotational position after the implant has rotated the LAA to the desired level of twist and closure or occlusion.

Figure 49A:
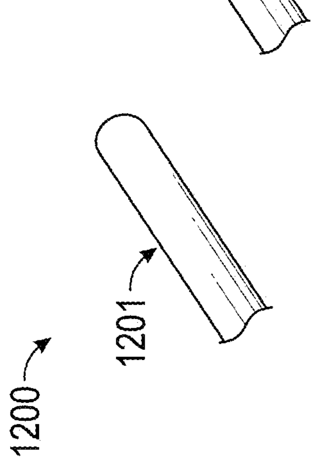
FIGS. 49A-49G show another embodiment of a treatment device for closing or occluding an LAA.
Figure 49B:
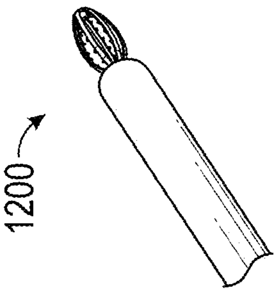
Figure 49C:
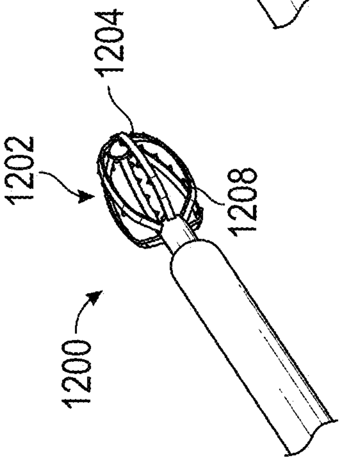
Figure 49D:
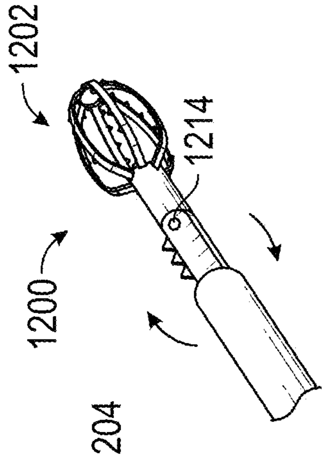
Figure 49E:
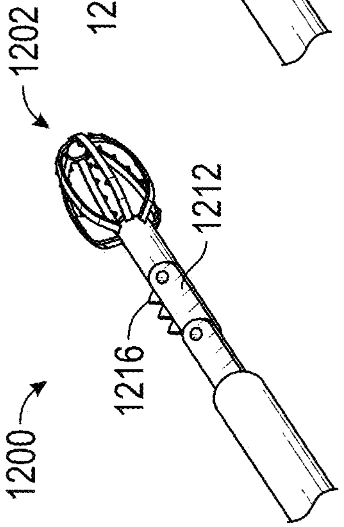
Figure 49F:
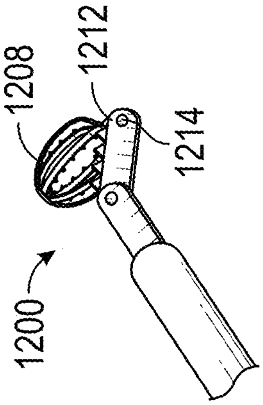
Figure 49G:
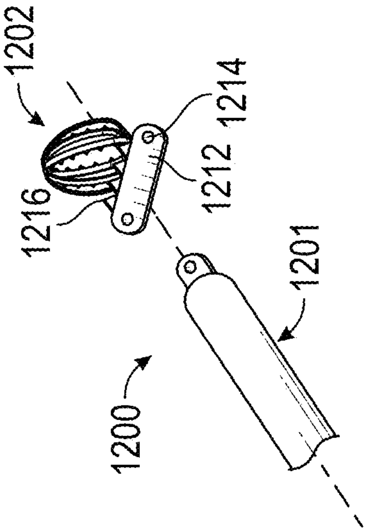
Figures 50A, 50B, 50C, 50D, 50E, 50F:
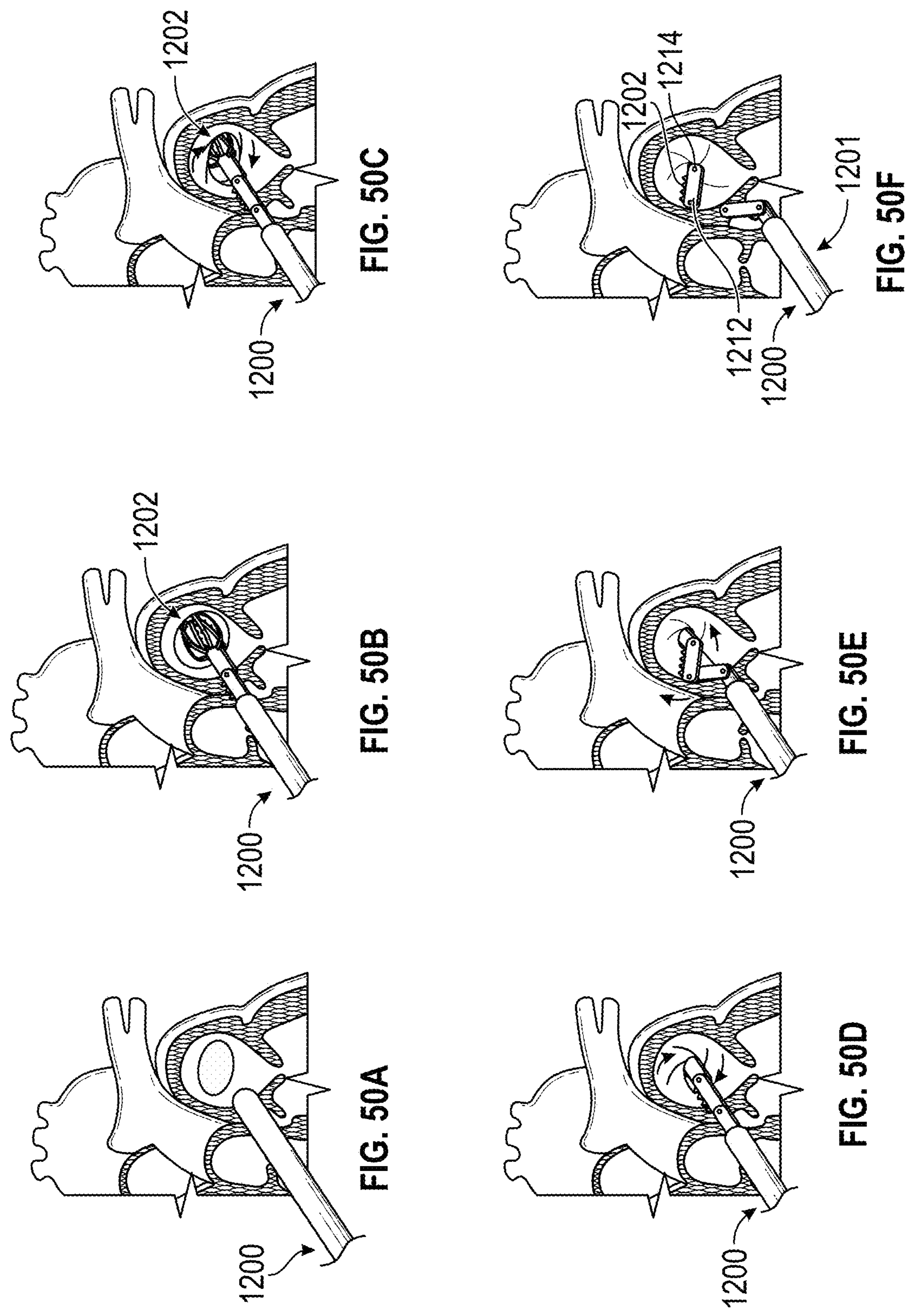
FIGS. 50A-50F show some stages or steps of an exemplifying deployment procedure of the expandable implant of FIGS. 49A-49G for treatment of an LAA.

FIGS. 50A-50F show some exemplifying stages of an embodiment of a deployment procedure of the expandable implant 1202 of FIGS. 49A-49G as the implant 1202 is being deployed into an LAA. In any embodiments, the implant 1202 can be advanced into the LAA, expanded, and then rotated from a first rotational position to a second rotational position so as to twist the LAA and cause an ostium and/or other tissue of the LAA to constrict or occlude about a portion of the implant 1202. The implant or any implant disclosed herein can be configured to be rotated clockwise (and can be rotated clockwise and/or counter-clockwise during any procedures disclosed herein) to twist and close or substantially close the ostium of the LAA or constrict the ostium of the LAA about a portion of the implant 1202. After the desired level of occlusion is reached, the securing element 1212 can be rotated or folded (such as, for example and without limitation, about an axis or a hinge 1214) to a lateral side of the LAA so as to be approximately perpendicular to the axial centerline of the implant, and forced into engagement with the tissue adjacent to the LAA adjacent to the ostium of the LAA to prevent unwinding of the implant and the ostium of the LAA. A body portion of the securing element 1212 can also have tissue anchors 1216 thereon or coupled or integrally formed therewith that can engage with, penetrate, and/or grip the tissue of the LA and/or LAA that has constricted as a result of the twisting of the LAA. In any embodiments disclosed herein, the securing element 1212 can be configured to be biased toward and/or securable in a second, locked state (such as is shown in FIG. 49G or FIG. 50F, using springs, shape memory material, sutures, ties, or other components. The delivery device can be disconnected from the implant and removed from the patient's body after deployment of the securing element 1212, as shown in FIG. 50F.

Figure 51:
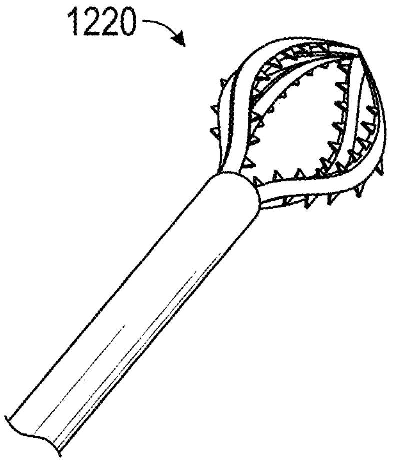
FIG. 51 shows another embodiment of a contact member that can be used with any treatment device embodiments disclosed herein.
Figure 52:
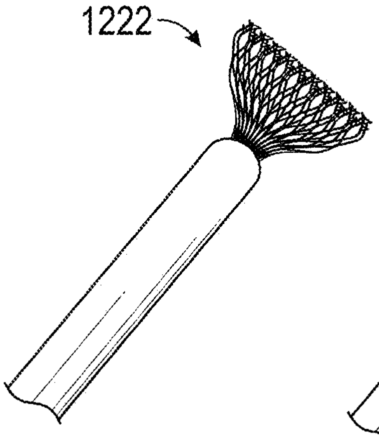
FIG. 52 shows another embodiment of a contact member that can be used with any treatment device embodiments disclosed herein.
Figure 53:
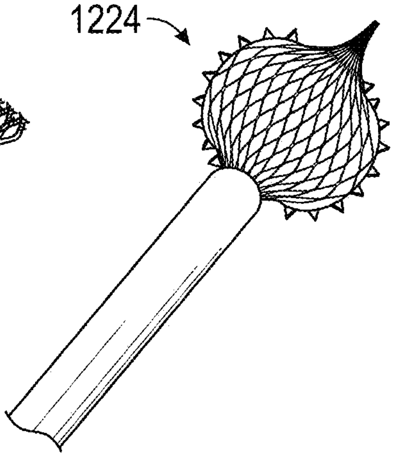
FIG. 53 shows another embodiment of a contact member that can be used with any treatment device embodiments disclosed herein.

FIGS. 51, 52, and 53 show additional embodiments of implant devices 1220, 1222, and 1224 (note that implant devices are also referred to herein as implants) that can be used with any of the embodiments of the treatment devices or procedures disclosed herein to treat an LAA. The implant device 1220 shown in FIG. 51 can have ribbons or struts made from Nitinol or any other suitable material which are configured to expand to an approximately spherical or elongated spherical shape, and which can be covered with small barbs or cleats (or other tissue anchors). The tissue anchors can be pointing in one or both circumferential directions. The implant device shown in FIG. 52 can have a stent-like body made from Nitinol or any other suitable material which can self-expand or be balloon expandable to an approximately spherical or elongated spherical shape. The body of the implant can be covered uniformly or otherwise with small barbs or cleats (or other tissue anchors). The implant device 1224 shown in FIG. 53 can have a woven wire body, which can be made from stainless steel, Nitinol or any other suitable material, and which can be configured to expand to an approximately spherical or elongated spherical shape. The body of the implant device 1224 can be covered uniformly or otherwise with small barbs or cleats (or other tissue anchors).

Figure 54:
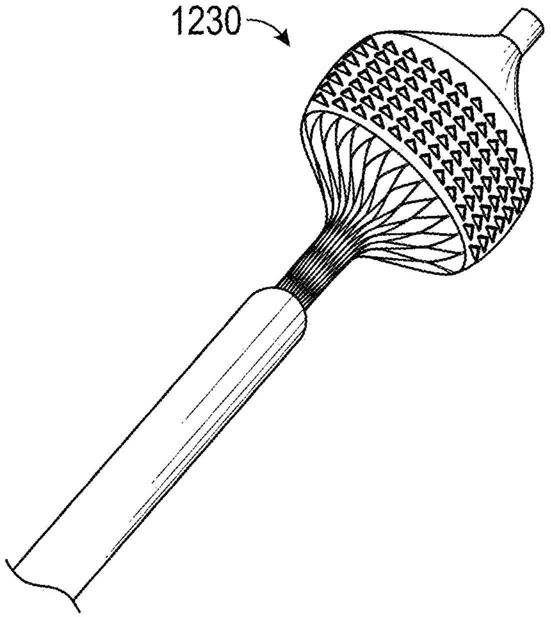
FIG. 54 shows another embodiment of a contact member that can be used with any treatment device embodiments disclosed herein.

FIG. 54 shows another embodiment of an implant device 1230 which can expand (or be expanded) to an approximately spherical or elongated spherical shape. For example and without limitation, the implant device 1230 can be configured to cover an inflatable balloon that can be inflated to expand the implant device 1230 into contact with the tissue of the LAA when the implant device 1230 is in a desired position within the LAA. The implant body 1230 covered with small barbs or cleats or other tissue anchors.

Figure 55:
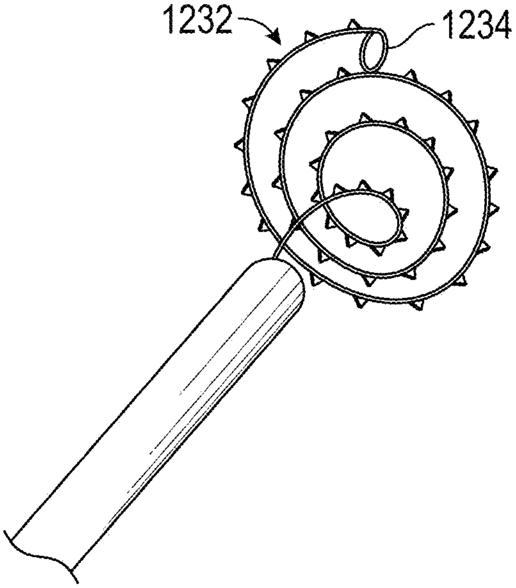
FIG. 55 shows another embodiment of a contact member that can be used with any treatment device embodiments disclosed herein.

FIG. 55 shows another embodiment of an implant device 1232 that can be used with any of the treatment device embodiments disclosed herein. In some embodiments, the implant device 1232 can have spiral shaped body at least when in a second, expanded state that can be used to exert the torque and twisting effect on the LAA. The implant device 1232 can be made from Nitinol, and can be covered with or have a plurality of small barbs, cleats, or other tissue anchors. The implant device 1232 can be self-expanding and can have a half-dome shape when in the second state. In some embodiments, the implant device 1232 can have a rounded end 1234 that can be approximately the same size as an internal lumen of the delivery system, or can be smaller, or larger and expandable.

Figure 55A:
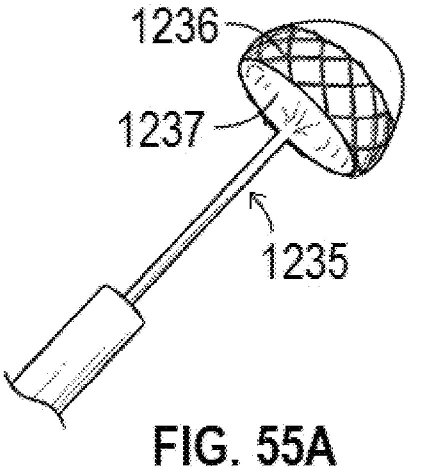
FIGS. 55A-55C show additional embodiments of implants that can be used with any treatment device embodiments disclosed herein.

FIG. 55A shows another embodiment of a treatment device having an implant device 1235 that can be used with any of the treatment device embodiments disclosed herein. In some embodiments, the implant device 1235 can have contact member 1236 that can have a generally cylindrically shaped structure, having a plurality of wires, struts or braids that can be laser cut from a hypotube, braided, woven, or formed using any other suitable technique known in the art. In some embodiments, the contact member 1236 can be shaped and formed like an expandable stent. The contact member 1236 can be mechanically expandable or self-expanding. As in any embodiments disclosed herein, the contact member 1236 can have a plurality of tissue barbs or anchors thereon configured to engage the tissue inside the LAA. As with any other implant embodiments disclosed herein, the implant 1235 can be configured to cause the LAA to twist upon a rotation of the implant, after the implant has been advanced into engagement with the LAA.

Further, any embodiments of the implant device 1235 can have an expandable member 1237 (such as a bladder or balloon) therein, the expandable balloon 1237 being selectively expandable to cause the expansion of the contact member 1236. In some embodiments, the expandable member 1237 can be sealable and removable from the delivery device so that the expandable member can remain in the LAA after the treatment procedure to occlude the LAA has been completed. In other embodiments, the treatment system having the implant device 1235 can be configured such that the implant device is removed either before or after the ostium of the LAA is secured in an occluded state.

Figure 55B:
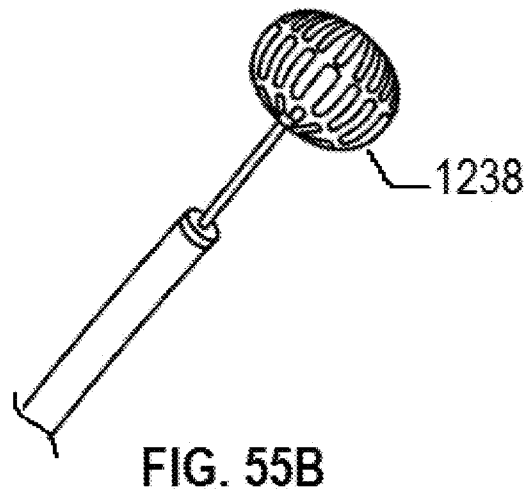

In other embodiments, the implant device of any embodiments disclosed herein can have a contact member that has a spherical shape. For example and without limitation, the implant device of any embodiments disclosed herein can have a generally spherical shaped contact member 1238 like as shown in FIG. 55B. The contact member 1238 can be made from a laser cut hypotube and formed into the desired shape and size, formed from one or more wires, or formed using any other suitable technique known in the art. As with any embodiments disclosed herein, the contact member 1238 can be closed on both ends, or open on one or more of the ends, and can be formed from Nitinol, stainless steel, or any other suitable material, and can be self-expanding, mechanically expandable, for example, balloon expandable, or otherwise. The contact member 1237 can have a plurality of tissue barbs or anchors thereon configured to engage the tissue inside the LAA.

Figure 55C:
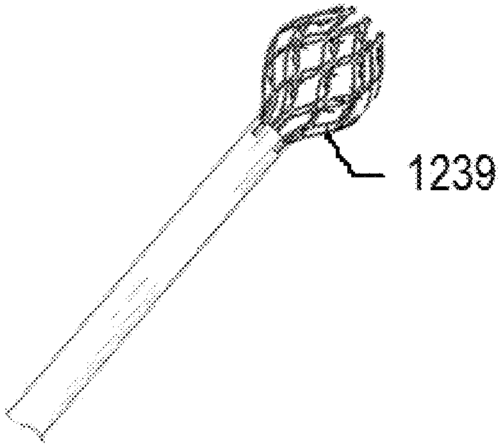

In other embodiments, the implant device of any embodiments disclosed herein can have a contact member that has a generally bulbous shape. For example and without limitation, the implant device of any embodiments disclosed herein can have a generally bulbous shaped contact member 1239 like as shown in FIG. 55C. The contact member 1239 can be open on a distal end thereof and can be made from a laser cut hypotube and formed into the desired shape and size, formed from one or more wires, or formed using any other suitable technique known in the art. As with any embodiments disclosed herein, the contact member 1238 can be formed from Nitinol, stainless steel, or any other suitable material, and can be self-expanding, mechanically expandable, for example, balloon expandable, or otherwise. The contact member 1239 can have a plurality of tissue barbs or anchors thereon configured to engage the tissue inside the LAA.

Figure 56A:
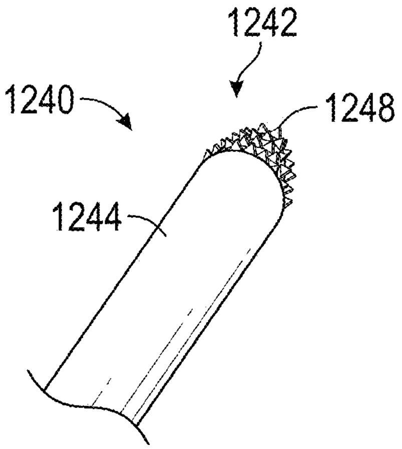
FIGS. 56A-56B show another embodiment of a contact member that can be used with any treatment device embodiments disclosed herein.
Figure 56B:
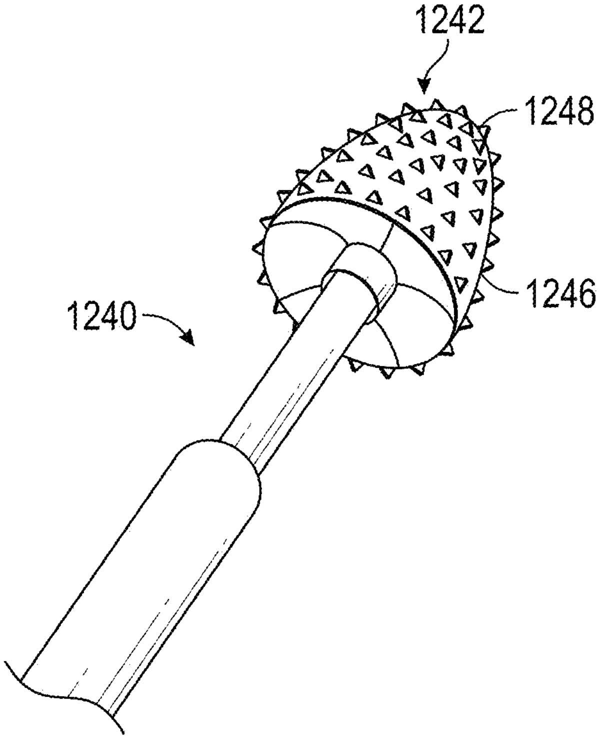
Figure 57A:
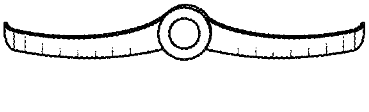
FIGS. 57A-57B show another embodiment of a securing element that can be used with any treatment device embodiments disclosed herein.
Figure 57B:
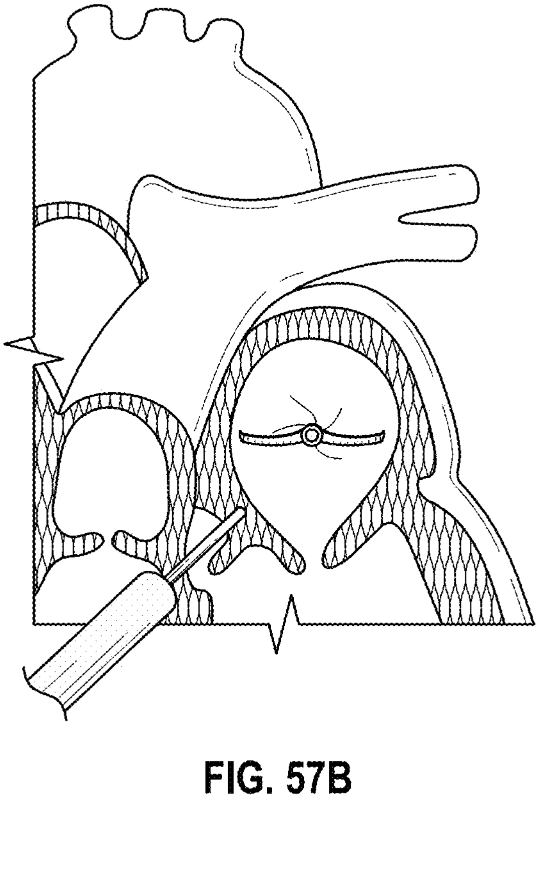

FIGS. 56A-56B show an embodiment of treatment device 1240 having an implant device 1242, with the implant device 1242 being mostly contained with a catheter body

1244 of the treatment device 1240 in FIG. 56A, and at least a contact member 1246 of the implant device 1242 being in a second, expanded state in FIG. 56B. The contact member 1246 can have a plurality of barbs or anchor members about an outside surface thereof, and can be configured to expand to an approximately spherical or elongated spherical shape. The contact member 1246 can be self-expanding, or mechanically expandable, and can have a half-dome shape with a rounded distal end portion 1248. In some embodiments, the rounded end portion 1248 can be approximately the same size as an internal lumen of the delivery system, or can be smaller, or larger and expandable.

FIGS. 57-61 show additional different embodiments of anchoring elements or securing elements that can be used with any of the other components of the implant device embodiments disclosed herein. FIG. 57A shows an embodiment of a double arm securing element. FIG. 57B shows the double arm securing element of FIG. 57A being advanced into the tissue of the LA and/or LAA adjacent to the ostium of the LAA that has constricted around a body portion of the implant device.

Figure 58A:
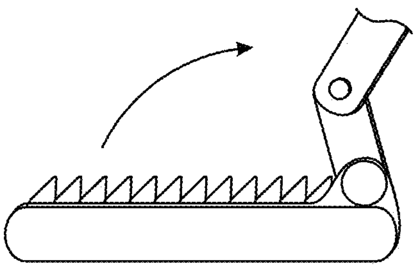
FIGS. 58A-58B show another embodiment of a securing element that can be used with any treatment device embodiments disclosed herein.
Figure 58B:
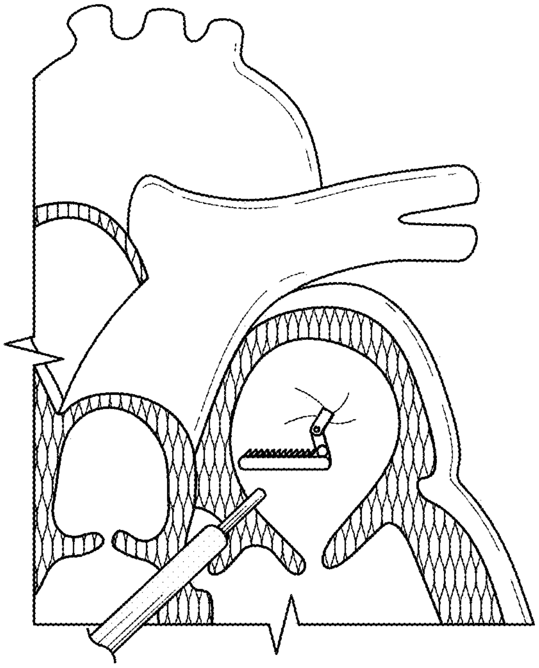
Figure 59A:
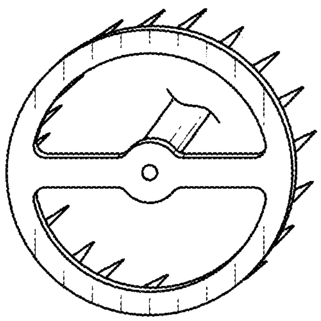
FIGS. 59A-59B show another embodiment of a securing element that can be used with any treatment device embodiments disclosed herein.
Figure 59B:
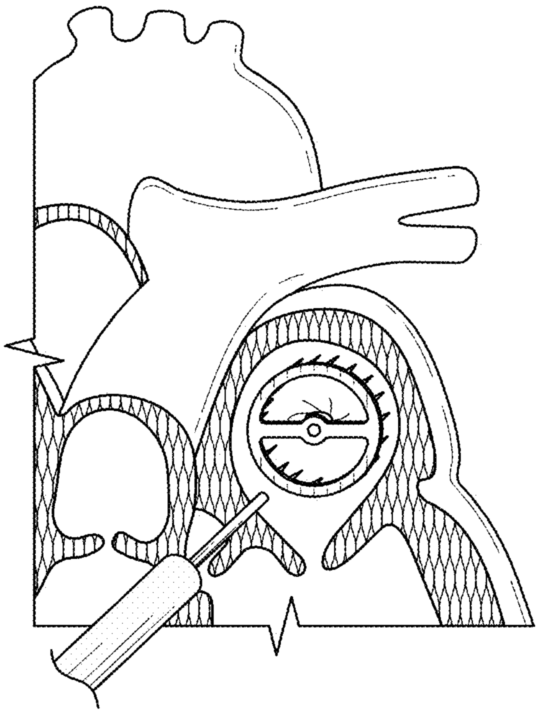

FIG. 58A shows an embodiment of a single folding clip anchor or securing element. FIG. 58B shows the single arm securing element of FIG. 58A being rotated against or clipped against the tissue of the LA and/or LAA adjacent to the ostium of the LAA that has constricted around a body portion of the implant device. In any embodiments, the securing element can be biased to remain in the secured or locked position. FIG. 59A shown an embodiment of a round disk anchor or securing element. FIG. 59B shows the round disk securing element of FIG. 59A being advanced toward the tissue of the LA and/or LAA adjacent to the ostium of the LAA that has constricted around a body portion of the implant device so that one or more tissue anchors of the securing element of FIG. 59A can engage with and/or penetrate into the tissue of the LA and/or LAA adjacent to the ostium of the LAA.

Figure 60A:
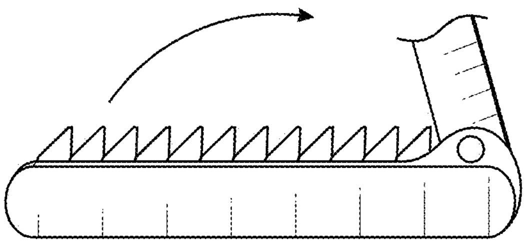
FIGS. 60A-60B show another embodiment of a securing element that can be used with any treatment device embodiments disclosed herein.
Figure 60B:
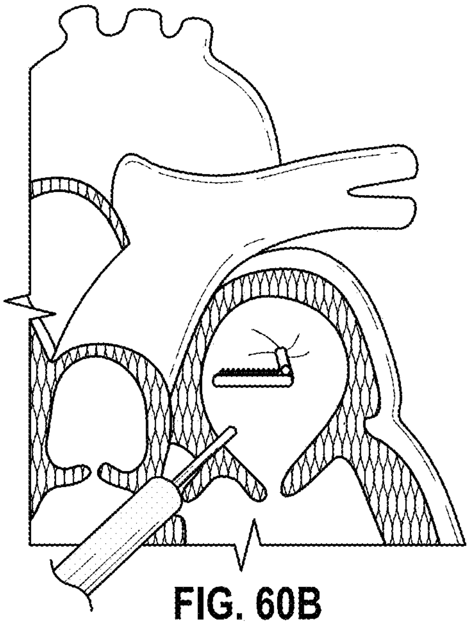
Figure 61A:
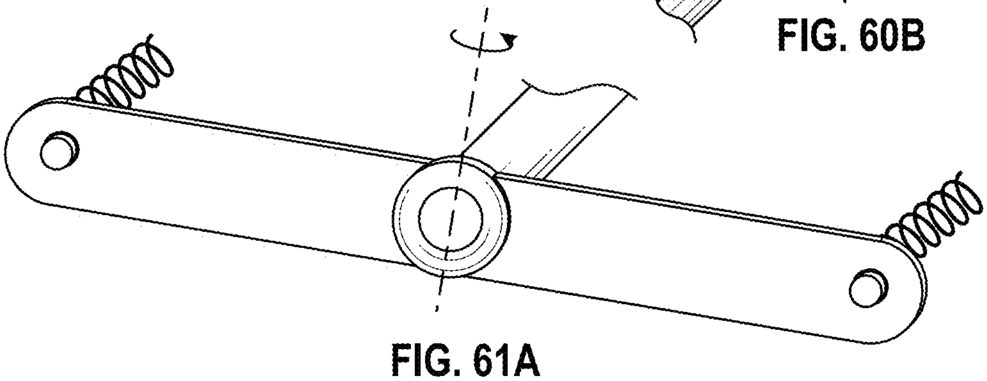
FIGS. 61A-61B show another embodiment of a securing element that can be used with any treatment device embodiments disclosed herein.
Figure 61B:
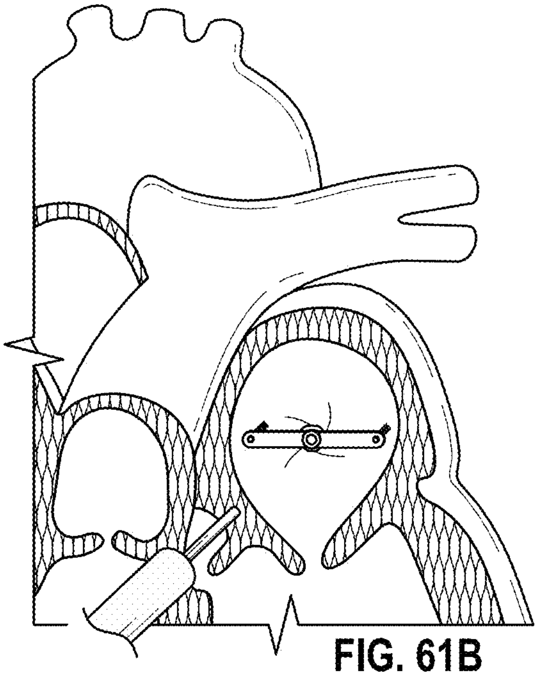

FIG. 60A shows an embodiment of a single folding clip anchor or securing element with a helical or screw type tissue anchor that can be used to engage with and/or penetrate into the tissue of the LA and/or LAA adjacent to the ostium of the LAA that has constricted around a body portion of the implant device. FIG. 60B shows the single folding clip anchor or securing element of FIG. 60A being rotated against or clipped against the tissue of the LA and/or LAA adjacent to the ostium of the LAA that has constricted around a body portion of the implant device. In any embodiments, the securing element can be biased to remain in the secured or locked position. FIG. 61A shows a double arm securing element with two helical or screw type tissue anchors. FIG. 61B shows the double arm securing element of FIG. 61A being rotated against the tissue of the LA and/or LAA adjacent to the ostium of the LAA that has constricted around a body portion of the implant device so that the tissue anchors on the arms can engage with and/or penetrate into the tissue. Both arms of the securing element of FIG. 61A-61B can collapse toward a body portion or axial centerline of the securing element, and can be configured to automatically deploy when extended past a distal end of the delivery catheter.

Figure 62A:
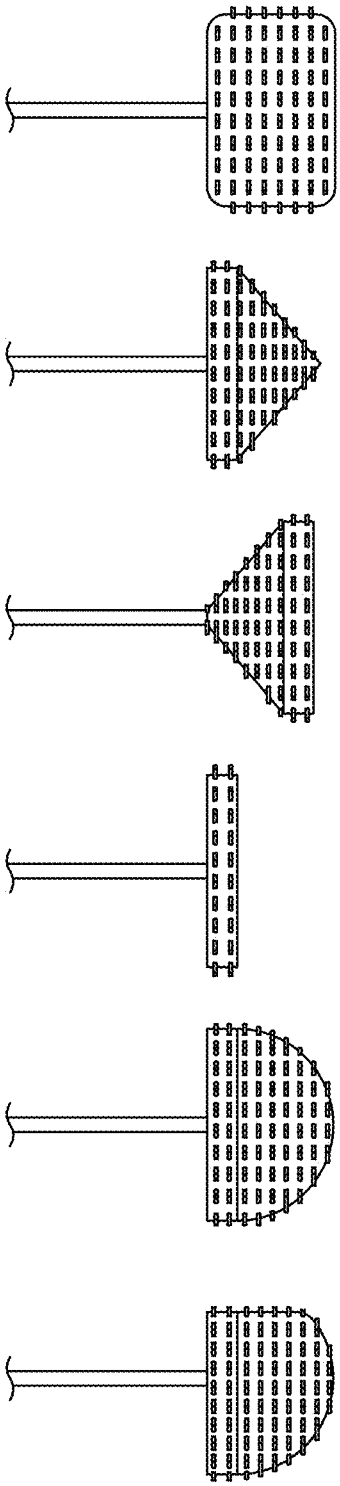
FIGS. 62A-62B show additional embodiments of contact members that can be used with any treatment device embodiments disclosed herein.
Figure 62B:
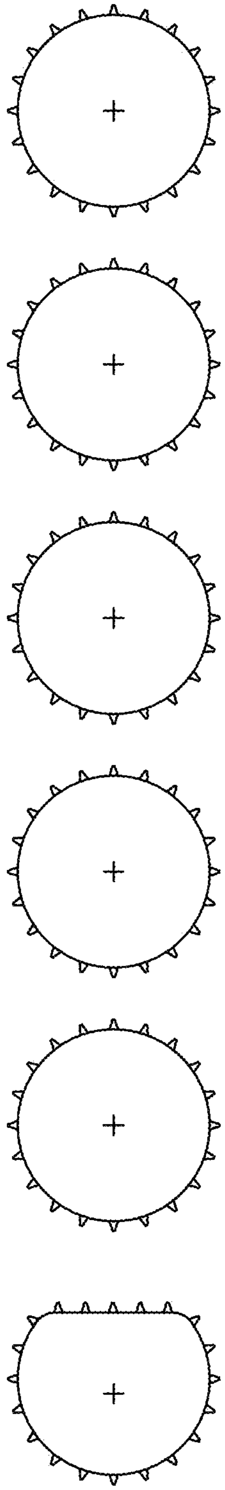

FIGS. 62A-62B show side view and end views of different embodiments of contact member that can be deployed within the LAA to engage the tissue of the LAA so as to cause the LAA to twist when a torque is applied to the contact member. FIGS. 62A-62B show embodiments of contact members having cylindrical or thick disc shaped body portions, spherical shaped body portions, conical shaped body portions, and semi-spherical and/or half-spherical shaped body portions that are configured to better engage or couple with LAA tissue. Any of the embodiments of the contact members shown in FIGS. 62A-62B can have a plurality of barbs, micro-barbs, or other tissue anchors on an outside surface thereof. Additionally, any of the embodiments of the contact members shown in FIGS. 62A-62B can have outside surfaces that are uniformly covered with barbs, micro-barbs, or other tissue anchors. Further, any of the embodiments of the body portions disclosed herein, including without limitation the half-sphere shaped body portion shown in FIGS. 62A-62B, can have a flat area on one portion thereof to allow for a lower profile.

Figure 62D:
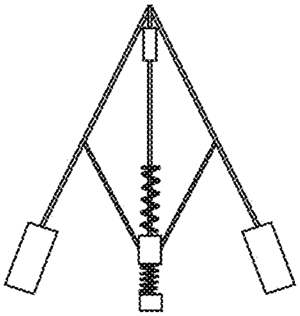
Figure 62D:
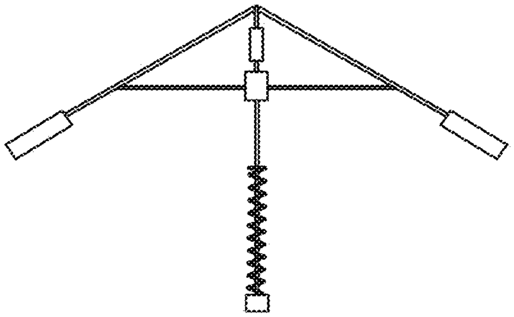
Figure 62D:
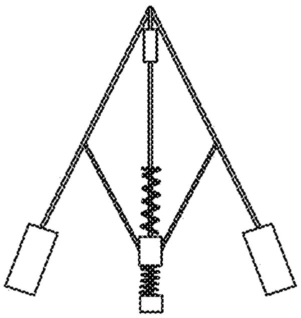
Figure 62D:
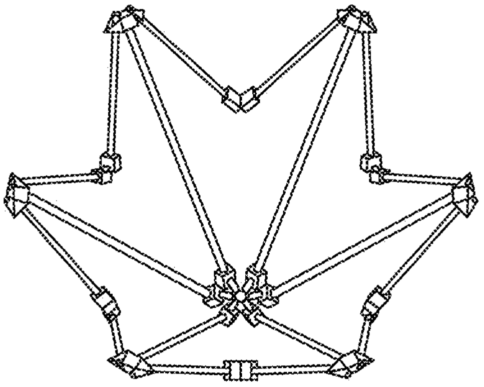
Figure 62E:
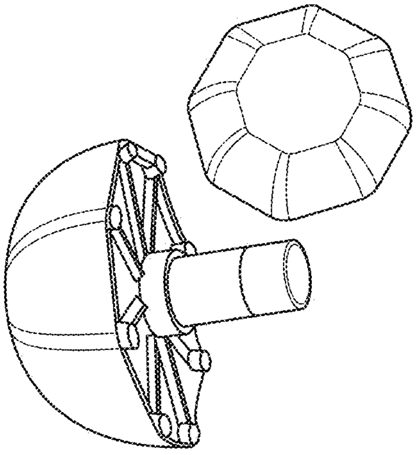
Figure 62F:
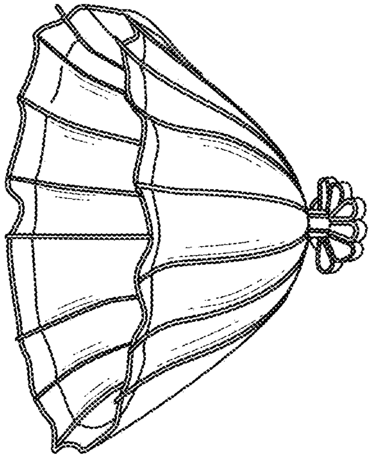
Figure 62I:
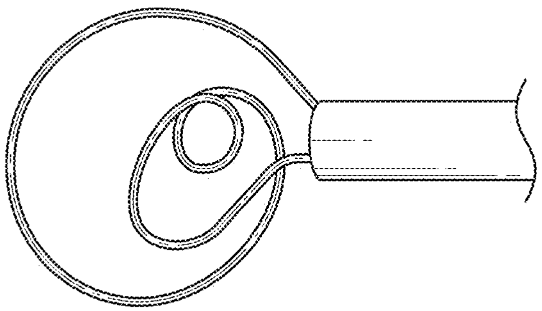
Figure 62J:
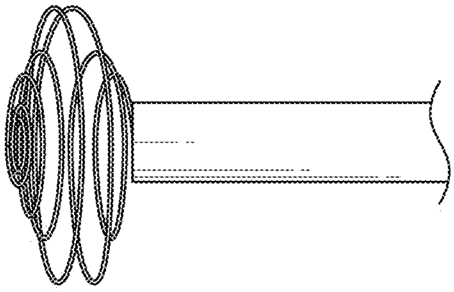
Figure 62K:
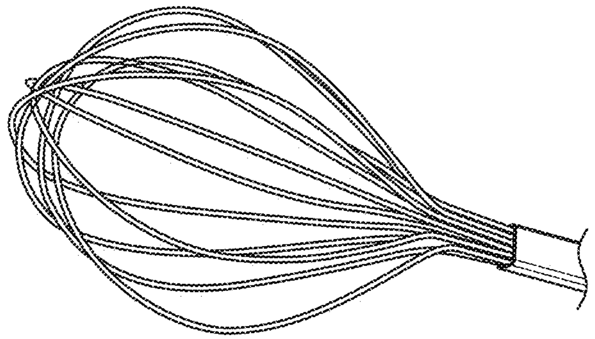
Figure 62L:
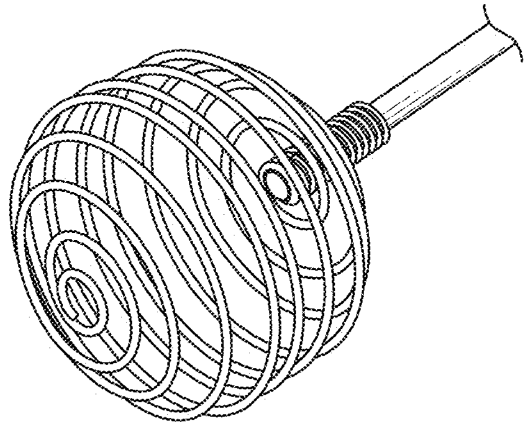
Figure 62M:
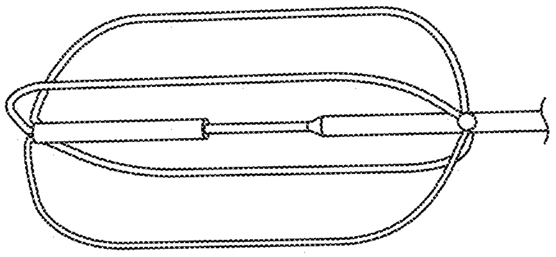
Figure 62N:
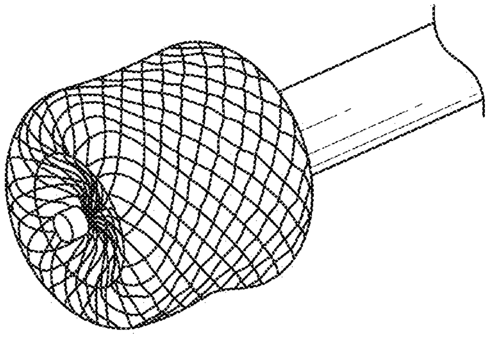
Figure 62O:
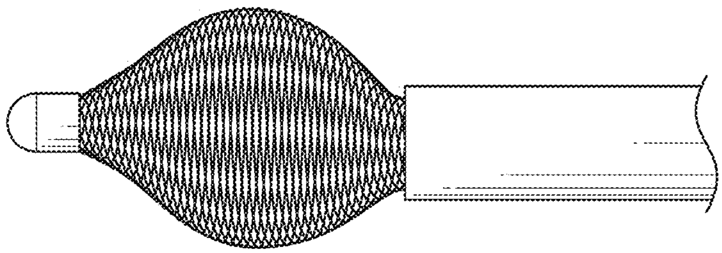
Figure 62P:
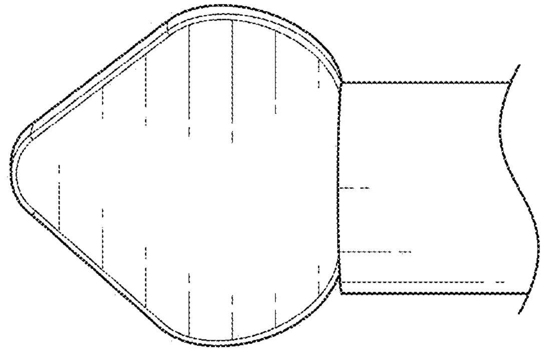
Figure 62Q:
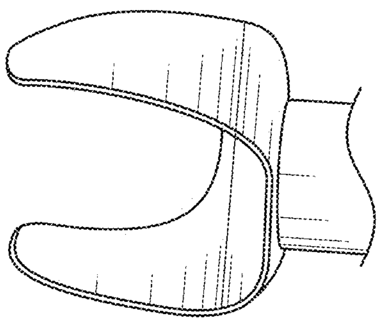
Figure 62T:
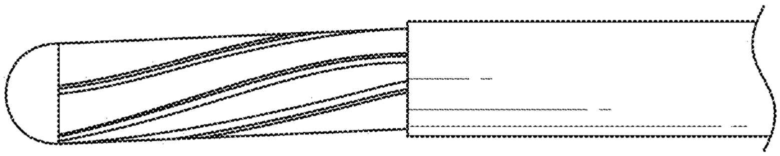
Figure 62T:
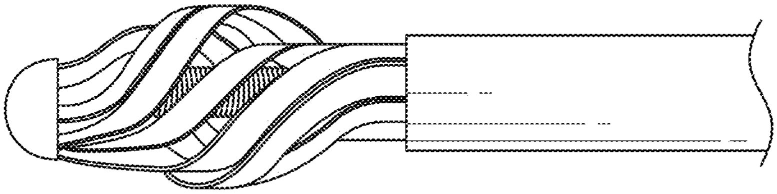
Figure 62T:
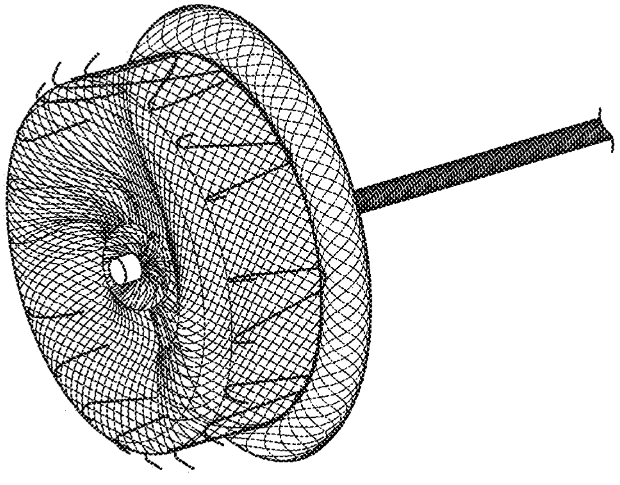
Figure 62U:
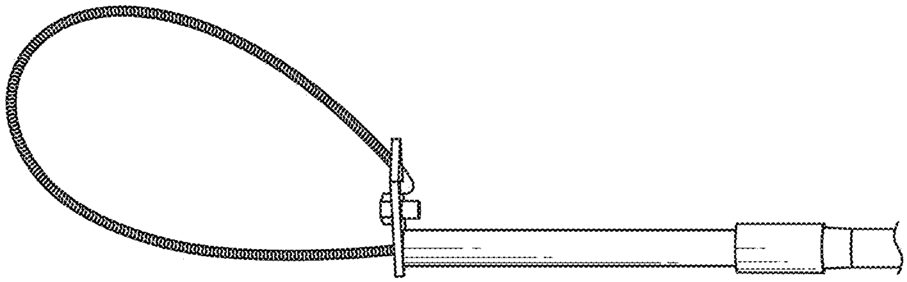
Figure 62V:
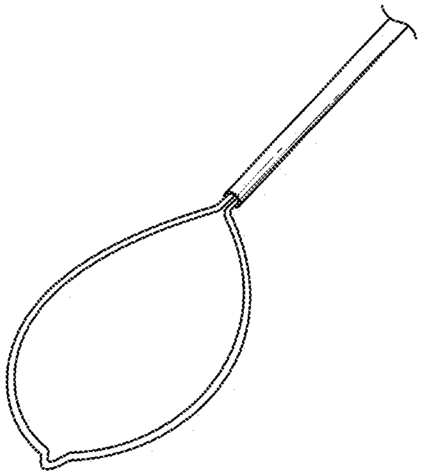
Figure 62W:
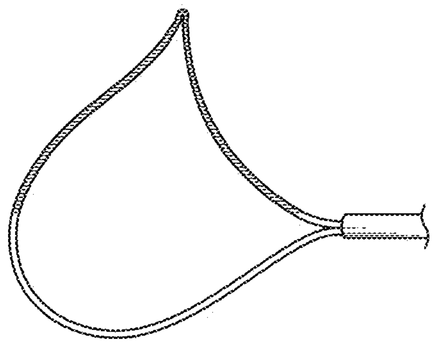
Figure 62X:
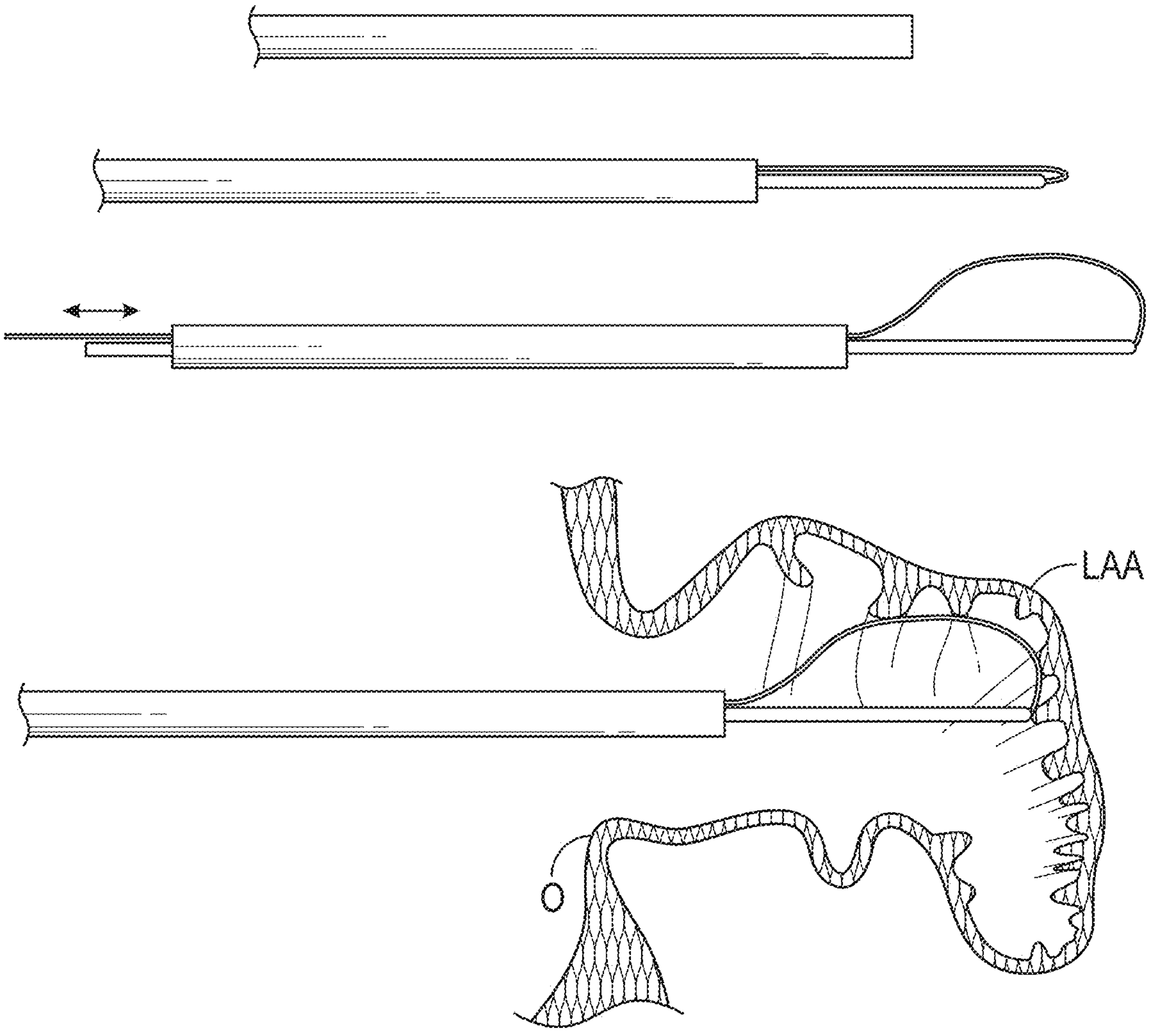
Figure 62Y:
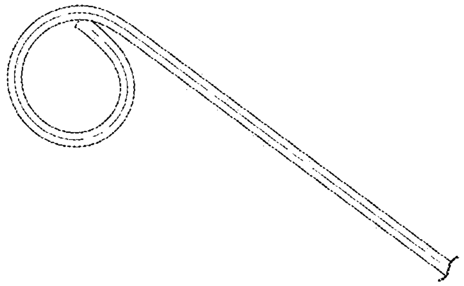
Figure 62Z:
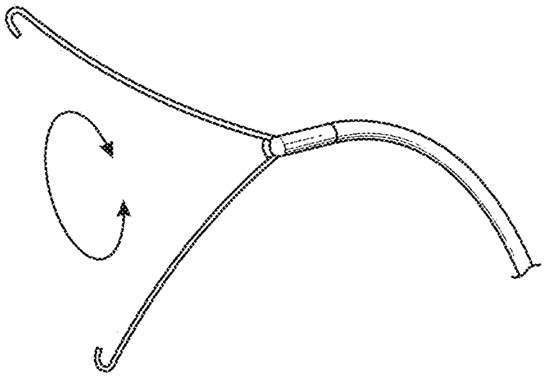

FIGS. 62C1-62Z show additional embodiments of contact members and/or implant devices that can be used with any of the embodiments of the treatment devices disclosed herein. Further, any of the contact member embodiments disclosed herein can have any of the features, components, or other details of any of the other contact member embodiments and/or implant device embodiments disclosed herein, including without limitation, tissue barbs, covers, and other features in combination with any of the components, features, and details disclosed for these embodiments below. Further, any of these devices shown in any of FIGS. 62C1-62Z can be configured to be removed from the LAA or to remain indefinitely in the LAA. Any of the embodiments of the contact members and/or implant devices shown in FIGS. 62C1-62Z can be configured to be expanded to grip the LAA for twisting the LAA occluded or closed. Some embodiments of the contact members and/or implant devices shown in FIGS. 62C1-62Z can be configured to be collapsed after a securing element is engaged with the tissue of the LAA and/or surrounding the LAA and/or the contact member to further reduce the remainder of the closed LAA pouch (e.g., to zero).

FIGS. 62C1-62C3 show an embodiments of a contact member have a tube extending through a middle thereof, a stretcher, and a runner. The contact member shown in FIGS. 62C1-62C3 can be expanded in a radial direction by advancing the runner in an axial direction along the tube, thereby causing the stretchers to extend outwardly so that arms or ribs can expand outwardly, for example against the tissue of the LAA. The contact member can be selectively secured in the expanded state and/or collapsed when desired. The hinges of this contact member can reduce the overall profile of the contact member for small passageway delivery. As with any contact member embodiments, the contact member shown in FIGS. 62C1-62C3 can have one or a plurality of tissue barbs on an outside surface thereof, such as at the ends of the ribs, as represented by the rectangular shaped objects at the ends of the ribs.

The contact member device shown in FIG. 62D can have a plurality of hinges and a plurality of struts to improve the collapsibility and, hence, the reduce the profile of the contact member when the contact member is in the collapsed state. In some embodiments, the contact member shown in FIG. 62D can be open on one end, can be enclosed on both ends such as with a sphere or elongated shaped member. The device of FIG. 62E can be open on one end and closed or sealed on the second end. The contact member shown in FIG. 62D can have a cover thereon configured to provide a seal to the opening of the LAA in a deployed or operable state. The contact member shown in FIG. 62F can be invertible so that the arms of the device can extend in either direction. A cover can be coupled with the arms of the device. The arms can be flexible and unrestrained at a distal end thereof, or can be retrained at a distal end thereof.

The contact member of FIG. 62G1-62G2 is shown extending from a distal end of a delivery catheter. The contact member can have a plurality of struts or arms, for example from 15-20 struts or arms, that extend out radially around the device. The arms can have a larger distal diameter or size as compared to a diameter or size of the device at or near a proximal end of the device. The device can have one or more tissue barbs or anchors having a spike like shape extending outwardly from each of the struts. Some embodiments of the contact member of FIGS. 62G1-62G2 can also be used to secure the LAA in the twisted state or configuration. In some embodiments, the user can deploy the contact member, rotate the contact member, and reduce a profile or size of the contact member so that the struts and/or tissue anchors on an outside surface of the contact member that are engaged with the tissue of the LAA can cause the LAA to collapse. The contact member shown in FIGS. 62G1-62G2 can therefore secure one or more folds in the tissue in this configuration. The user can axial advance the contact member to expand the contact member to the second state and engage the tissue of the LAA with the arms of the contact member, rotate the contact member to constrict the tissue of the LAA, and axially withdraw the contact member to contract the contact member, thereby causing the LAA to be secured by the contact member when the contact member is in the radially closed position. The contact member can thereafter by detached from the delivery device, in some embodiments. In some embodiments, this can be done with a Spiral Rib design.

FIGS. 62H1-62O show additional embodiments of contact members that can be used with any treatment devices disclosed herein. Some embodiments of the contact members, including the embodiments of the contact members shown in FIGS. 62N and 62O, can be configured to expand by shortening an axial length of an internal shaft, wire, suture, or other component of the contact member so that the outer structure of the contact member is caused to expand outwardly as the length of the outer structure is shortened. These contact members can be collapsed by increasing the length of the outer structure.

FIGS. 62H1 and 62H2 show another embodiment of a contact member that can have a helical spring shape having a closed end. The contact member shown in FIG. 62H can be attached to a distal portion of the LAA. When the contact member is deployed and released, the contact member can rotate and wind up LAA. A coil in the distal tip thereof can screw into the tissue of the LAA to secure the contact member and the LAA in the twisted or wound state. Other embodiments of the contact member can have tissue anchors, gripping features, and/or one or more clip mechanisms. To prevent the wire from rotating instead of the LAA, in some embodiments, the wire can have a square cross-section that runs through a keyway or square lumen, as shown in FIG. 62H2, that forces the twist to be at the coil tip and the LAA.

FIGS. 62P and 62Q show two different embodiments of a contact members having a fixed size and profile. The contact member shown in FIG. 62P can have a single smooth or blunt blade or plate and the contact member shown in FIG. 62Q can have a pair of blunt or smooth blades or plates that can extend in an axial direction to engage a tissue surface on the inside of the LAA.

The embodiments of the contact members of FIGS. 62R1-62R2, which are shown being deployed in FIGS. 62R3 and 62R4, can have one or more struts configured to provide visual feedback to the surgeon of when the contact member has made contact with the tissue of the LAA and, in some embodiments, approximately how much force is being applied to the visual indicator and, hence, the contact member. The visual indicator is configured to deflect and deform to provide such a visual indication. Some embodiments of the visual indicator are configured to deform before the struts or arms of the contact member do. This is a concept of have a visual indicator of tissue contact. Additionally, the contact members shown in FIGS. 62R1-62R4 can have rounded arms configured to provide some softer visual indicators. Visual indicators could be softer, flexible ribs that are radiopaque. When the surgeon sees the flexible indicators move, then this can indicate to the surgeon that the rest of the relatively stiff and non-deformable contact member is in contact with the tissue. The surgeon can then apply a rotation to the contact member to twist the contact member. The example in the figures shows indicator ribs (shown in darker, blue color) that can, in some embodiments, advance further forward than the gripping ribs. When the indicator ribs can be deformed proximally, to indicate that the device is touching the LAA. The surgeon can then apply a rotation to the contact member to twist the contact member.

The contact members shown in FIGS. 62S1 and 62S2 can have a low profile in a first state, for example, for delivery or withdrawal. The contact members can be self-expanding or can be mechanically activatable, for example and without limitation, by axially shortening the contact member, such as by a screw drive, to cause the ribs or arms of the contact member to expand outwardly. The coil direction can be designed for maximum grip—e.g. for a CCW grip direction, a left handed coil would engage and expand further when encountering rotational resistance. Any embodiments of the contact members disclosed herein can be designed for maximum grip—e.g. for a CCW grip direction, a left handed coil would engage and expand further when encountering rotational resistance.

The embodiments of the contact members shown in FIGS. 62U-62X can use a proximal pusher to advance and create a hoop inside the LAA. When the proximal pusher is tensioned, the hoop members would lay aligned with a small profile. One axial member may be relatively rigid, while the other member is more flexible to confirm to the tissue. After twisting up LAA and securing, this hoop could be detached and remain within the LAA or, in in other designs, the contact member could be removed through the center of the reduced LAA ostium.

Some embodiments of the contact members disclosed herein can have a shape of a ribbon or pigtail that are configured help engage tissue within the LAA. In some embodiments, device may have one or more of the contact members (i.e., one or more ribbons or elements) to help engage the implant with the tissue. In some embodiments, the tip of the pigtail can face proximally.

Figure 63:
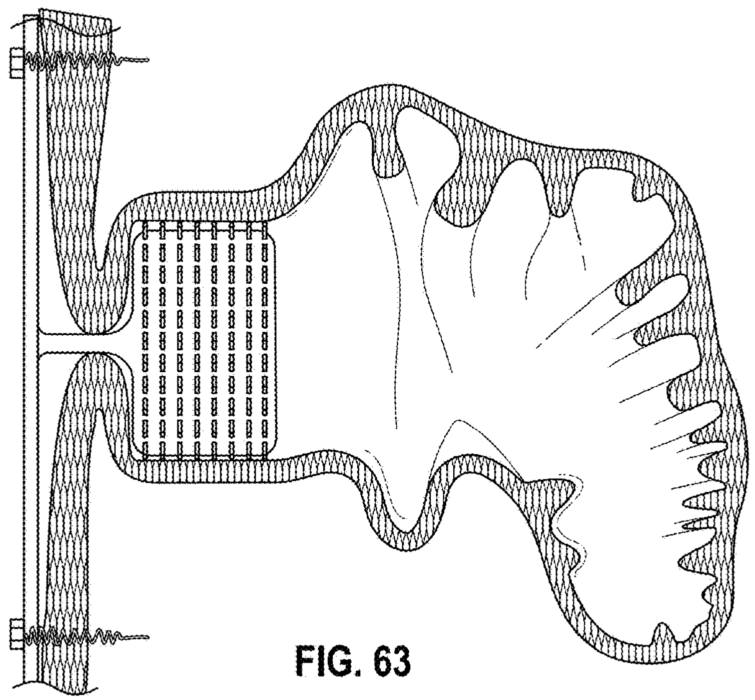
FIG. 63 shows a side view of an embodiment of a contact member.

FIG. 63 shows a side view of an embodiment of a contact member expanded against a tissue surface of the LAA, after a torque has been applied to the contact member that has caused a constriction of the tissue of the LA/LAA around a portion of the body of the implant device. FIG. 63 also shows the tissue anchors of the implant device advanced into the tissue of the LA/LAA to secure the LAA in the second rotational position.

Additionally, any of the implant embodiments disclosed herein can have drug coatings, fabric or other at least substantially impermeable coverings (such as and similar to, without limitation, cover member 121 or cover member 121' described above), seal elements (such as, without limitation, seal material 129 disclosed above), electrical contacts to eliminate the conduction of electrical signals causing Afib, or other features to improve the performance of the implant. Some embodiments of the implant can be transseptally delivered via catheter and a disconnectable element between the implant element and the delivery system which would allow for permanent disconnection and therefore permanent implantation of the implant. Additionally, in any embodiments disclosed herein, the implant can be delivered without the use of a catheter, such as surgically, or otherwise.

Some embodiments include a device for closing or occluding an LAA, having an expandable implant that is configured to move between a first state in which the implant is substantially collapsed and a second state in which the implant is expanded, and a catheter configured to advance the implant into the left atrial appendage. The implant can be advanced into the LAA when the implant is in the first state and to cause the implant to move from the first state to the second state so that at least some of the plurality of tissue anchors engage an inner wall surface of the left atrial appendage after the implant has been advanced into the left atrial appendage. Any embodiments of the implant or insert can have a plurality of tissue anchors on an outside surface thereof.

Additionally, the catheter can be configured to rotate the implant in a first direction from a first rotational position to a second rotational position so that the implant can twist the wall of the left atrial appendage. As mentioned above, the catheter can rotate the implant from as little as a quarter turn to more than one turn. In any embodiments, the delivery device (which can be, in any embodiments disclosed herein, a catheter or can be any other suitable deployment or surgical device or system) can be configured such that a user can rotate the implant as many times as is necessary or desired to close, occlude, or collapse the LAA on itself or about an outside surface of the implant.

Any embodiments of the implant can be self-expandable such that the implant automatically expands when a restraint is removed from the implant, such as when the implant automatically expands when the implant is advanced past a distal end of an outer sleeve of the catheter. The implant can be biased to remain in an expanded state after deployment into the left atrial appendage.

Additionally, any embodiments of the implant or systems disclosed herein can be configured such that the implant can engage or automatically engage with a tissue or tissue surface when rotated or turned in one (or a first) direction. The implant of any embodiments disclosed herein can also be configured to disengage with any tissue that it is engaged with when turned in a second direction (the second direction being opposite to the first direction). In this embodiment, a user can engage the tissue or wall surface of the LAA by rotating the implant in a first direction, and disengage (if needed for any reason, including without limitation repositioning the implant) by rotating the implant in a second direction, the second direction being opposite to the first direction.

In any embodiments, as has been described, the implant can be configured to prevent the contact member from rotating back to the first rotational position after the contact member has been fully deployed. For example, as described above, any embodiments of the implant can have a securing element or anchoring element that can be configured to engage with tissue surrounding the LAA, such as the tissue of an internal wall of the heart outside of the left atrial appendage. Some embodiments of the implant can have a securing element having a plurality of tissue anchors configured to engage with an internal wall of the heart adjacent to the left atrial appendage.

For example and without limitation, the implant of any device, apparatus, and method embodiments disclosed herein can include a securing element configured to engage with an internal wall of the heart outside of or adjacent to the left atrial appendage. The securing element can have one or a plurality of arms and/or tissue anchors configured to engage with an internal wall of the heart adjacent to the left atrial appendage, or can be configured to be sutured to or otherwise coupled with an internal wall of the heart adjacent to the left atrial appendage. In any embodiments, the implant can be configured to prevent or inhibit counter-rotation of the contact member or other portions of the implant back to the first rotational position after the contact member or other portion(s) of the implant has been fully deployed. In any embodiments, the implant can be configured to rotate or permit rotation of the contact member in a first direction from the first rotational position to the second rotational position, and to prevent or inhibit rotation of the implant in a second direction after the contact member or other portion of the implant has been fully deployed, the second direction being opposite to the first direction.

Any embodiments disclosed herein can include an implant for deployment within a cavity or vessel, having an expandable body (which can, but is not required to, have any of the features or characteristics of the contact member), a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Some embodiments of methods of closing or occluding an LAA using any embodiments of the implants disclosed herein will now be described. The method or procedure can include advancing a deployment device having an implant having an expandable member or contact member into the patient's left atrium, moving or expanding a portion of the implant from a first state to a second state within the left atrial appendage, wherein the expandable member or contact member is substantially collapsed in the first state and expanded in the second state, engaging a wall portion on an inside of the left atrial appendage with the expandable member or contact member (which can, but is not required to have one or more tissue anchors on an outside surface thereof), rotating the expandable member or contact member from a first rotational position to a second rotational position to twist the wall portion on the inside of the left atrial appendage, and preventing the expandable member or contact member from rotating back to the first rotational position. Any portion of the implant, including but not limited to the expandable member or contact member, can be self-expanding, wherein moving the expandable member or contact member from the first state to the second state comprises advancing the expandable member or contact member out of a distal end of the deployment device.

Additionally, in any embodiments disclosed herein, engaging a wall portion on an inside of the left atrial appendage can include engaging a wall portion on an inside of the left atrial appendage with one or more tissue anchors positioned on an outside surface of the expandable member or contact member or other portion of the implant. Further, preventing the implant from rotating back to the first rotational position can include engaging a tissue wall outside of the left atrial appendage with an anchor element or securing element. In some embodiments, the anchor element or securing element can be rotationally fixed to the expandable member or contact member and/or other portion of the implant to prevent relative movement between the anchor element and the expandable member or contact member and/or other portion of the implant. Preventing the expandable member or contact member and/or other portion of the implant from rotating back to the first rotational position can include engaging a tissue wall of the heart with an anchor element or securing element, wherein the anchor element can be rotationally fixed relative to the implant and configured to prevent the expandable member or contact member and/or other portion of the implant from rotating back to the first rotational position, or engaging an internal wall of the heart outside of the left atrial appendage with an anchor element or securing element. In any embodiments, the anchor element or securing element can include a plurality of tissue anchors on at least one surface thereof, the tissue anchors configured to engage with the internal wall of the heart outside of the left atrial appendage.

In any embodiments disclosed herein, the implant can be configured to automatically rotate from the first rotational position to the second rotational position after the contact member and/or other portion of the implant is in the second state, or can be activated to self-rotate at any desired time. For example and without limitation, the implant could have a spring or other torsional member configured to rotate the contact member and/or other portion of the implant or other portion of the body of the implant upon release or activation of the spring, or could be configured to be pre-wound or pre-twisted when the implant or contact member and/or other portion of the implant is in a first state. The self-rotation or self-twisting could be done, for example, after the contact member and/or other portion of the implant has been secured to a wall portion surrounding the LAA, and after a portion of the implant has engaged with at least a portion of an inside wall surface of the LAA so that the rotation or twisting of a portion of the implant causes a twisting of the LAA, thereby causing the ostium of the LAA to close or substantially close.

Therefore, in any embodiments, the implant can be configured to automatically rotate or self-rotate from the first rotational position to the second rotational position upon a release of a restraint holding the implant in the first rotational position, or upon a triggering or actuation of the rotational mechanism, which can be a spring or other torsional member. In some embodiments, a shaft extending through the implant can be configured to be wound or rotated relative to a securing portion or base of the implant, or can have a spring around the shaft, so that a rotation of the shaft relative to the securing portion or base of the implant as a result of the release of the torsion in the shaft or the spring surrounding at least a portion of the shaft, can result in the twisting of the LAA.

In other embodiments, the implant can have a shaft or body portion that extends from a base, wherein the shaft can be rotated (either manually, by the catheter, or can be self-rotating) relative to the base from the first rotational position to the second rotational position, and wherein a ratchet mechanism or other securing mechanism can be used to secure the shaft or body portion in the second rotational position relative to the base. The base can be configured to engage with and be secured to a wall or tissue of the heart surrounding the LAA before the shaft or body portion engages an inner wall portion of the LAA and before the shaft or body portion is rotated to the second rotational position.

Additionally, in any apparatus, implant device, method, or other embodiments disclosed herein, the second rotational position can be at least one-eighth or approximately one-eighth of a complete rotation (i.e., 45 degrees or approximately 45 degrees) relative to the first rotational position, one-quarter or approximately one-quarter of a complete rotation (i.e., 90 degrees or approximately 90 degrees) relative to the first rotational position, or at least one-half or approximately one-half of a complete rotation (i.e., 180 degrees or approximately 180 degrees) relative to the first rotational position, or wherein the second rotational position can be from one-eighth or approximately one-eighth of a complete rotation (i.e., 45 degrees or approximately 45 degrees) to one-half or approximately one-half of a complete rotation (i.e., 180 degrees or approximately 180 degrees) relative to the first rotational position. In any apparatus, implant device, method, or other embodiments disclosed herein, the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position, or from one-quarter or approximately one-quarter of a complete rotation (i.e., 90 degrees or approximately 90 degrees) to two, three, or more complete rotations or approximately one or more complete rotations (i.e., 360 degrees or approximately 360 degrees or more) relative to the first rotational position, one-eight or approximately one-eighth of a complete rotation (i.e., 45 degrees or approximately 45 degrees) to one, two, three, or more complete rotations or approximately one or more complete rotations (i.e., 360 degrees or approximately 360 degrees or more) relative to the first rotational position, or any value or ranges of values within any of the foregoing ranges. In any embodiments disclosed herein, the twisting movement or step can be accomplished by a torque catheter.

Further, in any apparatus, implant device, or method embodiments disclosed herein, the catheter can be configured to exert a torque on the implant to rotate the implant from the first rotational position until a threshold predetermined torque level is reached, or until the user decides to stop the rotation, whichever comes first. In some embodiments, the threshold predetermined torque level can be from 0.25 in-oz of torque or approximately 0.25 in-oz of torque to 10 in-oz of torque or approximately 10 in-oz of torque, or from 0.5 in-oz of torque or approximately 0.5 in-oz of torque to 5 in-oz of torque or approximately 5 in-oz of torque.

In any embodiments disclosed herein, without limitation, the contact member can have an outer diameter or size when in the first or collapsed state of from approximately 3 mm to approximately 8 mm (approximately 9 Fr to approximately 24 Fr), or from approximately 4 mm to approximately 6 mm, or of any values or ranges of values between any of the foregoing ranges, and/or a length (of the arm or strut members) from approximately 20 mm to approximately 60 mm, or from approximately 30 mm to approximately 50 mm, or of any values or ranges of values between any of the foregoing ranges. Further, in any embodiments disclosed herein, without limitation, the contact member can have an outer diameter or size when in the second or expanded state of from approximately 6 mm to approximately 14 mm (approximately 18 Fr to approximately 42 Fr), or of any values or ranges of values between any of the foregoing ranges, or from approximately 9 mm to approximately 11 mm, or of any values or ranges of values between any of the foregoing ranges, and/or a length (of the arm or strut members) from approximately 10 mm to approximately 40 mm, or from approximately 20 mm to approximately 30 mm, or of any values or ranges of values between any of the foregoing ranges.

In any embodiments disclosed herein, without limitation, the securing element can have an outer diameter or size when in the first or collapsed state of from approximately 3 mm to approximately 8 mm (approximately 9 Fr to approximately 24 Fr), or of any values or ranges of values between any of the foregoing ranges, or from approximately 4 mm to approximately 6 mm, and/or a length from approximately 4 mm to approximately 12 mm, or from approximately 6 mm to approximately 8 mm, or of any values or ranges of values between any of the foregoing ranges. Further, in any embodiments disclosed herein, without limitation, the securing element can have an outer diameter or size when in the second or expanded state of from approximately 6 mm to approximately 18 mm (approximately 18 Fr to approximately 54 Fr), or from approximately 9 mm to approximately 15 mm, or of any values or ranges of values between any of the foregoing ranges, and/or a length (of the arm or strut members) from approximately 4 mm to approximately 8 mm, or from approximately 4 mm to approximately 6 mm, or of any values or ranges of values between any of the foregoing ranges. Further, any embodiments of the securing elements disclosed herein can have tissue engaging tips or portions (i.e., the portion configured to penetrate or engage with the tissue) having a length of from approximately 0.2 mm to approximately 2 mm, or from approximately 0.5 mm to approximately 1 mm, or of any values or ranges of values between any of the foregoing ranges.

Some embodiments of the closure devices disclosed herein can be configured to more closely mimic the surgical type closure as compared to the conventional devices described above where the LAA in not plugged but closed with limited exposure of the device in the left atrium.

Figure 64:
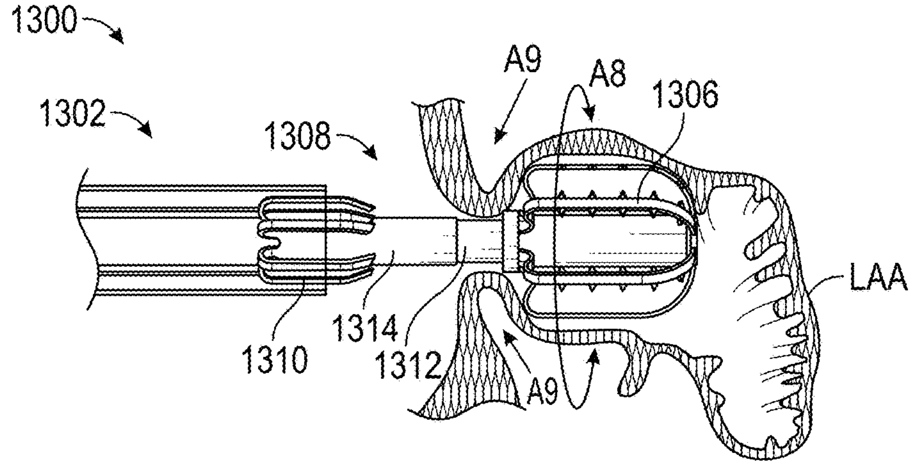
FIG. 64 shows another embodiment of a treatment device, showing the contact member being rotated to twist the LAA and cause a neck or opening of the LAA to constrict around a portion of the implant device.

FIG. 64 shows another embodiment of a treatment device 1300 having an implant device 1302 wherein the contact member 1304 is in a second, expanded state within the LAA and the securing element 1310 is in a first, contracted state. The retention element 1308 (also referred to herein as a retention element), used to retain the securing element 1310 in a desired axial position relative to the contact member 1304, is shown in a first, expanded state in FIG. 64. Any embodiments of the treatment device 1300 or implant device 1302 can have any of the components, features, or other details of any other treatment device or implant device embodiments disclosed herein, including without limitation any of the embodiments of the treatment device 100, 200, 300, 400, 500 or implant device 102, 202, 302, 402, 502 described above, including without limitation any details regarding the retention element of the treatment device 500 described above, in any combination with any of the components, features, or details of the treatment device 1300 or implant device 1302 disclosed herein. Similarly, any components, features, or other details of any of the other treatment device or implant device embodiments disclosed herein can have any of the components, features, or other details of any embodiments of the treatment device 1300 or implant device 1302 disclosed herein, in any combination, with any of the components, features, or details of the treatment device or implant device embodiments disclosed herein.

The contact member 1304 can have a plurality of struts or links 1306 that can have a plurality of tissue anchors 1307 thereon at a plurality of locations about the struts 1306 of the contact member 1304. In some embodiments, the tissue anchors 1307 can be the same as or similar to any of the tissue anchors 118 described above. As in any of the embodiments disclosed herein, the tissue anchors 1307 can be, but are not required to be, integrally formed with the struts 1306. The contact member 1304 can have a generally spherical or bulbous shape, or the shape of any of the other embodiments of contact members disclosed herein.

Similar to other embodiments described above, including the embodiment of the treatment device 500, any embodiments of the treatment device 1300 can have a suture or thread (not shown) that extends through an inside of the catheter body (such as through a lumen extending through the catheter) and/or a portion of the implant 1302 and loops around a pin or other fixed element on the implant 1302 (not shown), thereby permitting a user to retract or withdraw the suture to pull the contact member 1304 proximally relative to the securing element 1310, to keep the implant 1302 engaged with the delivery catheter, and/or to advance the securing element 1310 toward the contact member 1304 after the contact member 1304 has been used to twist the LAA. In some embodiments, the pin or other fixed element can be coupled with the contact member 1304 or with a portion of the implant 1302 (such as a shaft or body portion) that is coupled with the contact member 1304. In some embodiments, in this configuration, both ends of the suture can extend from a proximal end of the device 1300 such that a practitioner can grasp both ends of the suture to exert a proximally directed force around the pin or other fixed element to pull the contact member 1304 toward the securing element 1310 and/or to advance the securing element 1310 toward the contact member 1304 after the contact member 1304 has been used to twist the LAA.

In other embodiments, the securing element 1310 can be advanced toward the contact member 1304 using a portion of the catheter 1302 such as, for example and without limitation, a tube or sleeve (such as, without limitation, the second intermediate tube 157 of any of the embodiments of the treatment device 140 disclosed above) that can be advanced distally into contact with and engage a proximal end portion of the securing element 1310. The tube or sleeve of the catheter can be configured to be rotatable to adjust the rotational position of the securing element and/or maintain the securing element 1310 in a fixed rotational position relative to the anatomy, and/or to advance the securing element 1310 toward the contact member 1304 and into the tissue surrounding the implant 1302 after the LAA has been twisted. In any embodiments disclosed herein, the implant 1302 can be configured to be removed after the securing element 1310 is applied to the tissue that has been constricted by the twisting of the contact member 1304 so that the only portion of the implant device 1302 left in the LAA or the heart is the securing element 1310.

In any embodiments disclosed herein, the implant 1302 can have a first tube or body portion 1312 that is coupled with the contact member 1304 and a second tube or body portion 1314 that is coupled with the securing element 1310. In any embodiments disclosed herein, the first tube or body portion 1312 can be slidable (telescopically or otherwise) relative to a second tube or body portion 1314 so that a distance between the contact member 1304 and the securing element 1310 can be adjusted by the surgeon or other user of the treatment device 1300. In some embodiments, the first and/or second tubes 1312, 1314 can be configured to be indexed relative to one another so that the tubes are rotationally fixed to one another, for example using the slot and pin arrangement of any of the embodiments of the treatment device 500 disclosed above. In other embodiments, the first and/or second tubes 1312, 1314 can be configured to be rotatable relative to one another so that an angular orientation or position of the securing element 1310 can be adjusted relative to the contact member 1304 or vice-versa, and/or so that the securing element 1310 can be held in a stationary position or orientation as the contact member 1302 and the LAA are rotated by the surgeon or other user of the treatment device 1300.

In this configuration, when the contact member 1304 is rotated in a first direction (indicated by arrow A8 in FIG. 64, which can be in the clockwise or the counterclockwise direction), one or more or all of the struts 1306 and one or more or all of the tissue anchors 1307, if any, can engage the tissue of the LAA and cause the LAA to twist or rotate the LAA in the first direction A8. The twisting or rotation of the LAA in the first direction from a first rotational position to a second rotational position can result in the opening or ostium O of the LAA constricting in a radial direction (represented or identified by arrows A9 in FIG. 64) so that the opening O of the LAA is caused to move or constrict around an outside surface of the first tube or body portion 1312 or around a proximal portion of the contact member 1304. An operator can twist or rotate the contact member 1304 by twisting or rotating a portion of the catheter device coupled with the contact member 1304 or coupled with the first body portion or tube 1312 of the implant device 1302. The tightening or constriction of the opening O of the LAA around an outside surface of the first tube or body portion 1312 or around a proximal portion of the contact member 1304 or other portion of the implant device can result in the occlusion, or substantial occlusion, or substantial closing off of the interior portion of the LAA from LA, thereby substantially reducing the health risks associated with an open LAA.

Figure 65:
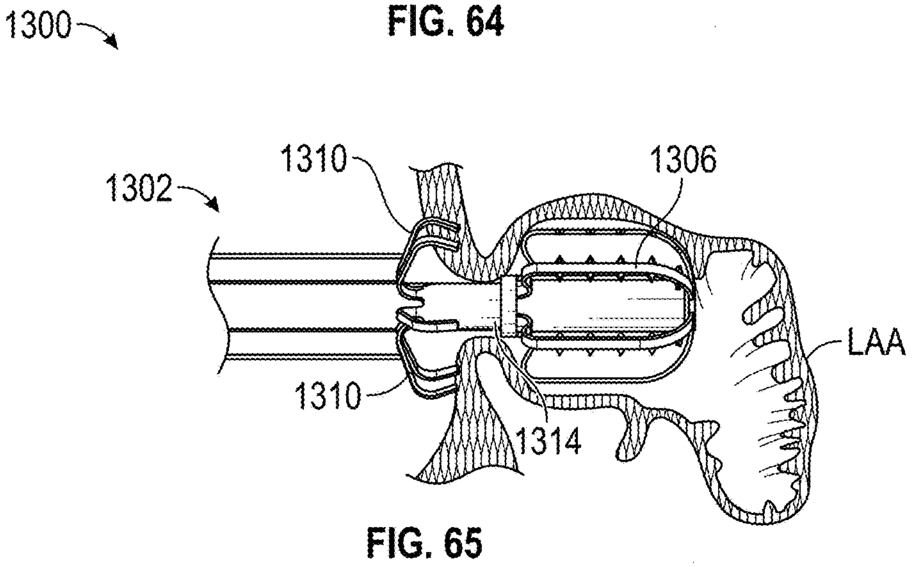
FIG. 65 shows the embodiment of the treatment device of FIG. 64, showing the securing element of the embodiment of the implant device being advanced into the tissue of the ostium of the LAA or adjacent to the ostium of the LAA.

Note that, as shown in FIG. 64, any embodiments of the treatment devices disclosed herein can be configured such that the securing element can be held in a first or collapsed state when the contact member is being rotated and, hence, the LAA is being twisted and the tissue of or adjacent to the ostium of the LAA is being constricted around the implant. This can reduce the risk of the securing element lacerating or otherwise damaging the tissue inside the heart during the twisting portions of the procedure. Thereafter, once the contact member and the LAA are in the desired rotational position, the securing element can be unrestrained or otherwise caused to move from the first collapsed position to the second expanded position. This can be achieved, in some embodiments, by removing a restraint (such as, without limitation, by retracting a sleeve, an outer sleeve, or other component of the catheter) surrounding the securing element after the contact member and the LAA are in the desired rotational position, as shown in FIGS. 64-65.

In some embodiments, the user can move the securing element 1310 from a first axial position toward the contact member 1304 to a second axial position by pulling back on or withdrawing the suture (again, while the contact member 1304 is held in a fixed position within the LAA, such as described above). This would be done after the desired level of twisting of the LAA has been achieved by torqueing or twisting the contact member 1304. With reference to FIG. 65 this can, in some embodiments, cause the securing element 1310 and second tube or body portion 1314 to advance distally relative to the contact member 1304 and the first tube or body portion 1312, thereby forcing the securing element into the tissue of the LAA or LA to hold the tissue in the closed, twisted, or contracted state.

Additionally, any embodiments of the device can be configured such that, as the securing element 1310 is advanced into the second rotational position, wherein the securing element 1310 engages with the tissue and holds the LAA in an occluded or closed position, a retention element can be used to prevent the securing element from moving away from the second rotational position (or away from the contact member 1304) toward the first rotational position. In any embodiments disclosed herein, the retention element can be used to bias or hold the securing element in the desired axial position relative to the contact member so as to secure or bias the tissue of and adjacent to the ostium of the LAA to remain in the constricted or occluded state.

For example and without limitation, some embodiments of the implant 1302 can have a ratchet mechanism configured to bias or secure the securing element to remain in any of a number of desired axial positions relative to the contact member. In some embodiments, for example, similar to the treatment device 500 disclosed herein, the first and/or second tube or body portion 1312, 1314 can have one or more tabs or other deflectable or deformable features (collectively referred to herein as tabs) formed in or coupled therewith configured to reversible or non-reversibly (i.e., removably or non-removably) engage with one or more recesses or openings (such as a plurality of openings aligned along a portion of a length of either the first or second tube or body portion) formed in the first and/or second tube or body portion 1312, 1314. For example and without limitation, one or more tabs or other deformable or deflectable features can be formed on or coupled with the first tube or body portion 1312 that are engageable with a plurality of openings or recesses that are formed in the second tube or body portion 1314. In some embodiments, the tabs can extend radially inward in a relaxed state. In this configuration the one or more tabs or other deflectable or deformable features can be configured such that the one or more tabs or other deflectable or deformable features engage with the one or more recesses or openings to permit the portion of the implant (such as, for example and without limitation, the second tube or body portion) to move toward the contact member and to prevent a movement away from the contact member.

As such, the tabs (which can be any other type of securing feature, such as ball and detent, or a zip tie type securing feature, or other deflectable or deformable feature) can be configured such that the securing element 1310 can freely move from the first, expanded position to the second, collapsed position, and to selectively prevent or inhibit movement from the second rotational position to the first rotational position, thereby essentially securing the securing element in the second rotational position. Further, in any embodiments disclosed herein, the treatment device 1300 can be configured such that the retention element is reversible or removable or otherwise such that a surgeon or other user can disengage the retention element and permit the securing element to move away from the contact member, such as for removal or repositioning of the implant device.

In some embodiments, the implant device 1302 can be configured such that the ratchet or retention element (including embodiments of the retention element having one or more tabs engageable with one or more of the recesses or openings are deflectable or deformable so that a surgeon or other user can disengage the one or more tabs from the one or more recesses or openings to move the securing element from the second rotational position to or toward the first rotational position, for example, to disengage the securing element from the tissue for repositioning, for re-twisting the LAA, or otherwise. For example, some embodiments of the implant device 1302 can be configured such that rotating or twisting the first or second tube or body portion 1312, 1314

(and, hence, the one or more tabs) relative to the other of the first or second tube or body portion 1312, 1314 can cause the tabs to disengage from the recesses or openings. In some embodiments, the catheter can have a core member that can be advanced into the first and/or second tube or body portion to contact and deflect the one or more tabs so as to disengage the one or more tabs from the one or more recesses or openings. Further, in any embodiments disclosed herein, one or more tabs can be formed in both axial directions so that the securing element can ratchet or be selectively securable in both axial directions. Further, in any embodiments disclosed herein, the tabs can be formed and configured so that the tabs can be moveable from a securing or engaging position to a non-securing (or sliding) state, as in the examples described above.

In other embodiments, the securing element and contact member can be held together using one or more sutures, wires, pins, or other components or fasteners, including, for example and without limitation, a suture with a slip knot which can be cinched during deployment. The suture can then be trimmed to length during final deployment, holding the securing element and contact member together to maintain the LAA in a closed or constricted state. Thereafter, the suture can be removed, and the remaining components of the deployment device can be withdrawn from the patient's body, leaving the implant 1302 in place.

FIGS. 66A-66I show another embodiment of treatment device 1400 for closing or occluding an LAA. In any embodiments disclosed herein, any components, features, or other details of the treatment device 1400 or implant device 1402 shown in FIGS. 66A-66I can have any of the components, features, or other details of any other treatment device embodiments or implant device embodiments disclosed herein, including without limitation any of the embodiments of the treatment device 100 or 140 or implant device 102 or 142 described above, in any combination with any of the components, features, or details of the treatment device 1400 or the implant device 1402 disclosed below. Similarly, any components, features, or other details of any of the other treatment device embodiments or implant device embodiments disclosed herein can have any of the components, features, or other details of any embodiments of the treatment device 1400 or implant device 1402 disclosed herein in any combination with any of the components, features, or details of the treatment device and/or implant device embodiments.

Figure 66A:
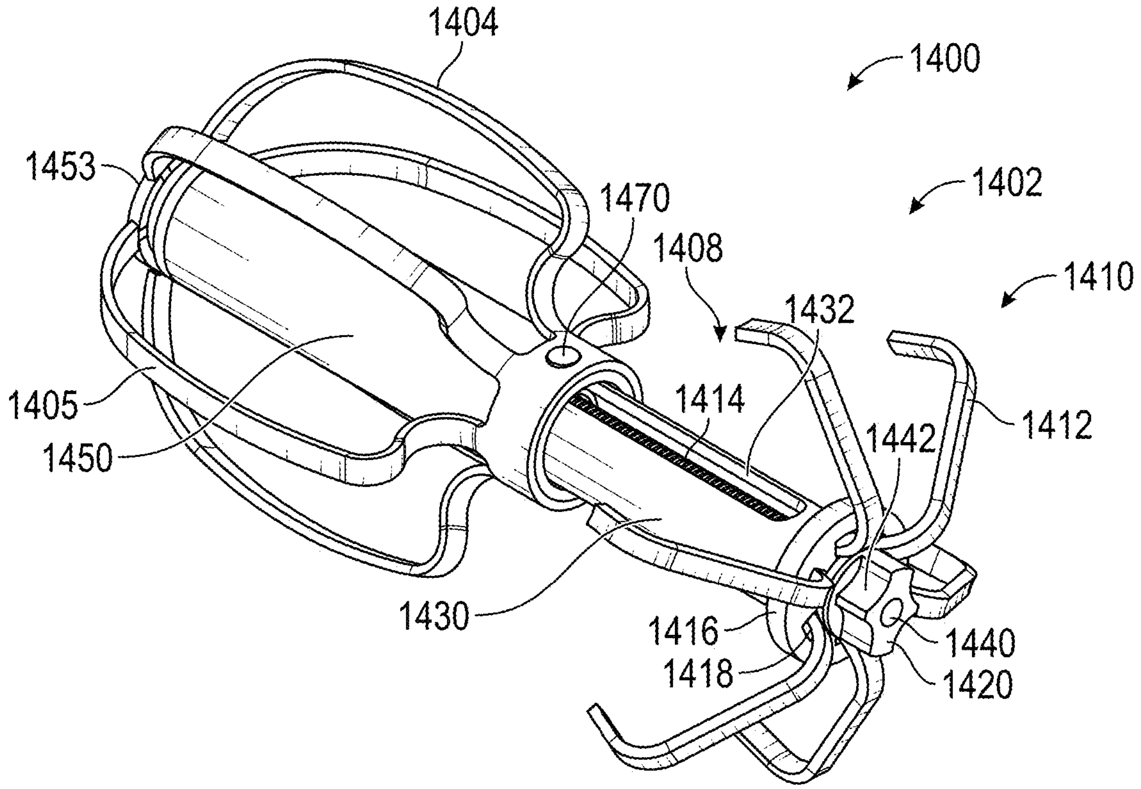
FIG. 66A shows an isometric view of another embodiment of an implant device for treating an LAA, showing a contact member in a second, expanded state, a securing element in a second, expanded state, and a retention element in a first rotational position in which the retention element is spaced apart from the contact member at a first distance.
Figure 66B:
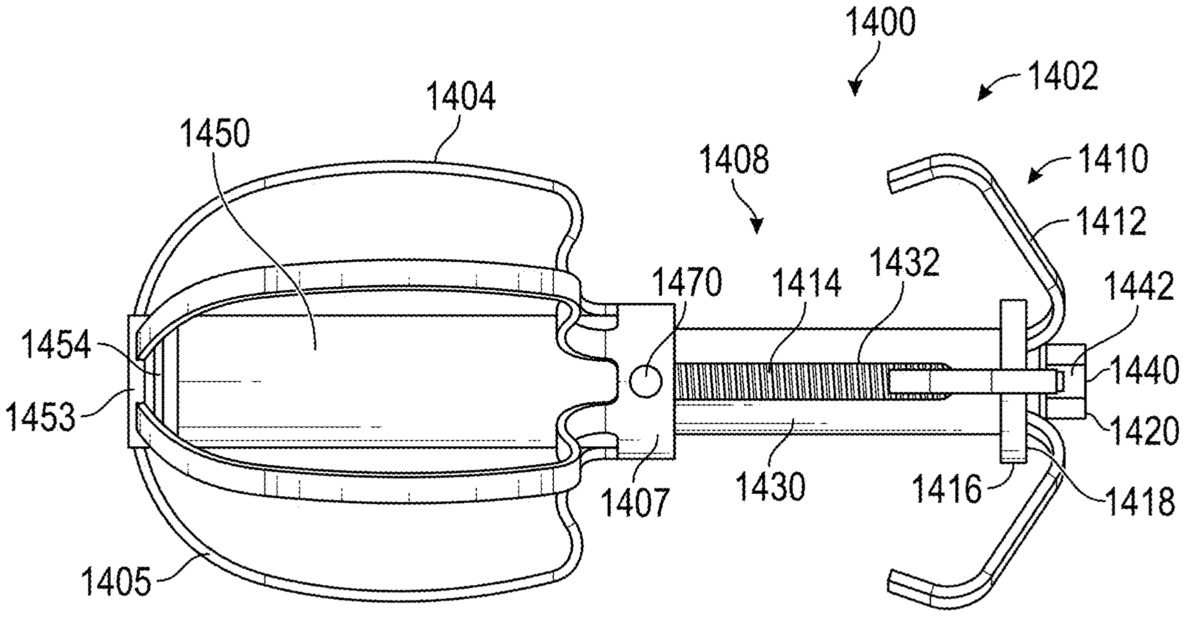
FIG. 66B shows a top view of the embodiment of the implant device shown in FIG. 66A.
Figure 66C:
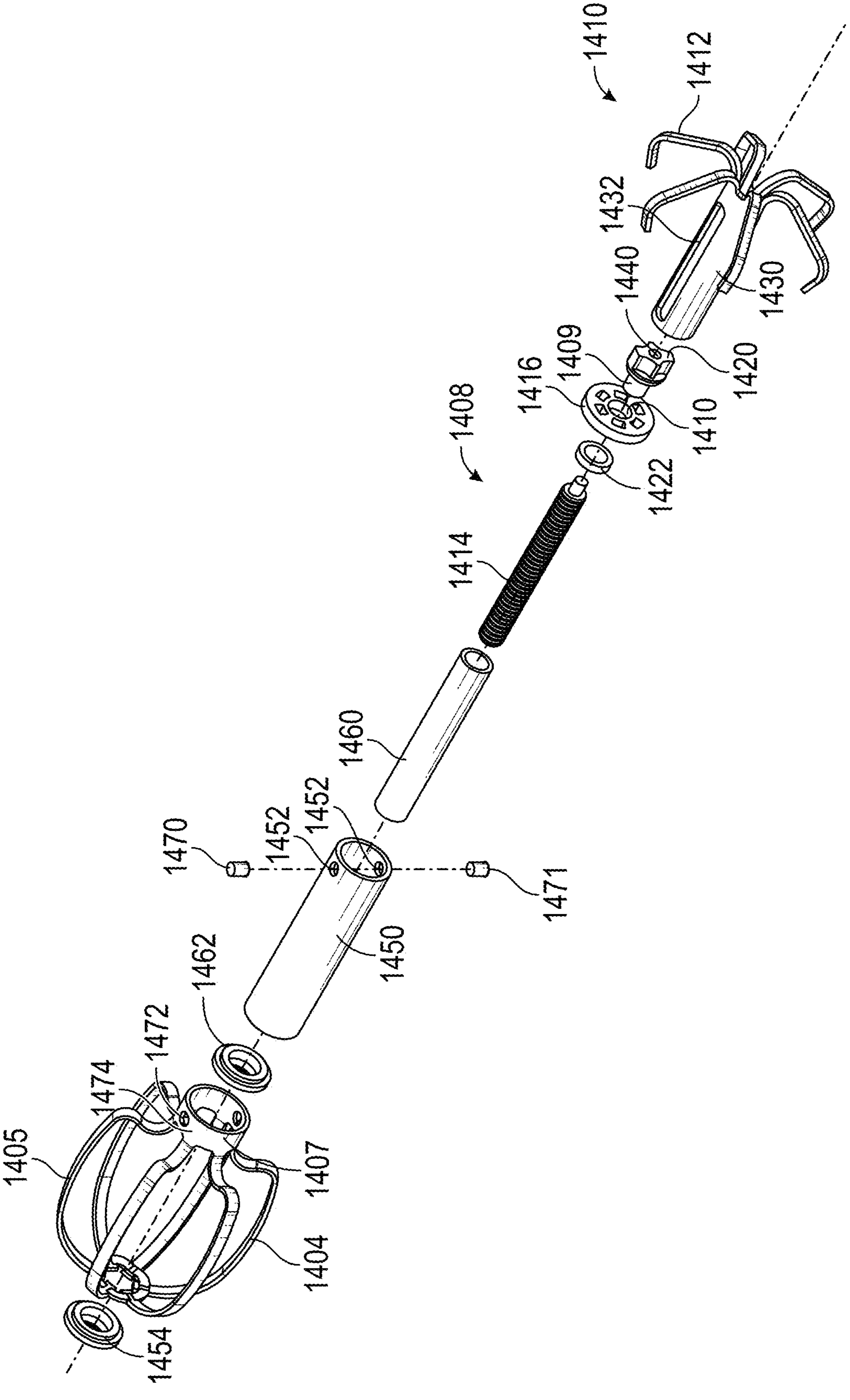
FIG. 66C shows an exploded view of the embodiment of the implant device shown in FIG. 66A, showing the contact member in the second, expanded state and the securing element in the second, expanded or unrestrained state.

In any embodiments of the treatment device 1400, including the embodiment of the treatment device 1400, the system can have an implant device 1402 having a contact member 1404 (also referred to herein as a contact element or an expandable implant member), a retention element 1408 (also referred to herein as a retention element), and a securing element 1410 (also referred to as a securing member) having one or more arms 1412 that can be coupled with and extend away from a body portion 1430 of the securing element 1412, as shown in FIG. 66C. In any embodiments, the securing element 1410 can have six arms 1412.

As will be described, the retention element 1408 can be used to retain or bias the securing element 1410 in a desired axial position relative to the contact member 1404. Further, the retention element 1408 of some embodiments is configured restrain the securing element 1410 in a first, collapsed state (also referred to herein as an unexpanded state), and to permit a surgeon or other user of the treatment device 1400 to carefully and precisely move the securing element 1410 between the first, collapsed state and a second, expanded or deployed state, and from the second, expanded state to the first, collapsed state in the event that the user wishes to remove the device from the patient, or otherwise.

Further, the retention element 1408 of some embodiments is configured to permit a surgeon or other user of the treatment device 1400 to carefully and precisely move the securing element 1410 in a distal direction, such as toward the contact member 1404, or from a first rotational position (wherein, for example and without limitation, the securing element 1410 is spaced further apart from the contact member 1404) to a second rotational position (wherein, for example and without limitation, the securing element 1410 is closer to the contact member 1404 as compared to the first rotational position). For example, the second rotational position of the securing element 1410 could be the position in which the securing element 1410 has engaged the tissue that has constricted as a result of the twisting of the contact member 1404 so as to maintain or bias such tissue in a constricted or occluded position or state. The retention element 1408 of some embodiments is further configured to permit a surgeon or other user of the treatment device 1400 to carefully and precisely move the securing element 1410 in a proximal direction, such as away from the contact member 1404, or from the second rotational position to the first rotational position. This can be very useful in either removing the device from the patient, for repositioning the securing element 1410, and/or for repositioning or reorienting (e.g., re-twisting) the contact member 1404.

As mentioned, in any embodiments, the retention element 1408 can also be used to restrain one or more arms 1412 of the securing element 1410 in the first, collapsed or restrained state. For example and without limitation, the retention element 1408 can have an arm restraint 1416 is movable from a first rotational position (which can be a first axial position) in which the arms 1412 of the securing element 1410 are restrained by the arm restraint 1416 in a first, restrained state (for example and without limitation, as shown in FIG. 66D) and a second rotational position (which can be a second axial position) in which the arms 1412 of the securing element 1410 are not restrained by the arm restraint 1416 and are permitted to move to the second, unrestrained state (for example and without limitation, as shown in FIG. 66E).

In some embodiments, the arm restraint 1416 can be in the shape of a disc. In some embodiments, the arm restraint 1416 and can have a plurality of openings 1418 therein that are each configured to receive an arm 1412 of the securing element 1410 therein. The arm restraint 1416 can have the same number of openings 1418 as the securing element 1410 can have arms 1412. The openings 1418 can be arranged in a radial pattern and each be sized and configured to surround one of the arms 1412, while permitting the arm restraint 1413 to slide relative to the securing element 1410 and the openings 1418 to slide relative to the arms 1412.

Figure 66D:
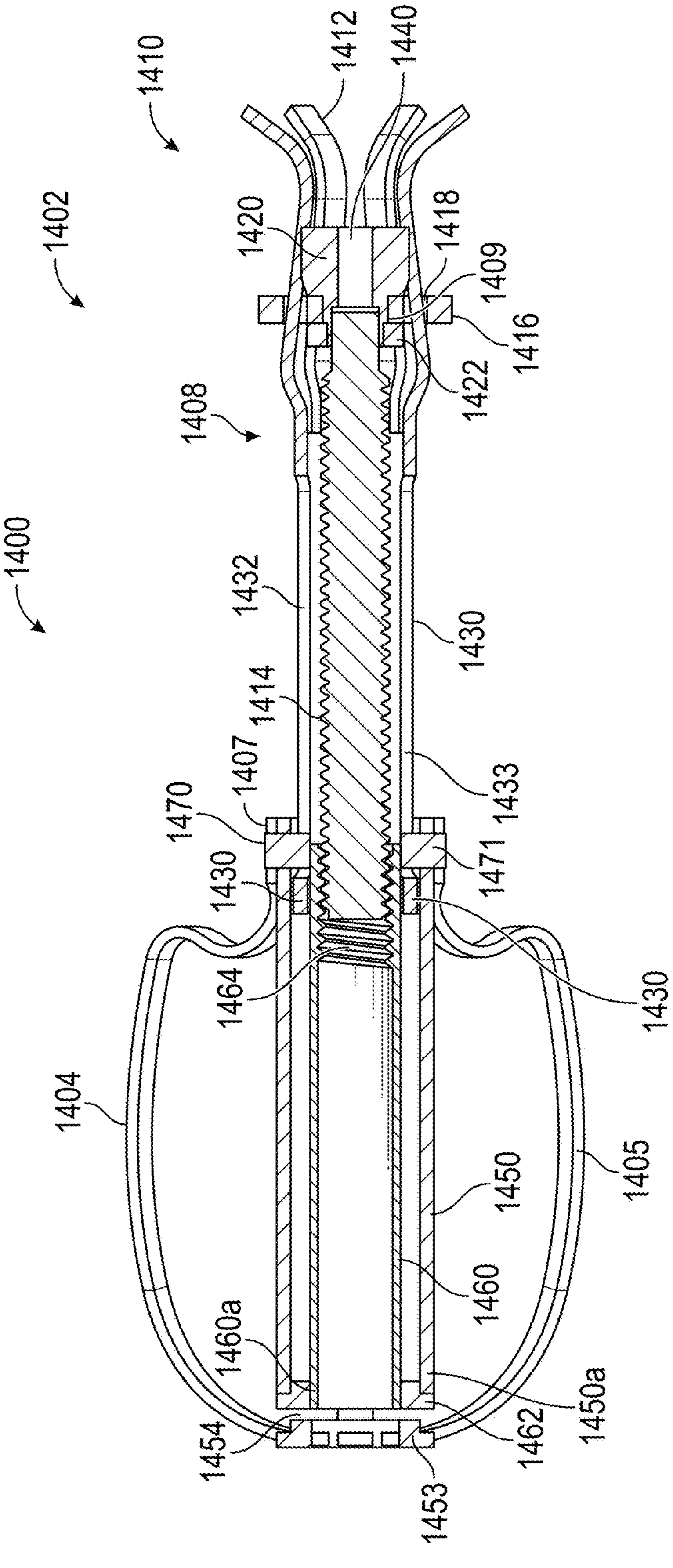
FIG. 66D shows a section view of the embodiment of the implant device shown in FIG. 66A taken through an axial centerline of the implant device, showing the contact member in the second, expanded state, the securing element in a first, collapsed or restrained state, and the retention element in the first rotational position in which the retention element is spaced apart from the contact member at the first distance.
Figure 66E:
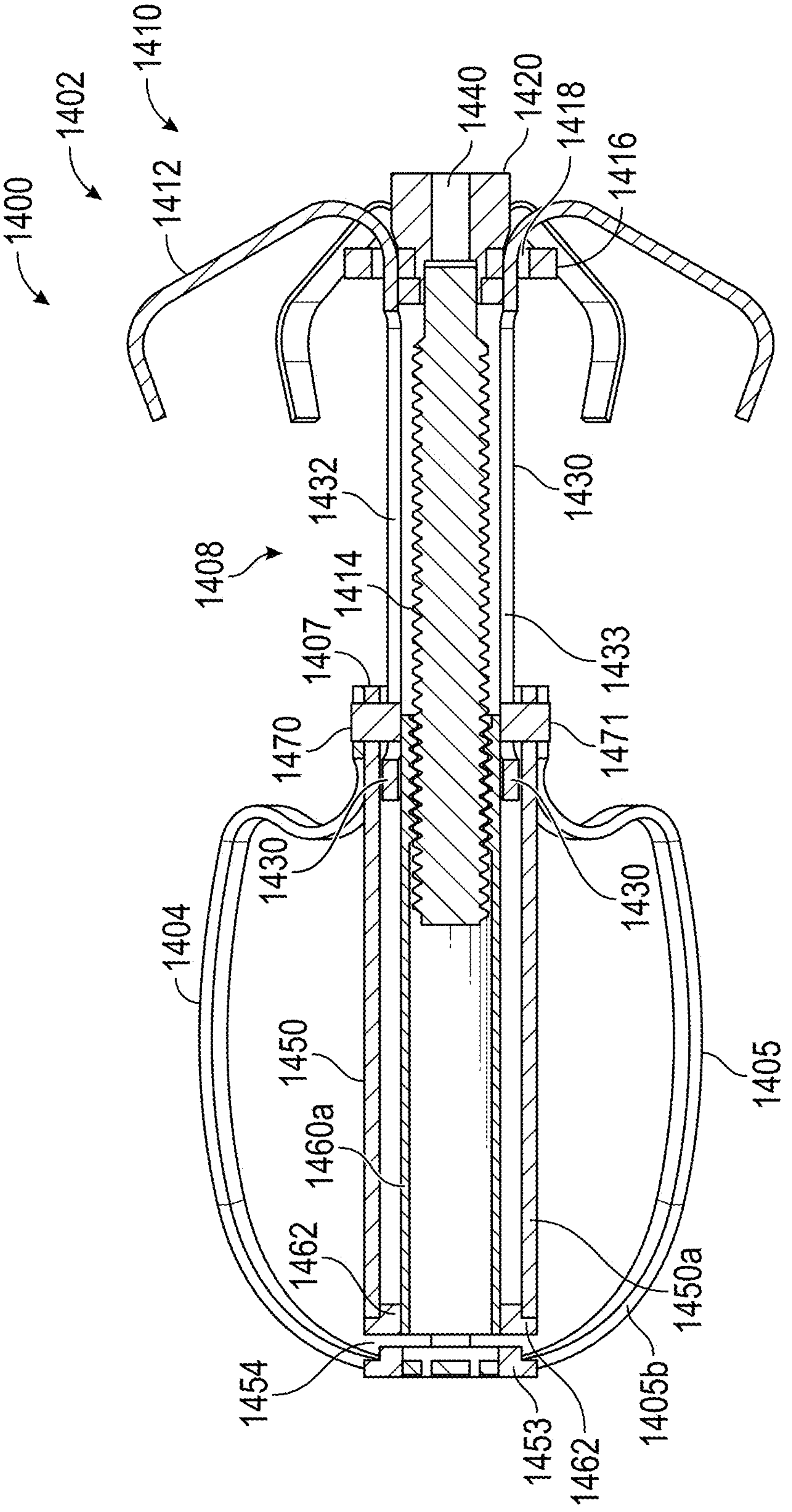
FIG. 66E shows a section view of the embodiment of the implant device shown in FIG. 66A taken through an axial centerline of the implant device, showing the contact member in the second, expanded state, the securing element in the second, expanded or unrestrained state, and the retention element in the first rotational position in which the retention element is spaced apart from the contact member at the first distance.
Figure 66F:
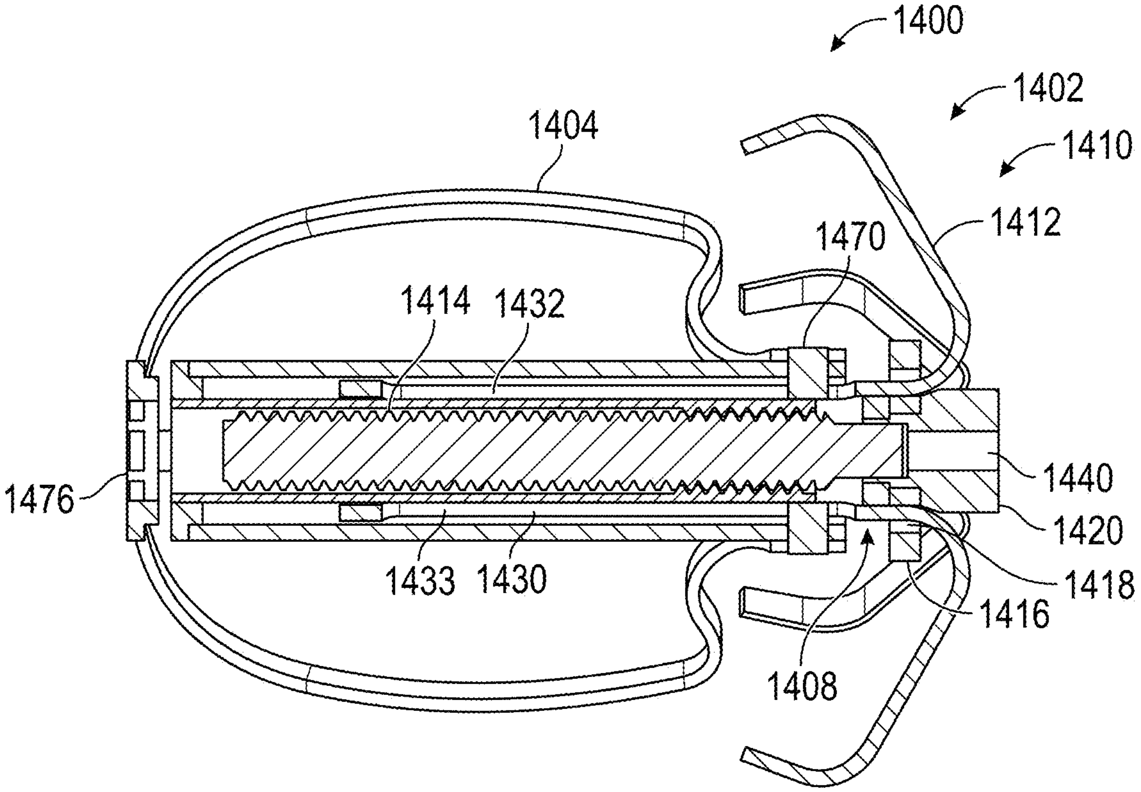
FIG. 66F shows a section view of the embodiment of the implant device shown in FIG. 66A taken through an axial centerline of the implant device, showing the contact member in the second, expanded state, the securing element in the second, expanded or unrestrained state, and the retention element in a second rotational position in which the retention element is spaced apart from the contact member at a second distance, wherein the second distance is smaller than the first distance when the retention element is in the first rotational position.

The arm restraint 1416 and the securing element 1410 can be configured such that, when the arm restraint 1416 is in a position that is approximately in a middle portion of an axial length of the securing element 1410, the arms 1412 will be folded back (or held in a folded back position by the arm restraint 1416) so as to generally point in a proximal axial direction and so that the securing element 1410 is in the first, collapsed state, for example and without limitation, as shown in FIG. 66D. The securing element 1410 in the first, collapsed state can have a much smaller overall diameter as compared to the securing element 1410 in the second, expanded state. For example and without limitation, the securing element 1410 can have an overall diameter that is at least 50% smaller in the first state that in the second state, or from 40% (or approximately 40%) to 60% (or approximately 60%) smaller in the first state than in the second state. When the arm restraint 1416 is in the first, collapsed state, an outer sleeve of the catheter can pass over and be advanced past the securing element 1410. In some embodiments, the treatment device 1400 can be configured such that the arm restraint 1416 can restrain or hold the arms 1412 in the first, collapsed state from a position that is adjacent to the unrestrained ends of the arms 1412 of the securing element 1410 (i.e., from a position adjacent to a proximal end of the securing element 1410 when the securing element 1410 is in the first, collapsed state), or near to the unrestrained ends of the arms 1412. Some embodiments of the treatment device 1400 will be configured such that the securing element 1410 is held in the first, restrained stated by the arm restraint 1416 within the catheter outer sleeve when the treatment device 1400 is assembled and packaged so that the treatment device 1400 is ready to be advanced into the LA or LAA without the need to move the arm restraint 1416 or change the securing element 1410 to the second, restrained position.

Further, the arm restraint 1416 and the securing element 1410 can be configured such that, when the arm restraint 1416 is in a position that is at or adjacent to a base portion of each of the arms 1412 (i.e., near a distal portion of the securing element 1410), the arms 1412 will be unrestrained by the arm restraint 1416 and permitted to expand to the second, unrestrained or expanded state. This is shown in FIG. 66E. In some embodiments, as the arm restraint 1416 moves from the first to the second rotational position, thereby permitting the arms 1412 of the securing element 1410 to move from the first to the second state or position, the ends of the arms 1412 can flip or change direction (e.g., from pointing in a proximal direction, when the securing element 1410 is in the first rotational position, to pointing in the distal direction, when the securing element 1410 is in the second rotational position, or from pointing generally or substantially in a proximal direction, when the securing element 1410 is in the first rotational position, to generally or substantially pointing in the distal direction, when the securing element 1410 is in the second rotational position).

In some embodiments, the head portion 1420 can have an annular recess 1409 formed therein that is configured to receive an arm restraint 1416 (also referred to herein as a restraining disk or restraining member) that can be configured to selectively restrain the one or more arms 1412 of the securing element 1410. In other embodiments, the annular recess 1409 can be formed in the threaded shaft 1414 (which is also referred to herein as a threaded member). The arm restraint 1416 can have an opening in a center thereof that can be slightly larger than an outside diameter of the annular recess so that the arm restraint 1416 can freely rotate (i.e., spin) in the annular recess 1409 relative to the head portion 1420 and the annular recess 1422. In some embodiments, a retainer 1422 can be coupled with the head portion 1420 or the shaft 1414 adjacent to a distal end of the annular recess 1409 to retain the arm restraint 1416 in a distal axial direction in the annular recess 1409. In some embodiments, the retainer 1422 can be welded, brazed, press fit, or otherwise secured to the head portion 1420 or the shaft 1414 adjacent to a distal end of the annular recess 1409, after the arm restraint 1416 has been advanced into the annular recess 1409. In other embodiments, the retention element 1408 can be configured such that the retainer 1422 is integrally formed with the head portion 1420 of the retention element 1408 and be configured such that the arm restraint 1416 can be pressed or forced over the retainer 1422 in the proximal direction during assembly into the annular recess 1409, while the retainer 1422 is configured to retain the arm restraint 1416 in the annular recess 1409 by preventing the arm restraint 1416 from moving in the distal axial direction away from the annular recess 1409.

The retention element 1408 can be configured such that, as the arm restraint 1416 is moved in a distal axial direction (i.e., toward the contact member 1404) by rotation of the threaded shaft 1414, the arms 1412 of the securing element 1410 will move from the first, collapsed state to the second, unrestrained or expanded state. For example and without limitation, the arm restraint 1416 can be moved from a position that is approximately in a middle portion of an axial length of the securing element 1410 when the securing element is in the first, collapsed state (as shown in FIG. 66D) to a more distal position wherein the arm restraint 1416 is positioned at or adjacent to a base or beginning portion of the arms 1412 of the securing element (as shown in FIG. 66E).

The implant 1402 can be configured such that the arm restraint 1416 will pass over the arms 1412 of the securing member 1410 toward the proximal ends of the arms 1412 so that the arms 1412 can move to the second, relaxed and expanded position, as shown in FIG. 66E. In some embodiments, the surgeon or user can controllably advance the arm restraint 1416 distally to unrestrain the securing element 1410 without advancing the securing element 1410 in the distal direction, thereby reducing the risk that the arms 1412 of the securing element 1410 will inadvertently lacerate or damage the tissue in the heart during the deployment of the securing element 1410.

In some embodiments, the body portion 1430 can have a tubular or generally tubular shape and have a first slot 1432 extending in an axial direction and a second slot 1433 extending in an axial direction. The first slot 1432 and the second slot 1433 can be parallel and can be positioned on mutually opposing sides of the body portion 1430 of the securing element 1410. In some embodiments, the body portion 1430 can be configured to have only one of the first and second slots 1430, 1432.

The first slot 1430 and/or the second slot 1432 can interact with a first pin 1470 and/or a second pin 1471, respectively, to prevent the body portion 1430 and, hence, the securing element 1410 from rotating relative to the contact member 1404. Further, the first slot 1430 and/or the second slot 1432 can interact with a first pin 1470 and/or a second pin 1471, respectively, to limit a range of axial movement of the body portion 1430 and, hence, limit a range of axial movement of the securing element 1410 relative to the contact member 1404. In some embodiments, the first pin 1470 and/or the second pin 1471 can be coupled with a body portion 1450 of the implant device 1402 and/or an annular base portion 1407 of the contact member 1404 from which the arms or struts 1405 of the contact member 1404 extend. The first and/or second pins 1470, 1471 can be used to couple the body portion 1450 to the contact member 1404 and to rotationally fix the body portion 1450 to the contact member 1404.

FIG. 66A shows the contact member 1404 in a second, expanded state. The contact member 1404 can have any of the components, features, or other details of any other contact member embodiments disclosed herein, including without limitation any of the embodiments of the contact member 144 described above, in any combination with any of the components, features, or details of the contact member 1404 disclosed herein. FIG. 66A also shows the securing element 1410 in a second, expanded or unrestrained state. In the section view of FIG. 66D, the securing element 1410 is shown in a first, contracted or restrained state as the securing element 1410 would be in when the securing element 1410 is within an outer sleeve of a catheter (not shown). As with any other embodiments disclosed herein, the contact member 1404 can be, but is not required to be, configured to automatically expand from a first, restrained state (such as within a catheter) to the second expanded state by advancing the contact member 1404 past a distal end of the delivery catheter (not shown) or by withdrawing or retracting a sheath (such as an outer sheath) of the delivery catheter. In some embodiments, the implant device 1402 and/or the contact member 1404 can be advanced distally out of the catheter past a distal end of an outer sleeve of the catheter by advancing a core member (not shown, but which can be similar to or have any of the same features or details as the core member 153 of the treatment device 140 described herein) of the catheter relative to the outer sleeve or sheath of the catheter, the core member being in communication with the implant device 1402. In this manner, the contact member 1404 of the implant device 1402 can be deployed within the LAA in an expanded state (i.e., expanded to the second state within the LA) or in the first state and then expanded to the second state within the LAA. The contact member 1404 can be advanced into the LAA to any desired depth within the LAA, including near or in contact with a distal wall of the LAA, the middle portion of the LAA, or otherwise by, for example and without limitation, holding the implant device 1402 in a stationary axial position by maintaining the core member of the catheter in a stationary axial position and retracting the outer sleeve of the catheter. In any embodiments disclosed herein, the contact member 1404 can be self-expanding in a radial direction so that, when a restraint is removed from the contact member 1404, the contact member 1404 can expand against an inner surface or wall of the LAA automatically. In other embodiments, the contact member 1404 can be mechanically expandable, such as by a balloon expander, so as to expand against inside surface or wall of the LAA.

In any embodiments, the contact member 1404 can have a plurality of arms or struts 1405 that are each configured to self-expand in a radial direction when a restraint has been removed from an outside surface of the contact member 1404. For example without limitation, any embodiments of the contact member disclosed herein can have six struts 1405, or between six and ten struts 1405, or from less than six to more than ten struts 1405. Further, in any embodiments, the contact member 1404 can have a plurality of tissue anchors (not shown) or other similar features coupled with or integrally formed with one or more of the struts 1405 configured to penetrate or engage the tissue of the LAA that are configured to penetrate into a tissue within the LAA when the contact member 1404 is expanded against the tissue of the LAA and/or when the contact member 1404 is rotated or twisted within the LAA. In other embodiments, as shown, the struts 1405 can be formed without any tissue anchors.

In this configuration, when the contact member 1404 is rotated in a first direction (which can be in the clockwise or the counterclockwise direction) after being expanded or moved against at least a portion of an inside surface of the LAA, one or more or all of the struts 1405 and one or more or all of the tissue anchors can engage the tissue of the LAA and cause the LAA to twist or rotate in the first direction. The twisting or rotation of the LAA in the first direction from a first rotational position to a second rotational position can result in the opening or ostium O of the LAA constricting in a radial direction so that the opening O of the LAA is caused to move or constrict around an outside surface of a proximal portion **1404*a* of the contact member 1404. An operator can twist or rotate the contact member 1404 by twisting or rotating the core member (not shown) of the catheter. The tightening or constriction of the opening O of the LAA around an outside surface of the proximal portion 1404*a* of the contact member 1404 or other portion of the implant device can result in the occlusion, or substantial occlusion, or substantial closing off of the interior portion of the LAA from the LA, thereby substantially reducing the health risks associated with an open LAA. In any embodiments disclosed herein, the contact member 1404 can be configured to be removed from the LAA without causing the opening or ostium of the LAA to open after the securing element is applied to the tissue that has been constricted by the twisting of the contact member 1404 so that the only portion of the implant device 1402 left in the LAA or the heart is the securing element 1410. In other embodiments, the contact member 1404** can remain positioned within the LAA after the procedure is completed.

As mentioned, the retention element 1408 can be used to couple the securing element 1410 to the contact member 1404 and to also allow a user (such as a surgeon) to move the securing element 1410 toward and away from the contact member 1404 with high adjustability and control. The treatment device 1400 can thus be configured to allow for the repositioning of the securing element 1410 and/or other components of the implant device 1402. In any embodiments, with reference to the figures, the retention element 1408 can comprise a threaded shaft 1414 that can be coupled with or integrally formed with a head portion 1420 that is rotationally and axially coupled with the threaded shaft 1414. In some embodiments, the threaded shaft 1414 can threadedly engage with an internal threaded portion 1464 of the sleeve component 1460. The sleeve component 1460 can be coupled with the body portion 1450 of the implant device 1402 and the contact member 1404. In some embodiments, the sleeve component 1460 can be axially and rotationally fixed to the body portion 1450 of the implant device 1402 and the contact member 1404. As illustrated, in some embodiments, a distal end portion **1460*a* of the sleeve component 1460 can be coupled with a distal end portion 1450*a* of the body portion 1450 of the implant device 1402. In some embodiments, a flange or insert 1462 or other attachment mechanism (such as welding, press fitting, brazing, etc.) can be used to couple the sleeve component 1460 with the body portion 1450 of the implant device 1402**.

In this configuration, as the threaded shaft 1414 is rotated and advanced in the distal direction, the annular recess 1409 and, hence, the arm restraint 1416 can be advanced in the distal direction. Once the arm restraint 1416 has been moved distally so as to be in contact with the body portion 1430, continued distal axial advancement of the threaded shaft 1414 and, hence, the arm restraint 1416 will cause the body portion 1430 and the securing element 1410 to be advanced distally toward the contact member 1404. As mentioned above, the first and/or second pins 1470, 1471 and the first and/or second slots 1432, 1433 can prevent the securing element 1410 from rotating while the threaded shaft 1414 is being rotated. In some embodiments, the first and/or second pins 1470, 1471 and the first and/or second slots 1432, 1433 can be used to limit a range of motion of the securing element 1410 in the axial direction. A distal end portion of the first and/or second slots 1432, 1433 can be used to limit a range of motion of the securing element 1410 in the proximal axial direction. A proximal end portion of the first and/or second slots 1432, 1433 can be used to limit a range of motion of the securing element 1410 in the distal axial direction.

In this configuration, the head portion 1420 can be rotated in a first direction (e.g., so that the head portion 1420 moves toward the contact member) to advance the securing element 1410 toward the contact member 1404, and rotated in a second, opposite direction to move the securing element 1410 away from the contact member 1404. The retention element 1408 can be configured to engage the securing element 1410 such that, when the retention element 1408 rotates, the securing element 1410 moves in an axial direction corresponding to the rotation of the retention element 1408, thus providing reversible and precise control over the position of the securing element 1410 relative to the contact member 1404. In some embodiments, the head portion 1420 can be rotated by rotating a core member of the catheter or other device of the catheter coupled with the head portion 1420 of the retention element 1408. An opening 1440 in some embodiments of the head portion 1420 can be threaded so that a core member or other component of the catheter can be selectively removably engaged with the head portion 1420 to maintain engagement between the catheter and the implant device 1402. The implant device 1402 can be removed or disengaged from the catheter by, for example and without limitation, disengaging a threaded projection (not shown) of the catheter device from the opening 1440 of the head portion 1420, which can be performed by holding the head portion 1420 in a fixed position with an intermediate components of the catheter device (for example and without limitation, the same component of the catheter device that is used to rotate the head portion 1420 of the retention element 1408) while rotating the threaded projection. Thus, once the securing element 1410 is in the desired axial position (for example, engaged with the tissue of the LA/LAA that has constricted as a result of the twisting of the contact member 1404), the implant 1402 can be removed from the catheter by disengaging the threaded projection from the retention element 1408 as described above, and the catheter can be removed from the LA. With the securing element 1410 engaged with the patient's tissue, the LAA can be prevented or biased from rotating to the first rotational position, which is the untwisted or relaxed position. In this configuration, the implant device 1402 can secure and maintain the LAA in a substantially or completely occluded or substantially or completely closed state.

Further, in any embodiments, the device can be configured such that the contact member 1404 can be removed from the patient's LAA after the securing element 1410 is engaged with the tissue sufficiently to hold the tissue in a closed or occluded state. In this configuration, the implant can have a plug or cover (such as or similar to the cover 178 coupled with the securing member 177) that can cover the opening in the implant 1402 that the contact member is withdrawn through, or be otherwise configured to plug or cover the opening in the implant that the contact member 1404 is withdrawn through.

Additionally, in some embodiments, the contact member 1404 can have a continuous and uninterrupted circumference at a proximal end **1404*a* that each of the strut members 1405 extend distally away from. Each of the strut members 1405 can be preformed into a curved shape such that the strut members 1405 are biased to expand to the second state when no external restraint or constraint is applied to the outside surface of the contact member 1404 (for example, when in a relaxed state). At a distal end, each of the strut members 1405 can, but are not required to, couple with a hub member 1453. Similar to the hub member 122 described above, the hub member 1453 can have a plurality of receptacles (not shown) configured to receive and constrain distal end portions 1405*b* of each of the strut members 1405. Additionally, each of the receptacles 163 can be configured to permit the distal end portions 1405*b* of each of the strut members 1405 to rotate relative to the hub member 1453 so that the distal end portions 1405*b* of the strut members 1405 can extend generally radially away from the hub member 1453 when the contact member 1404 is in the second, expanded state. The hub member 1453 can be configured to permit the distal end portions 1405*b* of each of the strut members 1405 to rotate relative to the hub member 1453 without resistance or significant resistance. In any embodiments, for example and without limitation, the distal ends of each of the strut members 1405 can have a tab or other feature (such as a T shaped termination or other increased width) (not shown) that can be secured to or otherwise engaged by each of a plurality of receptacles formed in the hub member 1453 so as to axially constrain the end portion of each of the strut members 1405**, while allow rotation about the end portion.

Further, in some embodiments, the implant 1402 can be configured to have a gap 1454 in the axial direction between the hub member 1453 and the distal end portion of the body portion 1450 of the implant device 1402 or the flange or insert 1462 coupled with the distal end portion of the body portion 1450 of the implant device 1402. In some embodiments, the gap 1454 can be used to permit a surgeon or user of the device to measure or monitor any axial loading on the distal end of implant device 1402. For example and without limitation, by monitoring or measuring a length of the gap 1454 in fluoroscopy or by other visual means, the user can determine how much axial loading is being applied to and end portion of the implant device 1402, such as by a wall of the LAA. The user can also, therefor, determine how much axial force is being applied to a wall of the LAA by monitoring or measuring the length of the gap 1454 and knowing how much load is required to deflect the gap by a discrete amount of the length of the gap 1454. In some embodiments, without limitation, the implant 1402 can be configured such that a force which may indicate a change in the length of the gap could be from 0.01 lbs. (or approximately 0.01 lbs.) or less to 0.25 lbs. (or approximately 0.25 lbs.) or more, or from 0.05 lbs. (or approximately 0.05 lbs.) to 0.1 lbs. (or approximately 0.1 lbs.) or more, or of any value or ranges of values within any of the foregoing ranges.

Any embodiments of the implants and/or delivery systems disclosed herein can be configured to be partially or completely self-expanding, balloon expandable or otherwise mechanically expandable using any known or later developed expansion devices, including without limitation balloon expansion devices typically used for implants, stents, stent grafts, angioplasty devices, or otherwise, or any of the expansion devices disclosed herein. Similarly, any embodiments of the implants and/or delivery systems disclosed herein can be configured to be partially or completely self-elongating, balloon elongatable or otherwise mechanically elongatable, be configured to be partially self-elongating and partially balloon or mechanically elongatable using, without limitation, balloon expansion devices typically used for implants, stents, stent grafts, angioplasty devices, or any of the expansion devices disclosed herein, or otherwise. For example and without limitation, some implant embodiments can be configured to be self-expanding and/or self-elongating to an intermediate size or shape, and then balloon or otherwise mechanically expanded and/or elongated to a final size or shape. Similarly, any such balloon or mechanical expansion devices and/or such devices disclosed herein can, in several embodiments, be used to elongate or complete the elongation of the ostium of the LAA beyond the elongation, if any, resulting from a self-expansion and/or self-elongation of the implant.

Figure 67A:
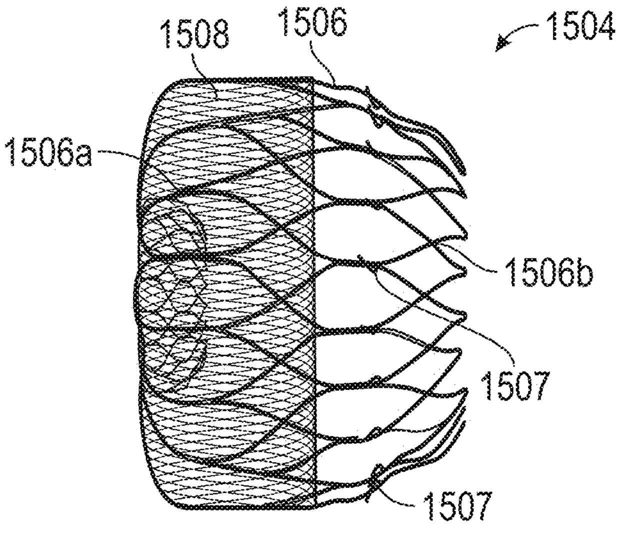
FIG. 67A shows an embodiment of a device that can be configured to be used as a contact member and/or a securing element in any of the treatment device embodiments disclosed herein.

Any embodiments of the treatment devices and/or implant devices disclosed herein can have any of a wide range of suitable implants (including, without limitation, any available or suitable LAA implants in the industry) for the contact member. FIG. 67A shows an example of a device that can be configured to be used as a contact member 1504 in any of the treatment device embodiments disclosed herein. In some embodiments, the contact member 1504 can have a self-expanding or mechanically expandable frame 1506. Some embodiments of the frame 1506 of the contact member 1504 can be made from metal wires, or be laser cut and formed from a solid tube of material, having a plurality of struts or frame members. In any embodiments, the frame 1506 can be made from stainless steel, Nitinol or any other suitable material.

Some embodiments of the contact member 1504 can have a generally tapering cylindrical shape (wherein a size or a diameter of the contact member 1504 decreases from the proximal to the distal end thereof), with the wire frame at a proximal end 1506*a* of the frame 1506 of the contact member 1504 extending toward the axial center of the frame 1506 so as to cover the proximal end 1506*a* of the frame. In some embodiments, the distal end 1506*b* of the frame 1506 can be generally open. The frame of the contact member 1504 can be flexible and conformable to the patient's anatomy in some embodiments, as in the illustrated embodiment, or can be more rigid in other embodiments. In some embodiments, the contact member 1504 can have a size, a shape, and/or other details similar to that of the WATCHMAN device by Boston Scientific, as is shown in FIG. 67A.

Some embodiments of the contact member 1504 can have a mesh cover or membrane 1508 (which can be, but is not required to be, a 160 micron membrane) over an outside surface, or a portion of the outside surface, of the frame 1506 of the contact member 1504. In any embodiments, the contact member 1504 can have a 21 mm size, a 24 mm size, a 27 mm size, a 30 mm size, or a 33 mm size. The contact member 1504 can also have a plurality of anchors 1507, for example and without limitation, 18 anchors, about an outside surface of the frame 1506 for engaging a tissue of the LAA.

FIGS. 67B-67F show an embodiment of a treatment device 1500 having the embodiment of the contact member 1504 shown in FIG. 67A for occluding the LAA. FIGS. 67B-67F also show an example of a treatment procedure that can be performed to occlude the LAA using the treatment device 1500. In any embodiments, the treatment device 1500 can have any of the features, components, and/or other details of any of treatment device embodiments disclosed herein, including without limitation, any of the embodiments of the treatment device 140 described above and shown in FIGS. 9A-9I, in place of or combination with any of the features, components, and/or other details disclosed herein of treatment device 1500.

Figure 67B:
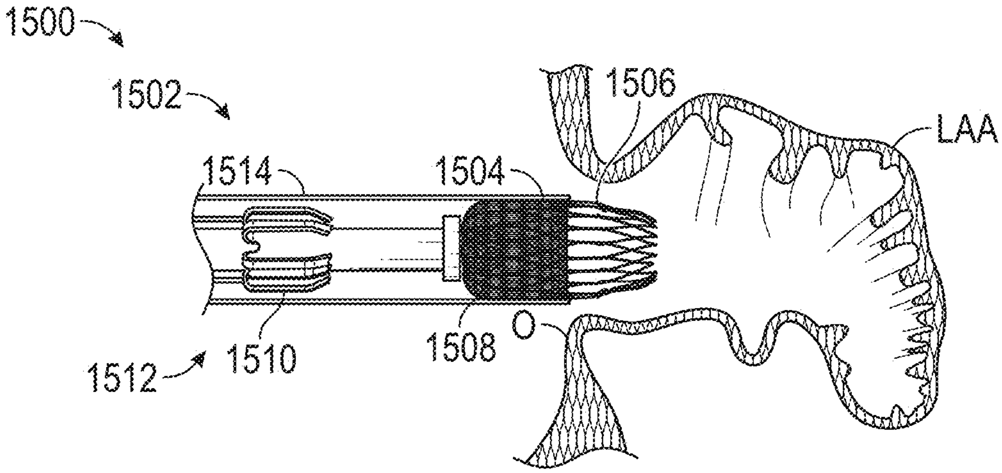
FIG. 67B shows an embodiment of a treatment device for occluding the LAA showing an implant device having a contact member in a collapsed state being advanced into the LAA.
Figure 67C:
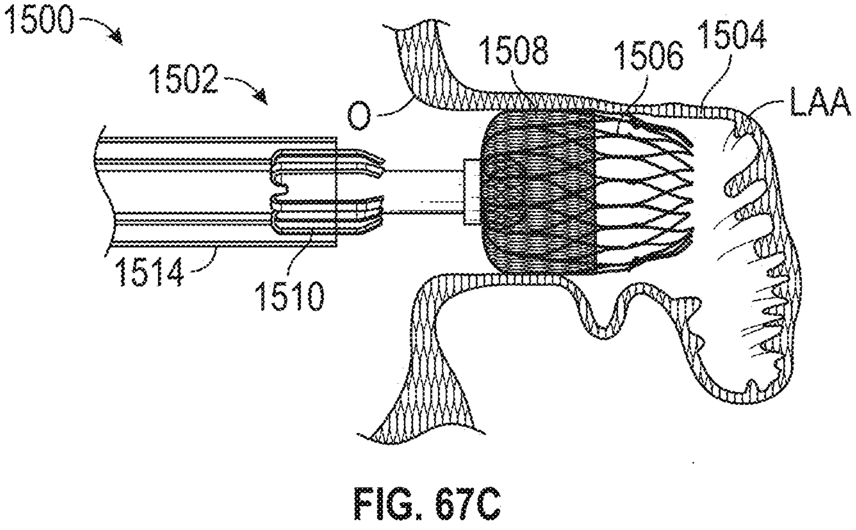
FIG. 67C shows the embodiment of the treatment device shown in FIG. 67B, showing the contact member being expanded within the LAA and engaging an inside surface of a wall portion of the LAA.
Figure 67D:
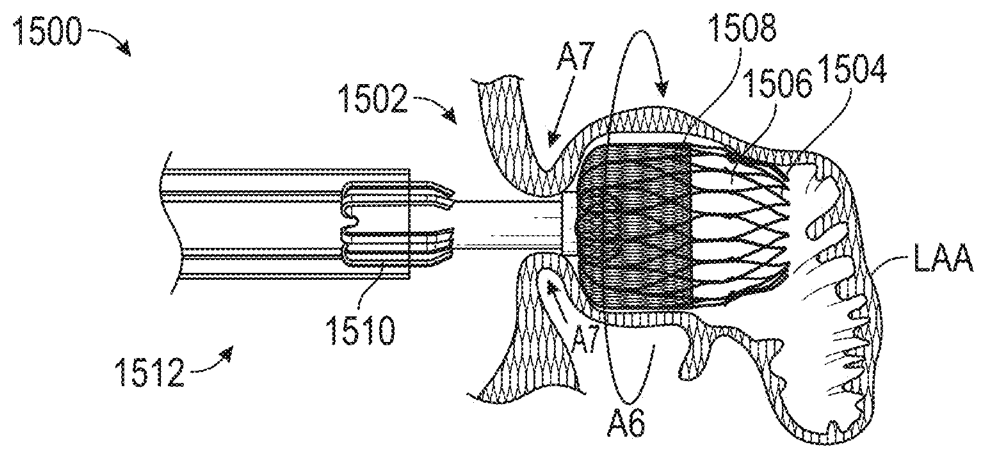
FIG. 67D shows the embodiment of the treatment device shown in FIG. 67B, showing the contact member being rotated to twist the LAA and cause a neck or opening of the LAA to constrict around a portion of the implant device.

FIG. 67B shows the treatment device 1500 being advanced into the LAA, showing the implant device 1502 having the contact member 1504 in a collapsed state. In any embodiments disclosed herein, the treatment device 1500 can have any of the components, features, or other details of any of the other treatment device embodiments disclosed herein and can be implanted or used using any of the steps or methods of any of the other embodiments disclosed herein. FIG. 67C shows the contact member 1504 being expanded within the LAA and engaging an inside surface of a wall portion of the LAA. FIG. 67D shows the contact member 1504 being rotated to twist the LAA and cause a neck or opening of the LAA to constrict around a portion of the implant device 1502. In this configuration, when the contact member 1504 is rotated in a first direction (indicated by arrow A6 in FIG. 67D, which can be in the clockwise or the counterclockwise direction), one or more or all of the struts of the frame 1506 of the contact member 1504 and one or more or all of the tissue anchors that the frame 1506 can have can engage the tissue of the LAA and cause the LAA to twist or rotate the LAA in the first direction A6. The twisting or rotation of the LAA in the first direction from a first rotational position to a second rotational position results in the opening or ostium O of the LAA constricting inwardly (identified by arrows A7 in FIG. 67D) so that the opening O of the LAA is caused to move or constrict around an outside surface of the implant device 1502.

Figure 67E:
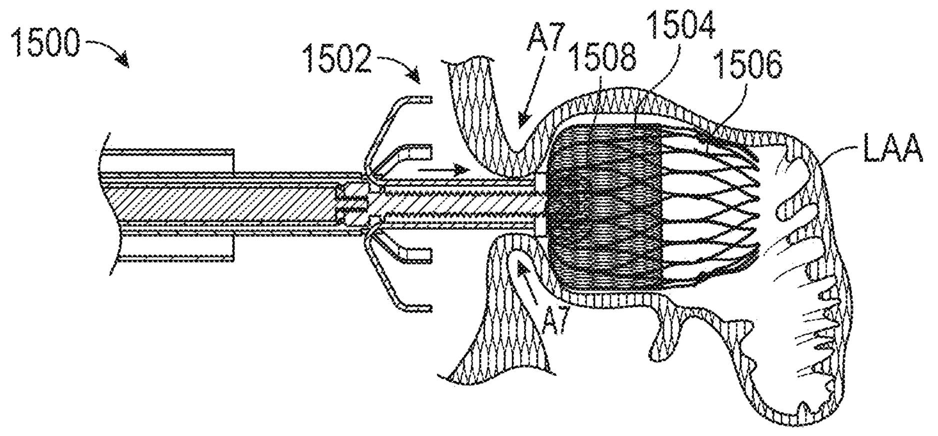
FIG. 67E shows the embodiment of the treatment device shown in FIG. 67B, showing a securing element of the embodiment of the implant device being advanced toward the contact member.
Figure 67F:
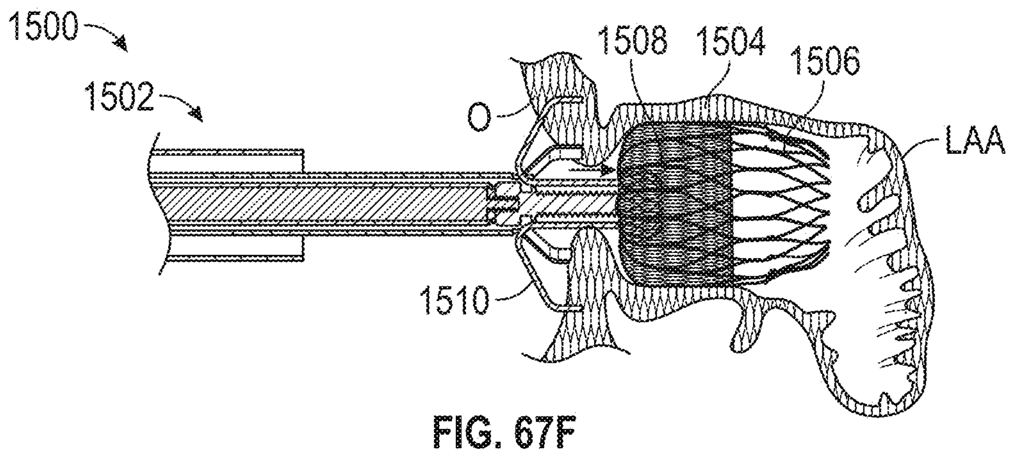
FIG. 67F shows the securing element of the treatment device shown in FIG. 67B engaged with the patient's tissue that has constricted as a result of the twisting of the LAA and/or adjacent to the patient's tissue that has constricted as a result of the twisting of the LAA.

FIG. 67E shows the securing element 1510 of the embodiment of the implant device 1502 being advanced toward the contact member 1504. FIG. 67F shows the securing element 1510 engaged with the tissue that has constricted as a result of the twisting of the LAA and/or the tissue adjacent to the tissue that has constricted as a result of the twisting of the LAA. In some embodiments, the contact member 1504 can remain in the LAA after the treatment procedure has been completed. In other embodiments, the contact member 1504 can be removed from the LAA and withdrawn with the delivery device. In any embodiments disclosed herein, the contact member can be expanded in the LA prior to being advanced into the LAA.

Figure 67G:
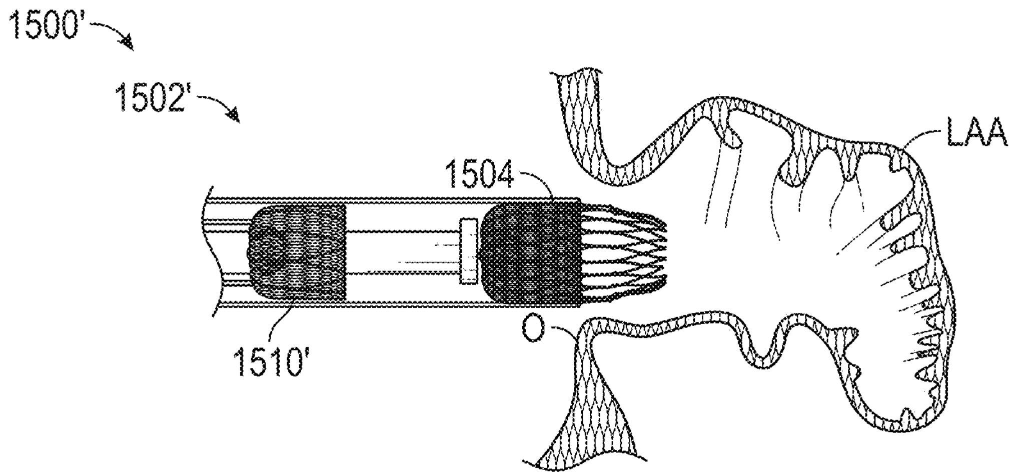
FIG. 67G shows another embodiment of a treatment device for occluding the LAA showing an implant device having a contact member shown in a collapsed state being advanced into the LAA and a securing element shown in FIG. 67A in a collapsed state within the delivery device.
Figure 67H:
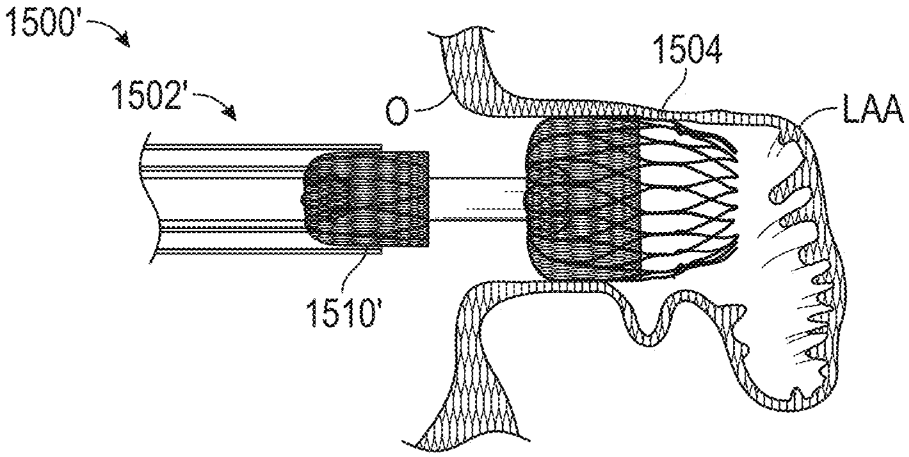
FIG. 67H shows the embodiment of the treatment device shown in FIG. 67G, showing the contact member being expanded within the LAA and engaging an inside surface of a wall portion of the LAA.
Figure 67I:
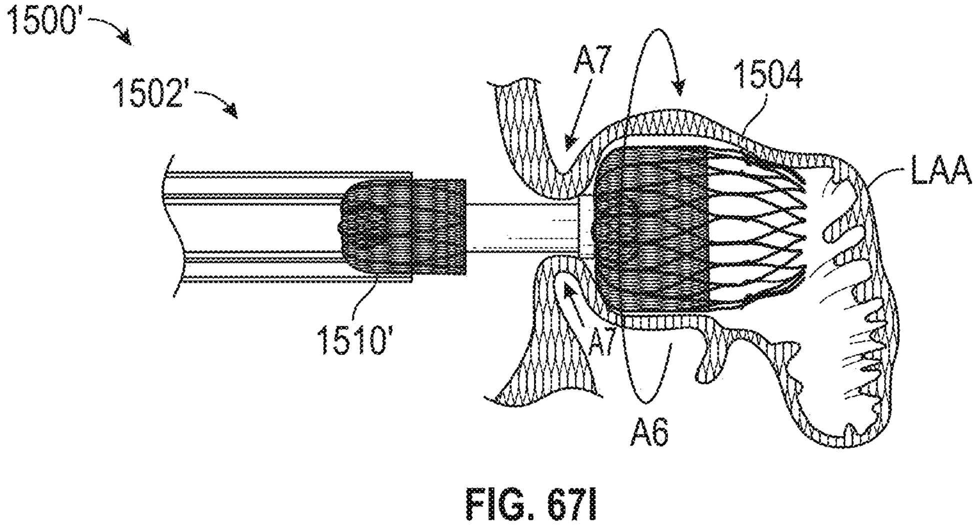
FIG. 67I shows the embodiment of the treatment device shown in FIG. 67G, showing the contact member being rotated to twist the LAA and cause a neck or opening of the LAA to constrict around a portion of the implant device.
Figure 67J:
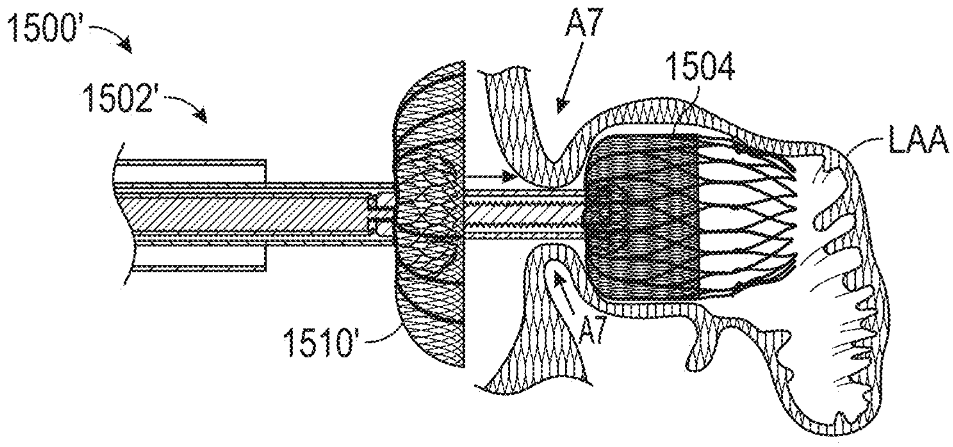
FIG. 67J shows the embodiment of the treatment device shown in FIG. 67G, showing a securing element being advanced toward the contact member.
Figure 67K:
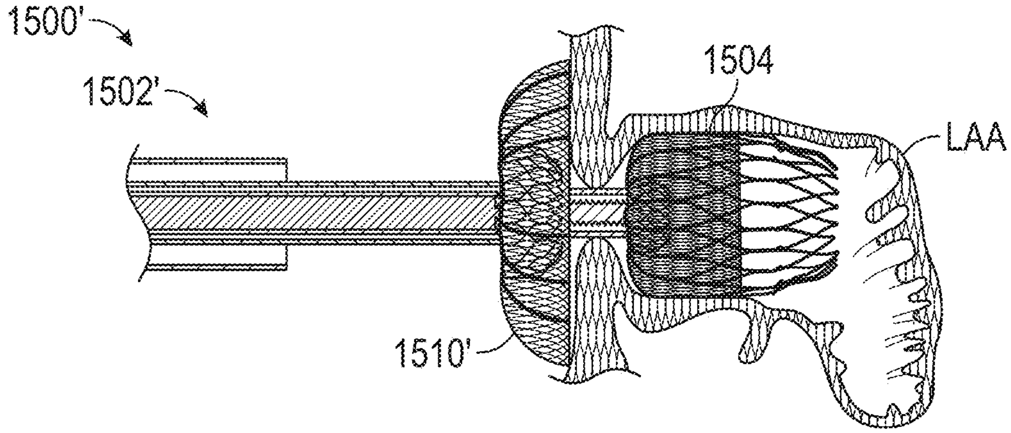
FIG. 67K shows the embodiment of the treatment device shown in FIG. 67G, showing the securing element engaged with the tissue that has constricted as a result of the twisting of the LAA and/or the tissue adjacent to the tissue that has constricted as a result of the twisting of the LAA.

FIG. 67G shows another embodiment of a treatment device 1500' for occluding the LAA showing an implant device 1502' having the contact member 1504 shown in FIG. 67A in a collapsed state being advanced into the LAA. In any embodiments disclosed herein, the treatment device 1500' can have any of the components, features, or other details of any of the other treatment device embodiments disclosed herein and can be implanted or used using any of the steps or methods of any of the other embodiments disclosed herein. The treatment device 1500' can also have a securing element 1510' that can have a structure and/or design that is similar to the embodiment of the implant device shown in FIG. 67G and FIG. 67A. In some embodiments, the securing element 1510' can be the same as a portion of the embodiment of the implant device shown in FIG. 67G. Therefore, in some embodiments, the securing element 1510' can have a size, a shape, and/or other details similar to that of the WATCHMAN device by Boston Scientific, as is shown in FIG. 67A, or a portion of the WATCHMAN device as is shown in FIG. 67A. In some embodiments, the securing element 1510' can have any of the components, features, and/or other details of any of the contact member embodiments disclosed herein, configured for use as a securing element. An end portion of the securing element 1510' can have a plurality of tissue anchors thereon to secure the securing element 1510' the patient's tissue that has constricted as a result of the twisting of the LAA. In some embodiments, the securing element 1510' can have a larger diameter or size as compared to the constricted ostium and/or compared with other embodiments of the securing elements disclosed herein and can be configured to engage with tissue that has constricted as a result of the twisting of the LAA and/or the tissue adjacent to the tissue that has constricted as a result of the twisting of the LAA FIG. 67H shows the treatment device 1500', showing the contact member 1504 being expanded within the LAA and engaging an inside surface of a wall portion of the LAA. FIG. 67I shows the embodiment of the treatment device 1500', showing the contact member 1504 being rotated to twist the LAA and cause a neck or opening of the LAA to constrict around a portion of the implant device 1502'. FIG. 67J shows the embodiment of the treatment device 1500' shown in FIG. 67G, showing the securing element 1510' in an expanded or second state being advanced toward the contact member 1504. FIG. 67K shows the securing element 1510' of the treatment device 1500' in an expanded or second state, and engaged with the patient's tissue that has constricted as a result of the twisting of the LAA. In this configuration, the securing element 1510' can inhibit the untwisting and/or the relaxation of the tissue that has contracted as a result of the twisting of the LAA.

Figure 67L:
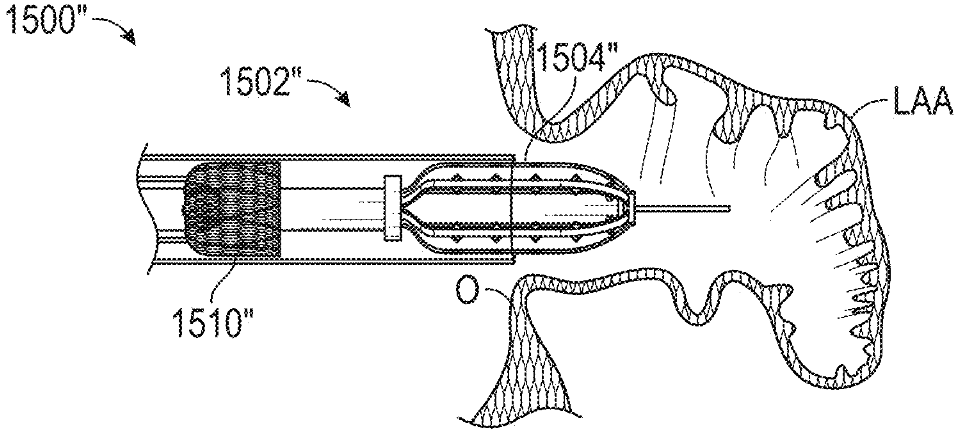
FIG. 67L shows another embodiment of a treatment device for occluding the LAA, showing an implant device having a contact member in a collapsed state being advanced into the LAA and a securing element in a collapsed state within the delivery device.

FIG. 67L shows another embodiment of a treatment device 1500" for occluding the LAA, showing an implant device 1502" having a contact member 1504" in a collapsed state being advanced into the LAA and a securing element 1510" in a collapsed state within the delivery device. In any embodiments disclosed herein, the treatment device 1500" can have any of the components, features, or other details of any of the other treatment device embodiments disclosed herein and can be implanted or used using any of the steps or methods of any of the other embodiments disclosed herein. Further, in any embodiments disclosed herein, the contact member 1504" can have any of the components, features, or other details of any of the other contact member embodiments disclosed herein, including without limitation any of the embodiments of the contact member 144 of the treatment device 140 described above. Further, in any embodiments, the securing element 1510" can be the same or have any of the same features or other details of any of the embodiments of the securing element 1510' described above.

Figure 67M:
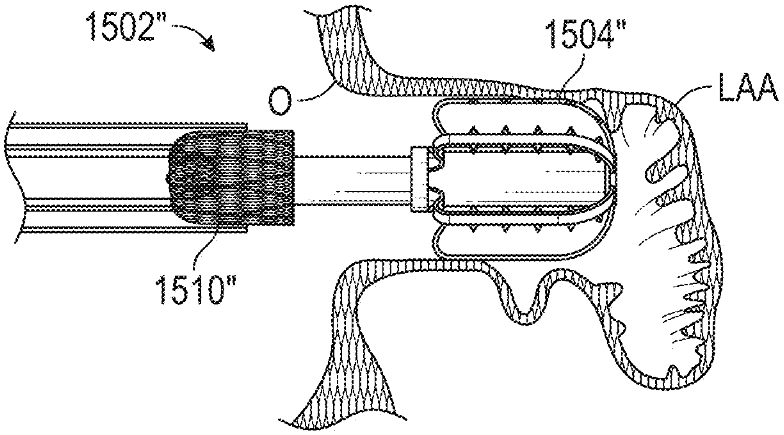
Figure 67N:
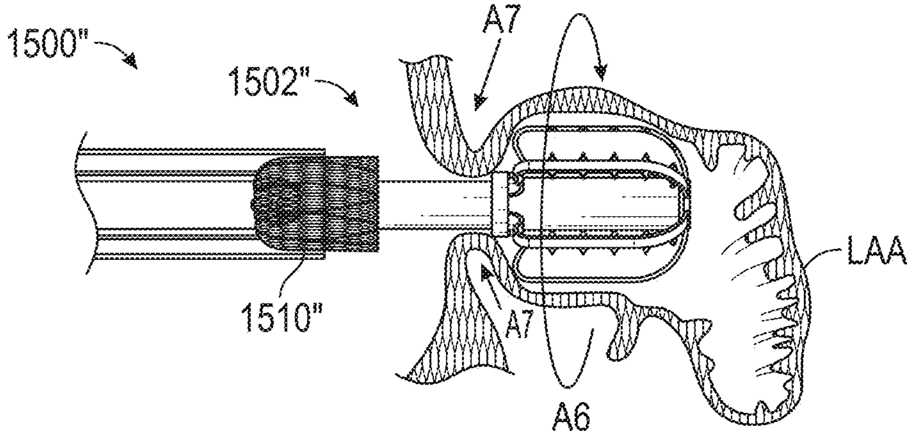
Figure 67O:
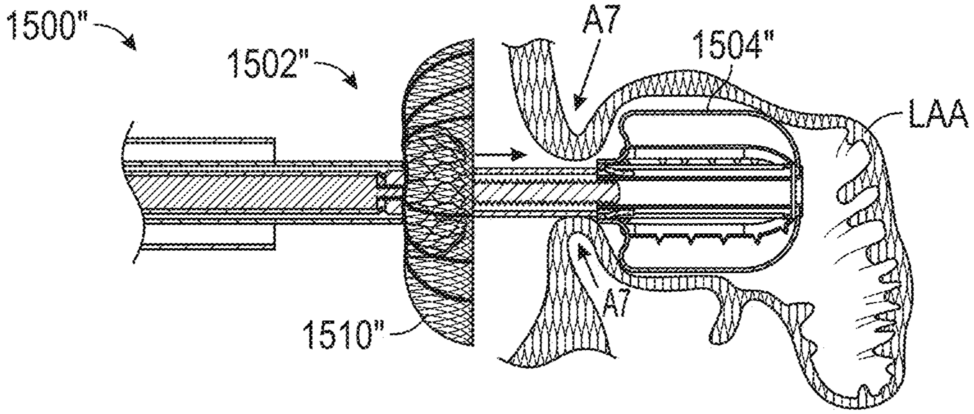
Figure 67P:
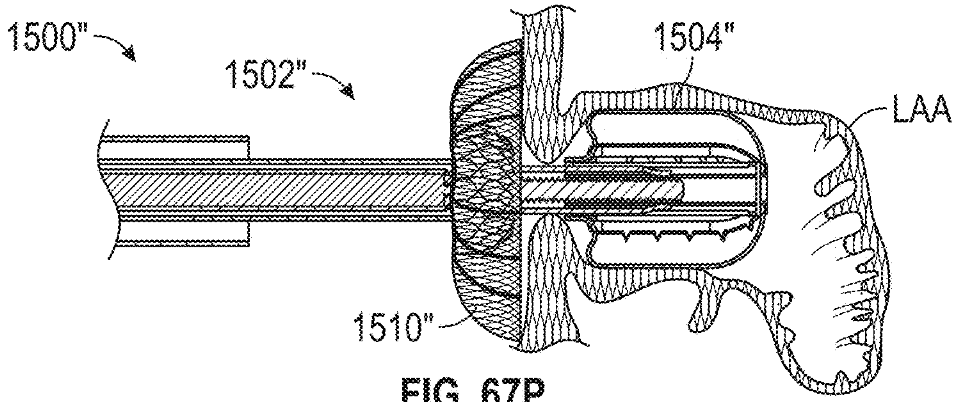

FIG. 67M shows the contact member 1504" of the treatment device 1500" being expanded within the LAA and engaging an inside surface of a wall portion of the LAA. FIG. 67N shows the contact member 1504" being rotated to twist the LAA and cause a neck or opening of the LAA to constrict around a portion of the implant device 1502". FIG. 67O shows securing element 1510" being advanced toward the contact member 1504". Finally, FIG. 67P shows the securing element 1510" of the treatment device 1500" shown in FIG. 67L in an expanded or second state, and engaged with the patient's tissue that has constricted as a result of the twisting of the LAA. In this configuration, the securing element 1510" can inhibit the untwisting and/or the relaxation of the tissue that has contracted as a result of the twisting of the LAA.

Figure 68A:
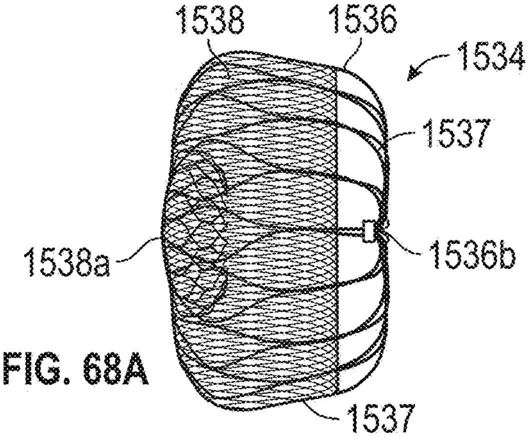

FIG. 68A shows an example of another embodiment of a device that can be configured to be used as a contact member and/or a securing element in any of the treatment device embodiments disclosed herein. In some embodiments, the contact member 1534 can have a self-expanding or mechanically expandable frame 1536. Some embodiments of the frame 1536 of the contact member 1534 can be made from metal wires, or be laser cut and formed from a solid tube of material, having a plurality of struts or frame members. In any embodiments, the frame 1536 can be made from stainless steel, Nitinol or any other suitable material.

Some embodiments of the contact member 1534 can have a generally tapering cylindrical shape (wherein a size or a diameter of the contact member 1504 decreases from the proximal to the distal end thereof), with the wire frame at a proximal end 1536*a* of the frame 1536 of the contact member 1534 extending toward the axial center of the frame 1536 so as to cover the proximal end 1536*a* of the frame. In some embodiments, the distal end 1536*b* of the frame 1536 can also be generally closed, converging on a hub or connector positioned along an axial centerline of the contact member 1534. The frame of the contact member 1534 can be flexible and conformable to the patient's anatomy in some embodiments, as in the illustrated embodiment, or can be more rigid in other embodiments. In some embodiments, the contact member 1534 can have a size, a shape, and/or other details similar to that of the WATCHMAN FLX device by Boston Scientific, as is shown in FIG. 68A.

Some embodiments of the contact member 1534 can have a mesh cover or membrane 1538 (which can be, but is not required to be, a 160 micron membrane made from PET) over an outside surface, or a portion of the outside surface, of the frame 1536 of the contact member 1534. In any embodiments, the contact member 1534 can have a 21 mm size, a 24 mm size, a 27 mm size, a 30 mm size, or a 33 mm size. The contact member 1534 can also have a plurality of anchors 1537, for example and without limitation, 18 anchors 1537, about an outside surface of the frame 1536 for engaging a tissue of the LAA.

FIGS. 68B-68F show an example of a treatment device 1530 having the embodiment of the contact member 1534 shown in FIG. 68A for occluding the LAA. FIGS. 68B-68F also show an example of a treatment procedure that can be performed to occlude the LAA using the treatment device 1530. In any embodiments disclosed herein, the treatment device 1530 can have any of the components, features, or other details of any of the other treatment device embodiments disclosed herein and can be implanted or used using any of the steps or methods of any of the other embodiments disclosed herein, including without limitation, any of the embodiments of the treatment device 140 described above and shown in FIGS. 9A-9I, in place of or combination with any of the features, components, and/or other details disclosed herein of treatment device 1530.

Figure 68B:
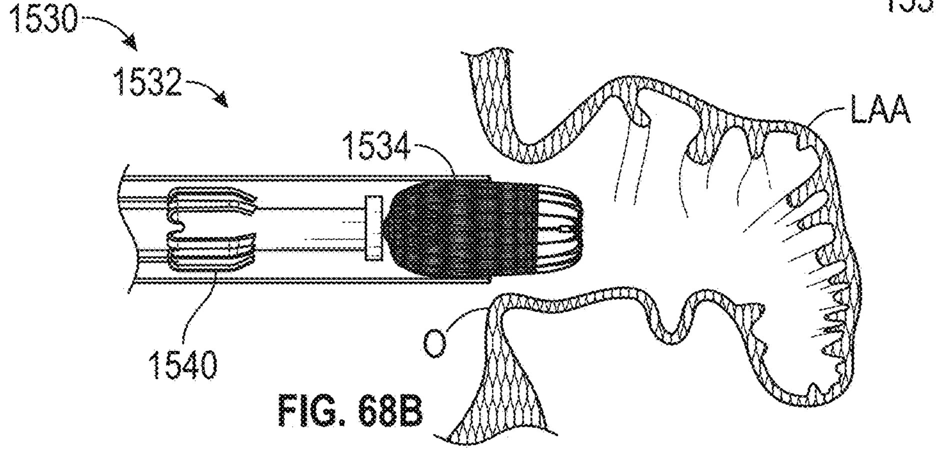
Figure 68C:
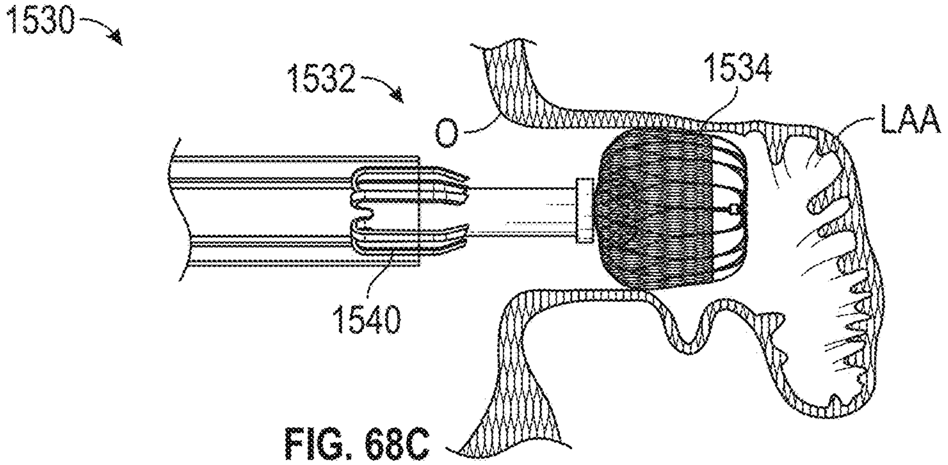
Figure 68D:
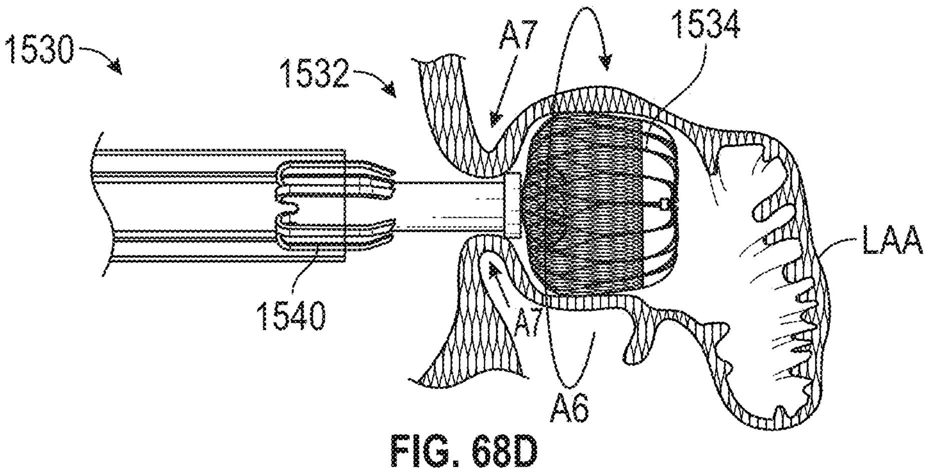

FIG. 68B shows the treatment device 1530 being advanced into the LAA, showing the implant device 1532 having the contact member 1534 in a collapsed state. FIG. 68C shows the contact member 1534 being expanded within the LAA and engaging an inside surface of a wall portion of the LAA. In any embodiments, the contact member 1534 or any contact member disclosed herein can be expanded within the LA before being advanced into the LAA. FIG. 68D shows the contact member 1534, that has engaged the tissue of the LAA, being rotated to twist the LAA and cause a neck or opening of the LAA to constrict around a portion of the implant device 1532. In this configuration, when the contact member 1534 is rotated in a first direction (indicated by arrow A6 in FIG. 68D, which can be in the clockwise or the counterclockwise direction), one or more or all of the struts of the frame 1536 of the contact member 1534 and one or more or all of the tissue anchors that the frame 1536 can have can engage the tissue of the LAA and cause the LAA to twist or rotate the LAA in the first direction A6. The twisting or rotation of the LAA in the first direction from a first rotational position to a second rotational position results in the opening or ostium O of the LAA constricting in a radial direction (identified by arrows A7 in FIG. 68D) so that the opening O of the LAA is caused to move or constrict around an outside surface of the implant device 1532.

Figure 68E:
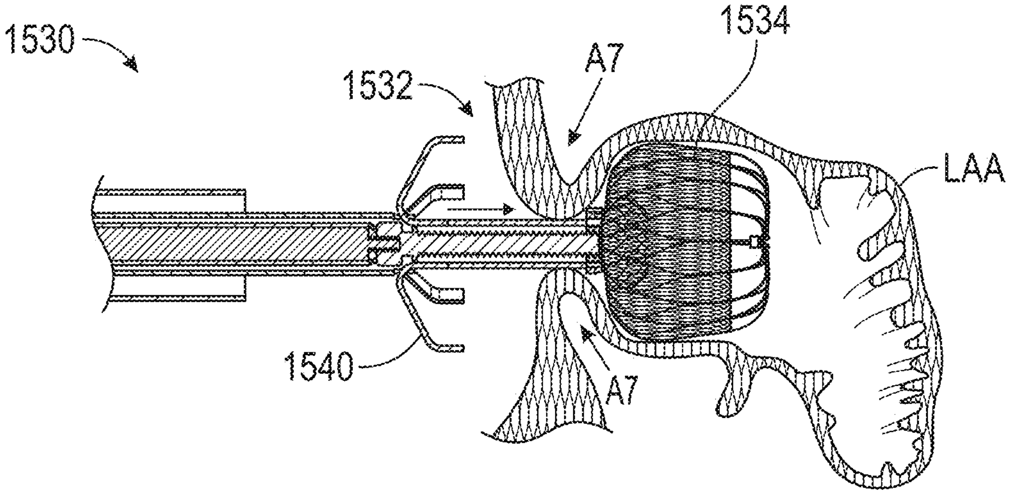
Figure 68F:
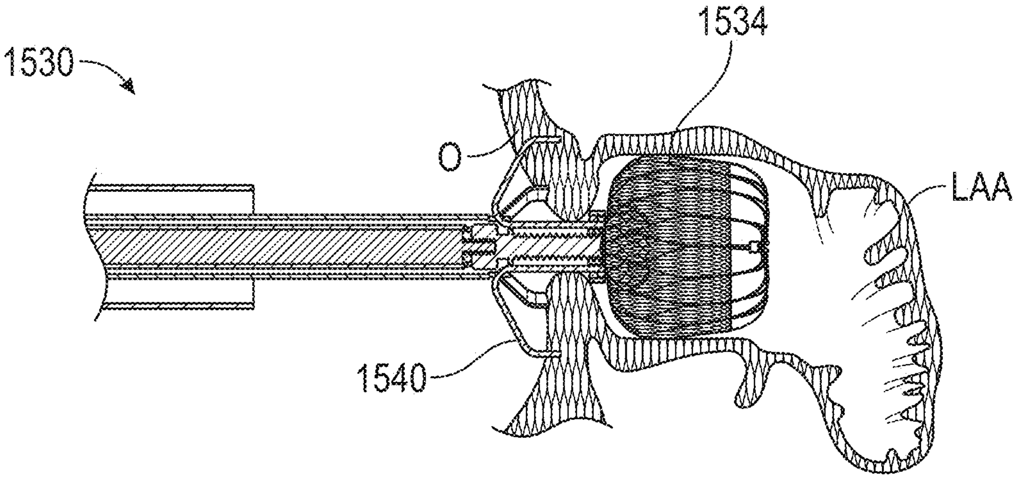

FIG. 68E shows an embodiment of a securing element 1540 of the embodiment of the implant device 1532 being advanced toward the contact member 1534. FIG. 68F shows the securing element 1540 of the treatment device 1530 shown in FIG. 68B engaged with the tissue that has constricted as a result of the twisting of the LAA and/or the tissue adjacent to the tissue that has constricted as a result of the twisting of the LAA. In some embodiments, the contact member 1534 can remain in the LAA after the treatment procedure has been completed. In other embodiments, the contact member 1534 can be removed from the LAA and withdrawn with the delivery device.

FIG. 69A shows an example of another embodiment of a device that can be used as a contact member and/or a securing element in any of the treatment device embodiments disclosed herein. In some embodiments, the contact member 1564 can have a self-expanding or mechanically expandable frame 1566. Some embodiments of the frame 1566 of the contact member 1564 can be made from metal wires, or be laser cut and formed from a solid tube of material, having a plurality of struts or frame members. In any embodiments, the frame 1566 can be made from stainless steel, Nitinol or any other suitable material.

Some embodiments of the contact member 1564 can have an approximately cylindrical shape, with the wire frame at a proximal end 1566*a* of the frame 1566 of the contact member 1564 extending toward the axial center of the frame 1566 so as to cover the proximal end 1566*a* of the frame. In some embodiments, the distal end 1566*b* of the frame 1566 can also be closed, with the various members of the frame 1566 converging at a hub or connector positioned along an axial centerline of the contact member 1564, or at a point along an axial centerline of the contact member. The frame of the contact member 1564 can be flexible and conformable to the patient's anatomy in some embodiments, or can be more rigid in other embodiments. In some embodiments, the contact member 1564 can have a size, a shape, and/or other details similar to that of the AMPLATZER AMULET LEFT ATRIAL APPENDAGE OCCLUDER by Abbott, as is shown in FIG. 69A.

Some embodiments of the contact member 1564 can have a mesh cover or membrane (not shown) over an outside surface, or a portion of the outside surface, of the frame 1566 of the contact member 1564. In any embodiments, the contact member 1564 can have a 16 mm size, an 18 mm size, a 20 mm size, a 22 mm size, a 25 mm size, a 28 mm size, a 31 mm size, or a 34 mm size. The contact member 1564 can also have a plurality of anchors 1567, for example and without limitation, 18 anchors 1567, about an outside surface of the frame 1566 for engaging a tissue of the LAA.

FIGS. 69B-69F show an example of a treatment device 1560 having the embodiment of the contact member 1564 shown in FIG. 69A for occluding the LAA. FIGS. 69B-69F also show an example of a treatment procedure that can be performed to occlude the LAA using the treatment device 1560. In any embodiments disclosed herein, the treatment device 1560 can have any of the components, features, or other details of any of the other treatment device embodiments disclosed herein and can be implanted or used using any of the steps or methods of any of the other embodiments disclosed herein. In some embodiments, the treatment device 1560 can have any of the features, components, and/or other details of any of treatment device embodiments disclosed herein, including without limitation, any of the embodiments of the treatment device 140 described above and shown in FIGS. 9A-9I, in place of or combination with any of the features, components, and/or other details disclosed herein of treatment device 1560.

FIG. 69B shows the treatment device 1560 being advanced into the LAA, showing the implant device 1562 having the contact member 1564 in a collapsed state. FIG. 69C shows the contact member 1564 being expanded within the LAA and engaging an inside surface of a wall portion of the LAA. FIG. 69D shows the contact member 1564 being rotated to twist the LAA and cause a neck or opening of the LAA to constrict around a portion of the implant device 1562. In this configuration, when the contact member 1564 is rotated in a first direction (indicated by arrow A6 in FIG. 69D, which can be in the clockwise or the counterclockwise direction), one or more or all of the struts of the frame 1566 of the contact member 1564 and one or more or all of the tissue anchors that the frame 1566 can have can engage the tissue of the LAA and cause the LAA to twist or rotate the LAA in the first direction A6. The twisting or rotation of the LAA in the first direction from a first rotational position to a second rotational position results in the opening or ostium O of the LAA constricting in a radial direction (identified by arrows A7 in FIG. 69D) so that the opening O of the LAA is caused to move or constrict around an outside surface of the implant device 1562.

FIG. 69E shows an embodiment of a securing element 1570 of the embodiment of the implant device 1562 being advanced toward the contact member 1564. FIG. 69F shows the securing element 1570 of the treatment device 1560 shown in FIG. 69B engaged with the tissue that has constricted as a result of the twisting of the LAA and/or the tissue adjacent to the tissue that has constricted as a result of the twisting of the LAA. In some embodiments, the contact member 1564 can remain in the LAA after the treatment procedure has been completed. In other embodiments, the contact member 1564 can be removed from the LAA and withdrawn with the delivery device.

FIG. 70A shows another embodiment of a device that can be used as a contact member and/or a securing element in any of the treatment device embodiments disclosed herein. Further, components of implant device 1592 can be used as a securing element and/or a retention element in any of the treatment device embodiments disclosed herein. In some embodiments, the implant device 1592 can have a contact member 1594, a securing element 1597, and a retention element 1598. The contact member 1594 can have an expandable frame 1596 that can be self-expanding or mechanically expandable. Some embodiments of the frame 1596 can be made from metal wires or be laser cut and formed from a solid tube of material. The frame 1596 can have a plurality of struts or frame members. In any embodiments, the frame 1596 can be made from stainless steel, Nitinol or any other suitable material. The contact member 1594 and/or implant device 1592 can have any of the same features, components, and/or other details of any embodiments of the contact member 1564 and/or the implant device 1592 disclosed above, in addition to or in place of any of the features, components, and/or other details described herein.

With reference to FIG. 70A, the implant device can also have a securing element 1597 and a retention element 1598 coupled with the contact member 1594. In some embodiments, the contact member 1594, the securing element 1598, and the retention element 1598 can be made from a wire mesh material. As with any other securing element embodiments disclosed herein, the securing element 1598 can be configured to inhibit a rotation of the contact member after the contact member has twisted the LAA, inhibit an opening of the tissue of or adjacent to the ostium of the LAA after the ostium of the LAA has been occluded, and/or can inhibit a rotation of the tissue of or adjacent to the ostium of the LAA after the ostium of the LAA has been twisted. Some embodiments of the securing element 1598 can have a cover or seal configured to inhibit the inflow or outflow of blood, emboli, or other substances into and out of the LAA through the ostium. The retention element 1598 can be used to couple the securing element 1598 and the contact member 1594 together, and can also be used to selectively bias the securing element 1598 toward the contact member 1594.

FIGS. 70B-70F show an example of a treatment device 1590 having the embodiment of the contact member 1594, securing element 1597, and retention element 1598 shown in FIG. 70A for occluding the LAA. FIGS. 70B-70F also show an example of a treatment procedure that can be performed to occlude the LAA using the treatment device 1590. In any embodiments disclosed herein, the treatment device 1590 can have any of the components, features, or other details of any of the other treatment device embodiments disclosed herein and can be implanted or used using any of the steps or methods of any of the other embodiments disclosed herein. After the LAA has been twisted and occluded, as shown in FIG. 70D, the securing element 1597 can be deployed from the delivery catheter and expanded to a second state, as shown in FIG. 70E. The retention element 1598 is shown in an expanded or partially expanded state in FIG. 70E. Thereafter, the securing element 1597 can be moved toward the tissue at the ostium of the LAA. This can be achieved by permitting the retention element 1598 to contract or can be achieved by contracting the retention element 1598 to a shortened or contracted state, as shown in FIG. 70F, to maintain the LAA in an occluded state or mostly occluded state. The securing element 1597 can have one or a plurality of tissue anchors configured to penetrate and engage the tissue that has constricted as a result of the twisting of the LAA and/or the tissue adjacent to the tissue that has constricted as a result of the twisting of the LAA, so as to increase the engagement of the securing element 1597 with the tissue. In some embodiments, the contact member 1594 can remain in the LAA after the treatment procedure has been completed. In other embodiments, the treatment system 1590 can be configured so that the contact member 1594 can be removed from the LAA and withdrawn with the delivery device.

FIG. 70G shows another embodiment of a treatment device 1590' that can be used to occlude an ostium to an LAA. Any embodiments of the treatment device 1590' disclosed herein can have any of the components, features, or other details of any of the other embodiments of the treatment devices or systems disclosed herein, including without limitation the embodiments of the treatment device 140, treatment device 140', and treatment devices 1590 disclosed herein, and can be implanted or used using any of the steps or methods of any of the other embodiments disclosed herein. With reference to FIGS. 70G-70K, the implant device 1592' of the treatment device 1590' can have a contact member 1594', a securing element 1597', and a retention element 1598'. In any embodiments disclosed herein, the contact member 1594' can have any of the components, features, or other details of any of the other contact member embodiments disclosed herein, including without limitation any of the embodiments of the contact member 144 of the treatment device 140 described above. Further, in any embodiments, the securing element 1597' can be the same or have any of the same features or other details of any of the embodiments of the securing element 1597 of the treatment device 1590 described above, and the retention element 1598' can be the same or have any of the same features or other details of any of the embodiments of the retention element 1598 of the treatment device 1590 described above.

FIGS. 70G-70K show an example of a method of treating an LAA using the treatment device 1590' for occluding the LAA. After the LAA has been twisted and occluded, as shown in FIG. 70I, the securing element 1597' can be deployed from the delivery catheter and expanded to a second state, as shown in FIG. 70J. The retention element 1598' is shown in an expanded or partially expanded state in FIG. 70J. Thereafter, the securing element 1597' can be moved toward the tissue at the ostium of the LAA. This can be achieved by permitting the retention element 1598' to contract or can be achieved by contracting the retention element 1598' to a shortened or a contracted or a partially contracted state, as shown in FIG. 70K, to maintain the LAA in an occluded state or mostly occluded state or otherwise inhibit the LAA from opening. As with securing element 1597, securing element 1597' can have one or a plurality of tissue anchors configured to penetrate and engage the tissue that has contracted and/or twisted as a result of the twisting of the LAA, so as to increase the engagement of the securing element 1597' with the tissue. In some embodiments, the contact member 1594' can remain in the LAA after the treatment procedure has been completed. In other embodiments, the treatment system 1590' can be configured so that the contact member 1594' can be removed from the LAA and withdrawn with the delivery device.

FIGS. 70L-70T show another embodiment of a treatment device 1650 for occluding the LAA, showing an implant device 1652 having a contact member 1654 in a collapsed state being advanced into the LAA. In other embodiments, the contact member 1654 can be expanded in the LA before being advanced into the LAA. Further, in any embodiments disclosed herein, the contact member can be configured such that the contact member is not expanded during the procedure—i.e., so that the contact member maintains a generally consistent or similar size and/or shape during the entire procedure.

In any embodiments disclosed herein, the treatment device 1650 can have any of the components, features, or other details of any of the other treatment device embodiments disclosed herein and can be implanted or used using any of the steps or methods of any of the other embodiments disclosed herein, including any embodiments of the treatment system 140 disclosed herein. Further, in any embodiments disclosed herein, the contact member 1654 can have any of the components, features, or other details of any of the other contact member embodiments disclosed herein, including without limitation any of the embodiments of the contact member 144 of the treatment device 140 described herein.

Figure 70M:
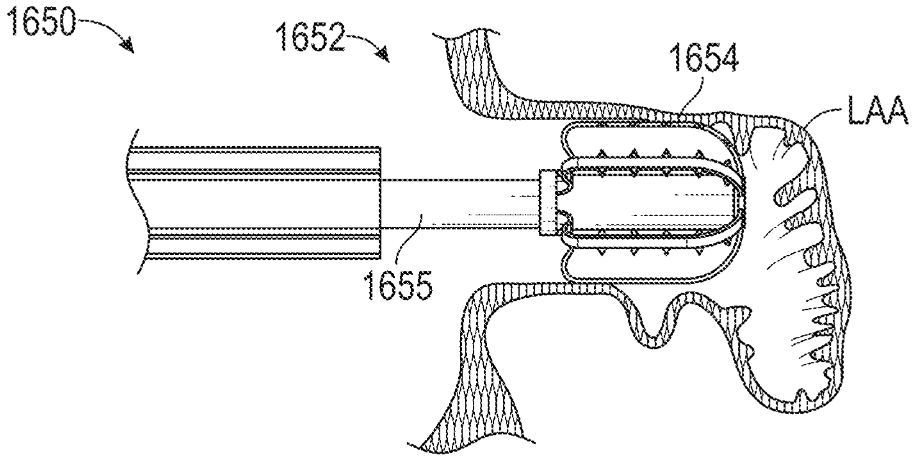
Figure 70N:
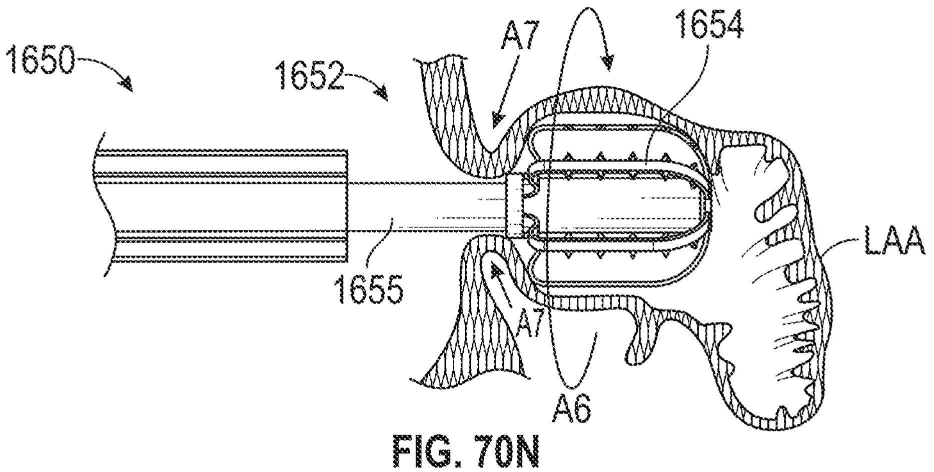
Figure 70O:
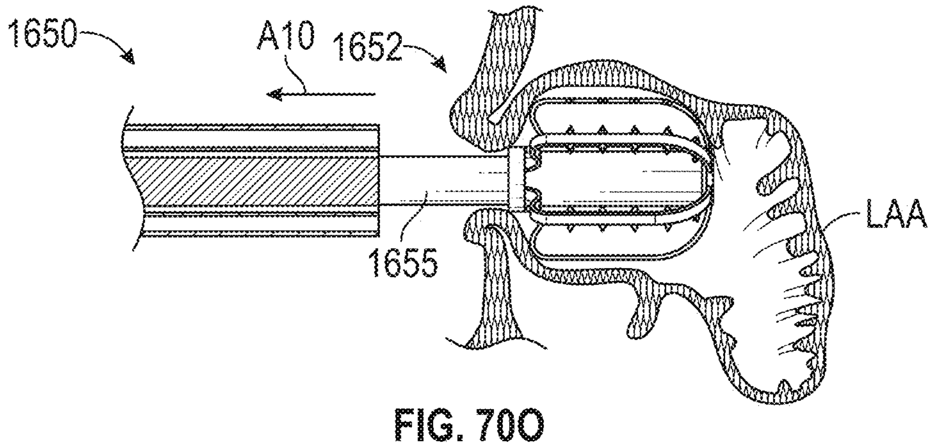
Figure 70P:
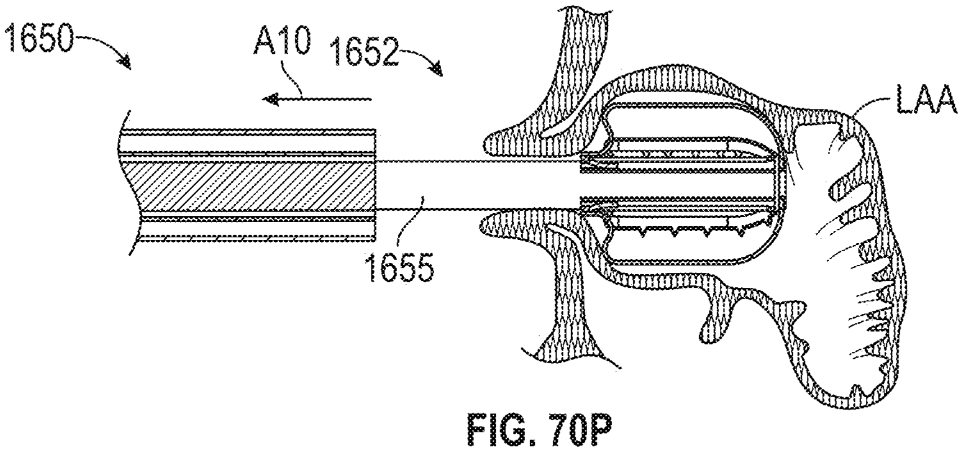

FIG. 70M shows the contact member 1654 of the treatment device 1650 engaging an inside surface of a wall portion of the LAA. FIG. 70N shows the contact member 1654 being rotated in direction A7 to twist the LAA and cause the tissue of the ostium or adjacent to the ostium of the LAA to constrict around a portion of the implant device 1652, for example and without limitation, in direction A7. Thereafter, after the tissue of the ostium or adjacent to the ostium of the LAA has constricted sufficiently around the implant device 1652, the user of the treatment device 1650 can retract or withdraw the contact member 1654 by withdrawing or retracting a core member 1655 of the delivery device in the direction indicated by arrow A10 of FIGS. 70O and 70P, for example and without limitation. As shown in FIG. 70O, this can cause a fold of tissue of the ostium and/or of tissue adjacent to the ostium of the LAA to extend into the LA. Further withdrawal of the core member 1655 and the contact member 1654 can increase a length of the fold of tissue that extends into the LA and that surrounds a portion of the implant device 1652.

Figure 70Q:
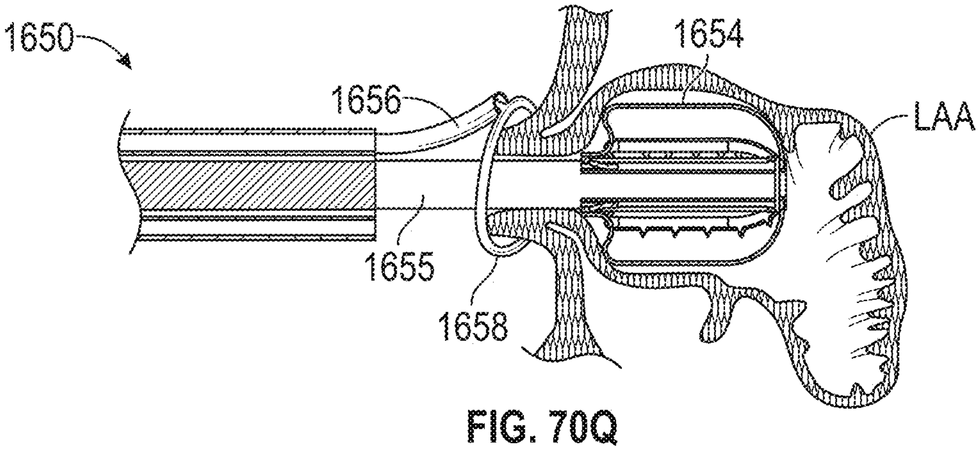
Figure 70R:
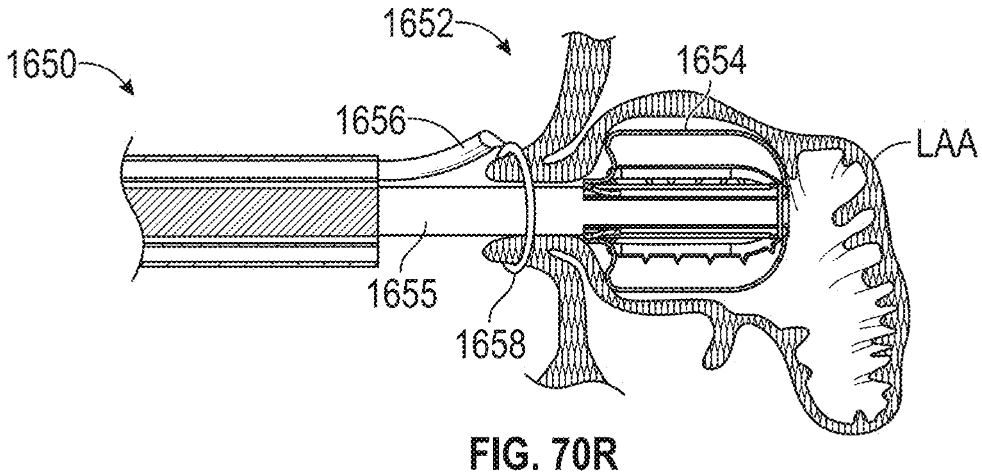
Figure 70S:
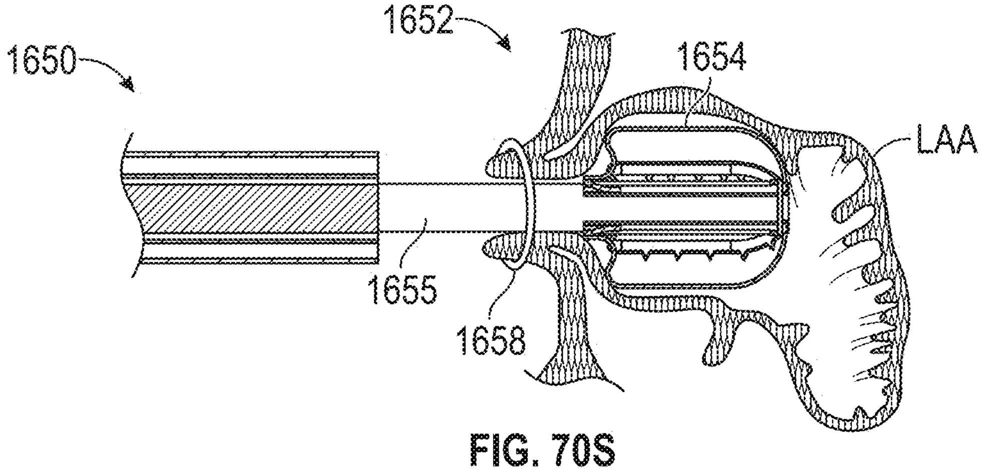
Figure 70T:
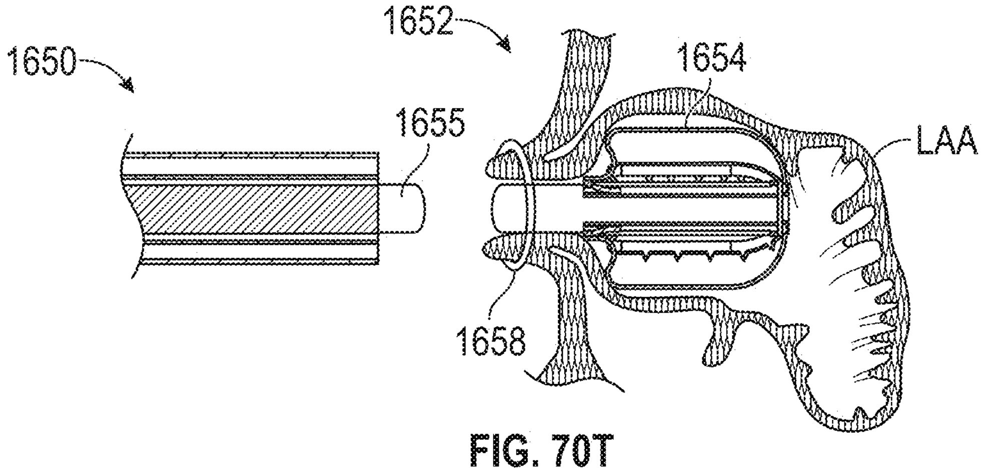

With reference to FIG. 70Q, in some embodiments, a delivery member 1656 that can be selectively coupled with a clamping element 1658 can be advanced past a distal end of the delivery catheter so that the claiming element 1658 passes over an outside surface of the tissue that is extending into the LA. In some embodiments, the clamping element 1658 can be configured to surround and constrict around the fold of tissue that extends into the LA and that surrounds a portion of the implant device 1652, so as to inhibit the fold of tissue from relaxing and/or inhibit the ostium of the LAA from expanding or opening up. The clamping element 1658 can be secured in a second or constricted state. In some embodiments, the clamping element 1658 can be a loop of material that can be cinched and secured. In some embodiments, the clamping element 1658 can have tissue grabbers, tissue anchors, roughened surface finish, and/or other features to inhibit the clamping element 1658 from becoming disengaged or decoupled from the tissue fold. In this configuration, the clamping element 1658 can inhibit the untwisting and/or the expansion of the tissue that has constricted around the implant device 1652 as a result of the twisting of the LAA and/or the retraction of the contact member 1654. Thereafter, with reference to FIG. 70T, the implant device 1652 can be decoupled from the core member 1655 so that the delivery device can be removed from the LA and from the patient.

FIG. 71A shows another embodiment of a treatment device 2000 for treating an LAA, showing an embodiment of an implant device 2004 within the LA being advanced past a distal end of the delivery device 2002 toward the LAA. As shown, the implant device 2004 can have a first implant member 2006 and a second implant member 2008 that can be supported within the delivery device 2002, for example within an outer sheath of the delivery device 2002. The first implant member 2006 and the second implant member 2008 of the implant device 2004 can be advanced into the target anatomy by advancing a first core member 2012 that can be selectively removably coupled with the first implant member 2006 and a second core member 2014 that can be selectively removably coupled with the second implant member 2008 toward the LAA, as shown in FIG. 71B. for example and without limitation, the first and second implant members 2006, 2008 can be selectively removable coupled with the first and second core members, respectively, so that the first and/or second implant members 2006, 2008 can remain in the left atrial appendage after the first and/or second core members 2012, 2014 have been withdrawn from the patient's heart.

In some embodiments, as is shown in FIG. 71C, the first core member 2012 coupled with the first implant member 2006 can be configured to cause a rotation of the first implant member when the first core member is rotated, and the second core member coupled with the second implant member can be configured to cause a rotation of the second implant member when the second core member is rotated. In any embodiments, the first and second core members 2012, 2014 can be independently rotated by a user of the device, so that the first and second implant members 2006, 2008 can also be independently rotated.

Therefore, in some embodiments, the device for treating a left atrial appendage can include an implant device 2004 having a first implant member 2006 configured to engage an inside tissue surface of a first portion of the left atrial appendage and a second implant member 2008 configured to engage an inside tissue surface of a second portion of the left atrial appendage. The first implant member 2006 can be configured to rotate in at least a first direction (e.g., in a clockwise direction) and the second implant member can be configured to rotate in at least a second direction (e.g., in a counter-clockwise direction), wherein the second direction is opposite to the first direction.

FIG. 71D shows the embodiment of the treatment device 2000 shown in FIG. 71A, showing a first and a second implant members 2006, 2008 of the implant device 2004 after occluding the LAA, the first and second implant members 2006, 2008 being secured together and disconnected from the delivery device 2002. Any embodiments of the treatment device 2000 can also have a securing element 2018 configured to inhibit a rotation of the first implant member 2006 and/or the second implant member 2008 in an operable state. In other embodiments, the first and second implant members 2006, 2008 can be configured to selectively lock or couple to one another without an additional securing element to inhibit a rotation of the first implant member 2006 and/or the second implant member 2008. For example and without limitations, the first and/or second implant members 2006, 2008 can have barbs, hook and loop fasteners, or other cooperating structures that, when in contact with the corresponding cooperating structure(s) of the other of the first and second implant members 2006, 2008 can inhibit the relative rotation of the first and second implant members 2006, 2008.

In any embodiments disclosed herein, the first and second implant members 2006, 2008 can have any of the features, components, or other details of any of the embodiments of the implant members or contact members disclosed herein, in place of or in combination with any of the features, components, and/or other details of any of the embodiments of the first and second implant members 2006, 2008 disclosed herein. In some embodiments, the first and second implant members 2006, 2008 can have gripping members, tissue anchors or barbs, roughened surface texture, and/or other features designed to improve the engagement of the first and second implant members 2006, 2008 with the tissue of the LAA. Further, any embodiments of the first and second implant members 2006, 2008 can be selectively expandable and collapsible. For example and without limitation, some embodiments of the treatment device 2000 can be configured such that the first and second implant members 2006, 2008 can be inflated so as facilitate the initial engagement of the first and second implant members 2006, 2008 with the tissue of the LAA. The first and second implant members 2006, 2008 can remain expanded or inflated during all or a portion of the rotation of the first and second implant members 2006, 2008. In other embodiments, the first and second implant members 2006, 2008 can be deflated as the tissue of the LAA is constricted or wrapped around the first and second implant members 2006, 2008, thereby reducing the size of the implant device 2004 that either can remain in the LAA after the procedure is completed, or removed from the LAA during the procedure.

Still other embodiments of the first and second implant members 2006, 2008 can be balloon expandable, wherein the expansion balloon can remain within the first and second implant members 2006, 2008 after the procedure is completed, or can be removed from the first and second implant members 2006, 2008 after the first and second implant members 2006, 2008 have been rotated. In other embodiments, the first and second implant members 2006, 2008 can be configured such that a size and/or a shape of the first and second implant members 2006, 2008 remains substantially fixed or constant during all stages of the procedure.

Novel embodiments of a method of occluding a left atrial appendage will now be described. In some embodiments, the method of occluding a left atrial appendage can include twisting a first portion of a tissue of the left atrial appendage in a first direction and twisting a second portion of the tissue of the left atrial appendage in a second direction that is opposite to the first direction. This twisting of the first portion of the tissue of the left atrial appendage in the first direction can cause a first portion of an ostium of the left atrial appendage to be drawn together so as to constrict the ostium of the left atrial appendage. Similarly, the twisting of the second portion of the tissue of the left atrial appendage in the second direction can cause a second portion of the ostium of the left atrial appendage to be drawn together so as to constrict the ostium of the left atrial appendage. With both the first portion and the portion of the tissue of the left atrial appendage being twisted, either in the same direction or in opposite directions, the ostium of the left atrial appendage can be occluded.

Some embodiments of the method of occluding a left atrial appendage can further include inhibiting the first portion and the second portion of the tissue of the left atrial appendage from untwisting, after such tissue has been twisted. This can inhibit the occluded ostium from opening up. In some embodiments, twisting the first portion of the tissue of the left atrial appendage in the first direction can be achieved by rotating a first implant member 2006 that is engaged with the second portion of the tissue in the first direction, and twisting the second portion of the tissue of the left atrial appendage in the second direction can be achieved by rotating a second implant member 2008 that is engaged with the second portion of the tissue in the second direction.

In any embodiments, the procedure or method can further include inhibiting the first implant member 2006 from rotating in the second direction, which is opposite to the first direction and/or inhibiting the second implant member 2008 from rotating in the first direction, which is opposite to the second direction. In some embodiments, this can be achieved by coupling the first implant member 2006 with the second implant member 2008 to inhibit the first and second implant members 2006, 2008 from rotating relative to one another. In other embodiments, the first implant member 2006 and the second implant member 2008 can have barbs, hook and loop fasteners, or other cooperating structures that, when in contact with the corresponding cooperating structure(s) of the other of the first and second implant members 2006, 2008, can inhibit the relative rotation of the first and second implant members 2006, 2008. In other embodiments, a separate securing element can be used to couple the first and second implant member 2006, 2008 together. In some embodiments, the securing element can have one or more sutures, loops, clamps, hooks, pins that can extend through substantially aligned holes through each of the first and second implant members 2006, 2008, or other fasteners that are configured to prevent the relative rotation of the first and second implant members 2006, 2008 in an operable state.

In any embodiments disclosed herein, the tissue of the LA or LAA that is constricted as a result of the LA being twisted can extend along a length of the implant device or upon an opposing tissue surface, or otherwise. In some embodiments, the length of the tissue of the LA or LAA that is constricted as a result of the LA being twisted and thus makes contact with the implant device or an opposing tissue surface can be longer than a clamp device, such as a ligation loop of other conventional designs. In some embodiments, the length of the tissue of the LA or LAA that is constricted as a result of the LA being twisted can be from 1 mm (or approximately 1 mm) to 15 mm (or approximately 15 mm) or more, or in some embodiments from 2 mm (or approximately 2 mm) to 10 mm (or approximately 10 mm), or in some embodiments from 2 mm (or approximately 2 mm) to 6 mm (or approximately 6 mm). Some of the embodiments disclosed here can be configured to twist the LAA down, which can recruit and encourage encourages the body's own tissue to close down on itself.

Additionally, some embodiments of the treatment devices disclosed herein can be configured to twist the tissue of the LAA and/or LA as the tissue is constricted by the twisting of the LAA. This can result in any leakage paths, if any, having a spiral path as opposed to a direct, linear path that is perpendicular to the ostium of the LAA. Thus, the leakage path, if any, in the tissue that has twisted and constricted may beneficially be longer and less likely to be open from one end to the other as a result of the twisting of the LAA as compared to potential leakage path lengths of conventional LAA treatment devices, e.g., treatment devices that clamp the ostium or neck of the LAA. Further, a portion of the implant device of some embodiments of the treatment devices disclosed herein are configured to remain in the ostium of the LAA after the tissue has been constricted. This can provide an improved seal as compared to some conventional treatment devices, for example and without limitation, for small central holes that may result from conventional epicardial LAA treatment devices.

FIG. 72A shows another embodiment of a treatment device 2020 for treating or occluding an LAA, showing an implant device having a first implant member 2022 and a second implant member 2024 positioned within the ostium of the LAA. In some embodiments, the first and second implant members 2022, 2024 can have a space therebetween, for example and without limitation, 1-2 mm. Some embodiments of the treatment device 2020 can have any of the features, components, or details of any of the other treatment device embodiments disclosed herein, for example and without limitation, any of the embodiments of the treatment device 2000 disclosed herein, in combination with or in place of any of the features, components, or other details disclosed herein for treatment device 2020. In some embodiments, the first and second implant members 2022, 2024 can be positioned so as to engage tissue surfaces of the LAA of or adjacent (e.g., distally adjacent) to the ostium of the LAA. The first and second implant members 2022, 2024 can be spread linearly to make contact with the ostium tissue, either with or without stretching or linearizing the tissue of the LAA or the tissue of the ostium of the LAA. The first and second implant members 2022, 2024 can then be rotated in opposite directions in some embodiments of the process, or in the same direction in other embodiments of the process, to draw the tissue of the ostium and/or adjacent to the ostium of the LAA together to constrict the ostium of the LAA, as shown in FIG. 72B. Thereafter, the first and second implant members 2022, 2024 can coupled or secured together to inhibit the first and second implant members 2022, 2024 from untwisting or counter-rotating and/or to inhibit the tissue that has twisted and constricted as a result of the rotation of the first and second implant members 2022, 2024 from untwisting or expanding. For example and without limitation, the shafts or body portions of the first and second implant members 2022, 2024 can coupled or secured together. Alternatively or additionally, the first and second implant members 2022, 2024 can be secured to the tissue using sutures, tissue anchors, or any of the embodiments of the securing elements disclosed herein.

In any embodiments disclosed herein, the treatment device can have a suction tube or suction member configured to selectively engage and grasp one or more tissue surfaces inside the LAA. Further, the contact member of any embodiments disclosed herein can be configured to selectively apply a suction force through one or more ports in the contact member, to initiate and/or increase the engagement of the contact member with the tissue of the LAA or otherwise. For example and without limitation, FIG. 73A shows an embodiment of a treatment device 2050 for treating or occluding an LAA, showing a deployment device 2052 having a suction member 2054 being advanced into the LAA. FIG. 73B shows the suction member 2054 of the treatment device 2050 being advanced toward a distal wall of the LAA. FIG. 73C shows the suction member 2054 engaging a distal wall of the LAA with suction and withdrawing a portion of the distal portion of the wall of the LAA in a proximal direction. In some embodiments, the wall of the LAA can be inverted or partially inverted by the withdrawal of the wall of the LAA. In some embodiments, the tissue of the LAA can be inverted or partially inverted and then twisted. In other embodiments, the tissue can be twisted before inverting the tissue. In some embodiments, the suction member 2054 can have a rounded tip or distal portion, and can be made from any suitable atraumatic material, such as a soft urethane like material. Suction can be communicated through the distal tip portion of the suction member 2054 through a single lumen or multiple pores throughout the distal portion of the suction member 2054.

In some embodiments, the suction member 2054 can be used in place of any of the embodiments of the contact member of any treatment device embodiments disclosed herein, for example and without limitation, to engage and twist the LAA. The tissue of or adjacent to the ostium of the LAA can be constricted in this manner around a body portion of the deployment device 2052. Thereafter, a securing element that can comprise any of the embodiments of the securing elements disclosed herein, one or more sutures, or other locking mechanisms, can be used to inhibit the tissue that has constricted as a result of the twisting of the LAA from untwisting or expanding. The suction member 2054 can remain within the LAA or can be removed.

FIG. 73D shows another embodiment of a treatment device 2070 for treating or occluding an LAA, showing the suction member 2074 engaging a distal wall of the LAA and withdrawing a portion of the distal portion of the wall of the LAA. In some embodiments, the suction member 2074 can have a funnel shape (as shown), a spherical shape, an elongated shape, or otherwise. Additionally, in any embodiments, the suction member can have one or a plurality of openings configured to communicate the source of suction to the tissue of the LAA. The openings can be radially oriented, axially oriented, and/or at any desired angle or position on the suction member. Further, in any embodiments disclosed herein, the suction member can have any number of tissue engaging features thereon, such as barbs, spikes, points, ridges, or any of the other features described in any other embodiments disclosed herein.

FIG. 73E shows another embodiment of a treatment device for treating or occluding an LAA, showing a clamp member surrounding a portion of the tissue that has been inverted by the withdrawal of the suction member. As shown in FIG. 73E, in some embodiments, the inverted tissue can be pulled through a clamp or a collar to secure the inverted tissue to occlude the LAA. In some embodiments, the clamp can have tissue anchors thereon that can prevent the tissue of the LAA from slipping out of the clamp.

Described below are novel devices, systems, and methods for closing the left atrial appendage (LAA) by closing the LAA with a device applied to an outside surface of the LAA. In some embodiments, the device is applied to the LAA within the pericardial space, as will be described in greater detail. The improved devices for closing or clamping the LAA disclosed herein can be configured to flatten and/or elongate the opening of the LAA, thereby resulting in an improved seal across the ostium of the LAA. The clamp device embodiments disclosed herein can result in reduced leakage out of the LAA and potentially reduce tissue damage that may result from radially constricting devices. In some embodiments, the device can be applied across or over a neck portion of the LAA in the pericardial space, using guidewires or other devices to advance the closure device into the pericardial space and to the LAA.

FIG. 74 is an anterior view of a heart illustrating the right ventricle RV, the left ventricle LV, and the left atrial appendage LAA. The methods and apparatuses of the present disclosure are intended to place a closure mechanism over or otherwise close off the base region BR of the left atrial appendage. By closing off the base region BR, the exchange of materials between the left atrial appendage LAA and the left atrium LA can be significantly reduced or stopped. Thus, the release of emboli from the left atrial appendage into the left atrium can be significantly reduced or stopped. FIG. 75 illustrates the heart, located within the pericardial space PS located beneath the patient's rib cage RC. FIG. 75 also illustrates a possible percutaneous access site for performing the methods of the present disclosure. The sternum S is located in the center of the rib cage RC and terminates at its lower end in the Xiphoid X. On either side of the Xiphoid are the costal cartilage CC, and the percutaneous access points for performing the procedures of the present disclosure will be located beneath the rib cage RC, and preferably between the Xiphoid X and an adjacent costal cartilage CC, preferably at the access location AL shown by a broken line.

Any embodiments of the devices, systems, and methods disclosed herein can include one or more guide devices having alignment elements that can be advanced toward the target location of the LAA to aid in positioning of a closure device, as will be described in more detail below. Some embodiments comprise advancing a first guide having a first alignment member into the left atrial appendage, advancing a second guide having a second alignment member into the pericardial space, approximately axially aligning the first and second alignment members, advancing an LAA closure device into the pericardial space and adjacent to the left atrial appendage using the second alignment member, and closing the left atrial appendage with the closure device. In some embodiments, only a single guide device can be used.

Any of the devices used in any of the methods described here may be advanced under any of a variety of visualization techniques, e.g., fluoroscopic visualization, ultrasound, etc. For example, the first guide, the second guide, or both guides may be advanced under fluoroscopic visualization in some variations. Similarly, any of the devices used in any of the methods described herein can be configured to be advanced over a guide element or guide wire. For example and without limitation, the first guide, the second guide, the closure device, any additional guide, and/or any combination thereof, may be advanced over a guidewire. In some variations, the second guide can be coupled to the closure device for at least a portion of the method or procedure.

For example and without limitation, FIGS. 76A-76F show the delivery stages of an exemplifying system 3100 for closing an LAA. Some embodiments of the system 3100 can include a delivery catheter 3102, a first guide device 3104, a second guide device 3106, and a clamp device 3110. In some embodiments, the delivery catheter 3102 can have an outer sheath and a guide sheath 3103 or a guide lumen for tracking over the second guide device 3106. In any embodiments disclosed herein, the guide lumen can be formed as part of a catheter body, or can be the opening extending axially through the guide sheath. FIG. 76A shows the transseptal magnetic guidewire in the distal appendage connected to an epicardial magnetic guidewire on the outside of the distal appendage. The multi-link clamp delivery system 3100 in the nonlimiting example shown in FIGS. 76A-76F is using this guidewire system to track the clamp device to the LAA. FIG. 76A shows the system 3100 after the first guide device 3104 has been advanced into the LAA toward a distal end of the LAA and the second guide device 3106 has been advanced into the pericardial space PS to an outside surface of the LAA and into alignment (generally) with the first guide device 3104.

In any embodiments disclosed herein, the guide devices (such as guide devices 3102, 3104) can include alignment elements (such as alignment elements 3114, 3116) that can be used to approximately or generally align a portion (such as a distal portion) of a first guide device with a portion (such as a distal portion) of a second guide device. The alignment elements can be, or can comprise, any suitable device or component that is configured to align with a tissue location or another object, including another alignment element. In some embodiments, the alignment elements can be used for axial alignment through a tissue wall (including elements or devices that do and that do not penetrate the tissue wall). For example, the alignment members can each or both comprise magnets, radiopaque markers, echogenic markings, members configured to produce one or more audible signals, interconnecting or interlocking members, one or more vacuum members, or the like or any combination of the foregoing. In any embodiments disclosed herein, the alignment members can have magnets at distal ends of the alignment members that can be configured or biased to axially align with one another.

After the one or more guide devices have been advanced into the target or desired location, the delivery catheter 3102 and/or the clamp device 3110 can be advanced over the guide device (such as guide device 3106 shown in FIGS. 76A-76F) through the pericardial space toward the LAA. FIG. 76B shows the embodiment of the multi-link clamp device 3110 opening or moving from a first closed state (as shown in FIG. 76A) toward an open state to fit over the LAA. The multi-link clamp device 3110 can be configured in different sizes and may be mechanically actuated to clamp down when placed at the target location. In some embodiments, the clamp members 3120 can be straight or flat along a length thereof, or can be curved, or otherwise.

In some embodiments, the clamp device 3110 (or any other clamp devices disclosed herein) can be configured to be biased toward an open position (i.e., can be configured to be a normally open clamp device) such that, when a restraint is removed from the clamp device 3110, the clamp device with automatically move to an open position. Such normally open clamp devices can be configured to move to an open state automatically when they are advanced past a distal end of the delivery catheter. Sutures or other constricting devices or mechanisms can be used to move the clamp device to the closed position and to maintain the clamp device in the closed position.

In some embodiments, the clamp device 3110 can be at least partially housed within the elongate body of the delivery catheter 3102 during advancement of the clamp device 3110 into the pericardial space. In any embodiments disclosed herein, the clamp device (including, without limitation, the clamp device 3110) can have or define a continuous aperture therethrough or an open-ended aperture. The clamp device of any embodiments disclosed herein can be configured to be clamped about or constricted over a neck portion of an LAA to isolate the LAA from the left atrium. The clamp device can have a generally flat configuration or clamping surface when the clamp is in the closed position, or can have a curved profile approximately or generally matching the contour of the closed neck portion of the LAA.

Figure 76F:
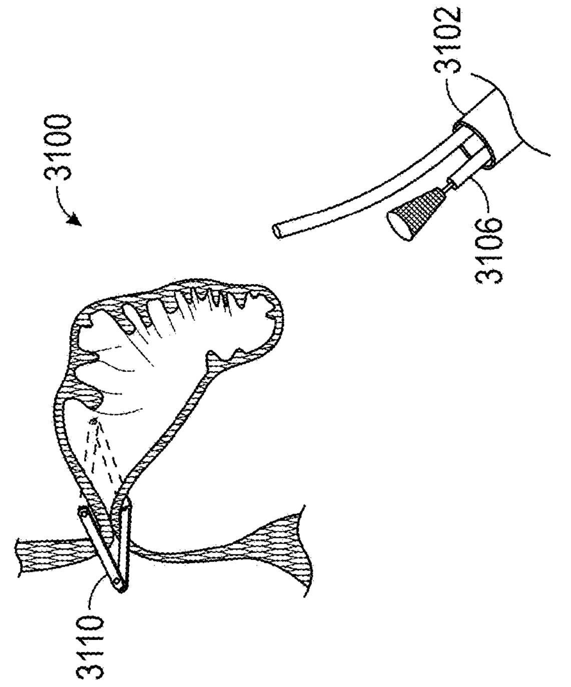
Figure 76E:
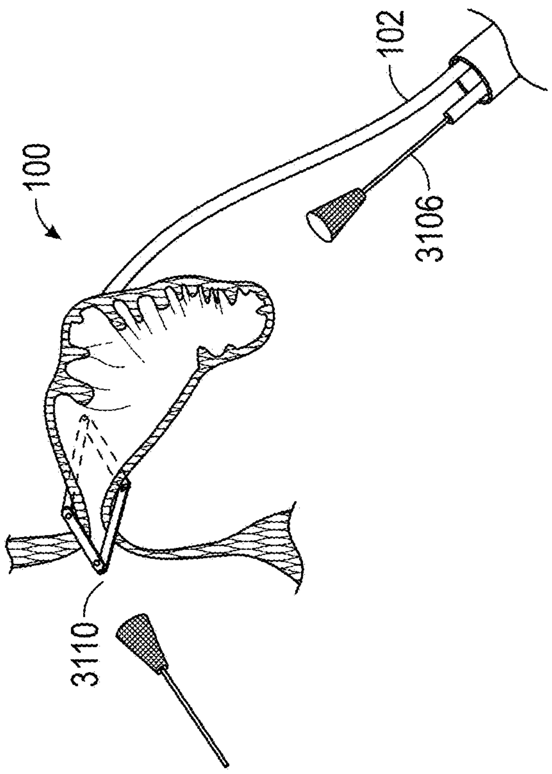

FIG. 76C shows the multi-link clamp device 3110 in an open position as the clamp device 3100 is being passed over the body of the LAA. FIG. 76D shows the multi-link clamp device 3110 positioned at a neck portion of the LAA. FIG. 76E shows the multi-link clamp device 3110 at least partially closed at the neck of the LAA. FIG. 76F shows the multi-link clamp device 3110 after the clamp device 3110 has been locked or secured about the neck portion of the LAA and released from the delivery catheter 3102.

FIGS. 77A-77E show the delivery stages of another embodiment of a clamp delivery system 3200 comprising a delivery catheter 3202, a first guide device 3204, a second guide device 3206, and a clamp device 3210 for closing an LAA. The deliver catheter 3202 can have a guide sheath 3203 or guide lumen. Any embodiments of the delivery system 3200 can have any of the same features, components, or other details of any other clamp delivery system embodiments disclosed herein, including without limitation any of the embodiments of the clamp delivery system 3200 disclosed above, in place of or in addition to any of the features, components, or other details disclosed below for delivery system 3200.

Figure 77B:
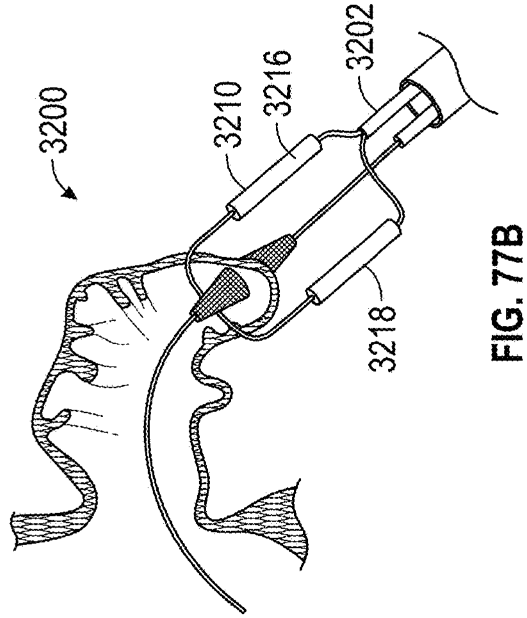
Figure 77A:
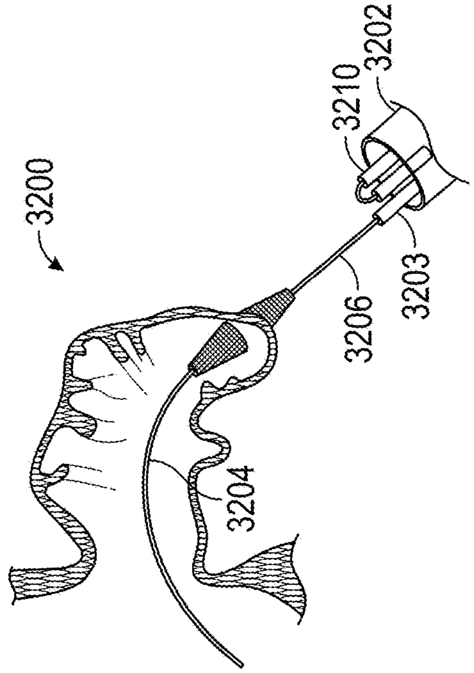
Figure 77D:
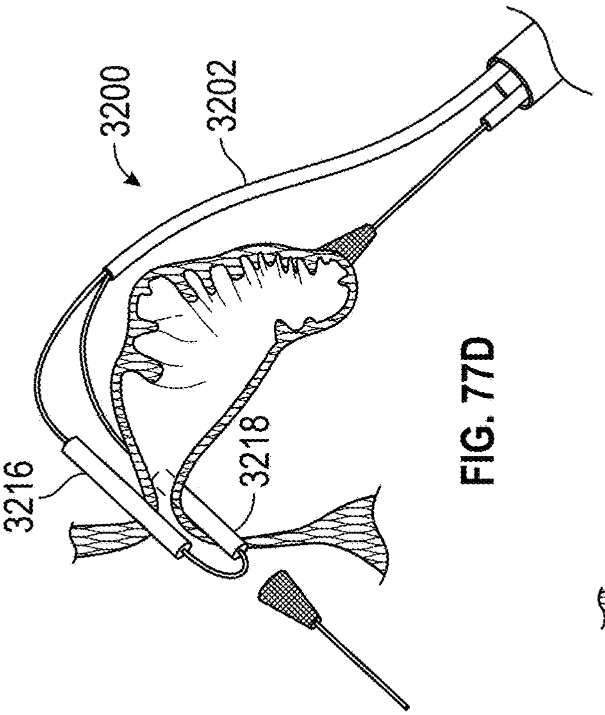
Figure 77C:
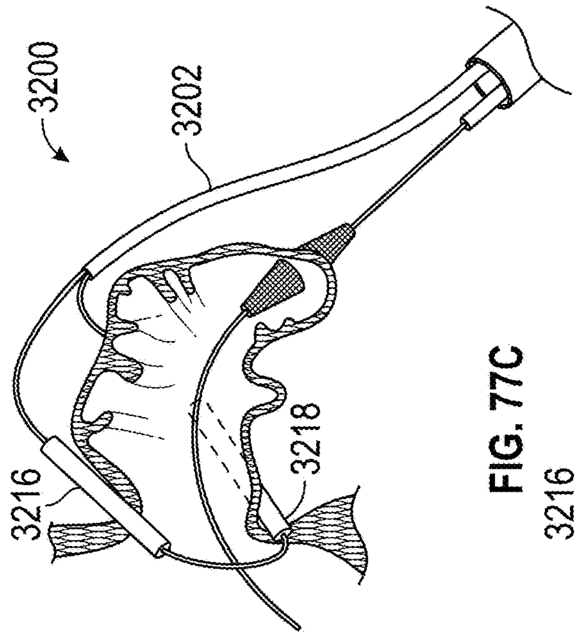
Figure 77E:
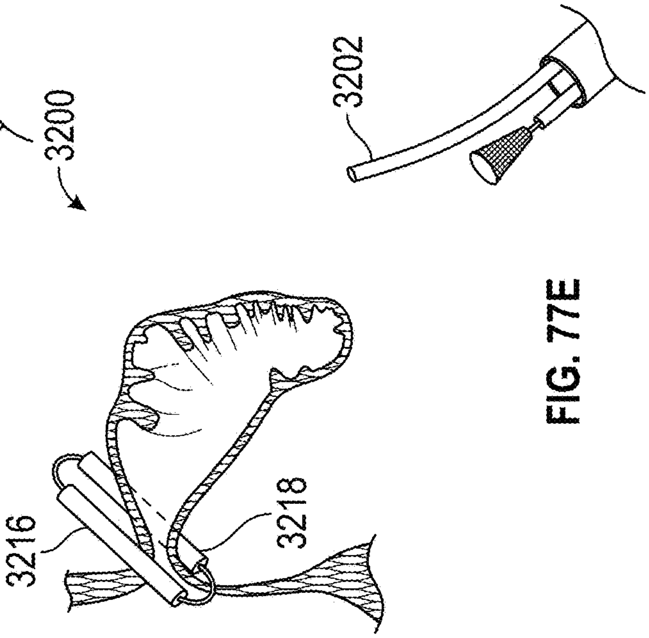

FIG. 77A shows the first guide device 3204 (which can be or comprise a transseptal magnetic guidewire) in the distal appendage aligned with or coupled with (through a distal wall of the LAA) the second guide device 3206 (which can be an epicardial magnetic guidewire) located on the outside of the distal appendage. The delivery catheter 3202 can track over the second guide device 3206 to direct the clamp device 3210 to the LAA. Any embodiments of the clamp device disclosed herein, such as without limitation claim device 3210, can have two bars or clamp members (for example, a first clamp member 3216 and a second clamp member 3218) that can be moved from a first open position, as shown in FIG. 77B to a closed position, as shown in FIG. 77D. As such, FIG. 77B shows the clamp device 3210 in an open position and being advanced toward the LAA. FIG. 77C shows the clamp device 3210 in an open position and being advanced over the body of the LAA toward the neck of the LAA. FIG. 77D shows the clamp device 3210 positioned at the neck of the LAA and partially collapsed or constricted about the neck of the LAA. FIG. 77E shows the clamp device 3210 after the clamp device 3210 has been locked or secured about the neck portion of the LAA and after the clamp device 3210 has been released from the delivery catheter.

Any embodiments of the clamp device 3210 can be provided in different sizes and/or shapes and can be mechanically actuated to clamp down when placed at the target location. Some embodiments of the clamp device 3210 can be adjustably cinched down at the lateral ends using a suture or otherwise to move the clamp device 3210 from the open state to the closed state. As such, any embodiments of the clamp device 3210 can include two rigid bars or clamping members (such as clamping members 3216, 3218) that can be configured to move together from an open state to a closed state. In the open state, the closure device can be passed over an outside surface of the LAA toward the neck region of the LAA. Once in the desired position, the clamp device 3210 can be moved from the open state to the closed state to flatten and substantially or completely close the opening of the LAA. The clamping members 3216, 3218 can be held together at the ends with a suture or other fastener, including a mechanical fastener, a spring, or otherwise, for maintaining the left atrial appendage in a flattened and substantially closed state after the LAA has been closed with the closure device. Alternatively, the closure device can comprise one or more multi-linkage rigid members held together at the ends with a suture for encircling the left atrial appendage after it has been closed with the closure device 3210.

FIGS. 78A-78E show the delivery stages of another embodiment of a clamp delivery system 3300 comprising a delivery catheter 3302, a first guide device 3304 (which can be a transseptal magnetic guidewire), a second guide device 3306 (which can be an epicardial magnetic guidewire), and a clamp device 3310 for closing an LAA. Any embodiments of the delivery system 3300 can have any of the same features, components, or other details of any other clamp delivery system embodiments disclosed herein, including without limitation any of the embodiments of the clamp delivery systems 100 or 200 disclosed above, in place of or in addition to any of the features, components, or other details disclosed below for delivery system 3300. Any embodiments of the clamp device 3310 can have a single bar clamp with a suture over a guidewire leading to the distal end of the LAA. The 1-bar clamp may come in different sizes, or shapes, and may be mechanically actuated through tensioning of the suture to clamp down when placed at the target location or may be adjustably cinched down at the lateral ends.

Figure 78A:
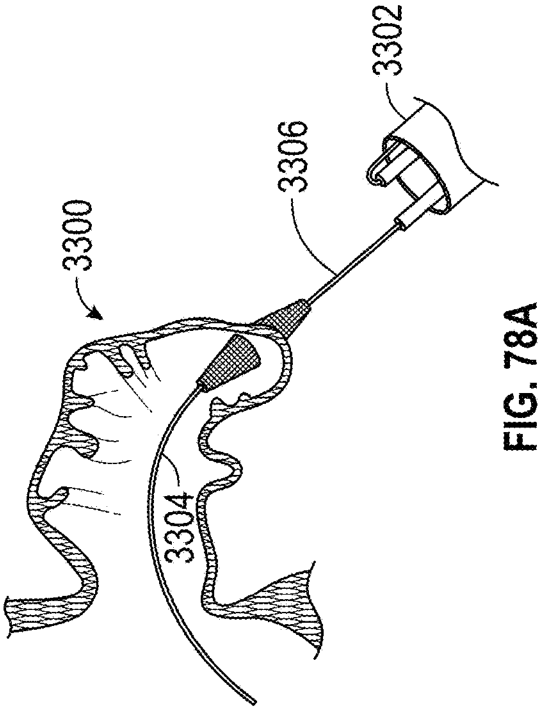
Figure 78B:
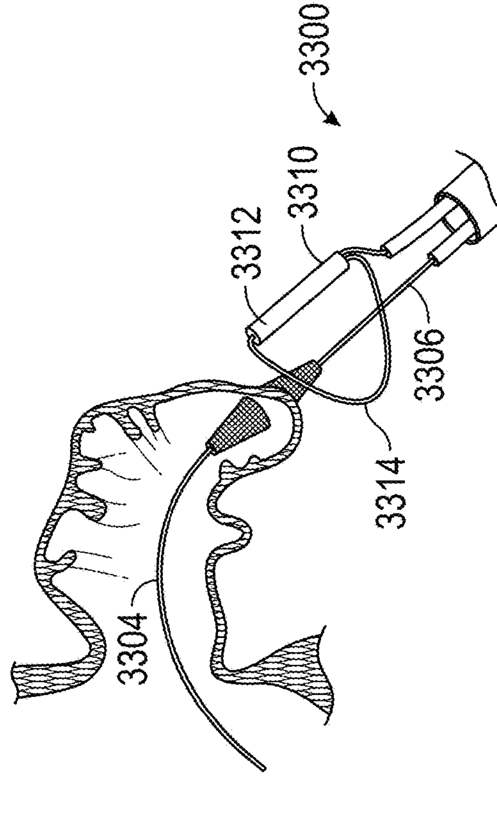
Figure 78C:
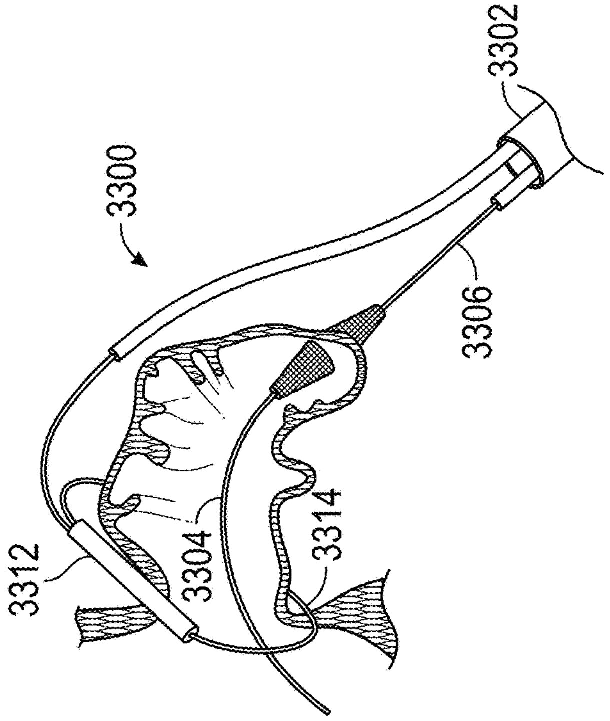
Figure 78D:
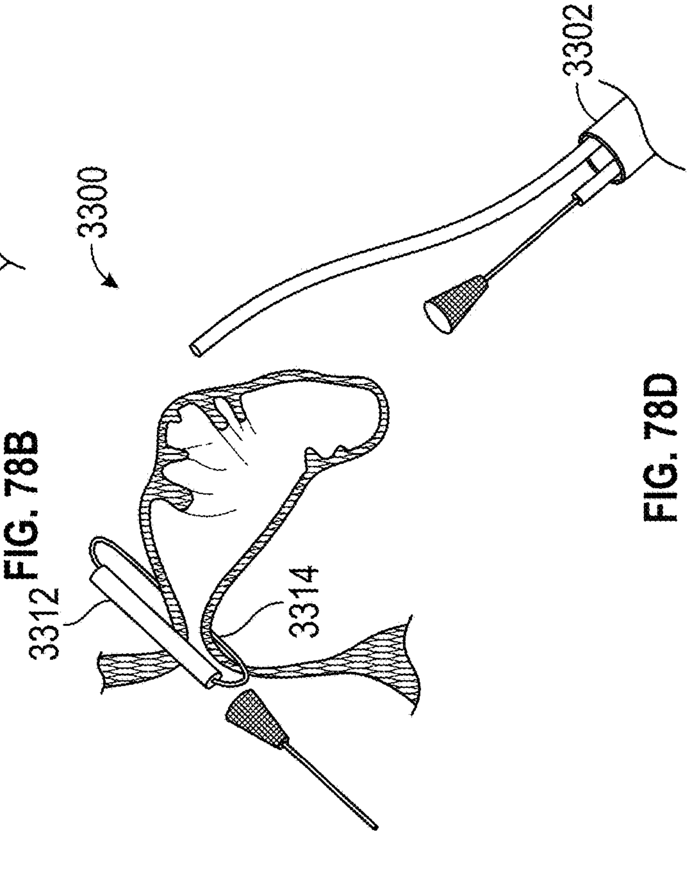
Figure 78E:
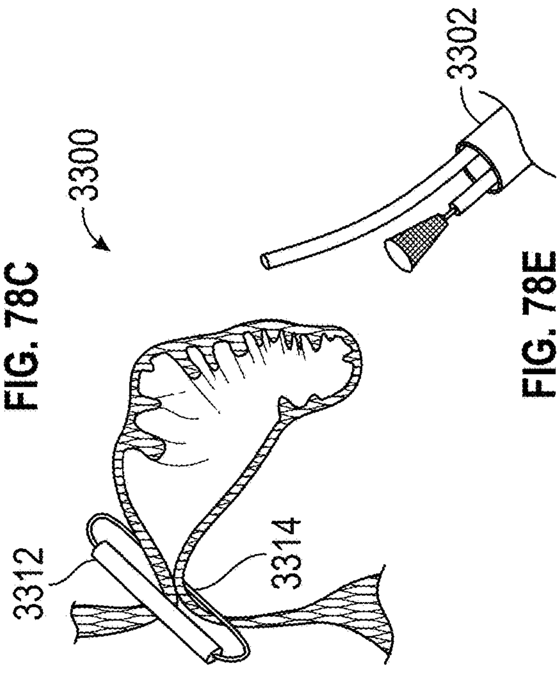

FIG. 78A shows the first guide device 3304 in the distal appendage connected to (through a distal wall of the LAA) or generally aligned with the second guide device 3306 positioned outside of the distal appendage. The embodiment of the one-bar suture clamp delivery system 3300 shown in FIG. 78A is using this guidewire system to track to the LAA. FIG. 78B shows the 1-bar clamp delivery system 3300 opening to fit over the LAA. FIG. 78C shows the embodiment of the clamp device 3310 in an open position and passing over the body of the LAA. FIG. 78D shows the embodiment of the clamp device 3310 closed at the neck of the LAA. FIG. 78E shows the embodiment of the clamp device 3310 locked, deployed, and released.

The clamp device 3310 can have a first rigid clamp member 3312 and a second flexible clamp member 3314. As shown, once in the desired position, the clamp device 3310 can be moved from the open state to the closed state by withdrawing the second flexible clamp member 3314 relative to the first rigid clamp member 3314 to flatten and substantially or completely close the opening of the LAA. The clamping members 3312, 3314 can be held together at the ends with a suture or other fastener, including a mechanical fastener, a spring, or otherwise, for maintaining the left atrial appendage in a flattened and substantially closed state after the LAA has been closed with the closure device.

Any embodiments of the clamp device disclosed herein can be configured to be movable between a first or open state and a second or closed state. In the first or open state, the clamp can have an opening therethrough that can be sized to enable the clamp to pass over the outside surface of the body of the LAA toward the neck of the LAA, as shown in FIG. 76C. Thereafter, as will be described, the clamp can be configured to be moved or be caused to automatically move to a second or closed state. In any embodiments disclosed herein, the clamp mechanism can be designed to be biased to the "normally open" state or condition where a spring (which can comprise or be a deformable wire, torsion spring, or other) can bias the clamp to be open. Activating the closure mechanism (which can be or can comprise a suture) can close the clamp. The clamp device can be configured such that, when tension is released from the closure mechanism, the clamp device can then return to the open state, or any configuration, state, or position between open and closed, based on the tension of the closure mechanism.

Any of the clamp device embodiments disclosed herein can be configured so that the clamp device can be held or maintained or locked in the closed or clamped position to maintain the LAA in a closed or substantially closed state after the procedure is completed. For example and without limitation, to lock or maintain any of the clamp device embodiments disclosed herein in the closed state, the suture can have a surgical slip knot on one end which can be tightened. This can also be done with two separate mechanisms where mechanism (1) can be used to open and close the clamp device, and mechanism (2) locks or secures the clamp device in the desired position. In this configuration, mechanism (2), which locks the clamp in the desired closed state can comprise or be a loop of suture with a surgical slip knot at the end which simply has sufficient slack in the line in the closed clamp configuration such that, when the clamp is open, the slack is removed. When this line is tightened, the slack is removed and the clamp is locked in the closed position. Then, in some embodiments, mechanism (1), which may just be a loop of suture without any slip knot, can be removed.

In some embodiments, closure of the clamping device could be achieved with just the locking suture alone. However, the addition of mechanism (1), which can be used to open and close the clamp device enables the surgeon to singularly or repeatedly reopen and reposition the clamp device after the clamp device has been closed. In some embodiments, the clamp can be configured to be a normally open type clamp, wherein the clamp is configured or biased to self-expand or automatically expand to the first or open state when the clamp is in a relaxed configuration. In this embodiment, for example and without limitation, the clamp can be configured to automatically move to the first or open state the clamp has been advanced past the distal end of the catheter sleeve.

In any embodiments disclosed herein, the clamp device (such as any embodiments of the clamp devices 3110, 3210, or 3310 disclosed herein) can be configured to be movable repeatedly between the open and closed states or positions. In this configuration, the clamp devices can be used to incrementally close or flatten the neck of the LAA, can be opened to release the LAA, repositioned, and then closed again, in any combination of steps.

In some embodiments, the clamp device can be configured to encircle the left atrial appendage without having a suture coupled to the clamp device. The closure element alone can be configured to capture and release the left atrial appendage (i.e., it can open and close around the left atrial appendage), which may help facilitate optimal closure of the left atrial appendage, prior to permanent exclusion. In any embodiments disclosed herein in which the clamp device comprises a suture, the suture can have a surgical slip knot. The slip knot can be used to hold or maintain the clamp device in the closed position, once the optimal position of the clamp device is achieved. The suture can optionally be coupled to the closure element or clamp device during advancement of the closure element or clamp device or, in other embodiments, the suture can be advanced into position about the clamp device after the clamp device has been positioned about the LAA.

FIGS. 79A-79H show another embodiment of a treatment device 3500 for occluding an LAA. With reference to FIGS. 79A-79H, some embodiments of the treatment device 3500 can have a first deployment device 3502 configured to twist and occlude the LAA and a second deployment device 3504 configured for epicardial ligation, as in any of the other embodiments disclosed herein. The first deployment device 3502 can have any of the components, features, and/or other details of any of the treatment device embodiments disclosed herein, including without limitation any embodiments of the treatment devices 100 and 140 described above, in place of or in combination with any of the components, features, and/or other details of any of the embodiments of the treatment device 3500 disclosed below. Further, the second deployment device 3504 can have any of the components, features, and/or other details of any of the treatment device embodiments disclosed herein, including without limitation any embodiments of the treatment devices 3100, 3200, and 3300 described above, in place of or in combination with any of the components, features, and/or other details of any of the embodiments of the treatment device 3500 disclosed below. Further, any of the treatment device embodiments disclosed herein can have any of the components, features, and/or other details of any of the embodiments of the first deployment device 3502 and the second deployment device 3504.

Figure 79A:
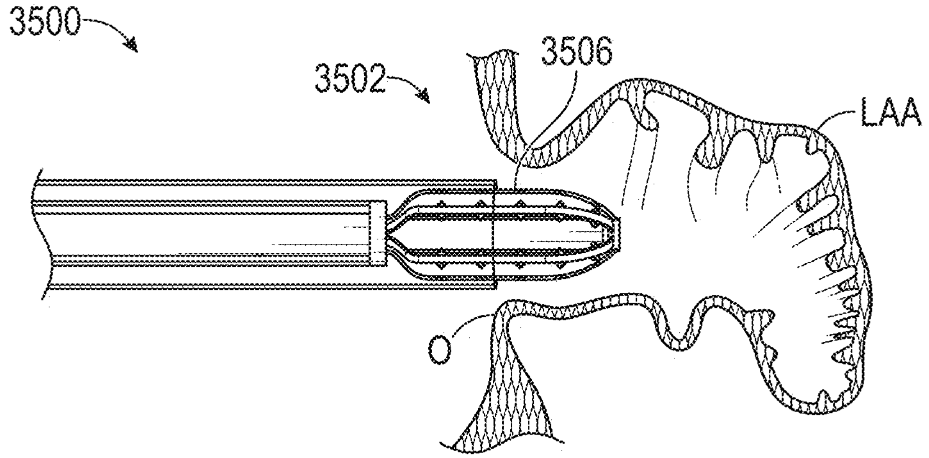
Figure 79B:
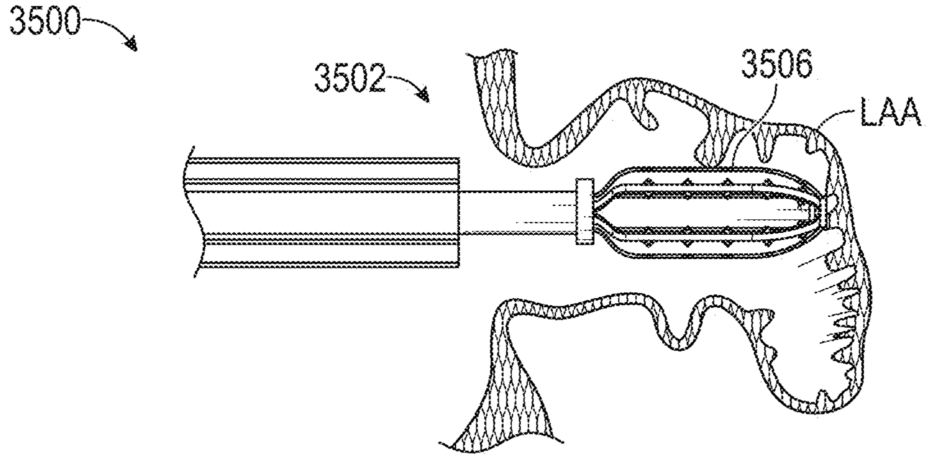
Figure 79C:
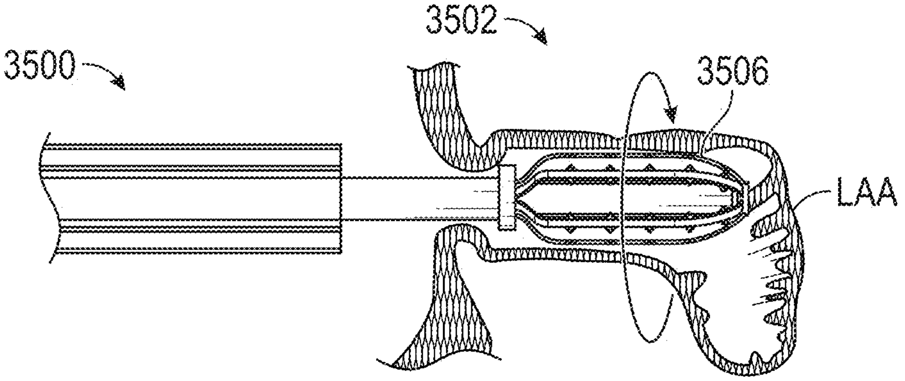
Figure 79D:
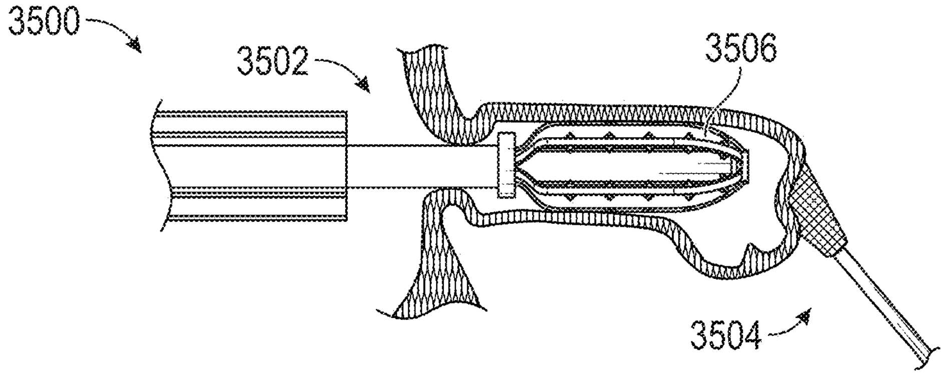
Figure 79E:
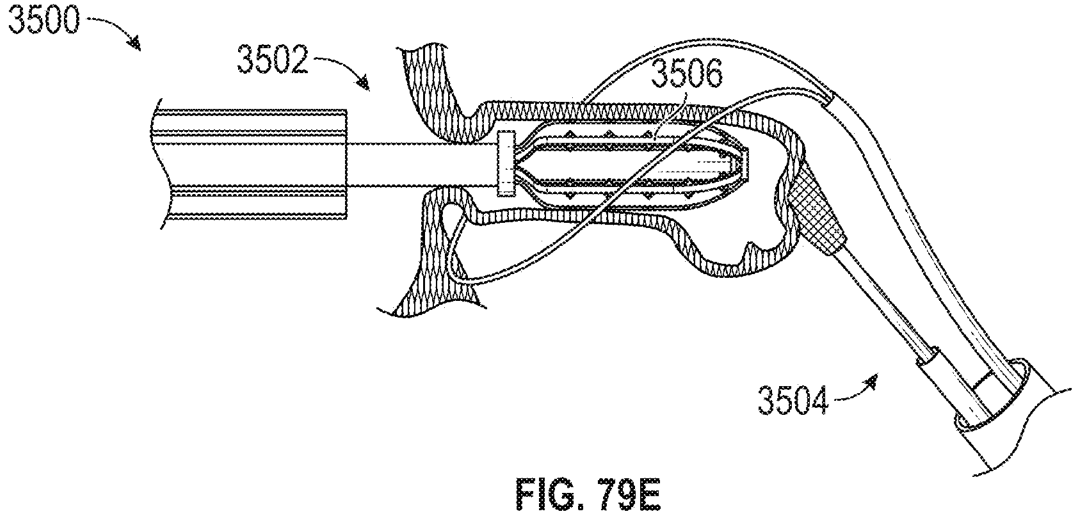
Figure 79F:
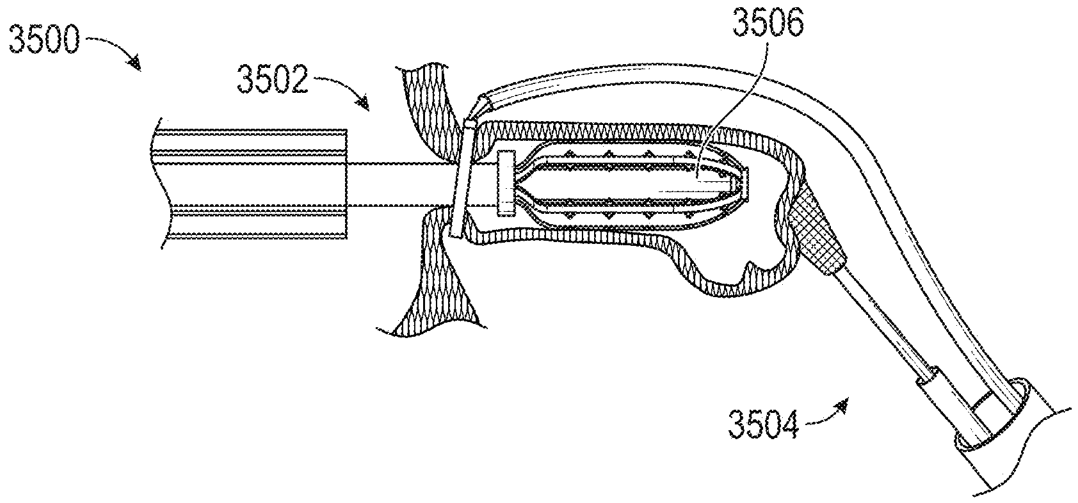

In this arrangement, the first deployment device 3502 can have a contact member 3506 that can be the same as any other contact member embodiments disclosed herein, including without limitation, contact member 104 or 144, that can be used to engage and twist the LAA, as shown in FIGS. 79B-79D. In any embodiments, the contact member 3506 can be configured to have a generally constant or fixed size throughout the procedure. Thereafter, once the tissue of the ostium and/or the tissue adjacent to the ostium of the LAA has constricted, a flexible loop or clamp member 3510 can be passed over the neck of the LAA, as shown in FIG. 79E. The clamp member 3510 can thereafter be closed and tightened around the neck of the LAA, further increasing the seal or level of occlusion between the LAA and the LA. In these embodiments, the clamp member can prevent the untwisting of the LAA and ensure a long-term-seal of the LAA, thereby overcoming the common leakage related drawbacks of other conventional epicardial ligation devices.

Figure 79G:
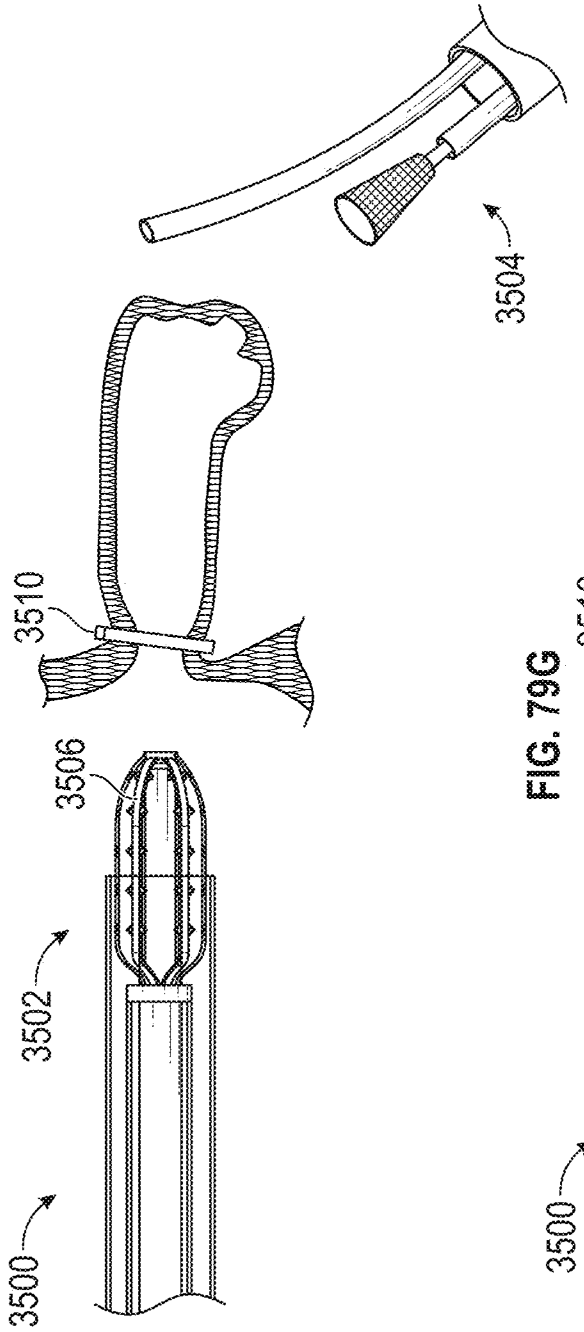
Figure 79H:
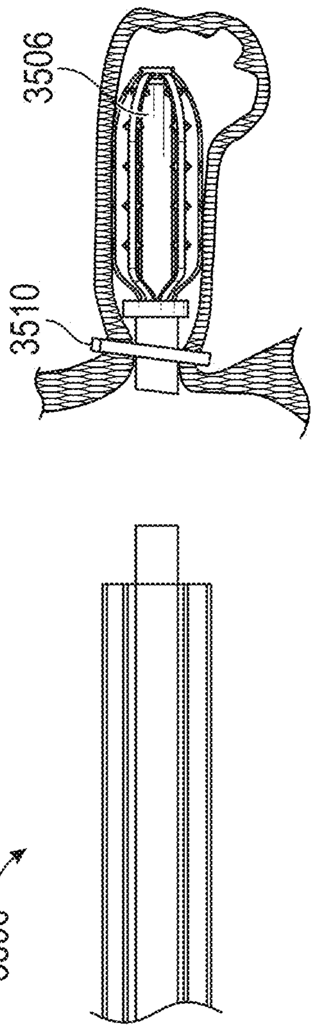

With reference to FIG. 79G, some embodiments of the treatment device 3500 can be configured such that the contact member 3506 is removed from the LAA prior to completion of the procedure. In some embodiments, the contact member 3506 can be removed after the clamp member 3510 has been passed over and partially tightened or snugged about the neck of the LAA. The clamp member 3510 can be tightened and secured as the contact member 3506 is removed. In other embodiments, as shown in FIG. 79H, the contact member 3506 can detached from the delivery device and can remain within the LAA.

Additionally, in any embodiments disclosed herein, the device can be configured so that the device has a low profile shape in the portion of the device that remains in the left atrium following implantation of the device and is otherwise configured to minimize the impact of the device on the overall volume of the left atrium and the flow of blood through the atrium. In some embodiments, the portion of the device that extends into the left atrium following implantation of the device can be minimized. For example and without limitation, the device of any embodiments disclosed herein can be configured such that only a small fraction of the overall length of the deployed device (for example and without limitation, approximately 10% or less, or approximately 15% or less, or in some embodiments approximately 20% or less of the overall length of the deployed device) extends into the left atrium following deployment.

Further, any embodiments of the devices and methods disclosed herein can be adapted or modified for use with robotic surgical devices or apparatuses. For example without limitation, any of the deployment catheters disclosed herein can be modified for use with such robotic surgical devices and apparatuses. All such applications of devices and methods disclosed herein for use with robotic systems are contemplated as forming part of the disclosure herein.

FIGS. 80A-80W show another embodiment of treatment device 4000 (also referred to herein as a treatment system) for closing or occluding an LAA. In any embodiments disclosed herein, any components, features, or other details of the treatment device 4000 or implant device 4002 shown in FIGS. 80A-80W can have any of the components, features, or other details of any other treatment device embodiments or implant device embodiments disclosed herein, including without limitation any of the embodiments of the treatment devices 100, 140 or implant devices 102, 104 described above, in any combination with any of the components, features, or details of the treatment device 4000 or implant device 4002 disclosed herein. Similarly, any components, features, or other details of any of the other treatment device embodiments or implant device embodiments disclosed herein can have any of the components, features, or other details of any embodiments of the treatment device 4000 or implant device 4002 disclosed herein in any combination with any of the components, features, or details of the treatment device and/or implant device.

In any embodiments of the treatment device 4000, including the embodiment of the treatment device 4000, the system can have an implant device 4002 having a contact member 4004 (also referred to herein as a contact element or an expandable implant member), a retention element 4008, and/or a securing element 4010 (also referred to as a securing member), and a retention element 4008. In some embodiments, the contact member 4004, the retention element 4008, and/or the securing element 4010 can be made from Nitinol. FIG. 80A shows the contact member 4004 and the securing element 4010 both in a first, contracted or restrained state within an outer sleeve 4014 of the catheter 4012. The implant device 4002 can be advanced distally out of the catheter 4012 past a distal end 4014_a_ of the outer sleeve 4014 by advancing a core member 4013 of the catheter 4012 so that the contact member 4004 of the implant device 4002 can be implanted or deployed within the LAA at any desired depth within the LAA, including near or in contact with a distal wall of the LAA, the middle portion of the LAA, or otherwise by, for example and without limitation, holding the implant device 4002 in a stationary axial position by maintaining the core member 4013 of the catheter 4012 in a stationary axial position and retracting the outer sleeve 4014 of the catheter 4012. In other embodiments, the outer sleeve 4014 can be held stationary and the core member 4013 can be advanced, thereby advancing the contact member 4004 past the distal end of the outer sleeve 4014 inside the LAA, LA, or otherwise. The contact member 4004 can be expanded or moved from the first state to the second state inside the LAA, inside the LA, as the contact member 4004 is moving into the LAA, or otherwise.

In any embodiments disclosed herein, the contact member 4004 can be self-expanding in a radial direction so that, when a restraint is removed from the contact member 4004, the contact member 4004 can expand against an inner surface or wall of the LAA automatically. In other embodiments, the contact member 4004 can be mechanically expandable, such as by a balloon expander, so as to expand against inside surface or wall of the LAA or can be a balloon type device that is selectively expandable.

In any embodiments, the contact member 4004 can have a plurality of arms or struts 4016 that can expand in a radial direction (for example and without limitation, self-expand in a radial direction when a restraint has been removed from an outside surface of the contact member 4004). Any embodiments of the contact member 4004 disclosed herein can have six struts 4016, or from four to ten struts 4016, or from six to eight struts 4016, or from less than four to more than ten struts 4016. Further, in any embodiments, the contact member 4004 can have a plurality of tissue anchors 4018 or other similar features configured to penetrate or engage the tissue of the LAA that are configured to penetrate into a tissue within the LAA when the contact member 4004 is expanded against the tissue of the LAA and/or when the contact member 4004 is rotated or twisted within the LAA. In any embodiments disclosed herein, the tissue anchors or teeth (also referred to as nubs) of the contact member can be formed at an angle directed toward a proximal end of the contact member. For example and without limitation, the tissue anchors can be angled back toward the proximal end of the contact member by 5 degrees or approximately 5 degrees, or from 2 degrees or approximately 2 degrees to 15 degrees or approximately 15 degrees, or from 5 degrees or approximately 5 degrees to 10 degrees or approximately 10 degrees, or of any value within the foregoing ranges or to and from any values within the foregoing ranges. In any embodiments disclosed herein, the anchors can have a proximal surface that is angled back toward the proximal end of the contact member by an angle of 5 degrees or approximately 5 degrees, or from 2 degrees or approximately 2 degrees to 15 degrees or approximately 15 degrees or more, or from 5 degrees or approximately 5 degrees to 10 degrees or approximately 10 degrees, or of any value within the foregoing ranges or to and from any values within the foregoing ranges.

In this configuration, when the contact member 4004 is rotated in a first direction (as indicated by arrow A10 in FIG. 81A, which can be in the clockwise or the counterclockwise direction), one or more or all of the struts 4016 and one or more or all of the tissue anchors 4018, if any, can engage the tissue of the LAA and cause the LAA to twist or rotate the LAA in the first direction. The twisting or rotation of the LAA in the first direction from a first rotational position to a second rotational position can result in the opening or ostium O of the LAA constricting in a radial direction (identified by arrows A11 in FIG. 81B) so that the opening O of the LAA is caused to move or constrict around an outside surface of the implant device 4002 (for example, without limitation, around the contact member 4004, retention element 4008, or other surface of the implant device 4002). An operator can twist or rotate the contact member 4004 by twisting or rotating the core member 4013 of the catheter 4012. The tightening or constriction of the opening O of the LAA around an outside surface of the proximal portion 4004*a* of the contact member 4004 or other portion of the implant device 4002 can result in the occlusion, or substantial occlusion, or substantial closing off of the interior portion of the LAA from the remaining chambers within the heart, thereby substantially reducing the health risks associated with an open LAA. In any embodiments disclosed herein, the implant 4002 can be configured to be removed after the securing element is applied to the tissue that has been constricted by the twisting of the contact member so that the only portion of the implant device 4002 left in the LAA or the heart is the securing element 4010.

The retention element 4008 can be used to couple the securing element 4010 to the contact member 4004 and to also allow a user (such as a surgeon) to move the securing element 4010 toward and away from the contact member 4004. In any embodiments, the retention element 4008 can have helical threads on an outer surface thereof. In any embodiments, the retention element 4008 can comprise a threaded shaft 4009. In this configuration, the retention element 4008 can be rotated in a first direction to advance the securing element 4010 toward the contact member 4004, and rotated in a second, opposite direction to move the securing element 4010 away from the contact member 4004. The retention element 4008 can be configured to engage the securing element 4010 such that, when the retention element 4008 rotates, the securing element 4010 moves in an axial direction corresponding to the rotation of the retention element 4008. In some embodiments, the securing element 4010 can be configured to spin freely relative to the contact member 4004 and the retention element 4008, even when the retention element 4008 and/or the contact member 4004 is being rotated. For example and without limitation, with reference to FIGS. 80R and 80S, the retention element 4008 can have an annular recess 4019 near or adjacent to a proximal end 4008*a* thereof that can be configured to receive the securing element 4010. In some embodiments, the recess 4019 can be configured to receive an annular base portion 4011 of the securing element 4010. The recess 4019 can be configured to constrain or inhibit an axial movement (e.g., longitudinal movement) of the securing element 4004 while permitting the securing element 4004 to freely rotate about the axial centerline of the retention element 4008.

In some embodiments, the securing element 4010 can be keyed or indexed to the contact member 4004 and/or the retention element 4008 so that the securing element 4010 and the contact member 4004 and/or the retention element 4008 can rotate dependently and simultaneously. For example, in some embodiments, the securing element 4010 can have a body portion having one or more tabs or projections that extend into a channel or recess formed in a body portion of the contact member 4004 and/or the retention element 4008. One or more channels can be formed in an axial orientation such that the projection(s) of the securing element 4010 can freely move in an axial direction relative to the contact member 4004 and/or the retention element 4008. However, a narrow width of the channel(s) relative to the projection(s) can prevent the projection(s) and, hence, the securing element 4010, from rotating relative to the contact member 4004 and/or the retention element 4008. In some embodiments, the securing element 4010 can be configured to be selectively rotationally fixed to the retention element 4008, or selectively rotationally fixed to the retention element 4008 so that the securing element 4010 can freely rotate relative to the contact member 4004 and/or retention element 4008 in a first state or configuration and be prevented from rotation relative to the contact member 4004 and/or retention element 4008 in a second state or configuration.

In some embodiments, the base portion 4011 can extend into the annular recess 4019 so as to axially lock or engage the securing element 4010 with the retention element 4008. The interaction of the base portion 4011 with the annular recess 4019, wherein the walls of the annular recess contact and push the base portion 4011, can cause the retention element 4008 to move the securing element 4010 when the retention element 4008 is rotated. The contact member 4004 can have an internally threaded body portion 4005 that can threadedly engages the threads of the retention element 4008 so that the retention element 4008 threads into and out of the threaded body portion 4005. In this configuration, the retention element 4008 can thread into and out of the contact member 4004 to cause the securing element 4010 to move relative to the contact member. As shown in FIG. 80S, the retention element 4008 is nearly completely threaded into the contact member 4004 and into the cavity or space 4023 within the body portion 4005 of the contact member 4004 such that the securing element 4010 is moved into nearly full engagement with the contact member 4004. As the retention element 4008 is rotated in the second direction, the threaded shaft 4009 of the retention element 4008 will move out of the space 4023 within the contact member 4004 and move the securing element 4010 away from the contact member 4004.

With reference to FIG. 80J, an intermediate sleeve 4025 can be advanced distally so that a distal end portion 4025*b* of the intermediate sleeve 4025 can couple with and engage a proximal end portion 4008*a* of the retention element 4008 and/or a proximal end portion 4010*a* of the securing element 4010. For example and without limitation, as shown in FIGS. 80J and 80N, teeth, projections or tabs 4029 on a distal end portion 4025*b* of the intermediate sleeve 4025 can couple with or be advanced into recesses or depressions 4031 between the arms or struts 4030 of the securing element 4010 and/or, in some embodiments, the distal end portion 4025*b* can have recesses or notches 4033 in a distal end portion 4025*b* of the intermediate sleeve 4025 that can be configured to couple with projections or a head 4017 at a proximal end portion 4008*a* of the retention element 4008 so that the intermediate sleeve 4025 can be rotationally coupled with the retention element 4008 and/or the securing element 4010 when the distal end portion 4025*b* of the intermediate sleeve 4025 is advanced distally into engagement with the retention element 4008 and/or the securing element 4010. Once the intermediate sleeve 4025 is rotationally coupled with the retention element 4008 and/or the securing element 4010, a rotation of the intermediate sleeve 4025 can cause the simultaneous and equal rotation of the retention element 4008 and/or the securing element 4010. In embodiments where the securing element 4010 is rotationally coupled with the retention element 4008, a rotation of the intermediate sleeve 4025 can cause the simultaneous and equal rotation of the retention element 4008 and the securing element 4010.

In some embodiments, the intermediate sleeve 4025 can be configured such that, when the intermediate sleeve 4025 is engaged with the proximal end portion 4010*a* of the securing element 4010, the retention element 4008 and/or the securing element 4010 can be maintained in a fixed rotational position by maintaining the intermediate sleeve 4015 in a fixed rotational position while, for example and without limitation, the contact member 4004 is rotated, or can be rotated in the first or second direction by rotating the intermediate sleeve 4025 in the first or second direction. In some embodiments, the intermediate sleeve 4025 can be moved axially and rotated independently of the other tubes or sleeves of the catheter 4012.

Additionally, in any embodiments, the system 4000 can be configured so that the implant device 4002 is biased or selectively secured in the proximal direction relative to the catheter 4012. For example and without limitation, as shown in FIG. 80T, some embodiments of the system 4000 can have a suture or thread 4032 (also referred to herein as a retention line) that extends through an inside of the catheter 4012 (e.g., inside of the core member 4013, such as through a lumen 4037 of the core member 4013) and loops around the pin 4034, thereby permitting a user to retract or withdraw the suture to pull the implant device 4002 or the contact member 4004 proximally relative to the catheter 4012 or the core member 4013. In some embodiments, the core member 4013 can have one or more slots 4036 formed in a distal end portion 4013*b* of the core member 4013. The one or more slots 4036 can be configured to engage and/or receive the pin 4034 so that the core member 4013 can rotationally engage the pin 4034 and, hence, the contact member 4004. In this configuration, when the core member 4013 is engaged with the pin 4034 and, hence, the contact member 4004 (such as by withdrawing or retracting the retainer line 4032), any rotation of the core member 4013 can cause a simultaneous and equal rotation of the contact member 4004.

Both ends of the retainer line 4032 can extend from a proximal end of the device 4000 such that a practitioner can grasp both ends of the retainer line 4032 to exert the biasing force around the pin 4034 to maintain the pin against a proximal end of the slot 4036 formed within the distal end 4013*b* of the core member 4013. When the implant device 4002 is ready to be released from the core member 4013, the practitioner can simply release one end of the retainer line 4032 and retract or withdraw the other end of the retainer line 4032 until the retainer line 4032 no longer forms a loop and/or no longer wraps around the pin 4034, thereby removing the biasing force or retaining force from the retainer line 4032 and the contact member 4004. After removing the biasing force or retaining force from the retainer line 4032 and/or removing the proximally directed force from the contact member 4004, the core member 4013 can be withdrawn relative to the implant device 4004, while the contact member 4004 can remain stationary within the LAA. This may be done after the contact member 4004 and/or the securing element 4010 have been fully deployed or implanted into the LAA and/or tissue adjacent to the LAA. In any embodiments disclosed herein, the pin or cross member 4034 can be configured to permit a guidewire to pass through a distal end portion of the implant device 4002 without obstruction. For example without limitation, an opening larger than an outside diameter of a guidewire can be formed in the pin 4034 to permit a guidewire to pass therethrough, or the pin 4034 can be formed in two parts, with a sufficiently large space therebetween.

In any embodiments, the catheter 4012 can be selectively coupled with or engaged with the retention element 4008 so that the catheter 4012 can rotate the retention element 4008 toward and away from the contact member 4004. In some embodiments, the intermediate sleeve 4025 can engage with the retention element 4008 (e.g., a head portion of the threaded shaft 4009) to rotate the retention element 4008 to advance or withdraw the securing element 4010 relative to the contact member 4004 and/or the tissue of the ostium or the LA that has constricted around the implant 4002 as a result of the twisting of the contact member 4004.

Figure 81A:
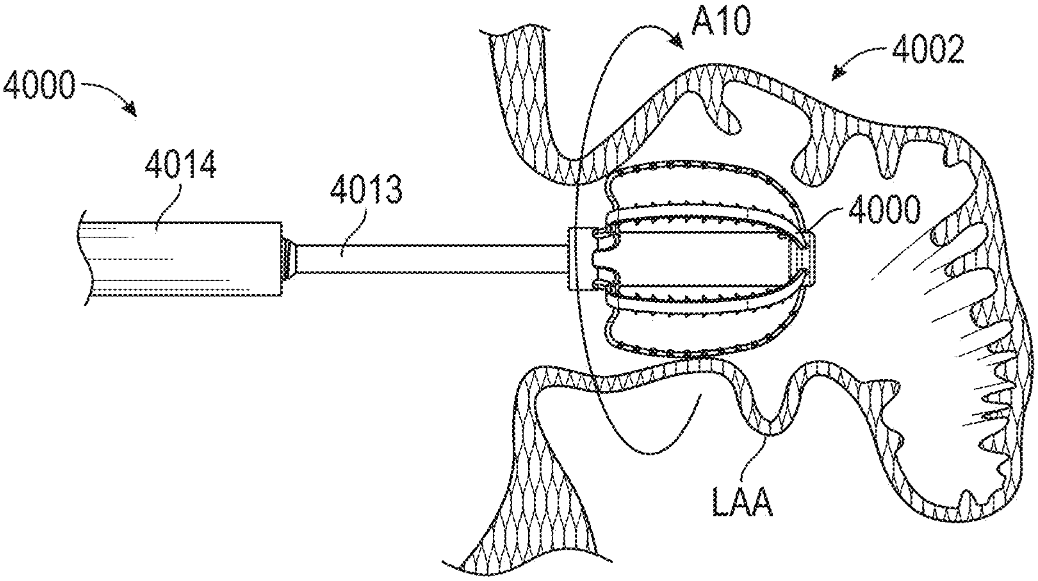
Figure 81B:
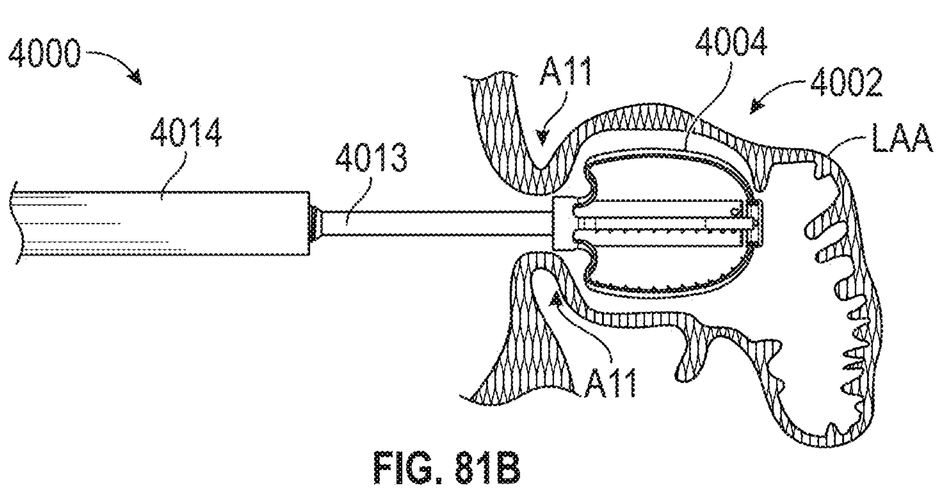
Figure 81C:
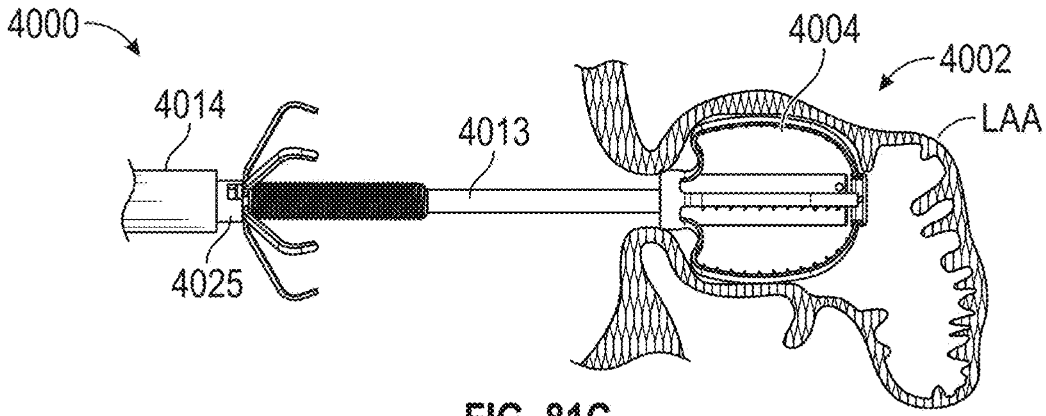
Figure 81D:
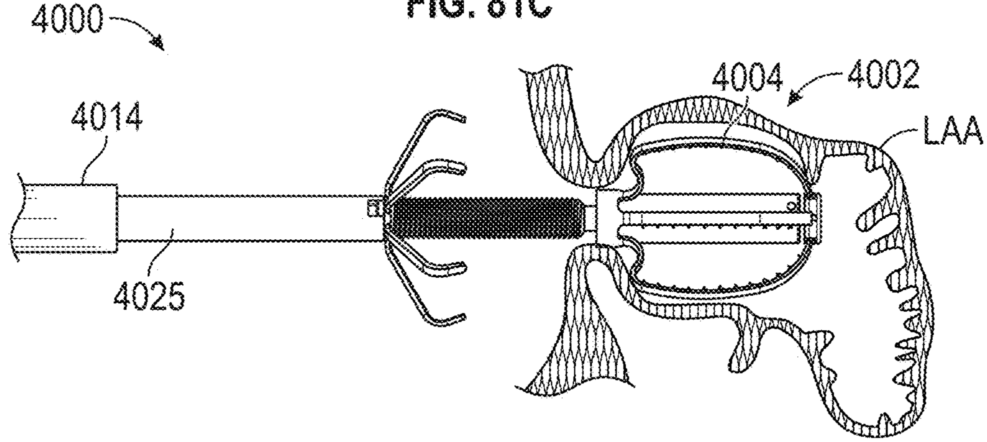
Figure 81E:
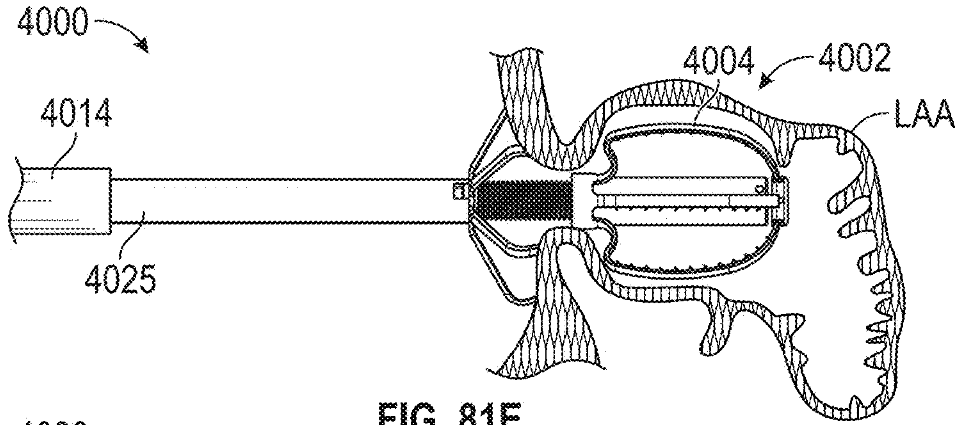
Figure 81F:
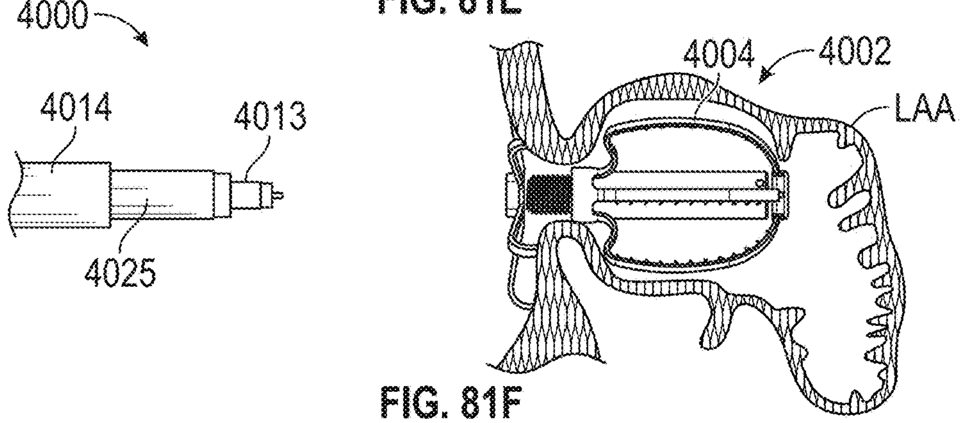

Once the securing element 4010 is in the desired axial position (for example, engaged with the tissue of the LA/LAA that has constricted as a result of the twisting of the contact member 4004), the implant 4002 can be removed from the catheter 4012 and the catheter can be removed from the LA. With the securing element 4010 engaged with the patient's tissue, as illustrated in FIG. 81F, the LAA can be prevented from rotating to or toward the first rotational position, which is the untwisted or relaxed position, or away from the second rotational portion. In this configuration, the implant device 4002 can secure and maintain the LAA in a substantially or completely occluded or substantially or completely closed state.

Further, in any embodiments, the device 4000 can be configured such that the contact member 4004 can be removed from the patient's LAA after the securing element 4010 is engaged with the tissue sufficiently to hold the tissue in a closed or occluded state such that the securing element 4010 and/or the retention element is the only component remaining within the body following the completion of the implant procedure. In this configuration, in some embodiments, the implant 4002 can have a plug or cover that can be coupled with the securing element 4010 that can cover any openings that may exist in the implant 4002 that the contact member is withdrawn through. The contact member 4004 can be a balloon that can be deflated and removed through an opening in the implant 4002 after the ostium of the LAA has been occluded or constricted.

In some embodiments, the contact member 4004 can have a continuous and uninterrupted circumference at a proximal end 4004*a* of the contact member 4004 that each of the strut members 4016 extend distally away from. Each of the strut members 4016 can be preformed into a curved shape such that the strut members 4016 are biased to expand to the second state when no external restraint or constraint is applied to the outside surface of the contact member 4004 (for example, when in a relaxed state). At a distal end 4004*b* of the contact member 4004, each of the strut members 4016 can, but are not required to, couple with a hub 4040. The hub member 4040 can have a plurality of slots or receptacles 4042 configured to receive and constrain distal end portions 4016*b* of each of the strut members 4016. Additionally, each of the receptacles 4042 can be configured to permit the distal end portions 4016*b* of each of the strut members 4016 to rotate relative to the hub 4040 so that the distal end portions 4016*b* of the strut members 4016 can extend generally radially away from the hub 4040 when the contact member 4004 is in the second, expanded state. The hub 4040 can be configured to permit the distal end portions 4016*b* of each of the strut members 4016 to rotate relative to the hub 4040 without resistance or significant resistance when the contact member moves between the first and second states (e.g., between contracted and expanded states). In any embodiments, the distal ends 4016*b* of each of the strut members 4016 can have a tab or other feature (such as a T shaped termination or other increased width) that locks into, is secured by, or is otherwise engaged by each of the receptacles 4042 so as to axially constrain the end portion of each of the strut members 4016, while allow rotation about the end portion 4016*b* of the struts 4016. In some embodiments, the distal end portion of the contact member (such as, without limitation, the contact member 4004) can be configured to be atraumatic or otherwise reduce a risk of injury to the tissue of the body. For example and without limitation, in some embodiments, the hub (such as hub 4040, as shown in FIG. 80B) of the contact member can have rounded or smooth corners (e.g., a radius) on a distal surface thereof configured to reduce a risk of damage to the tissue of the LAA or body.

In some embodiments, a method of treating an LAA can include any combination of the following: advancing a catheter 40122 and LAA (as shown in FIG. 80A), retracting an outer sheath 4014 of the catheter 4012 relative to the implant 4002 or advancing the implant 4002 relative to the outer sheath 4014 (as shown in FIG. 80B), advancing the contact member 4004 into the LAA and rotating the contact member 4004 to twist the LAA to a constricted or occluded state, holding the twisted LAA closed and further retracting the outer sleeve 4014 of the catheter 4012 to deploy or release the securing element 4010 (as shown in FIG. 80D), and/or continuing to hold the twisted LAA closed and advancing the securing element 4010 toward the contact member 4004, for example and without limitation by rotating the retention element 4008 and, hence, the securing element 4010, relative to the contact member 4004 (as shown in FIGS. 80E-80F). In some embodiments, the arms 4030 of the securing element 4010 can pass between and interlock with the struts 4016 of the contact member 4004 so as to prevent or at least inhibit the rotation of the securing element 4010 relative to the contact member 4004 (as shown in FIG. 80G). This can, in some embodiments, effectively rotationally coupled the securing element 4010 with the contact member 4004. In some embodiments, a method of treating an LAA can include any combination of the following in any combination with the foregoing steps: removing the inner core 4013 from the implant 4002 (as shown in FIG. 80H) and the retainer line 4032 to release the implant 4002 (as shown in FIG. 80I).

FIG. 80J shows an isometric view of an expanded contact member 4004 separated or decoupled from the retention element 4008 and the securing element 4010. FIG. 80K shows an isometric view of the expanded securing element 4010 being advanced toward the expanded contact member 4004. This can be done, for example and without limitation, after the LAA has been twisted by rotating the contact member 4004. FIG. 80L shows an isometric view of the deployed securing element 4010 at least partially engaged with (e.g., at least partially threaded into) the expanded contact member 4004. As a securing element 4010 is advanced toward the contact member 4004, with reference to FIG. 80M, the securing element 4010 can compress the twisted tissue of the LAA together or to the contact member 4004. FIG. 80N shows an isometric view of the securing element 4010 fully engaged with (e.g., fully threaded into) the contact member 4004. FIG. 80N also shows the inner core 4013 and the intermediate sleeve 4025 decoupled from or disengaged from the implant device 4002 and also shows the retainer line 4032 coupled with the contact member 4004. FIG. 80O is an isometric cross-sectional view of the treatment device 4000 shown in the state of the treatment device 4000 shown in FIG. 80O. FIG. 80P shows the retainer line 4032 released from the contact member 4004. FIG. 80Q shows an isometric cross-sectional view of the contact member 4004, and FIG. 80R shows an isometric cross-sectional view of the retention element 4008 and the securing element 4010. FIG. 80S shows an isometric cross-sectional view of the implant 4002 in an implanted or released state.

FIG. 80T shows a cross-sectional view of the securing element 4010 separated from or not yet engaged with the contact member 4004. FIG. 80U shows a cross-sectional view of the securing element 4010 completely or substantially completely engaged with the contact member 4004, the catheter 4012 still engage with the implant 4002. FIG. 80V shows a cross-sectional view of the securing element 4010 completely or substantially completely engaged with the contact member 4004, with the catheter 4012 decoupled from the implant 4002, while the retainer line 4032 is still coupled with the contact member 4004. FIG. 80W shows the catheter 4012 and the retainer line 4032 completely decoupled from the implant 4002. In some embodiments, the implant 4002 is fully recapturable at any point prior to the removal of the retainer line 4032, for example without limitation, by following a sequence of steps that is the reverse of the sequence of steps used for deployment.

In any embodiments of the treatment device disclosed herein, including without limitation any embodiments of the treatment device 4000, the implant can have a securing element having arms of any desired shape, including arms having a spiral shape, a helical shape, or otherwise. Additionally, in any embodiments of the treatment device disclosed herein, including without limitation any embodiments of the treatment device 4000, the securing element can be rotationally fixed to the other components of the implant, including the retention element. For example and without limitation, FIGS. 82A-82E show another example embodiment of the treatment device 4000 having a contact member 4002, a retention element 4058, and a securing element 4060 that can have a plurality of spiral shaped arms. The contact member 4004 can have an internally threaded body portion 4005 that can threadedly engages the threads of the retention element 4008 so that the retention element 4008 threads into and out of the threaded body portion 4005. The securing element 4060 can have one or more arms 4062 (e.g., six arms 4062, or from four to eight arms 4062, or any other number of arms) that have a helical, spiral, or twisted shape. In some embodiments, the arms 4062 can be curved in a first direction, which can be a longitudinal direction (e.g., toward the contact member 4002). The arms 4062 can also be curved in a circumferential direction. Some embodiments of the securing element 4060 can have a spiraled star like shape, like shown in FIGS. 82A-82E. In some embodiments, the arms 4062 of the securing element 4060 can be curved in a direction that is opposite the direction of the threading and rotation of the retention element 4058 so that the arms 4062 will point in a direction that is away from the direction of rotation of the securing element 4060 when the retention element 4058 and the securing element 4060 are rotated so as to engage the securing element 4060 with the tissue that has contracted as a result of the twisting of the contact member 4002 and/or the LAA. In this configuration, in some embodiments, the arms 4062 can atraumatically drag against the tissue that has contracted as a result of the twisting of the contact member 4002 and/or the LAA as the securing element 4060 is advanced toward or into the tissue, and can be configured to prevent untwisting of the tissue in the opposing direction once engaged. In some embodiments, the arms 4062 can be flexible so as to bend or flex in a circumferential direction when the securing element 4060 is rotated and the arms 4062 make contact with the tissue that has constricted as a result of the twisting of the LAA and/or the contact member 4004. In some embodiments, the arms 4062 can be rigid or substantially rigid in an axial direction.

In any embodiments disclosed herein, any components, features, or other details of the treatment device 4000 or implant device 4002 shown in FIGS. 82A-82E can have any of the components, features, or other details of any other treatment device embodiments or implant device embodiments disclosed herein, including without limitation any of the embodiments of the treatment devices 100, 140, 4000 or implant devices 102, 104, 4002 described above, in any combination with any of the components, features, or details of the treatment device 4000 or implant device 4002 disclosed herein. Similarly, any components, features, or other details of any of the other treatment device embodiments or implant device embodiments disclosed herein can have any of the components, features, or other details of any embodiments of the treatment device 4000 or implant device 4002 of FIGS. 82A-82E disclosed herein in any combination with any of the components, features, or details of the other embodiments of the treatment device and/or implant device.

Figure 82A:
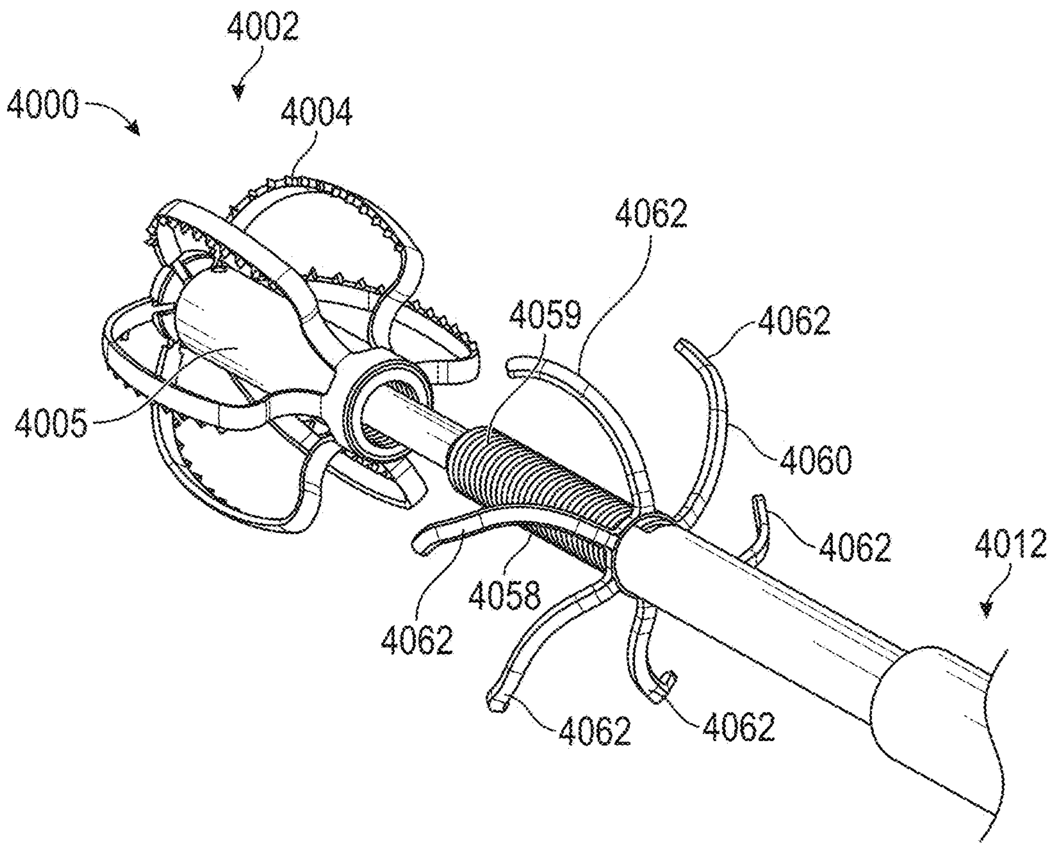
Figure 82B:
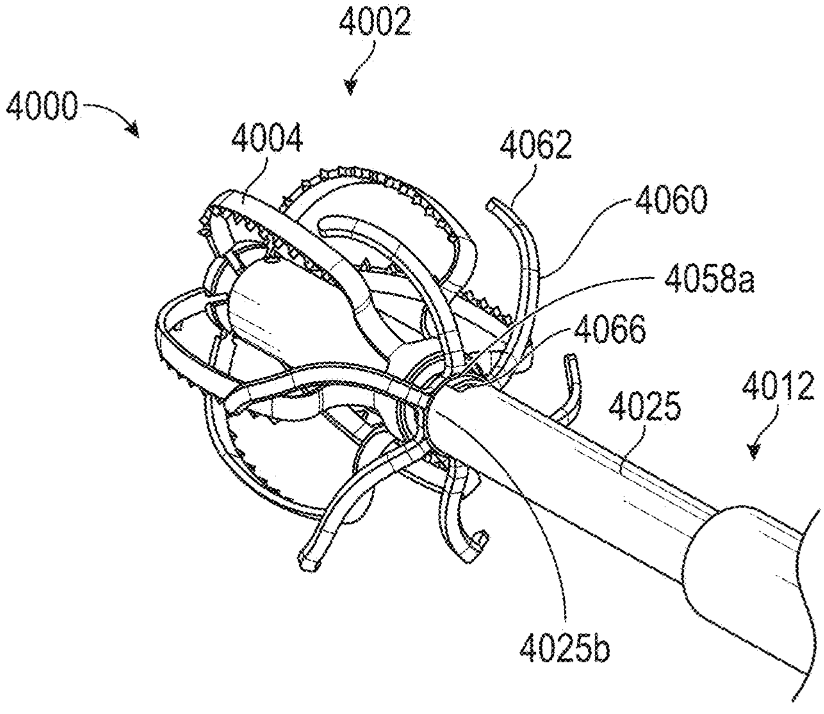
Figure 82C:
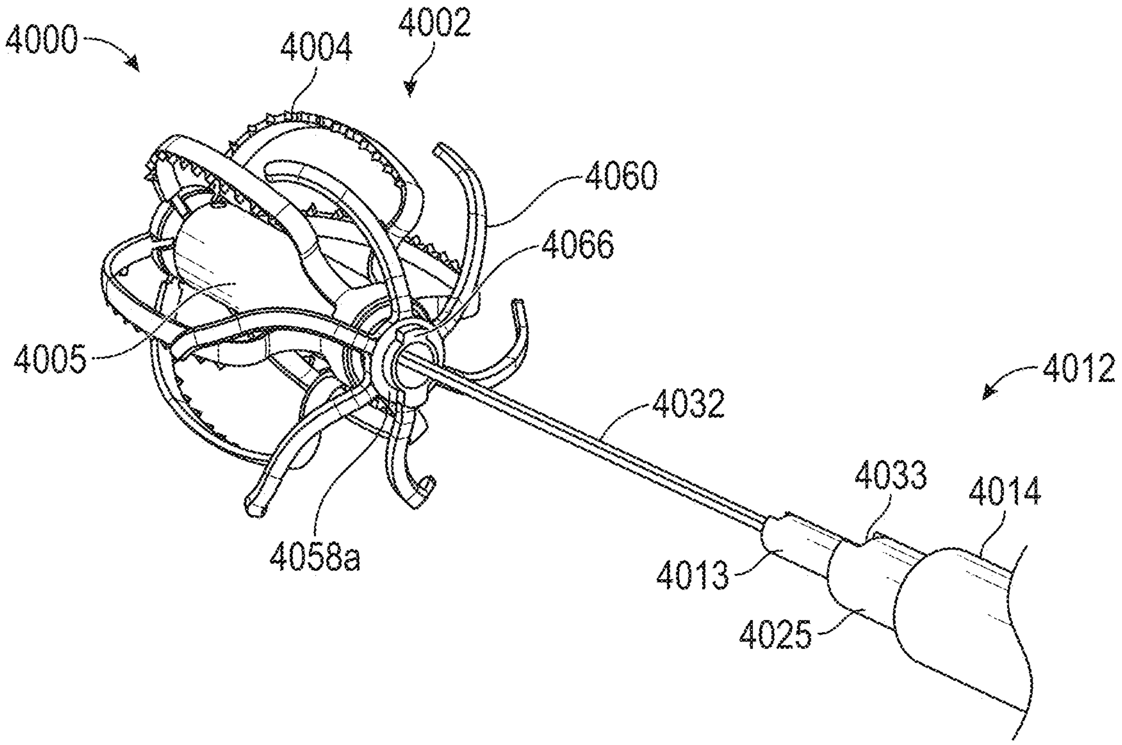
Figure 82D:
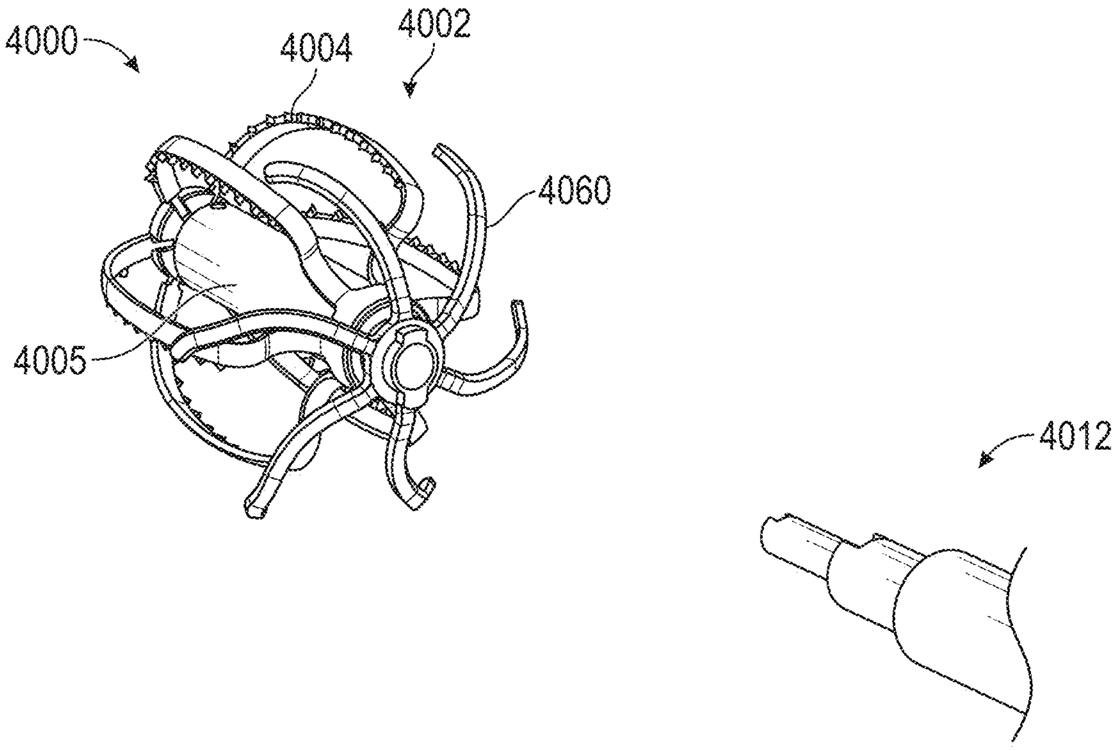
Figure 82E:
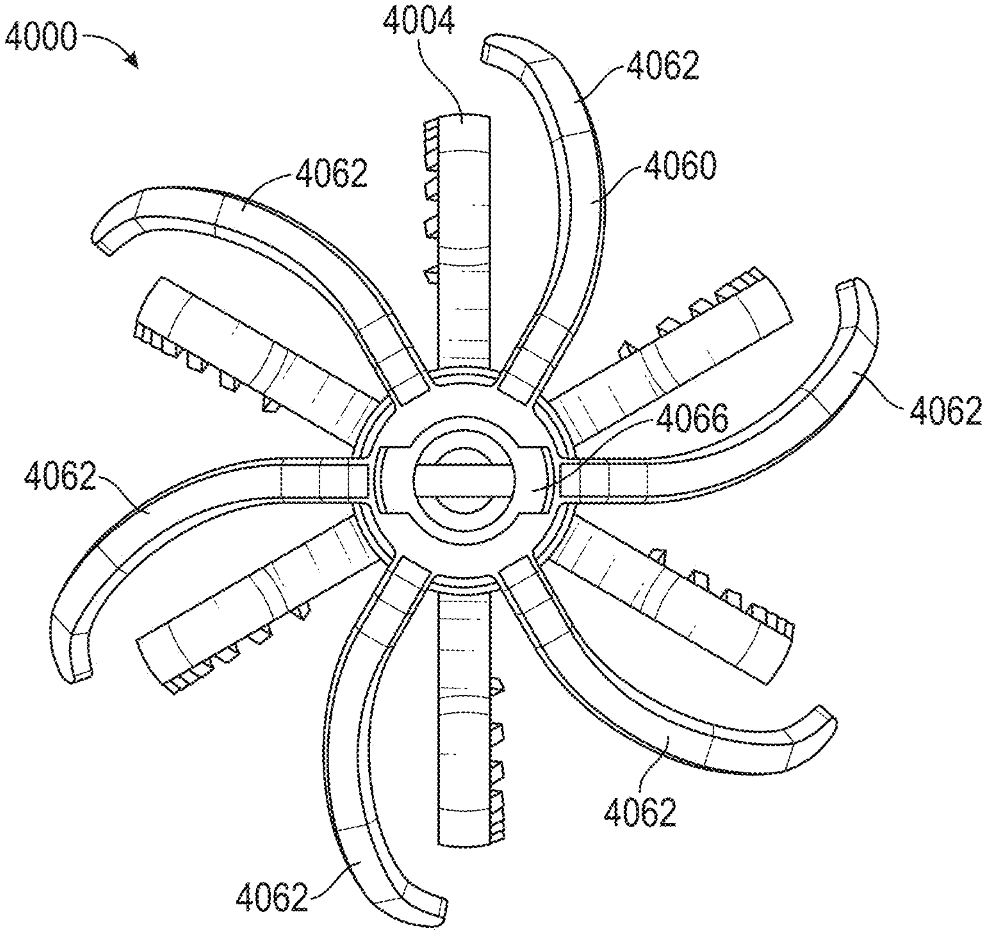

FIG. 82A shows an isometric view of a securing element 4060 that has been expanded (e.g., is in the second state) separated from a contact member 4004 that is also in an expanded, second state. The securing element 4060 and the contact member 4004 have not yet been coupled or joined. FIG. 82B shows an isometric view of the expanded securing element 4060 fully engaged with (e.g., threaded into) the contact member 4004. This can be done after the LAA tissue has been twisted and constricted (e.g., constricted around the implant 4002). The securing element 4060 can compress the tissue that has constricted. The implant 4002 as shown is still coupled with the delivery catheter 4012. FIG. 82C shows the retainer line 4032 coupled with the implant 4012, while the inner core 4013 and the intermediate member 4025 have been withdrawn from engagement from the implant 4012. In FIG. 82D, the retainer line 4032 has been removed and withdrawn from engagement with the implant 4002. FIG. 82E shows an end view of the implant 4002 in a fully deployed state.

In some embodiments, the arms 4062 and the other components and features of the securing element 4060 can be permanently or otherwise non-removably coupled with the retention element 4058 so that the arms 4062 and the other components and features of the securing element 4060 are rotationally fixed to the retention element 4058 so that any rotation of the retention element 4058 will cause the simultaneously rotation of the arms 4062 and the other components and features of the securing element 4060. In some embodiments, the retention element 4058 can be fixed to an outer surface of a threaded shaft 4059 of the retention element 4058, or can be integrally formed with the threaded shaft 4059 of the retention element 4058.

In some embodiments, a distal end portion 4025*b* of the intermediate sleeve 4025 can couple with and engage a proximal end portion 4058*a* of the retention element 4058 and/or a proximal end portion 4060*a* of the securing element 4060. For example and without limitation, the distal end portion 4025*b* can have recesses or notches 4033 in a distal end portion 4025*b* of the intermediate sleeve 4025 that can be configured to couple with projections or a head 4066 at a proximal end portion 4058*a* of the retention element 4058 and/or a proximal end portion 4060*a* of the securing element 4060 so that the intermediate sleeve 4025 can be rotationally coupled with the retention element 4058 and/or the securing element 4060 when the distal end portion 4025*b* of the intermediate sleeve 4025 is advanced distally into engagement with the retention element 4058 and/or the securing element 4060. Once the intermediate sleeve 4025 is rotationally coupled with the retention element 4058 and/or the securing element 4060, a rotation of the intermediate sleeve 4025 can cause the simultaneous and equal rotation of the retention element 4058 and/or the securing element 4060. In embodiments where the securing element 4060 is rotationally coupled with the retention element 4058, a rotation of the intermediate sleeve 4025 can cause the simultaneous and equal rotation of the retention element 4058 and the securing element 4060.

In any embodiments, the implant 4002 shown in FIGS. 82A-82E can be configured to be recapturable (e.g., collapsed and/or removed or repositioned). In some embodiments, the arms 4062 of the securing element 4060 can have sharp tips, barbs, and/or other features to penetrate the tissue and retain the arms 4062 in the tissue. In other embodiments, the arms 4062 of the securing element 4060 can have rounded tips and a smooth outside surface without barbs so that the securing element 4060 can be removed from the tissue to recapture and/or reposition the securing element 4060. In some embodiments, the implant 4002 can be configured such that the implant 4002 can be recapturable at any point prior to the removal of the suture 4032 due to the rounded atraumatic tips of the securing element 4060, which can also be configured to fold over in a reverse order to the deployment sequence shown in FIGS. 82A-82E.

In any embodiments of the treatment device disclosed herein, including without limitation any embodiments of the treatment device 4000, the body portion of the contact member can have one or more deflectable tabs instead of or in addition to the threaded internal surface thereof that can engage with external threads or ridges on an outside surface of the retention element so that the retention element can be axially advanced into an inside space within the body portion of the contact member and the deflectable tabs can prevent or at least inhibit the retention element from axially withdrawing from engagement with the body portion of the contact member. For example and without limitation, FIGS. 83A-83J show another example embodiment of the treatment device 4000 having a contact member 4072 having one or more deflectable tabs 4074 (e.g., two deflectable tabs 4074) in a body portion 4076 thereof, a retention element 4008, and a securing element 4010.

In any embodiments disclosed herein, any components, features, or other details of the treatment device 4000 or implant device 4002 shown in FIGS. 83A-83J can have any of the components, features, or other details of any other treatment device embodiments or implant device embodiments disclosed herein, including without limitation any of the other embodiments of the treatment devices 100, 140, 4000 or implant devices 102, 104, 4002 described herein, in any combination with any of the components, features, or details of the treatment device 4000 or implant device 4002 shown in FIGS. 83A-83J. Similarly, any components, features, or other details of any of the other treatment device embodiments or implant device embodiments disclosed herein can have any of the components, features, or other details of any embodiments of the treatment device 4000 or implant device 4062 of FIGS. 83A-83J disclosed herein in any combination with any of the components, features, or details of the other embodiments of the treatment device and/or implant device disclosed herein.

In some embodiments, the deflectable tabs 4074 can be integrally formed with the body portion 4076 of the contact member 4072. For example, a proximal end portion 4074*a* of the deflectable tabs 4074 can be attached to or integrally formed with the the body portion 4076 of the contact member 4072. In some embodiments, the one or more deflectable tabs 4074 (e.g., two deflectable tabs 4074) in the body portion 4076 of the contact member 4072 can extend in an axial direction of the body portion 4076. The deflectable tabs 4074 can be biased to align with the body portion 4076 of the contact member 4072 when the deflectable tabs 4074 are in a relaxed state. A distal end portion 4074*b* of the deflectable tabs 4074 can be configured to deflect away (e.g., radially away) from the body portion 4076 of the contact member 4072 when a radially outward force is exerted on the distal end portion 4074*b* of the deflectable tabs 4074, for example by the ridges or threads 4080 of the retention element 4008 contacting the teeth or projections 4082 on the distal end portion 4074*b* of the deflectable tabs 4074 as the retention element 4008 is advanced into the body portion 4076 of the contact member 4072.

In some embodiments, the deflectable tabs 4074 can be configured to deflect outwardly and permit the advancement of the retention element 4008 into the body portion 4076 of the contact member 4072, but be configured to inhibit (e.g., prevent) the axial movement of the retention element 4008 in an axial direction away from the contact member 4072 (e.g., in a direction in which the retention element 4008 withdraws from the contact member 4072). In other embodiments, the deflectable tabs 4074 and the retention element 4008 can be configured such that, if an operator wishes to withdraw the retention element 4008 from the contact member 4072, the retention element 4008 can be rotated to unthread or withdraw the retention element 4008 from the contact member 4072. In other words, the deflectable tabs 4074 can be configured to threadably engage with the threads or ridges 4080 of the retention element 4008. In this configuration, the retention element 4008 can be threadably engaged with and/or threadably disengaged from the contact member 4072. In other embodiments, the deflectable tabs 4074 and the retention element 4008 can be configured such that an operator can withdraw the retention element 4008 from the contact member 4072 by exerting an axial force on the retention element 4008 that overcomes the locking or engaging force of the deflectable tabs 4074 on the threads or ridges 4080 of the retention element 4008.

Figure 83A:
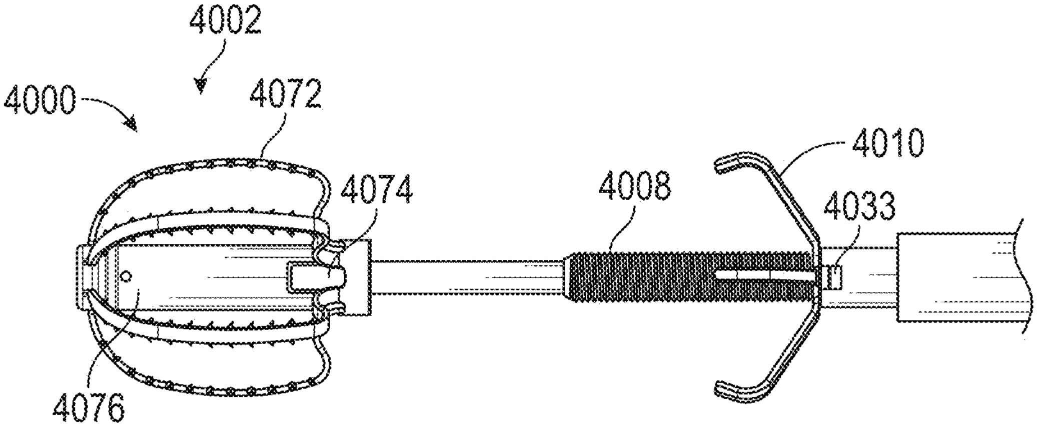
Figure 83B:
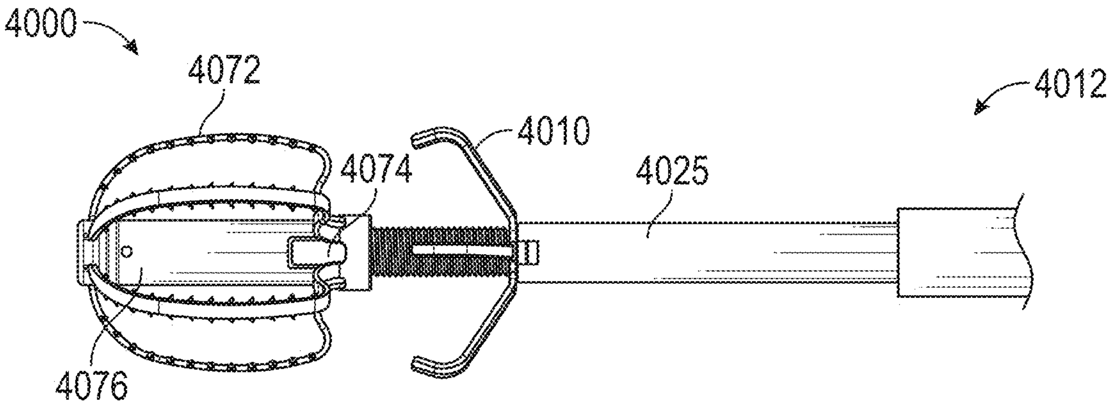
Figure 83C:
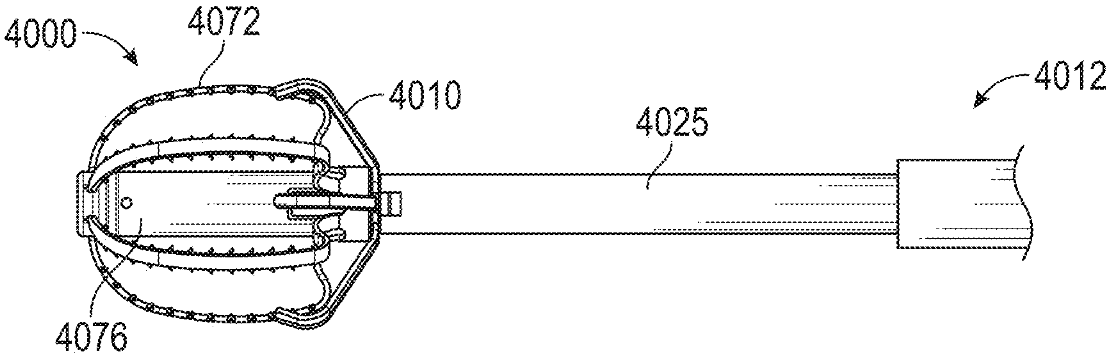

FIG. 83A shows a side view of a securing element 4010 that has been expanded (e.g., is in the second state) separated from a contact member 4072 that is also in an expanded, second state. The securing element 4010 and the contact member 4072 have not yet been coupled or joined. FIG. 83B shows a side view of the retention element 4008 and the expanded securing element 4010 partially engaged with (e.g., partially threaded or otherwise advanced into) the contact member 4072. This can be done after the LAA tissue has been twisted and constricted (e.g., constricted around the implant 4002). The securing element 4010 can compress the tissue that has constricted. The implant 4002 as shown is still coupled with the delivery catheter 4012. FIG. 83C shows a side view of the retention element 4008 and the expanded securing element 4010 fully engaged with (e.g., threaded or otherwise advanced into) the contact member 4072.

Figure 83D:
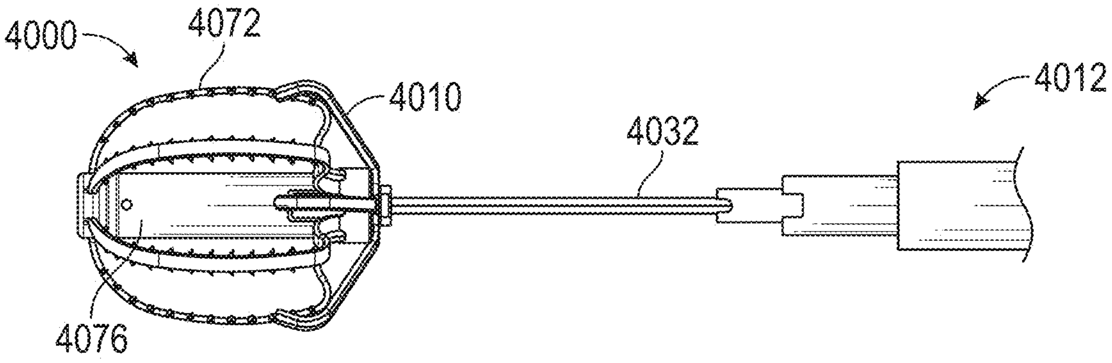
Figure 83E:
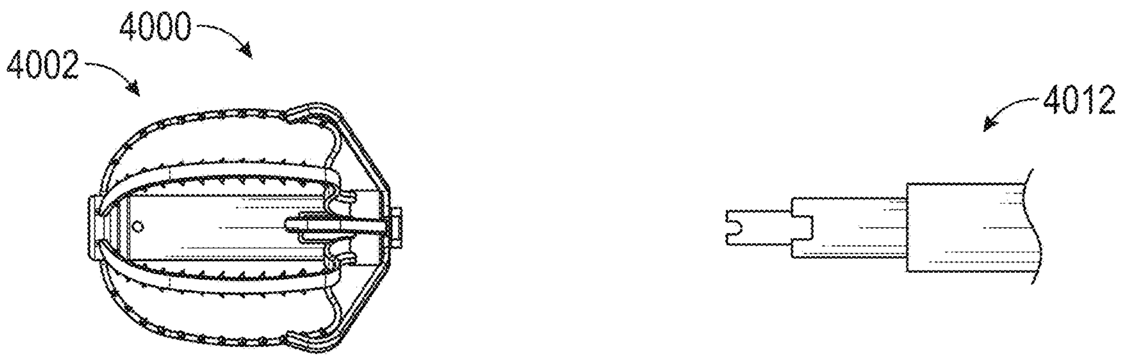
Figure 83F:
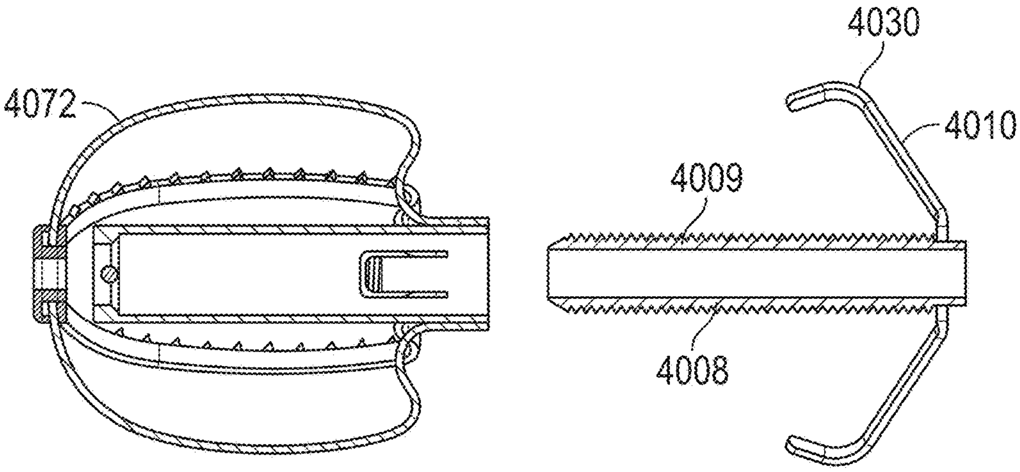
Figure 83G:
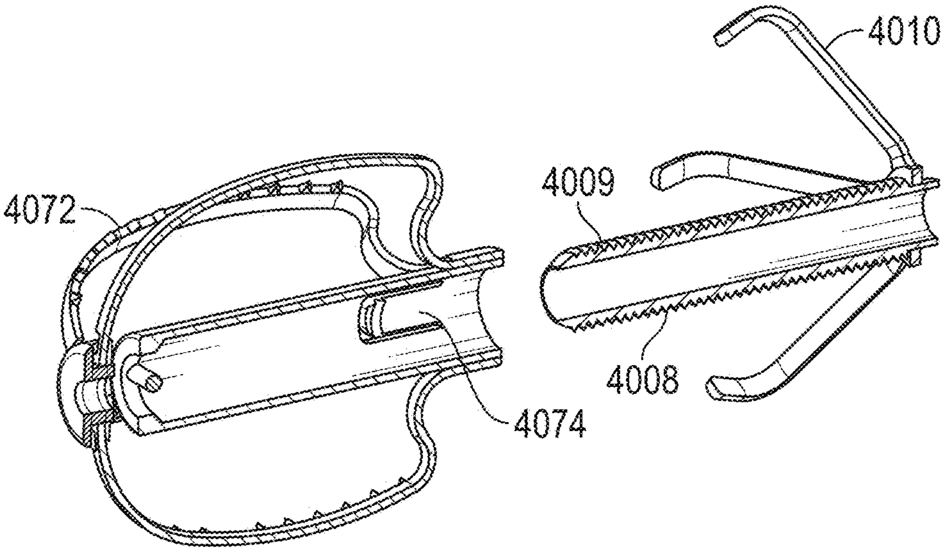
Figure 83H:
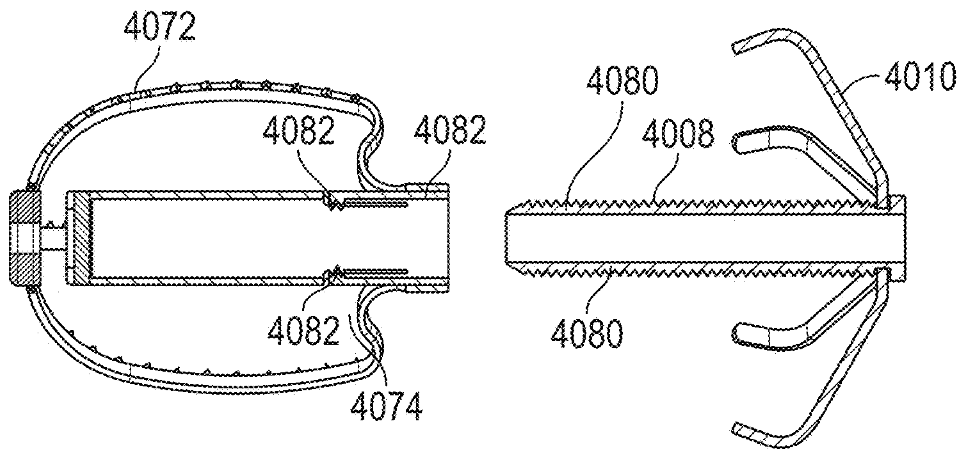
Figure 83I:
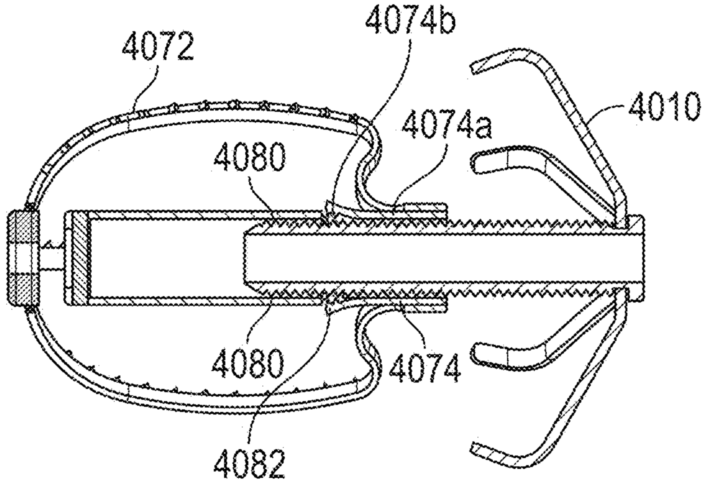
Figure 83J:
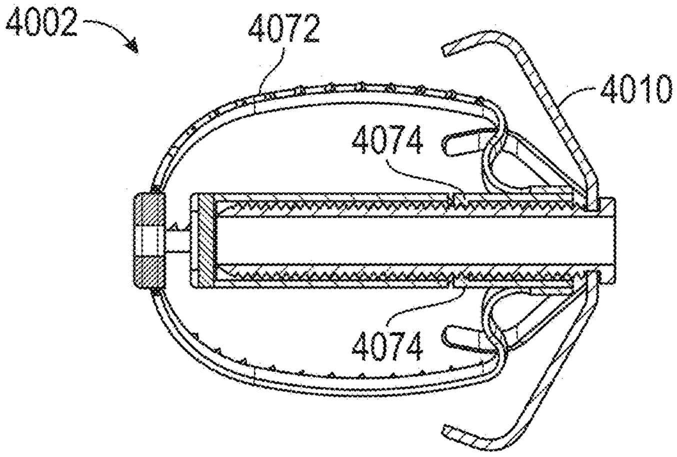

FIG. 83D shows the retainer line 4032 coupled with the implant 4012, while the inner core 4013 and the intermediate member 4025 have been withdrawn from engagement from the implant 4012. In FIG. 83E, the retainer line 4032 has been removed and withdrawn from engagement with the implant 4002. FIGS. 83F and 83G show a section view and an isometric view, respectively, of the implant 4002 in a decoupled but fully expanded state.

In some embodiments, the securing element 4010 can be configured to spin freely relative to the retention element 4008, even when the retention element 4008 is being rotated. In some embodiments, the securing element 4010 can be permanently or otherwise non-removably coupled with the retention element 4008 so that the securing element 4010 is rotationally fixed to the retention element 4008 and so that any rotation of the retention element 4008 will cause the simultaneously rotation of the arms 4030 and the other components and features of the securing element 4010. In some embodiments, the retention element 4008 can be fixed to an outer surface of a threaded shaft 4009 of the retention element 4008, or can be integrally formed with the threaded shaft 4009 of the retention element 4008.

In some embodiments, the deflectable tabs 4074 can be configured to have an increased friction or exert an increased force on an outside surface of the retention element 4008 to resist or inhibit a rotation of the retention element 4008 relative to the contact member 4004. In other embodiments, the outside surface of the retention element 4008 can have detents, recesses, or other depressions that can be configured to interact with projections, points, teeth, or other features on the deflectable tabs 4074 that can be configured to resist a rotation of the retention element 4008 relative to the deflectable tabs 4074 and, hence, the contact member 4004. In other embodiments, the contact member 4004 and the retention element 4008 can be indexed, keyed, or otherwise configured to rotationally locked together and prevent a rotation of the retention element 4008 relative to the contact member 4004.

FIGS. 84A-84B show another embodiment of a retention element 4092 that can be used with any of the embodiments of the treatment device or the implant device disclosed herein, including without limitation the embodiments of the treatment device 4000 or implant device 4002 disclosed herein. In some embodiments, the retention element 4092 can have a multi-tapered body 4094 including a plurality of tapering ridges 4096 that taper toward the distal end 4094*b* of the body 4094. The contact member used with the retention element 4092 can have one or more deflectable tabs configured to engage with ridges 4096. The ridges 4096 can be configured to more easily deflect the deflectable tabs of the contact member when the retention element 4092 is advanced into the contact member so that the retention element 4092 can be more easily advanced into the contact member 4004. The ridges 4096 can be configured to inhibit (e.g., prevent) withdrawal of the retention element 4092 from or relative to the contact member to maintain the axial position of the securing element 4010 relative to the contact member after implantation of the securing element 4010.

In any embodiments of the treatment device disclosed herein, including without limitation any embodiments of the treatment device 4000, the retention element and the securing element can be configured such that the securing element can be automatically changed or moved from a first state in which the securing element can rotate freely relative to the contact member and/or the retention element (such as, for example and without limitation, during deployment of the contact member) to a second state in which the securing element is rotationally locked or coupled with the retention element (such as and without limitation after implantation of the securing element into the tissue). For example and without limitation, FIGS. 85A-85I show another example embodiment of the treatment device 4000 having a contact member 4004, a retention element 5008, and a securing element 5010. The retention element 5008 can threadedly engage with the contact member 4004, as in any of the other embodiments of the implant disclosed herein, including without limitation the embodiments of the implants disclosed in FIG. 80A. In some embodiments, the retention element 5008 and the contact member 4004 can have any of the locking features of any of the other embodiments of the implants disclosed herein, including without limitation the embodiments of the implants disclosed in FIG. 83A.

In any embodiments disclosed herein, any components, features, or other details of the treatment device 4000 or implant device 4002 shown in FIGS. 85A-85I can have any of the components, features, or other details of any other treatment device embodiments or implant device embodiments disclosed herein, including without limitation any of the other embodiments of the treatment devices 100, 140, 4000 or implant devices 102, 104, 4002 described herein, in any combination with any of the components, features, or details of the treatment device 4000 or implant device 4002 shown in FIGS. 85A-85I. Similarly, any components, features, or other details of any of the other treatment device embodiments or implant device embodiments disclosed herein can have any of the components, features, or other details of any embodiments of the treatment device 4000 or implant device 4062 of FIGS. 85A-85I disclosed herein in any combination with any of the components, features, or details of the other embodiments of the treatment device and/or implant device disclosed herein.

Figure 85A:
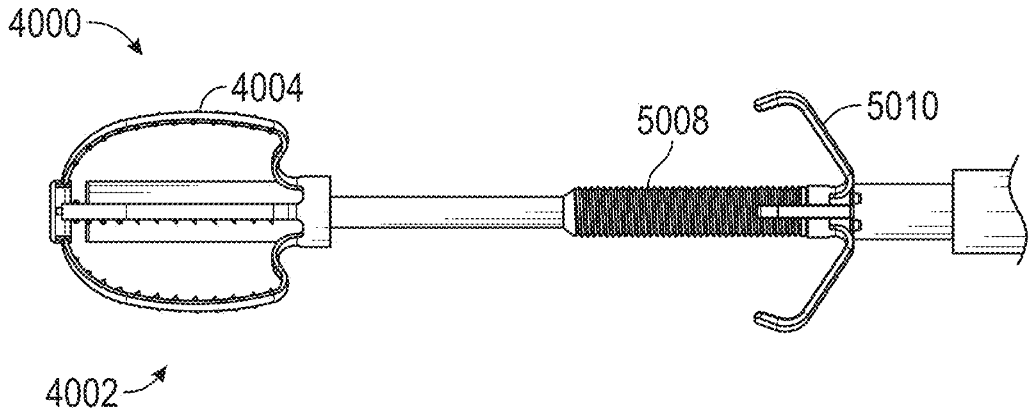
Figure 85B:
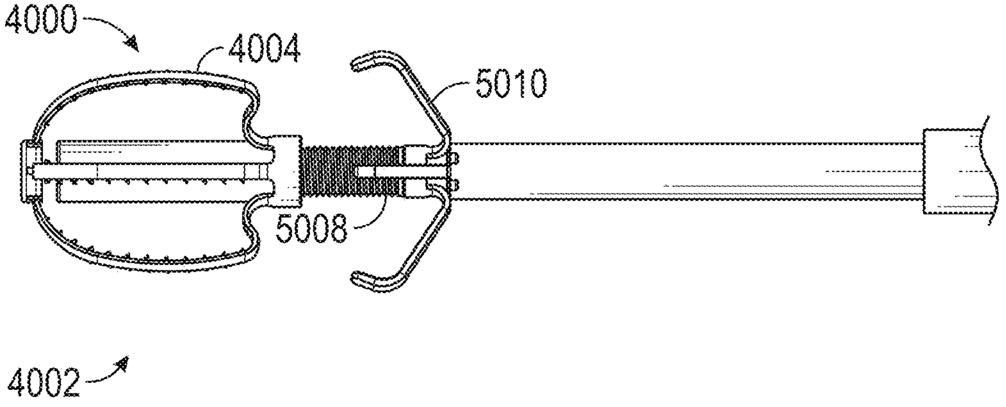
Figure 85C:
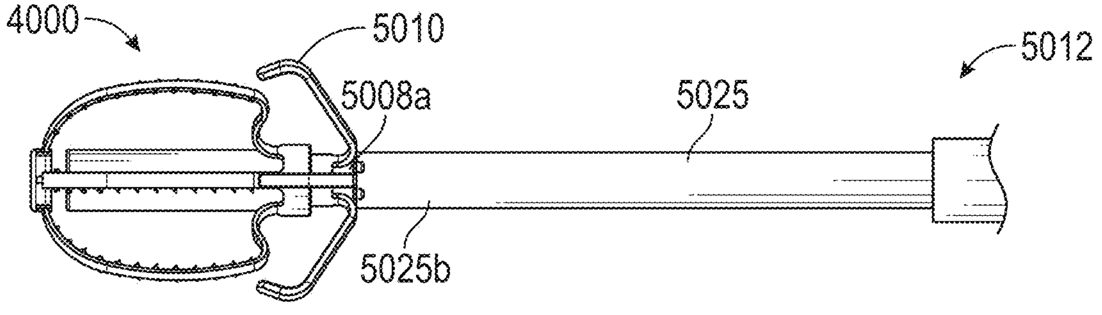

FIG. 85A shows a side view of the device 4000, in which the securing element 5010 that has been expanded (e.g., is in the second state) is separated from the contact member 4004 that is also in an expanded, second state. The securing element 5010 and the contact member 4004 have not yet been coupled or joined. FIG. 85B shows a side view of the retention element 5008 and the expanded securing element 5010 partially engaged with (e.g., partially threaded or otherwise advanced into) the contact member 4004. This can be done after the LAA tissue has been twisted and constricted (e.g., constricted around the implant 4002). The securing element 4010 can compress the tissue that has constricted. The implant 4002 as shown is still coupled with the delivery catheter 5012. FIG. 85C shows a side view of the retention element 5008 and the expanded securing element 5010 fully engaged with (e.g., threaded or otherwise advanced into) the contact member 4004. FIG. 85C also shows a distal end portion 5025*b* of the intermediate member 5025 of the catheter 5012 engaged with a proximal end portion 5008*a* of the retention element 5008.

Figure 85D:
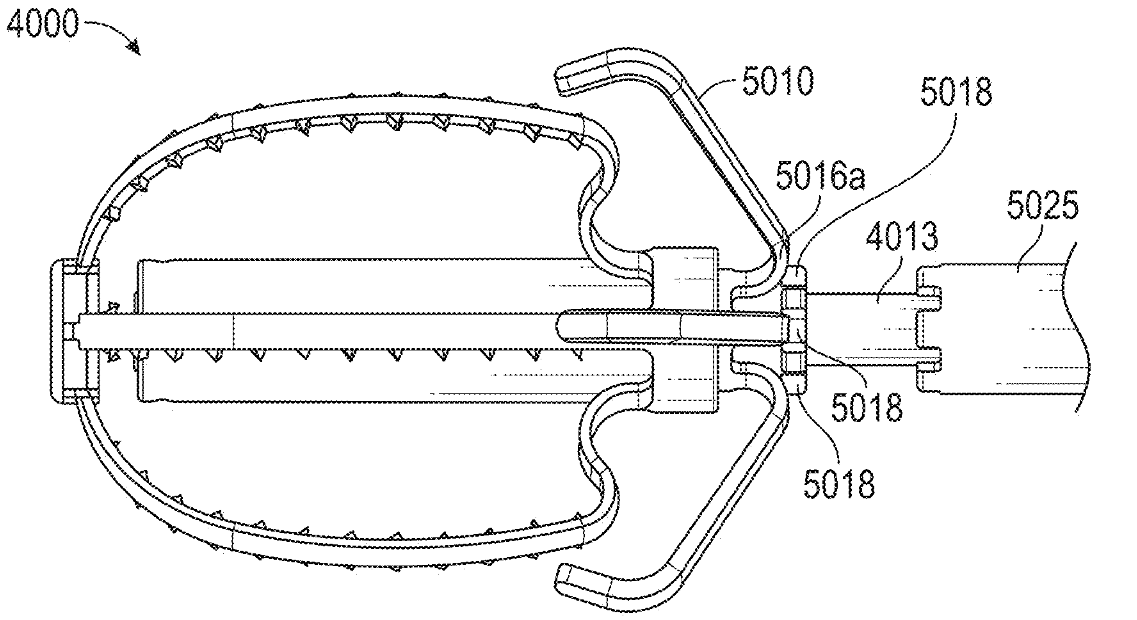

FIG. 85D shows the intermediate member 5025 partially withdrawn from engagement from the proximal end portion 5008*a* of the retention element 5008. In some embodiments, the intermediate member 5025 can be withdrawn from the retention element 5008 after the securing element 5010 has been implanted into the tissue that has compressed (e.g., the tissue of the LA and/or the ostium of the LAA) as a result of the twisting of the contact member 4004 and/or the LAA.

Figure 85E:
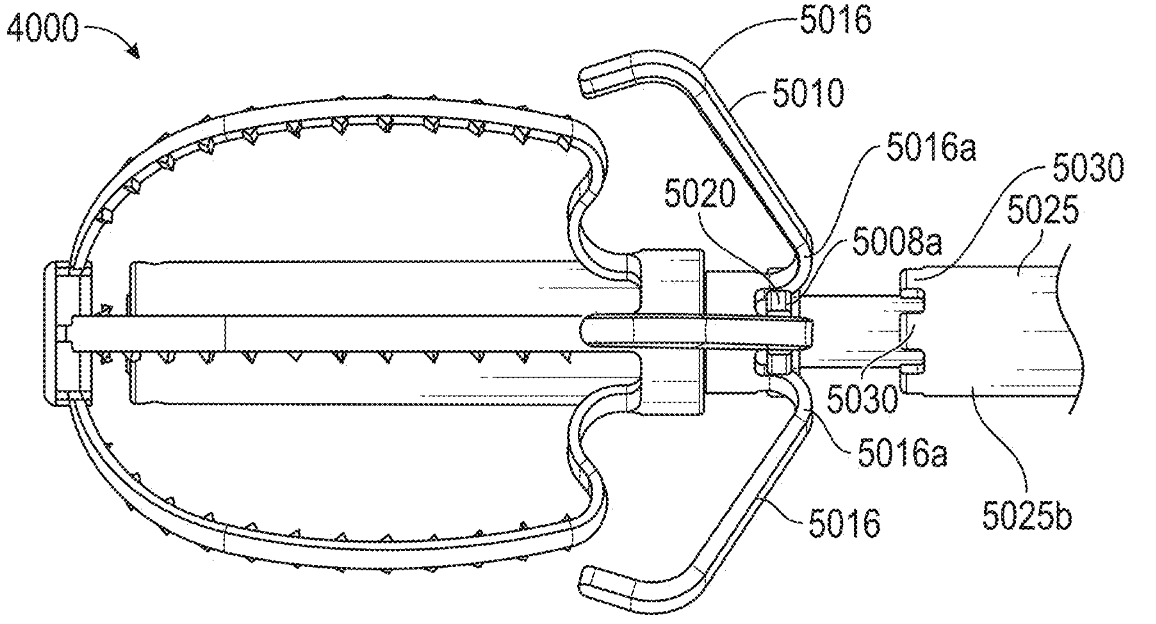

With reference to FIG. 85E, after the intermediate member 5025 is partially withdrawn from engagement from the proximal end portion 5008*a* of the retention element 5008, the securing element 5010 can move away from the contact member 4004 as a result of a biasing force in the implant 4002 (such as, for example and without limitation, as a result of a spring member or other axially resilient member), as a result of the expansion of the tissue that the securing element 5010 has penetrated into and/or engaged with, or otherwise.

Figure 85F:
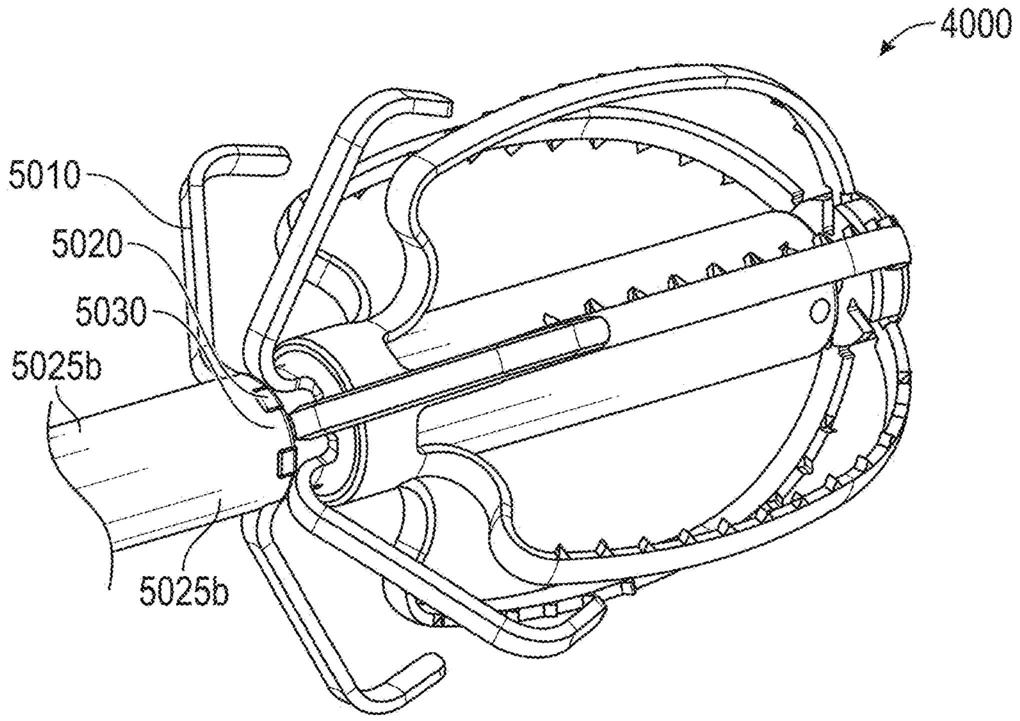

FIG. 85F shows an isometric view of the device 4000, showing the distal end portion 5025*b* of the intermediate member 5025 in engagement with the proximal end portion 5008*a* of the retention element 5008.

Figure 85G:
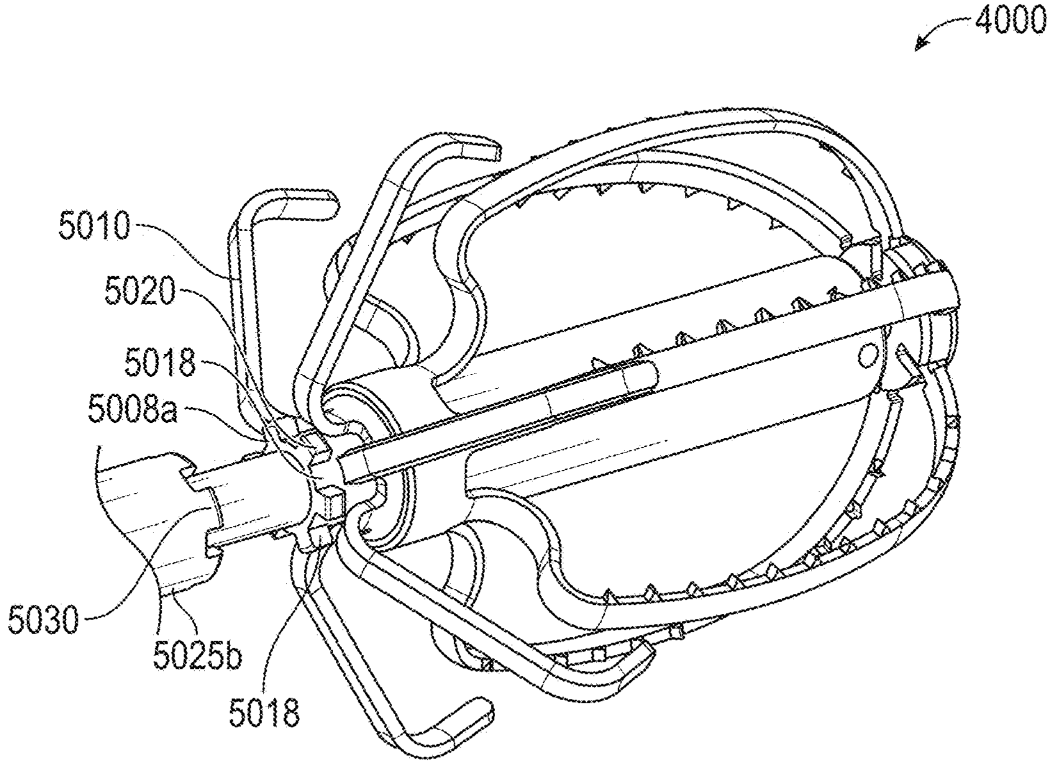

FIG. 85G shows an isometric view of the device 4000, showing the distal end portion 5025*b* of the intermediate member 5025 withdrawn from the proximal end portion 5008*a* of the retention element 5008, but before the retention element 5008 has moved in the proximal direction away from the contact member 4004.

Figure 85H:
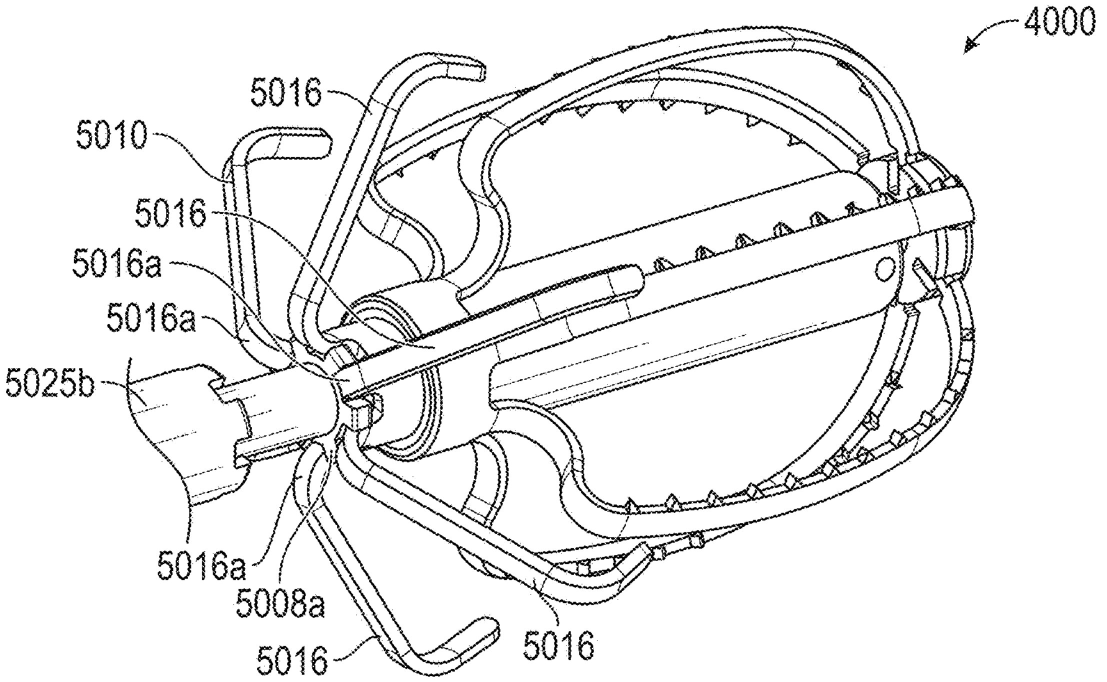

FIG. 85H shows an isometric view of the device 4000, showing the distal end portion 5025*b* of the intermediate member 5025 withdrawn from the proximal end portion

Figure 85I:
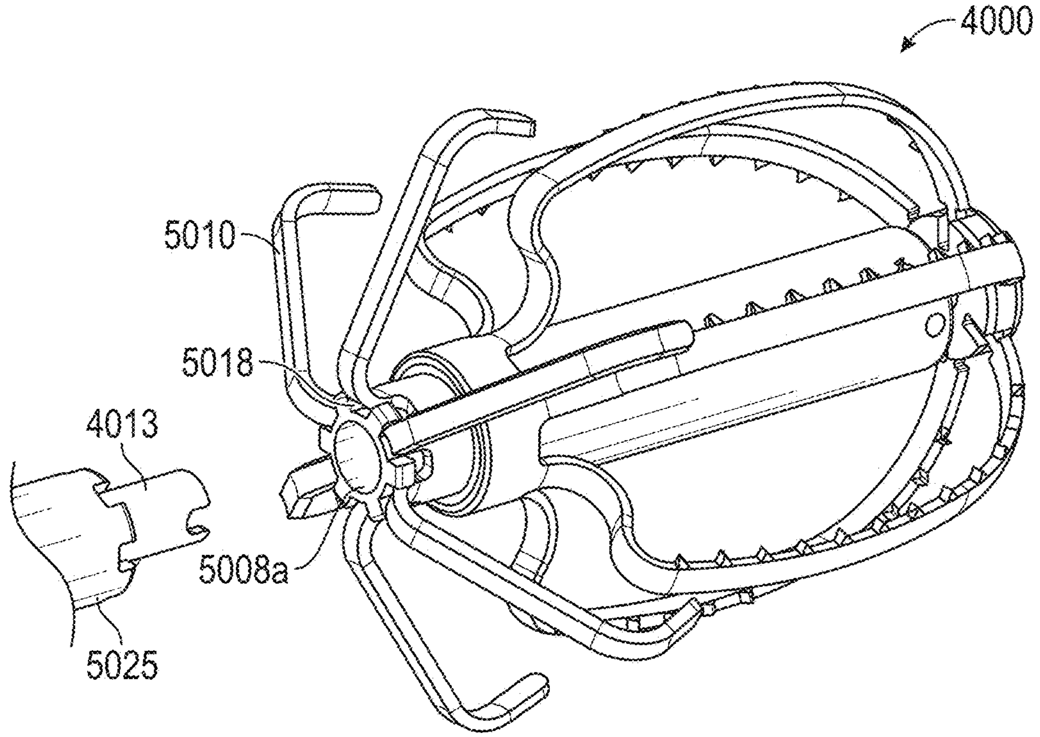

5008*a* of the retention element 5008 and showing the retention element 5008 withdrawn in a proximal axial direction from the contact member 4004 so that the proximal end portions 5016*a* of the arms 5016 of the securing element have been received by or moved into engagement with notches or recesses 5018 formed in a proximal end portion 5008*a* of the retention element 5008. The recesses 5018 can be formed between projections 5020 in the proximal end portion 5008*a* of the retention element 5008. In some embodiments, the proximal end portion 5008*a* of the retention element 5008 can be castellated or have one or more castellated features. FIG. 85I shows the inner core 4013 and the intermediate member 5025 withdrawn from the implant 4002.

In some embodiments, the securing element 5010 can be configured to move axially between a first, distal state or position (as shown in FIG. 85G) and a second, proximal state or position (as shown in FIG. 85H) relative to the retention element 5008. In some embodiments, the securing element 5010 can be configured to spin freely relative to the retention element 5008 when the securing element 5010 is in the first state or position, such that, for example and without limitation, the securing element 5010 can be held in a fixed rotational state or position as the contact member 4004 is rotated or, in some embodiments, as the retention element 5008 and the securing element 5010 are advanced toward the contact member 4004 by rotating and threadedly engaging the retention element 5008 into the contact member 4004. The securing element 5010 can be rotationally coupled with the retention element 5008 when the securing element 5010 is in the second state or position so that the securing element 5010 is unable to rotate relative to the retention element 5008 when the securing element 5010 is in the second state or position.

Some embodiments of the implant 4002 can be fully recapturable at any point prior to the removal of the retaining line (which can be a suture, as in other embodiments disclosed herein) by moving the securing element 5010 in a distal axial direction to the first position of the securing element 5010 so that the arms 5016 of the securing element 5010 are not engaged by the recesses 5018 of the retention element 5008.

In some embodiments, the notches or recesses 5018 can be configured to receive the projections 5030 formed in the distal end portion 5025*b* of the intermediate member 5025. This can permit the intermediate member 5025 to rotationally engage with or lock with the retention element 5008 so that a torsional force or rotation applied to the intermediate member 5025 can be transferred to the retention element 5008, for example and without limitation, to rotationally advance the retention element 5008 toward the contact member 4004.

FIGS. 86A-86I show another embodiment of a treatment device 6000 having an implant 6002 having a contact member 6004, and retention element 6008, and securing element 6010. In any embodiments disclosed herein, the implant device 6002 can have any of the components, features, or other details of any other treatment device embodiments or implant device embodiments disclosed herein, including without limitation any of the other embodiments of the treatment devices 100, 140, 4000 or implant devices 102, 104, 4002 described herein, in any combination with any of the components, features, or details of the implant device 6002 shown in FIGS. 86A-86I. Similarly, any components, features, or other details of any of the other treatment device embodiments or implant device embodiments disclosed herein can have any of the components, features, or other details of any embodiments of the implant device 6002 disclosed herein in any combination with any of the components, features, or details of the other embodiments of the treatment device and/or implant device disclosed herein.

FIG. 86A shows an isometric view of the implant device 6002, in which the securing element 6010 that has been expanded (e.g., is in the second state) is spaced apart from the contact member 6004 that is also in an expanded, second state. FIG. 86B shows a side view of the implant device 6002 and the expanded securing element 6010 spaced apart from the implant device 6002. FIG. 86C shows an end view of the implant device 6002.

With reference to FIGS. 86A-86I, in some embodiments of the implant 6002, the securing element 6010 can be axially secured to the retention element 6008. Some embodiments of the retention element 6008 can have a threaded shaft 6009 that is positioned within a body portion 6011 of the securing element 6010. The threaded shaft 6009 can be permitted to rotate freely within the body portion 6011 of the securing element 6010. The threaded shaft 6009 can also be threadedly coupled with the contact member 6004. In this configuration, rotating the threaded shaft 6009 in a first direction can cause the securing element 6010 to advance axially toward the contact member 6004. Rotating the threaded shaft 6009 in a second direction which is opposite to the first direction can cause the securing element 6010 to withdraw or move axially away from the contact member 6004.

With reference to FIG. 86C, some embodiments, the securing element 6010 can have a plurality of arms or struts 6016 extending away from a proximal end portion 6011*a* of the body portion 6011 of the securing element 6010. In some embodiments, the plurality of struts 6016 can each initially bend radially outwardly at a proximal end portion 6016*c* thereof and can each have a distal end portion 6016*b* that is, and the second or expanded state of the securing element 6010, positioned closer to the contact member 6004 than the proximal end portion 6016*a* of the struts 6016. Each of the struts 6016 can have a middle section 6016*c* that, in a second or expanded state, angles outwardly at an angle that is angled forward toward the contact member. In some embodiments, the middle section 6016*c* can angle forward at an angle that is 45° (or approximately 45°) relative to an axial or longitudinal axis of the body portion 6011 of the securing element 6010, or from 35° (or approximately 35°) to 60° (or approximately 60°) relative to the axial or longitudinal axis of the body portion 6011.

In any embodiments of the securing element 6010 disclosed herein, each of the struts 6016 can have one or more interconnections with adjacent struts 6016 along a length of each of the struts 6016. For example and without limitation, with respect to FIG. 86C, each of the struts 6016 can have a first interconnection 6020 at an end portion 6016*b* of each of the struts 6016, wherein the first interconnection 6020 is an interconnection between the distal end portions 6016*b* of two adjacent struts 6016. Additionally, in some embodiments, each of the struts 6016 can also have a second interconnection 6022 in a middle portion 6016*c* of each of the struts 6016, wherein the second interconnection 6022 is an interconnection between the middle portions 6016*c* of two adjacent struts 6016. In this configuration, each of the struts 6016 of the securing element 6010 can have a first and a second interconnection along a length thereof with an adjacent strut 6016. The interconnections 6020, 6022 can provide additional rigidity and strength to the entire securing element 6010. Additionally, in some embodiments, each of the interconnections 6020, 6022 can also provide an additional point of securement of each of the struts 6016 to the securing element 6010 so that, if a strut becomes from or broken, the first interconnection 6020 and/or the second interconnection 6022 can couple or secure the broken or fractured strut 6016 to the securing element 6010 and prevents the broken or fractured strut 6016 from flowing into the patient's heart or blood stream. Additionally, in some embodiments, each of the struts 6016 can have a sharp distal end portion 6016*b* wherein, in some embodiments, the distal end portion 6016*b* can have two struts that coupled together at the distal end portion 6016*b* of the struts. The distal end portion 6016*b* can have a sharp point that is designed to penetrate tissue. Additionally, in some embodiments, the distal end portion 6016*b* of each of the struts can have a sloped or angled surface 6030 that can assist with the penetration of the distal end portion 6016*b* into the tissue.

In some embodiments, the first and/or second interconnections 6020, 6022 can increase a rigidity of the securing element 6010, at least torsionally. In some embodiments, with the more torsionally rigid configuration having interconnections, the struts 6016 can be made thinner in cross-sectional size, which can improve tissue ingrowth into the securing element 6010 in some embodiments and/or reduce a weight of the securing element 6010. In some embodiments, the cross-sectional area or size of the struts 6016 can be the same as or approximately the same as a 2-0 suture.

In some embodiments, the retention element 6008 can have a head 6030 coupled with the threaded shaft 6009, the head 6030 being configured to couple with an end portion of an intermediate member of the catheter (not shown) so that a rotation or torque applied to the intermediate member can cause an equal rotation or torque to be applied to the head 6030 and the threaded shaft 6009 of the retention element 6008. In some embodiments, the retention element 6008 can be axially coupled with the body portion 6011 of the securing element 6010 so that the retention element 6008 and the securing element 6010 move together in either axial direction. For example and without limitation, in some embodiments, the retention element 6008 can have a first retainer 6035 that can be coupled with (e.g., welded to, press fit, or otherwise attached to) a distal end 6009*b* of the threaded shaft 6009 and a second retainer 6036 that can be positioned within and be axially constrained within the slot 6038 formed in the body portion 6011 of the securing element 6010. A collar member 6037 can fit around an outside surface of the body portion 6011 of the securing element 6010 to radially constrain the second retainer 6036 within the slot 6038.

The first retainer 6035 can prevent a proximal axial movement of the threaded shaft 6009 (i.e., in the proximal direction, away from the contact member 6004) relative to the body portion 6011 of the securing element 6010. Because the second retainer 6036 can have an opening 6039 axially therethrough that is smaller than the major diameter of the threaded portion of the threaded shaft 6008, the second retainer 6036 can prevent a distal axial movement of the threaded shaft 6009 (i.e., in the distal direction, toward the contact member 6004) relative to the body portion 6011 of the securing element 6010. An outside diameter of the first retainer 6035 can be greater than the diameter of the opening 6037 in the second retainer 6036 to prevent the first retainer 6035, which is coupled with an end portion 6009*b* of the threaded shaft 6009, from passing through the opening 6037. In this configuration, any axial movement of the retention element 6008 will cause the simultaneous and equal axial movement of the securing element 6010.

In some embodiments, a post member 6040 can be threadedly engaged with the shaft 6009 and be configured to translate along the longitudinal slot 6042 formed in the body portion 6011 of the securing element 6010. In this configuration, as the threaded shaft 6009 is rotated in a first direction, the post member 6040 can move axially in a first direction (e.g., a distal axial direction) and so that, as the threaded shaft 6009 is rotated in a second direction, which is opposite to the first direction, the post member 6040 can move axially in a second direction (e.g., a proximal axial direction) which is opposite to the first direction. The post member 6040 can be coupled with a proximal end portion 6004*a* of the contact member 6004 such that, as the post 6040 is moved axially relative to the securing element 6010, the securing element 6010 can simultaneously and equally move in an axial direction relative to the contact member 6004. In this configuration, the securing element 6010 can be moved toward or away from the contact member 6004 by rotating the head portion 6030 of the threaded shaft 6009 of the retention element 6008.

With reference to FIG. 86I, some embodiments of the contact member 6004 can have a hub 6050 at a distal end portion 6004*b* of the contact member 6004 that can couple with the distal end portions 6018*b* of the struts 6018. The hub 6050 can couple with the distal end portions 6018*b* of the struts 6018 so as to secure the hub 6050 with the distal end portions 6018*b* of the struts 6018 in an axial direction. The hub 6050 can be configured to permit the distal end portions 6018*b* of the struts 6018 to rotate relative to the hub 6050. In some embodiments, the hub 6050 can include a first disc member 6052, a retention element 6054, and a second disc member 6056. The first disc member 6052 can have an opening 6053 axially therethrough for a guidewire or other instrument to pass through and can be configured to constrain the distal end portions 6018*b* of the struts 6018 in the slots 6058 formed in the retention element 6054 in the distal axial direction. The retention element 6054 can also have an opening 6060 axially therethrough for a guidewire other instrument pass through. The slots 6058 can be configured to engage with the tabs or other T-shaped features 6066 formed on the distal end portion 6018*b* of the struts 6018 and to permit the distal end portions 6018*b* to rotate relative to the retention element 6054. The second disc member 6056 can also have slots 6064 therein to permit a rotation of the distal end portions 6018*b* of the struts 6018 and to axially restrain the distal end portions 6018*b* of the struts 6018 in a proximal axial direction.

A proximal end portion of the contact member 6004 can have a first collar member 6070 and a second collar member 6072. In some embodiments, the first and second collar members 6070, 6072 can be formed separately and can be coupled together, such as by welding, so that the first and second collar members 6070, 6072 do not move relative to one another. In other embodiments, the first and second collar members 6070, 6072 could be made as a single component. In some embodiments, the first collar member 6070 can be used to at least inhibit (e.g., prevent) a rotational movement of the first collar member 6070 relative to the contact member 6004. For example and without limitation, the tabs that project in the axial direction toward the contact member 6004 can engage with one or more spaces in the contact member 6004 (e.g., one or more spaces between the struts of the contact member 6004) to at least inhibit (e.g., prevent) a rotational movement of the first collar member 6070 relative to the contact member 6004.

In some embodiments, the second collar member 6072 can be used to at least inhibit (e.g., prevent) an axial movement of the second collar member 6072 relative to the contact member 6004. For example and without limitation, the tabs formed on the second collar member 6072 that project in the radial inward direction toward the contact member 6004 can engage with one or more end surfaces or walls formed in the contact member 6004 to at least inhibit (e.g., prevent) an axial movement of the second collar member 6072 relative to the contact member 6004. Together, the first and second collar members 6070, 6072 can be used to limit the rotational and axial movement of the first and second collar members 6070, 6072 relative to the contact member 6004. The first collar member 6070 can be made by laser cutting the part from a tube of material. The second collar member 6072 can be machined. In some embodiments, the first and second collar members 6070, 6072 constrain the post 6040 to the contact member 6004 so that the post 6040 cannot become disengaged from the contact member 6004.

In this configuration, as the retention element 6008 is rotated first direction, the securing element 6010 can be advanced toward the contact member 6004 so as to engage with and/or compress any tissue that has constricted or closed as a result of the twisting of the contact member 6004 or the LAA. The distal tips **6016*b* of the arms 6016 of the securing element 6010** can penetrate into the tissue that has been can compress or otherwise inhibit (e.g., prevent) the tissue that has constricted from opening back up or expanding.

FIGS. 86J-86L show another embodiment of a treatment device 6100 having an implant 6102 having a contact member 6104, and retention element 6108, and securing element 6110. In any embodiments disclosed herein, the implant device 6102 can have any of the components, features, or other details of any other treatment device embodiments or implant device embodiments disclosed herein, including without limitation any of the other embodiments of the treatment devices 100, 140, 4000, 6000 or implant devices 102, 104, 4002, 6002 described herein, in any combination with any of the components, features, or details of the implant device 6102 shown in FIGS. 86J-86L. Similarly, any components, features, or other details of any of the other treatment device embodiments or implant device embodiments disclosed herein can have any of the components, features, or other details of any embodiments of the implant device 6102 disclosed herein in any combination with any of the components, features, or details of the other embodiments of the treatment device and/or implant device disclosed herein.

With reference to FIGS. 86J-86L, any embodiments of the contact member 6104 disclosed herein can have a plurality of tissue anchors or teeth 6118 (also referred to as nubs) or other similar features configured to penetrate or engage the tissue of the LAA. The tissue anchors 6118 can be configured to penetrate into a tissue within the LAA when the contact member 4004 is expanded against the tissue of the LAA and/or when the contact member 4004 is rotated or twisted within the LAA. The tissue anchors 6118 can be positioned on one side of the struts 6106 of the contact member 6104, for example, to point in the direction of intended rotation of the contact member 6104. In other embodiments, the tissue anchors 6118 can be positioned on both sides of the struts 6106 of the contact member.

In any embodiments disclosed herein, the tissue anchors or teeth 6118 of the contact member can be asymmetrical or otherwise be formed at an angle (such as angle A, shown in FIG. 86K). In some embodiments, as shown, the tissue anchors 6118 can be directed toward a proximal end **6104*a* of the contact member 6104 by an angle A. In this arrangement, in some embodiments, the tissue anchors can be angled toward an ostium. For example and without limitation, the anchors can have a proximal surface that is angled back toward the proximal end of the contact member by an angle A of 5 degrees or approximately 5 degrees, or from 2 degrees or approximately 2 degrees to 15 degrees or approximately 15 degrees or more, or from 5 degrees or approximately 5 degrees to 10 degrees or approximately 10 degrees, or of any value within the foregoing ranges or to and from any values within the foregoing ranges. In some embodiments, angling the tissue anchors toward the proximal end of the contact member can improve the engagement (e.g., grip) of the tissue anchors in the tissue of the LAA as the retention element and/or the securing element are drawn toward the contact member, which can cause the contact member to be pulled toward the ostium of the LAA. In other embodiments, the tissue anchors 6118 can have a distal surface that can be angled toward a distal end 6104*b* of the contact member 6104**, or can have a mix of tissue anchors having a proximal surface angled toward the proximal end of the contact member, tissue anchors having a distal surface angled toward the distal end of the contact member, and/or symmetrically shaped tissue anchors.

In some embodiments, a length of any of the tissue anchors disclosed herein (for example and without limitation, the tissue anchors 6118), measured from the base of the tissue anchor to a distal tip of the tissue anchor along a centerline of the tissue anchor, can be 0.6 mm, or approximately 0.6 mm. In some embodiments, the length of the tissue anchors can be 0.5 mm, or from 0.4 mm (or approximately 0.4 mm, or less than 0.4 mm) to 0.8 mm (or approximately 0.8 mm, or more than 0.8 mm), or from 0.5 mm (or approximately 0.5 mm) to 0.7 mm (or approximately 0.7 mm), or of any value or range of values within any of the foregoing ranges.

With reference to FIGS. 86J-86L, in some embodiments, the tissue anchors 6118 can be positioned along a length of the struts 6108 of the contact member 6104 from the proximal end **6104*a* of the contact member 6104 to the distal end 6104*b* of the contact member 6104, or near or adjacent to the proximal end 6104*a* of the contact member 6104 to a point that is adjacent to or near to the distal end 6104*b* of the contact member 6104. In some embodiments, the tissue anchors 6118 can be positioned along at least 80% of a length of the struts 6108 of the contact member 6104, or from 60% (or approximately 60%, or less than 60%) to 100% (or approximately 100%) of the length of the struts 6108 of the contact member 6104**, or of any values or ranges of values within the foregoing ranges.

The securing element 6110 shown in FIGS. 86J-86L is shown in an expanded state (e.g., is in the second state) and spaced apart from the contact member 6104 that is also in an expanded, second state. In some embodiments of the implant 6102, similar to the implant 6002 described above, the securing element 6110 can be axially secured to the retention element 6108. Some embodiments of the retention element 6108 can have a threaded shaft) that can be positioned within a body portion of the securing element 6110. The threaded shaft 6109 can be permitted to rotate freely within the body portion 6111 of the securing element 6110. The threaded shaft 6109 can also be threadedly coupled with the contact member 6104. In this configuration, rotating the threaded shaft 6109 in a first direction can cause the securing element 6110 to advance axially toward the contact member 6104. Rotating the threaded shaft 6109 in a second direction which is opposite to the first direction can cause the securing element 6110 to withdraw or move axially away from the contact member 6104. With reference to FIG. 86K, the securing element 6110 can have a bend radius or radius of curvature (represented by R in FIG. 86K) near a base of the struts of the securing element 6110 that can be 1.0 mm (or approximately 1.0 mm) in size, or from 0.8 mm (or approximately 0.8 mm, or less than 0.8 mm) to 1.0 mm (or approximately 1.0 mm, or more than 1.0 mm), or from 0.6 mm (or approximately 0.6 mm, or less than 0.6 mm) to 1.4 mm (or approximately 1.4 mm, or more than 1.4 mm), or of any values or ranges of values within the foregoing ranges. In any embodiments disclosed herein, the securing element (including securing element 6110) can have an overall outside diameter (represented by D in FIG. 86L) of 13 mm (or approximately 13 mm), or from 10 mm (or approximately 10 mm, or less than 10 mm) to 20 mm (or approximately 20 mm, or more than 20 mm), or from 12 mm (or approximately 12 mm) to 17 mm (or approximately 17 mm), or of any values or ranges of values within the foregoing ranges.

In some embodiments, with reference to FIG. 86K, the space 6112 between the struts (also referred to herein as arms) of the securing element 6110 can be configured to reduce the stress in the struts and allow for a better stress and/or strain distribution along a length of the base portion of the struts of the securing element 6110. By increasing the length of the space between the struts of the securing element 6110, the struts are able to bend or flex more in the base portion of the struts, therein optimizing the stress and/or strain distribution along a length of the base portion of the struts.

In some embodiments, the retention element 6108 can have a head 6130 coupled with (e.g., integrally formed with) the threaded shaft 6109, the head 6130 being configured to couple with an end portion of an intermediate member of the catheter (not shown) so that a rotation or torque applied to the intermediate member can cause an equal rotation or torque to be applied to the head 6130 and the threaded shaft 6109 of the retention element 6108. In some embodiments, the retention element 6108 can be axially coupled with the body portion 6111 of the securing element 6110 so that the retention element 6108 and the securing element 6110 move together in either axial direction. For example and without limitation, in some embodiments, the retention element 6108 can have a first retainer 6135 that can be coupled with (e.g., welded to, press fit, or otherwise attached to) a distal end 6109*b* of the threaded shaft 6109 and a second retainer 6136 that can be positioned within and be axially constrained within the slot 6138 formed in the body portion 6111 of the securing element 6110.

The first retainer 6135 can prevent a proximal axial movement of the threaded shaft 6109 (i.e., in the proximal direction, away from the contact member 6104) relative to the body portion 6111 of the securing element 6110. Because the second retainer 6136 can have an opening axially therethrough that is smaller than the major diameter of the threaded portion of the threaded shaft 6108, the second retainer 6136 can prevent a distal axial movement of the threaded shaft 6109 (e.g., in the distal direction, toward the contact member 6104) relative to the body portion 6111 of the securing element 6110. In this configuration, any axial movement of the retention element 6108 will cause the simultaneous and equal axial movement of the securing element 6110. A proximal end portion of the contact member 6104 can have a collar member 6170. In some embodiments, the collar member 6170 can be used to constrain the post 6140 to the contact member 6104 so that the post 6140 cannot become disengaged from the contact member 6104.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device for treating a left atrial appendage of a left atrium, comprising:

an implant comprising:

(a) a contact member including a tissue engaging feature configured to engage an inside tissue surface of the left atrial appendage and to rotate about a longitudinal axis in at least a first direction from a first position to at least a second position so as to rotate and thus twist the left atrial appendage when the contact member is engaged with the inside tissue surface of the left atrial appendage; and (b) a securing element configured to move between a first position in which the securing element is decoupled from the contact member and a second position in which the securing element is coupled with the contact member, wherein the securing element is proximal to the contact member, and wherein a distal-most end of the contact member is rotationally fixed to the securing element about the longitudinal axis to thereby maintain the twist of the left atrial appendage.

2. The device of claim 1, wherein the contact member is configured to rotate at least in the first direction from the first position to the second position when a torque is applied to the contact member.

3. The device of claim 1, wherein the contact member is configured to rotate at least in the first direction from the first position to at least the second position to twist the left atrial appendage and reduce a size of an ostium of the left atrial appendage from a first size to a second size when the contact member is engaged with the inside tissue surface or the left atrial appendage.

4. The device of claim 3, wherein the implant is configured to inhibit the ostium of the left atrial appendage from enlarging back to the first size.

5. The device of claim 1, wherein the device is configured such that the contact member can be removed from the left atrial appendage after the securing element has been moved to the second position, and wherein the securing element is configured to prevent a rotation of the tissue of the left atrium and/or the left atrial appendage that has been constricted as a result of the rotation of the contact member from the first position to the second position.

6. The device of claim 1, wherein the contact member is configured to move between a first state and a second state, wherein an outside dimension of the contact member is greater in the second state than in the first state.

7. The device of claim 6, wherein the contact member is self-expandable such that the contact member will automatically expand from the first state to the second state when a restraint is removed from the implant without further intervention from a user.

8. The device of claim 6, wherein the contact member is configured to automatically move from the first state to the second state when a restraint is removed from the contact member, and wherein the contact member is configured to engage a wall portion of the left atrial appendage when the contact member is in the second state and advanced into the left atrial appendage.

9. The device of claim 1, wherein the contact member has a plurality of tissue anchors on an outer surface thereof.

10. The device of claim 9, wherein the plurality of tissue anchors of the contact member have a proximal facing surface that is angled toward a proximal end of the contact member at an angle from 2 degrees to 10 degrees.

11. The device of claim 1, wherein the device is configured to cause a tissue of the left atrium and/or the left atrial appendage to constrict around an outer surface of a body portion of the implant when the contact member is rotated to the second position.

12. The device of claim 11, wherein the securing element is configured to engage with the tissue that has constricted around the outer surface of the body portion of the implant to prevent rotation of the implant in a second direction that is opposite to the first direction.

13. The device of claim 1, wherein, in an operable position, the securing element is configured to at least inhibit the contact member from rotating back to the first position.

14. The device of claim 1, wherein the securing element is configured to prevent a rotation of at least a portion of the left atrial appendage in a second direction when the securing element is implanted in a tissue surface surrounding an ostium of the left atrial appendage, wherein the second direction is opposite to the first direction.

15. The device of claim 1, wherein the securing element is configured to at least expand from a first state to a second state, wherein an outside dimension of the securing element is greater in the second state than in the first state.

16. The device of claim 1, wherein the securing element comprises a plurality of arms.

17. The device of claim 16, wherein at least an end portion of each of the plurality of arms of the securing element point generally away from the contact member when the securing element is in a first state and point generally toward the contact member when the securing element is in a second state.

18. The device of claim 16, comprising a restraint configured to be movable in an axial direction relative to at least a portion of the securing element between a first axial position in which the plurality of arms of the securing element are restrained by the restraint and a second axial position in which the plurality of arms of the securing element are not restrained by the restraint, wherein the second axial position is closer to the at least a portion of the securing element than the first axial position.

19. The device of claim 18, wherein the restraint is configured to be movable in the axial direction relative to at least a portion of the securing element from the second position in which the plurality of arms of the securing element are not restrained by the restraint to the first position in which the plurality of arms of the securing element are restrained by the restraint to facilitate repositioning and/or removal of the implant.

20. The device of claim 18, comprising a threaded member configured such that rotating the threaded member will cause the restraint to move from the first position to the second position.

21. The device of claim 20, wherein the restraint is rotatable relative to the threaded member so that the restraint is not forced to rotate as the threaded member is rotated.

22. The device of claim 1, wherein the securing element comprises a plurality of struts and a plurality of interconnections between adjacent struts of the plurality of struts.

23. The device of claim 1, wherein the securing element has a helical shape and is configured to rotate about a body portion of the implant during an implantation procedure.

24. The device of claim 1, wherein the securing element is movable between a first state in which the securing element can spin freely relative to the contact member and a second state in which the securing element is rotationally locked to the contact member.

25. The device of claim 24, wherein one of the securing element and the contact member has recesses and the other of the securing element and the contact member has protrusions configured to selectively engage with the recesses such that the protrusions are spaced apart from the recesses when the securing element is in the first state and the protrusions are engaged with the recesses when the securing element is in the second state.

26. The device of claim 1, further comprising a retention element configured to selectively couple the securing element to the contact member at any of a range of selectable distances when the securing element is in the second position.

27. The device of claim 26, wherein the retention element comprises a threaded shaft configured to threadedly engage with the contact member, the threaded shaft being coupled with the securing element.

28. The device of claim 26, wherein the retention element is adjustable so as to move the securing element between at least a first position and a second position, wherein the securing element is closer to the contact member when the retention element is in the second position as compared to when the retention element is in the first position.

29. The device of claim 28, wherein the retention element comprises a threaded member, wherein a rotation of the threaded member in a first direction causes the securing element to move toward the contact member and a rotation of the threaded member in a second direction causes the securing element to move away from the contact member.

30. The device of claim 28, wherein the retention element is configured to slide at least in an axial direction over an inner core component of a delivery catheter.

31. The device of claim 1, wherein the second position of the contact member is at least one-quarter of a complete rotation relative to the first position.

32. The device of claim 1, wherein the second position of the contact member is at least one-half of a complete rotation relative to the first position.

33. The device of claim 1, comprising a catheter selectively coupled with the contact member and configured to exert a torque on the contact member to rotate the contact member from the first position until a threshold predetermined torque level is reached.

34. A device for occluding an anatomical structure, comprising: an implant comprising: (a) a contact member including a tissue engaging feature configured to grip an inside tissue surface of the anatomical structure and to thereby rotate about a longitudinal axis in at least a first direction from a first position to at least a second position so as to twist the anatomical structure when the contact member is gripped against the inside tissue surface of the anatomical structure, wherein a distal-most end of the contact member is configured to rotate with a proximal-most end of the contact member during the rotation about the longitudinal axis; and (b) a securing element configured to move between a first position in which the securing element is decoupled from the contact member and a second position in which the securing element is coupled with the contact member, wherein the securing element is rotatably coupled to the contact member to thereby be configured to maintain the twist of the anatomical structure.

35. A device for twisting an anatomical structure, comprising:

an implant comprising:

(a) a contact member including a tissue engaging feature configured to engage an inside tissue surface of the anatomical structure and to rotate about a longitudinal axis in at least a first direction from a first position to at least a second position so as to twist the anatomical structure when the contact member is engaged with the inside tissue surface of the anatomical structure; and (b) a securing element configured to move between a first position in which the securing element is decoupled from the contact member and a second position in which the securing element is coupled with the contact member, wherein the securing element is rotatably coupled to the contact member to thereby be configured to maintain the twist of the anatomical structure.

* * * * *